US012807966B2

(12) United States Patent
Fisher et al.

(10) Patent No.: US 12,807,966 B2
(45) Date of Patent: Nov. 24, 2026

(54) TRIPLE HELIX TERMINATOR FOR EFFICIENT RNA TRANS-SPLICING

(71) Applicant: The Trustees of the University of Pennsylvania, Philadelphia, PA (US)

(72) Inventors: Krishna J. Fisher, Durham, NC (US); Jean Bennett, Philadelphia, PA (US)

( * ) Notice: Subject to any disclaimer, the term of this patent is extended or adjusted under 35 U.S.C. 154(b) by 1184 days.

(21) Appl. No.: 17/604,228

(22) PCT Filed: Apr. 17, 2020

(86) PCT No.: PCT/US2020/028797
§ 371 (c)(1),
(2) Date: Oct. 15, 2021

(87) PCT Pub. No.: WO2020/214973
PCT Pub. Date: Oct. 22, 2020

(65) Prior Publication Data

US 2022/0204989 A1 Jun. 30, 2022

Related U.S. Application Data

(60) Provisional application No. 62/835,164, filed on Apr. 17, 2019.

(51) Int. Cl.
*C12N 15/86* (2006.01)
*A61K 48/00* (2006.01)
(Continued)

(52) U.S. Cl.
CPC .............. *C12N 15/86* (2013.01); *A61K 48/00* (2013.01); *A61K 48/005* (2013.01); (Continued)

(58) Field of Classification Search
CPC ............. C12N 2320/33; C12N 15/102; C12N 15/113; C12N 2830/36; C12N 2830/42
See application file for complete search history.

(56) References Cited

U.S. PATENT DOCUMENTS 5,478,745 A 12/1995 Samulski et al.
6,013,487 A 1/2000 Mitchell
(Continued)

FOREIGN PATENT DOCUMENTS

WO WO 2000/015822 A1 3/2000
WO WO 2005/033321 A2 4/2005
(Continued)

OTHER PUBLICATIONS

Wilusz, J. E., JnBaptiste, C. K., Lu, L. Y., Kuhn, C. D., Joshua-Tor, L., & Sharp, P. A. (2012). A triple helix stabilizes the 3' ends of long noncoding RNAs that lack poly(A) tails. Genes & development, 26(21), 2392-2407. https://doi.org/10.1101/gad.204438.112 (Year: 2012).*

(Continued)

*Primary Examiner* — Kimberly Chong
*Assistant Examiner* — Africa M McLeod
(74) *Attorney, Agent, or Firm* — Howson & Howson LLP; Colleen M. Schaller

(57) ABSTRACT

A nucleic acid trans-splicing molecule is provided that can replace an exon in a targeted mammalian ocular gene carrying a defect or mutation causing an ocular disease with an exon having the naturally-occurring sequence without the defect or mutation. The trans-splicing molecule includes a 3' transcription terminator domain which enhances the efficiency of trans-splicing. The 3' TTD comprises a triple helix domain and a tRNA-like domain.

16 Claims, 21 Drawing Sheets

Specification includes a Sequence Listing.

hhRz = Hammerhead Ribozyme
Comp14 = Truncated derivative of MALAT1 triple helix terminator
NB = Random Sequence Binding Domain (Non-Binding)

(51) Int. Cl.

| | |
|---|---|
| ***A61P 27/02*** | (2006.01) |
| ***C12N 15/10*** | (2006.01) |
| ***C12N 15/113*** | (2010.01) |

(52) U.S. Cl.

CPC ............ *C12N 15/113* (2013.01); *A61P 27/02* (2018.01); *C12N 15/102* (2013.01); *C12N 2320/33* (2013.01); *C12N 2750/14143* (2013.01); *C12N 2830/36* (2013.01); *C12N 2830/42* (2013.01); *C12N 2830/50* (2013.01)

(56) References Cited

U.S. PATENT DOCUMENTS

| | | | |
|---|---|---|---|
| 6,083,702 | A | 7/2000 | Mitchell et al. |
| 6,280,978 | B1 | 8/2001 | Mitchell et al. |
| 7,282,199 | B2 | 10/2007 | Gao et al. |
| 7,399,753 | B2 | 7/2008 | Mitchell et al. |
| 7,561,972 | B1 | 7/2009 | Welch et al. |
| 7,561,973 | B1 | 7/2009 | Welch et al. |
| 7,629,322 | B2 | 12/2009 | Kleinschmidt et al. |
| 7,888,112 | B2 | 2/2011 | Hermanson et al. |
| 8,053,232 | B2 | 11/2011 | Puttaraju et al. |
| 9,717,749 | B2 | 8/2017 | Wilusz et al. |
| 2006/0246422 | A1 | 11/2006 | Mitchell et al. |
| 2013/0059901 | A1 | 3/2013 | Bauer et al. |
| 2018/0369412 | A1 | 12/2018 | Mitchell et al. |

FOREIGN PATENT DOCUMENTS

| | | | | |
|---|---|---|---|---|
| WO | WO 2014/062801 | | 4/2014 | |
| WO | WO 2014/124282 A1 | | 8/2014 | |
| WO | WO-2017087900 A1 | * | 5/2017 | ........... A61K 48/005 |
| WO | WO 2019/027869 | | 2/2019 | |
| WO | WO 2019/204514 A1 | | 10/2019 | |

OTHER PUBLICATIONS

Dewan, A., Liu, M., Hartman, S., Zhang, S. S., Liu, D. T., Zhao, C., Tam, P. O., Chan, W. M., Lam, D. S., Snyder, M., Barnstable, C., Pang, C. P., & Hoh, J. (2006). HTRA1 promoter polymorphism in wet age-related macular degeneration. Science (New York, N.Y. ), 314(5801), 989-992. (Year: 2006).*

Khan, Arif O., et al. "A Deep Intronic CLRN1 (USH3A) Founder Mutation Generates an Aberrant Exon and Underlies Severe Usher Syndrome on the Arabian Peninsula." Scientific Reports, vol. 7, No. 1, May 3, 2017, www.ncbi.nlm.nih.gov/pmc/articles/PMC5431179/, https://doi.org/10.1038/s41598-017-01577-8. (Year: 2017).*

Wilusz, J. E., et al. "A Triple Helix Stabilizes the 3' Ends of Long Noncoding RNAs That Lack Poly(A) Tails." Genes & Development, vol. 26, No. 21, Oct. 16, 2012, pp. 2392-2407, https://doi.org/10.1101/gad.204438.112. Accessed May 15, 2019. Supplemental information. (Year: 2012).*

Avale, "Trans-splicing correction of tau isoform imbalance in a mouse model of tau mis-splicing," Hum. Mol. Genet., vol. 22(13):2603-11, Jul. 2013.

Beal et al., Second structural motif for recognition of DNA by oligonucleotide-directed triple-helix formation, Science, vol. 251: 1360-1363, Mar. 1991.

Beltran et al., "rAAV2/5 gene-targeting to rods: dose-dependent efficiency and complications associated with different promoters," Gene Ther., vol. 17(9):1162-1174, Sep. 2010.

Brown et al., "Structural insights into the stabilization of MALAT1 noncoding RNA by a bipartite triple helix," Nature Structural and Molecular Biology, vol. 21, 633-642, Jul. 2014.

Brown et al., Formation of triple-helical structures by the 3'-end sequences of MALAT1 and MENβ noncoding RNAs, Proc. Natl. Acad. Sci. USA, vol. 109:19202-7, Nov. 2012.

Buske et al., Triplexator: Detecting nucleic acid triple helices in genomic and transcriptomic data, Genome Res., vol. 22:1372-1382, Jul. 2012.

Cai et al., "A 350 bp region of the proximal promoter of Rds drives cell-type specific gene expression," Exp Eye Res., vol. 91(2):186-94, Aug. 2010.

Cash et al., "Pyrimidine motif triple helix in the Kluyveromyces lactis telomerase RNA pseudoknot is essential for function in vivo," Proc. Natl. Acad. Sci USA, vol. 110:10970-5, Jul. 2013.

Dooley et al., "Spliceosome-Mediated Pre-mRNA trans-Splicing Can Repair CEP290 mRNA," Molecular Therapy: Nucleic Acids, vol. 12:294-308, Sep. 2018.

Leiden University Medical Center, "MYO7A (MYO7A)—coding DNA reference sequence," last modified Feb. 17, 2010, retrieved on Feb. 19, 2022, from https://grenada.lumcnl/LOVD2/Usher_montpellier/refseq/MYO7A_codingDNA.html.

Fisher et al., "Transduction with recombinant adeno-associated virus for gene therapy is limited by leading-strand synthesis," J. Virol., vol. 70:520-532, Jan. 1996.

Gilbert et al., "Structure of the SAM-II riboswitch bound to S-adenosylmethionine," Nat. Struct. Mol. Biol., vol. 15:177-82, Feb. 2008.

Gruber et al., "The design and optimization of RNA trans-splicing molecules for skin cancer therapy," Mol. Oncol., vol. 7(6):1056, Dec. 2013.

Kachi et al., "Equine infectious anemia viral vector-mediated codelivery of endostatin and angiostatin driven by retinal pigmented epithelium-specific VMD2 promoter inhibits choroidal neovascularization," Human Gene Therapy, vol. 20:31-9, Jan. 2009.

Kay et al., "Viral vectors for gene therapy: the art of turning infectious agents into vehicles of therapeutics," Nat. Medic, vol. 7(1):33-40, Jan. 2001.

Kozak et al., "An analysis of 5'-noncoding sequences from 699 vertebrate messenger RNAs," Nucleic Acids Res., vol. 15 (20): 8125-8148, Oct. 1987.

Lambard et al.," Expression of rod-derived cone viability factor: dual role of CRX in regulating promoter activity and cell-type specificity," PLoS One, vol. 5(10):e13075, Oct. 2010.

Liberman et al., "Structure of a class II preQ1 riboswitch reveals ligand recognition by a new fold," Nat. Chem. Biol., vol. 9:353-5, Jun. 2013.

McLaughlin et al., "Adeno-associated virus general transduction vectors: analysis of proviral structures," J. Virol., vol. 62:1963, Jun. 1988.

Mitton-Fry et al., "Poly(A) tail recognition by a viral RNA element through assembly of a triple helix," Science, vol. 330:1244-7, Nov. 2010.

Morrissey et al., "PRE-1, a cis element sufficient to enhance cone- and rod-specific expression in differentiating zebrafish photoreceptors," BMC Dev, Biol, vol. 11:3, Jan. 2011.

Mussolino et al., "AAV-mediated photoreceptor transduction of the pig cone-enriched retina," Gene Ther, vol. 18(7):637-45, Jul. 2011.

NCBI Reference Sequence Database, NP_078939.3—probable aminopeptidase NPEPL 1 isoform 1 [*Homo sapiens*], May 2004.

NCBI Reference Sequence Database, NC_000011.9—*Homo sapiens* chromosome 11, GRCh37.p13 Primary Assembly, Jun. 2009.

NCBI Reference Sequence Database, NC_000012.12—*Homo sapiens* chromosome 12, GRCh38.p13 Primary Assembly, Feb. 2014.

NCBI Reference Sequence Database, NG_009073.1—*Homo sapiens* ATP binding cassette subfamily A member 4 (ABCA4), RefSeqGene on chromosome 1, Sep. 2019.

NCBI Reference Sequence Database, NM_000260.3—*Homo sapiens* myosin VIIA (MYO7A), transcript variant 1, mRNA, May 2008.

NCBI Reference Sequence Database, NM_000350.2—*Homo sapiens* ATP binding cassette subfamily A member 4 (ABCA4), mRNA, Jun. 2006.

NCBI Reference Sequence Database, NM_025114.3—*Homo sapiens* centrosomal protein 290 (CEP290), mRNA, Jul. 2006.

NCBI Reference Sequence Database, NP_000251.1—myosin VIIA [*Homo sapiens*], Oct. 2006.

NCBI Reference Sequence Database, NP_000341.2—retinal-specific phospholipid-transporting ATPase ABCA4 [*Homo sapiens*], Jun. 2006.

(56) References Cited

OTHER PUBLICATIONS

NCBI Reference Sequence Database, NR_002819—*Homo sapiens* metastasis associated lung adenocarcinoma transcript 1 (MALAT1), transcript variant 1, long non-coding RNA, Nov. 2016.
Nicoud et al., "Development of photoreceptor-specific promoters and their utility to investigate EIAV lentiviral vector mediated gene transfer to photoreceptors," J. Gene Med, vol. 9(12):1015-23, Dec 2007.
Thompson et al., "CLUSTAL W: improving the sensitivity of progressive multiple sequence alignment through sequence weighting, position-specific gap penalties and weight matrix choice," Nucleic Acid Res., vol. 22(22):4673-4680, Nov. 1994.
Puttaraju et al., "Spliceosome-mediated RNA trans-splicing as a tool for gene therapy," Nat Biotechnol., vol. 17:246-252, Mar. 1999.
Rindt et al., "Replacement of huntingtin exon 1 by trans-splicing," Cell Mol. Life Sci., vol. 69(24):4191, Dec. 2012.
Theimer et al., "Structure of the human telomerase RNA pseudoknot reveals conserved tertiary interactions essential for function," Mol Cell, vol. 17:671-82, Mar. 2005.
Tycowski et al., "Conservation of a triple-helix-forming RNA stability element in noncoding and genomic RNAs of diverse viruses," Cell Rep., vol. 2:26-32, Jul. 2012.
Walther et al., "Viral vectors for gene transfer: a review of their use in the treatment of human diseases," Drugs, 60(2):249-271, Aug. 2000.
Wilusz et al., "3' end processing of a long nuclear-retained noncoding RNA yields a tRNA-like cytoplasmic RNA," Cell, vol. 135(5): 919-932, Nov. 2008.
Wilusz et al., "A triple helix stabilizes the 39 ends of long noncoding RNAs that lack poly(A) tails," Genes and Develop, vol. 26(21):2392-2407, Aug. 2012.
Zhang et al., "Identification and Characterization of a Class of MALAT1-like Genomic Loci," Cell Reports, vol. 19, 1723-1738, May 2017.
Zuker, "Mfold web server for nucleic acid folding and hybridization prediction," Nucleic Acids Res., vol. 31(13): 3406-3415, Jul. 2002.
International Search Report and Written Opinion issued on International Patent Application No. PCT/US2020/028797, dated Jul. 22, 2020.
International Preliminary Report on Patentability issued on International Patent Application No. PCT/US2020/028797, dated Sep. 28, 2021.
Extended European Search Report dated Dec. 22, 2022 issued in corresponding European Patent Application No. 20791307.0.

* cited by examiner

FIG. 4B
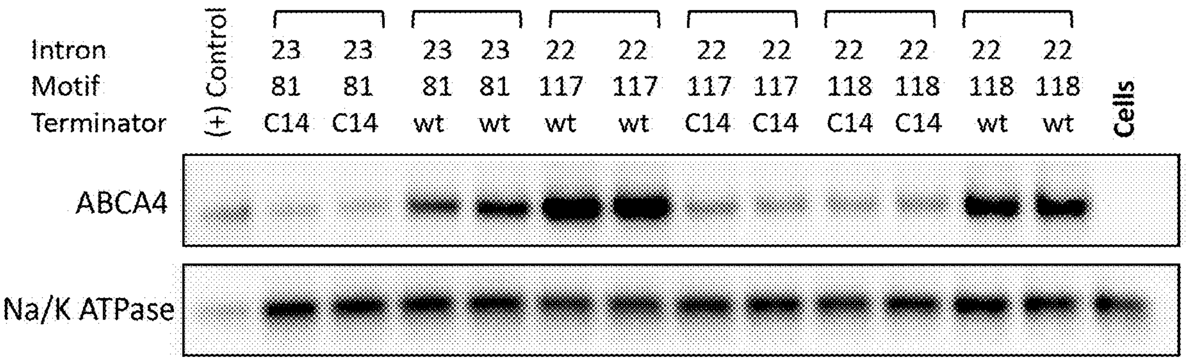
wt = native wild-type MALAT1 triple helix terminator
C14 = Comp14 derivative of MALAT1 triple helix terminator
Brackets indicate experimental replicates.
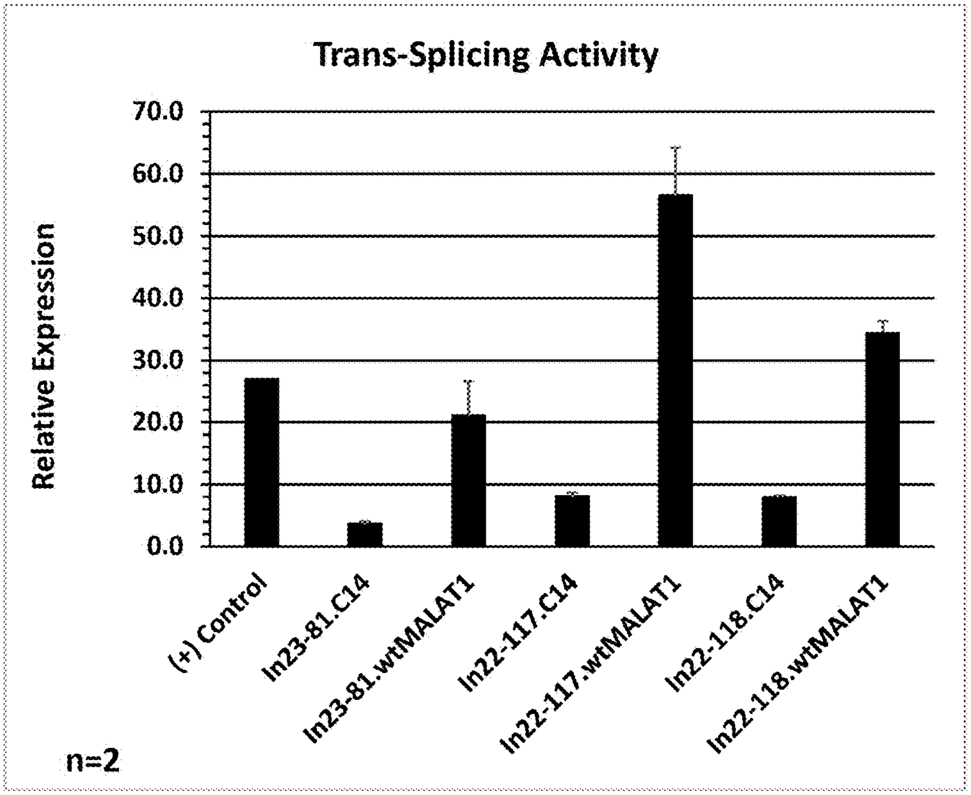

FIG. 5A

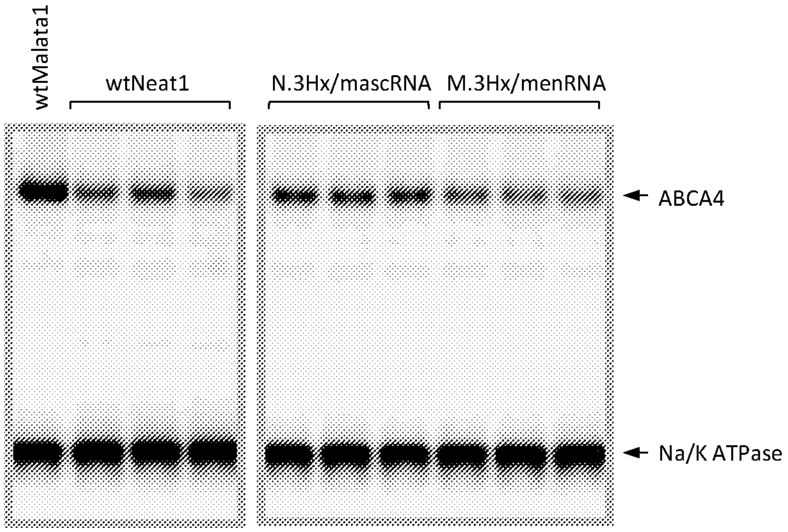

- wtMalat1 = Triple Helix Terminator from the Human Malat1 lncRNA
- wtNeat1 = Triple Helix Terminator from the Human Neat1 lncRNA
- N.3Hx/mascRNA = Chimeric Triple Helix Terminator; Triple Helix Domain from human Neat1 Fused to mascRNA from human Malat1
- M.3Hx/menRNA = Chimeric Triple Helix Terminator; Triple Helix Domain from human Malat1 Fused to menRNA from human Neat1
- Brackets indicate experimental replicates.

FIG. 5B

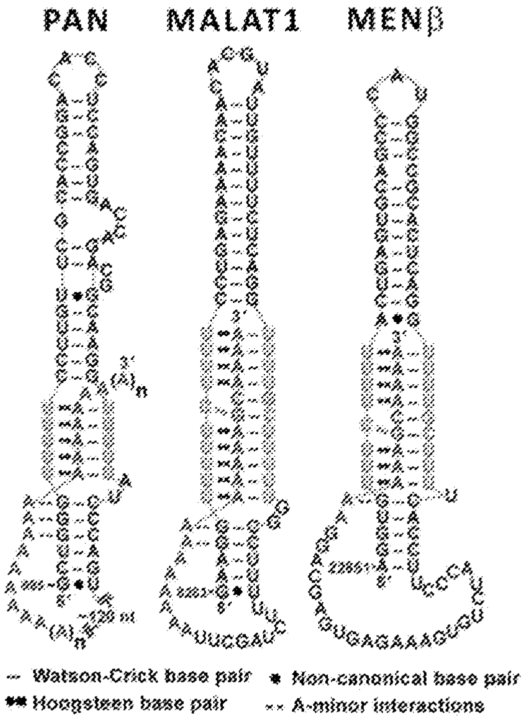

Folded conformation of the Malat1 mascRNA and its sequence conservation across difference species. The location of a G-to-A point mutation that was inserted to test the importance of this domain is indicated with a red arrow. As shown in the Western blot in FIG. 5B, this single point mutation ablated trans-splicing activity of an RTM that targets the ABCA4 gene.

Human MALAT1 3' Triple Helix Terminator with mascRNA

SEQUENCE LISTING

```
<160> NUMBER OF SEQ ID NOS: 37

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1

gtaagagagc tcgttgcgat attat                                           25


<210> SEQ ID NO 2
<211> LENGTH: 7
<212> TYPE: DNA
<213> ORGANISM: Artificial Sequence
<220> FEATURE:
<223> OTHER INFORMATION: Synthetic Construct

<400> SEQUENCE: 2

tactaac                                                                7


<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3

tactaactgg tacctcttct tttttttctg cag                                  33


<210> SEQ ID NO 4
<211> LENGTH: 5
<212> TYPE: DNA
<213> ORGANISM: Artificial Sequence
<220> FEATURE:
<223> OTHER INFORMATION: Synthetic Construct

<400> SEQUENCE: 4

caggt                                                                  5


<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5

tggtacctct tctttttttt ctg                                             23


<210> SEQ ID NO 6
<211> LENGTH: 150
<212> TYPE: DNA
<213> ORGANISM: Artificial Sequence
<220> FEATURE:
```

<223> OTHER INFORMATION: Synthetic Construct

<400> SEQUENCE: 6
tcactgttta atctgttaat tcatctgagc attttgaggg tgtagtcgct tgattttatc 60
ctagagagtg tgtgagtcac acacagagag gagcagaacc tccaagggtc cctttggctt 120
gtcatcaatt atgtggcagc tgtaggttct 150

<210> SEQ ID NO 7
<211> LENGTH: 8779
<212> TYPE: DNA
<213> ORGANISM: Homo sapiens

<400> SEQUENCE: 7
cgcagcctgc agcccgagac ttctgtaaag gactggggcc ccgcaactgg cctctcctgc 60
cctcttaagc gcagcgccat tttagcaacg cagaagcccg gcgccgggaa gcctcagctc 120
gcctgaaggc aggtcccctc tgacgcctcc gggagcccag gtttcccaga gtccttggga 180
cgcagcgacg agttgtgctg ctatcttagc tgtccttata ggctggccat tccaggtggt 240
ggtatttaga taaaaccact caaactctgc agtttggtct tggggtttgg aggaaagctt 300
ttatttttct tcctgctccg gttcagaagg tctgaagctc atacctaacc aggcataaca 360
cagaatctgc aaaacaaaaa cccctaaaaa agcagaccca gagcagtgta aacacttctg 420
ggtgtgtccc tgactggctg cccaaggtct ctgtgtcttc ggagacaaag ccattcgctt 480
agttggtcta ctttaaaagg ccacttgaac tcgctttcca tggcgatttg ccttgtgagc 540
actttcagga gagcctggaa gctgaaaaac ggtagaaaaa tttccgtgcg ggccgtgggg 600
ggctggcggc aactgggggg ccgcagatca gagtgggcca ctggcagcca acggcccccg 660
gggctcaggc ggggagcagc tctgtggtgt gggattgagg cgttttccaa gagtgggttt 720
tcacgtttct aagatttccc aagcagacag cccgtgctgc tccgatttct cgaacaaaaa 780
agcaaaacgt gtggctgtct tgggagcaag tcgcaggact gcaagcagtt gggggagaaa 840
gtccgccatt ttgccacttc tcaaccgtcc ctgcaaggct ggggctcagt tgcgtaatgg 900
aaagtaaagc cctgaactat cacactttaa tcttccttca aaaggtggta aactatacct 960
actgtccctc aagagaacac aagaagtgct ttaagaggta ttttaaaagt tccgggggtt 1020
ttgtgaggtg tttgatgacc cgtttaaaat atgatttcca tgtttctttt gtctaaagtt 1080
tgcagctcaa atctttccac acgctagtaa tttaagtatt tctgcatgtg tagtttgcat 1140
tcaagttcca taagctgtta agaaaaatct agaaaagtaa aactagaacc tatttttaac 1200
cgaagaacta ctttttgcct ccctcacaaa ggcggcggaa ggtgatcgaa ttccggtgat 1260
gcgagttgtt ctccgtctat aaatacgcct cgcccgagct gtgcggtagg cattgaggca 1320
gccagcgcag gggcttctgc tgagggggca ggcggagctt gaggaaaccg cagataagtt 1380
tttttctctt tgaaagatag agattaatac aactacttaa aaaatatagt caataggtta 1440
ctaagatatt gcttagcgtt aagtttttaa cgtaatttta atagcttaag attttaagag 1500
aaaatatgaa gacttagaag agtagcatga ggaaggaaaa gataaaaggt ttctaaaaca 1560
tgacggaggt tgagatgaag cttcttcatg gagtaaaaaa tgtatttaaa agaaaattga 1620
gagaaaggac tacagagccc cgaattaata ccaatagaag ggcaatgctt ttagattaaa 1680
atgaaggtga cttaaacagc ttaaagttta gtttaaaagt tgtaggtgat taaaataatt 1740
tgaaggcgat cttttaaaaa gagattaaac cgaaggtgat taaaagacct tgaaatccat 1800
gacgcaggga gaattgcgtc atttaaagcc tagttaacgc atttactaaa cgcagacgaa 1860
aatggaaaga ttaattggga gtggtaggat gaaacaattt ggagaagata gaagtttgaa 1920
gtggaaaact ggaagacaga agtacgggaa ggcgaagaaa agaatagaga agatagggaa 1980
attagaagat aaaaacatac ttttagaaga aaaaagataa atttaaacct gaaaagtagg 2040
aagcagaaga aaaaagacaa gctaggaaac aaaaagctaa gggcaaaatg tacaaactta 2100
gaagaaaatt ggaagataga aacaagatag aaaatgaaaa tattgtcaag agtttcagat 2160
agaaaatgaa aaacaagcta agacaagtat tggagaagta tagaagatag aaaaatataa 2220
agccaaaaat tggataaaat agcactgaaa aaatgaggaa attattggta accaatttat 2280
tttaaaagcc catcaattta atttctggtg gtgcagaagt tagaaggtaa agcttgagaa 2340
gatgagggtg tttacgtaga ccagaaccaa tttagaagaa tacttgaagc tagaagggga 2400
agttggttaa aaatcacatc aaaaagctac taaaaggact ggtgtaattt aaaaaaaact 2460
aaggcagaag gcttttggaa gagttagaag aatttggaag gccttaaata tagtagctta 2520
gtttgaaaaa tgtgaaggac tttcgtaacg gaagtaattc aagatcaaga gtaattacca 2580
acttaatgtt tttgcattgg actttgagtt aagattattt tttaaatcct gaggactagc 2640
attaattgac agctgaccca ggtgctacac agaagtggat tcagtgaatc taggaagaca 2700
gcagcagaca ggattccagg aaccagtgtt tgatgaagct aggactgagg agcaagcgag 2760
caagcagcag ttcgtggtga agataggaaa agagtccagg agccagtgcg atttggtgaa 2820
ggaagctagg aagaaggaag gagcgctaac gatttggtgg tgaagctagg aaaaaggatt 2880
ccaggaagga gcgagtgcaa tttggtgatg aaggtagcag gcggcttggc ttggcaacca 2940
cacggaggag gcgagcaggc gttgtgcgta gaggatccta gaccagcatg ccagtgtgcc 3000
aaggccacag ggaaagcgag tggttggtaa aaatccgtga ggtcggcaat atgttgtttt 3060
tctggaactt acttatggta accttttatt tattttctaa tataatgggg gagtttcgta 3120
ctgaggtgta aagggattta tatggggacg taggccgatt tccgggtgtt gtaggtttct 3180
ctttttcagg cttatactca tgaatcttgt ctgaagcttt tgagggcaga ctgccaagtc 3240
ctggagaaat agtagatggc aagtttgtgg gttttttttt tttacacgaa tttgaggaaa 3300
accaaatgaa tttgatagcc aaattgagac aatttcagca aatctgtaag cagtttgtat 3360
gtttagttgg ggtaatgaag tatttcagtt ttgtgaatag atgacctgtt tttacttcct 3420
caccctgaat tcgttttgta aatgtagagt ttggatgtgt aactgaggcg ggggggagtt 3480
ttcagtattt ttttttgtgg gggtgggggc aaaatatgtt ttcagttctt tttcccttag 3540
gtctgtctag aatcctaaag gcaaatgact caaggtgtaa cagaaaacaa gaaaatccaa 3600
tatcaggata atcagaccac cacaggttta cagtttatag aaactagagc agttctcacg 3660
ttgaggtctg tggaagagat gtccattgga gaaatggctg gtagttactc tttttttcccc 3720
ccaccccctt aatcagactt taaaagtgct taacccctta aacttgttat tttttacttg 3780
aagcattttg ggatggtctt aacagggaag agagagggtg ggggagaaaa tgtttttttc 3840
taagattttc cacagatgct atagtactat tgacaaactg ggttagagaa ggagtgtacc 3900
gctgtgctgt tggcacgaac accttcaggg actggagctg cttttatcct tggaagagta 3960
ttcccagttg aagctgaaaa gtacagcaca gtgcagcttt ggttcatatt cagtcatctc 4020
aggagaactt cagaagagct tgagtaggcc aaatgttgaa gttaagtttt ccaataatgt 4080
gacttcttaa aagttttatt aaaggggagg ggcaaatatt ggcaattagt tggcagtggc 4140
ctgttacggt tgggattggt ggggtgggtt taggtaattg tttagtttat gattgcagat 4200
aaactcatgc cagagaactt aaagtcttag aatggaaaaa gtaaagaaat atcaacttcc 4260
aagttggcaa gtaactccca atgatttagt ttttttcccc ccagtttgaa ttgggaagct 4320
gggggaagtt aaatatgagc cactgggtgt accagtgcat taatttgggc aaggaaagtg 4380
tcataatttg atactgtatc tgttttcctt caaagtatag agcttttggg gaaggaaagt 4440
attgaactgg gggttggtct ggcctactgg gctgacatta actacaatta tgggaaatgc 4500
aaaagttgtt tggatatggt agtgtgtggt tctcttttgg aattttttttc aggtgattta 4560
ataataattt aaaactacta tagaaactgc agagcaaagg aagtggctta atgatcctga 4620
agggatttct tctgatggta gcttttgtat tatcaagtaa gattctattt tcagttgtgt 4680
gtaagcaagt tttttttttag tgtaggagaa atacttttcc attgtttaac tgcaaaacaa 4740
gatgttaagg tatgcttcaa aaattttgta aattgtttat tttaaactta tctgtttgta 4800
aattgtaact gattaagaat tgtgatagtt cagcttgaat gtctcttaga gggtgggctt 4860
ttgttgatga gggaggggaa acttttttttt tttctataga ctttttttcag ataacatctt 4920
ctgagtcata accagcctgg cagtatgatg gcctagatgc agagaaaaca gctccttggt 4980
gaattgataa gtaaaggcag aaaagattat atgtcatacc tccattgggg aataagcata 5040
accctgagat tcttactact gatgagaaca ttatctgcat atgccaaaaa attttaagca 5100
aatgaaagct accaatttaa agttacggaa tctaccattt taaagttaat tgcttgtcaa 5160
gctataacca caaaaataat gaattgatga gaaatacaat gaagaggcaa tgtccatctc 5220
aaaatactgc ttttacaaaa gcagaataaa agcgaaaaga aatgaaaatg ttacactaca 5280
ttaatcctgg aataaaagaa gccgaaataa atgagagatg agttgggatc aagtggattg 5340
aggaggctgt gctgtgtgcc aatgtttcgt ttgcctcaga caggtatctc ttcgttatca 5400
gaagagttgc ttcatttcat ctgggagcag aaaacagcag gcagctgtta acagataagt 5460
ttaacttgca tctgcagtat tgcatgttag ggataagtgc ttatttttaa gagctgtgga 5520
gttcttaaat atcaaccatg gcactttctc ctgacccctt ccctagggga tttcaggatt 5580
gagaaatttt tccatcgagc ctttttaaaa ttgtaggact tgttcctgtg ggcttcagtg 5640
atgggatagt acacttcact cagaggcatt tgcatcttta aataatttct taaaagcctc 5700
taaagtgatc agtgccttga tgccaactaa ggaaatttgt ttagcattga atctctgaag 5760
gctctatgaa aggaatagca tgatgtgctg ttagaatcag atgttactgc taaaatttac 5820
atgttgtgat gtaaattgtg tagaaaacca ttaaatcatt caaaataata aactattttt 5880
attagagaat gtatactttt agaaagctgt ctccttattt aaataaaata gtgtttgtct 5940
gtagttcagt gttggggcaa tcttgggggg gattcttctc taatctttca gaaactttgt 6000
ctgcgaacac tctttaatgg accagatcag gatttgagcg gaagaacgaa tgtaacttta 6060
aggcaggaaa gacaaatttt attcttcata aagtgatgag catataataa ttccaggcac 6120
atggcaatag aggccctcta aataaggaat aaataacctc ttagacaggt gggagattat 6180
gatcagagta aaaggtaatt acacatttta tttccagaaa gtcaggggtc tataaattga 6240
cagtgattag agtaatactt tttcacattt ccaaagtttg catgttaact ttaaatgctt 6300
acaatcttag agtggtaggc aatgttttac actattgacc ttatataggg aagggagggg 6360
gtgcctgtgg ggttttaaag aattttcctt tgcagaggca tttcatcctt catgaagcca 6420
ttcaggattt tgaattgcat atgagtgctt ggctcttcct tctgttctag tgagtgtatg 6480
agaccttgca gtgagtttat cagcatactc aaaatttttt tcctggaatt tggagggatg 6540
ggaggagggg gtggggctta cttgttgtag cttttttttt ttttacagac ttcacagaga 6600
atgcagttgt cttgacttca ggtctgtctg ttctgttggc aagtaaatgc agtactgttc 6660
tgatcccgct gctattagaa tgcattgtga aacgactgga gtatgattaa aagttgtgtt 6720
ccccaatgct tggagtagtg attgttgaag gaaaaaatcc agctgagtga taaaggctga 6780
gtgttgagga aatttctgca gttttaagca gtcgtatttg tgattgaagc tgagtacatt 6840
ttgctggtgt atttttaggt aaaatgcttt ttgttcattt ctggtggtgg gaggggactg 6900
aagcctttag tcttttccag atgcaacctt aaaatcagtg acaagaaaca ttccaaacaa 6960
gcaacagtct tcaagaaatt aaactggcaa gtggaaatgt ttaaacagtt cagtgatctt 7020
tagtgcattg tttatgtgtg ggtttctctc tcccctccct tggtcttaat tcttacatgc 7080
aggaacactc agcagacaca cgtatgcgaa gggccagaga agccagaccc agtaagaaaa 7140
aatagcctat ttactttaaa taaaccaaac attccatttt aaatgtgggg attgggaacc 7200
actagttctt tcagatggta ttcttcagac tatagaagga gcttccagtt gaattcacca 7260
gtggacaaaa tgaggaaaac aggtgaacaa gctttttctg tatttacata caaagtcaga 7320
tcagttatgg gacaatagta ttgaatagat ttcagcttta tgctggagta actggcatgt 7380
gagcaaactg tgttggcgtg gggtggagg ggtgaggtgg gcgctaagcc ttttttaag 7440
atttttcagg taccctcac taaaggcacc gaaggcttaa agtaggacaa ccatggagcc 7500
ttcctgtggc aggagagaca acaaagcgct attatcctaa ggtcaagaga agtgtcagcc 7560
tcacctgatt tttattagta atgaggactt gcctcaactc cctctttctg gagtgaagca 7620
tccgaaggaa tgcttgaagt acccctgggc ttctcttaac atttaagcaa gctgtttta 7680
tagcagctct taataataaa gcccaaatct caagcggtgc ttgaagggga gggaaagggg 7740
gaaagcgggc aaccactttt ccctagcttt tccagaagcc tgttaaaagc aaggtctccc 7800
cacaagcaac ttctctgcca catcgccacc ccgtgccttt tgatctagca cagacccttc 7860
acccctcacc tcgatgcagc cagtagcttg gatccttgtg ggcatgatcc ataatcggtt 7920
tcaaggtaac gatggtgtcg aggtctttgg tgggttgaac tatgttagaa aaggccatta 7980
atttgcctgc aaattgttaa cagaagggta ttaaaaccac agctaagtag ctctattata 8040
atacttatcc agtgactaaa accaacttaa accagtaagt ggagaaataa catgttcaag 8100
aactgtaatg ctgggtggga acatgtaact tgtagactgg agaagatagg catttgagtg 8160
gctgagaggg cttttgggtg ggaatgcaaa aattctctgc taagactttt tcaggtgaac 8220
ataacagact tggccaagct agcatcttag cggaagctga tctccaatgc tcttcagtag 8280
ggtcatgaag gtttttcttt tcctgagaaa acaacacgta ttgttttctc aggttttgct 8340
ttttggcctt tttctagctt aaaaaaaaaa aaagcaaaag atgctggtgg ttggcactcc 8400
tggtttccag gacggggttc aaatccctgc ggcgtctttg ctttgactac taatctgtct 8460
tcaggactct ttctgtattt ctccttttct ctgcaggtgc tagttcttgg agttttgggg 8520
aggtgggagg taacagcaca atatctttga actatataca tccttgatgt ataatttgtc 8580
aggagcttga cttgattgta tattcatatt tacacgagaa cctaatataa ctgccttgtc 8640
tttttcaggt aatagcctgc agctggtgtt ttgagaagcc ctactgctga aaacttaaca 8700
attttgtgta ataaaaatgg agaagctcta aattgttgtg gttcttttgt gaataaaaaa 8760
atcttgattg gggaaaaaa 8779

<210> SEQ ID NO 8
<211> LENGTH: 22743
<212> TYPE: DNA

<213> ORGANISM: Homo sapiens

<400> SEQUENCE: 8
ggagttagcg acagggaggg atgcgcgcct gggtgtagtt gtgggggagg aagtggctag 60
ctcagggctt caggggacag acagggagag atgactgagt tagatgagac gaggggggcgg 120
gctgggggtg cgagaaggaa gcttggcaag gagactaggt ctaggggac cacagtgggg 180
caggctgcat ggaaaatatc cgcagggtcc cccaggcaga acagccacgc tccaggccag 240
gctgtcccta ctgcctggtg gagggggaac ttgacctctg ggagggcgcc gctcttgcat 300
agctgagcga gcccgggtgc gctggtctgt gtggaaggag gaaggcaggg agaggtagaa 360
ggggtggagg agtcaggagg aataggccgc agcagccctg gaaatgatca ggaaggcagg 420
cagtgggtgc agggctgcag gagggccggg agggctaatc ttcaacttgt ccatgccagc 480
agccccttttt tttccagacc aagggctgtg aacccgcctg gggatgaggc ctggtcttgt 540
ggaactgaac ttagctcgac ggggctgacc gctctggccc agggtggtat gtaattttcg 600
ctcggcctgg gacggggccc aggccgggcc cagcctggtg gagcgtccag gtctgggtgc 660
gaagccaggc ccctgggcgg aggtgagggg tggtctgagg agtgatgtgg agttaaggcg 720
ccatcctcac cggtgactgg tgcggcacct agcatgtttg acaggcgggg actgcgaggc 780
acgctgctcg ggtgttgggg acaacattga ccaacgcttt attttccagg tggcagtgct 840
ccttttggac ttttctctag gtttggcgct aaactcttct tgtgagctca ctccacccct 900
tcttcctccc tttaacttat ccattcactt aaaacattac ctggtcatct ggtaagcccg 960
ggacagtaag ccgagtggct gttggagtcg gtattgttgg taatggtgga ggaagagagg 1020
ccttcccgct gaggctgggg tggggcggat cggtgttgct tgcctgcaga gagggtgggg 1080
agtgaatgtg cacccttggg tgggcctgca gccatccagc tgaaagttac aaaaatgctt 1140
catggaccgt ggtttgttac tatagtgttc ctcatggcga gcagatggaa ccgggagaca 1200
tggagtccct ggccagtgtg agtcctagca ttgcaggagg ggagaccctg gaggagagag 1260
cccgcctcaa ttgatgcctg cagattgaat ttccagaggc ttaggaggag gaagttctcc 1320
aatgttctgt ttccaggcct tgctcaggaa gccctgtatt caggaggcta ccatttaaag 1380
tttgcagatg agcttatggg gggcaatctt aaaaagtcca cagcagatgc atccggctcg 1440
aggggccatc agctttgaat aaatgcttgt tccagagccc atgaatgcca gcaggcaccc 1500
ctcctttcct ggggtaaagg ttttcagatg ctgcatcttc taaattgagc ctccggtcat 1560
actagttttg tgcttggaac cttgcttcaa gaagatccct aagctgtaga acattttaac 1620
gttgatgcca caacgcagat tgatgccttg tagatggagc ttgcagatgg agccccgtga 1680
cctctcacct acccacctgt ttgcctgcct tcttgtgcgt ttctcggaga agttcttagc 1740
ctgatgaaat aacttggggc gttgaagagc tgtttaattt taaatgcctt agactgggga 1800
tatattagag gaagcagatt gtcaaattaa gggtgtcatt gtgttgtgct aaacgctggg 1860
agggtacaag ttggtcattc ctaaatctgt gtgtgagaaa tggcaggtct agtttgggca 1920
ttgtgattgc attgcagatt actaggagaa gggaatggtg ggtacaccgg tagtgctctt 1980
ttgttcttgc ttcgtttttt taaacttgaa ctttacttcg ttagatttca taatactttc 2040
ttggcattct agtaagagga ccctgaggtg ggagttgtgg gggacgggga gaaggggaca 2100
gcttggcacc ggtcccgtgg gcgttgcagt gtgggggatg gggtatgca gcttggcact 2160
ggtactggga gggatgaggg tgaagaaggg gagagggttg gttagagata cagtgtgggt 2220
ggtgggggtg gtaggaaatg caggttgaag ggaattctct ggggctttgg ggaatttagt 2280

```
gcgtgggtga gccaagaaaa tactaattaa taatagtaag ttgttagtgt tggttaagtt   2340
gttgcttgga agtgagaagt tgcttagaaa ctttccaaag tgcttagaac tttaagtgca   2400
aacagacaaa ctaacaaaca aaaattgttt tgctttgcta caaggtgggg aagactgaag   2460
aagtgttaac tgaaaacagg tgacacagag tcaccagttt tccgagaacc aaagggaggg   2520
gtgtgtgatg ccatctcaca ggcaggggaa atgtctttac cagcttcctc ctggtggcca   2580
agacagcctg tttcagaggg ttgttttgtt tggggtgtgg gtgttatcaa gtgaattagt   2640
cacttgaaag atgggcgtca gacttgcata cgcagcagat cagcatcctt cgctgcccct   2700
tagcaactta ggtggttgat ttgaaactgt gaaggtgtga ttttttcagg agctggaagt   2760
cttagaaaag ccttgtaaat gcctatattg tgggctttta acgtatttaa gggaccactt   2820
aagacgagat tagatgggct cttctggatt tgttcctcat ttgtcacagg tgtcttgtga   2880
ttgaaaatca tgagcgaagt gaaattgcat tgaatttcaa gggaatttag tatgtaaatc   2940
gtgccttaga aacacatctg ttgtcttttc tgtgtttggt cgatattaat aatggcaaaa   3000
tttttgccta tctagtatct tcaaattgta gtctttgtaa caaccaaata accttttgtg   3060
gtcactgtaa aattaatatt tggtagacag aatccatgta cctttgctaa ggttagaatg   3120
aataatttat tgtattttta atttgaatgt ttgtgctttt taaatgagcc aagactagag   3180
gggaaactat cacctaaaat cagtttggaa aacaagacct aaaaagggaa ggggatgggg   3240
attgtgggga gagagtgggc gaggtgcctt tactacatgt gtgatctgaa aaccctgctt   3300
ggttctgagc tgcgtctatt gaattggtaa agtaatacca atggcttttt atcatttcct   3360
tcttcccttt aagtttcact tgaaatttta aaaatcatgg ttatttttat cgttgggatc   3420
tttctgtctt ctgggttcca tttttaaat gtttaaaaat atgttgacat ggtagttcag   3480
ttcttaacca atgacttggg gatgatgcaa acaattactg tcgttgggat ttagagtgta   3540
ttagtcacgc atgtatgggg aagtagtctc gggtatgctg ttgtgaaatt gaaactgtaa   3600
aagtagatgg ttgaaagtac tggtatgttg ctctgtatgg taagaactaa ttctgttacg   3660
tcatgtacat aattactaat cacttttctt cccctttaca gcacaaataa agtttgagtt   3720
ctaaactcat tagaattgtt gtattgctat gttacatttc tcgaccccta tcacattgcc   3780
ttcataacga ctttggatgt atcttcatat tgtagattta ggtctagatt tgctagctcc   3840
aagtaattaa ggccatgtag gagagcatgg taaccacaga tagaactggt attatcccaa   3900
gtggtctgca gactgctgag tggggatggg atctgctctc tgttgagagt tggtaatcat   3960
tggtttgaaa tgtgatgaaa ccactcaagc caatgaaggt gggtgtgtag gtggggagta   4020
ctttgccata atattttaaa acattacctg gttagagttc taagtggtac ttatttttgt   4080
ttggttaggg gaaagcctga ataaaaacag aaatggacac ataatatgca tattccatag   4140
tctttgggag gctggaatgt gcctgggatt tgggtctaag tgtatgcgta attcttacct   4200
cactaaagaa tttgccttgt ttttttcctt ttggtgagtg actaaaacgt ctgggcttcc   4260
ctgtgtgcgt gctacagtaa gcaagcagag gctgtgcaaa ggtgtgagca ggatcacgtg   4320
gaatctggag gatacatctt ggcttgcaaa ctgcctctgt ctcctgggtg ggactgttct   4380
gtccttgcac tgctgttctg tgttacctct tggggtgtaa ggttttgctt acaggagaca   4440
aactttgggc gtagaatgga agccactgcc agcctctgtg ctgagaagga aggtgcttgt   4500
ttcaaaggga gcagcaaggg aggcttgttc tactcacctg ggcctgtttg cctgagaagg   4560
ggagataagg gctgaactgg gactagccag ggggaccaac acaaatggtg ggggatcatg   4620
```

-continued

```
acctgaagga ttctttcctt cccatgagct gcagggctgg ttgccgtcct tgcaactgtg   4680
tcttatttgc ctgtgccgtt atatcttggt gacccctcca cgtgtacact actgacaaac   4740
gggtggagtg ctggggagaa gtcactgtgc cgcccaccta gtaaaccttc tgtctgtgct   4800
catggcatct ccaagatggg gcactgctgt gtgcagaatc cagggtcctc tttctgcttg   4860
caactccttt ccctggatgc cccagaaaca atccaggcct cctttcctat cttacccctt   4920
tgctttgctt tttaccccag cacctctata accgccttct cttcttttca gaactccttg   4980
tttctcgtcc tgttttttat gattacaaaa ctcttgcttc caccctggaa gataactgct   5040
atagatgcct gtatgtaaat ggtgctgtct ccagcaactg gcatgctgaa gaagaattga   5100
ttcacggggt ataaatgttg gggattggaa gtggggatga aatggcactt gttgatacag   5160
gagcagagag gtgaggccga ctgctgaaga cagctcgcca ccctccttgc ctccactcca   5220
atccaggggc tggggccaca ttctttgcct tcatttatcc tcagatcagg tgagatcgac   5280
aggaggtgtt gatggcagtg ccagcaatta ttgctaatcc gtttgcatcc ttatgcatag   5340
atctgaattc agactttgtg aatttccaga ggtgtgggta atataataga attcagtgag   5400
tgggcatggc tgatcttgtg caaattaaaa gttatggggc ataagaatag caaaagttga   5460
acttctttta aaaaggaaag taccctgaga gccagtattg gttgaggctc ttcagtatgc   5520
ccaggttggc agcactgaga accgcaggaa cggcctgttg ttacaaaaag gagattgact   5580
cagctgccct tggtgcatct gactgactat gactgctgag agattccaag gacccttaat   5640
gccagggcta acctctccat gtgcagtgag acctctggag gaagtgtcat cctctggctt   5700
tgtgtggtac tcattatggt gcagtgcggg catgaaatga agacacccaa ataggcttac   5760
agatacgata tgttttaaat gttcgtattt aacaaaaaca tactgacact gtttggaaat   5820
ggcaacagga agatagcaaa atgaatacta acattacgaa aagatgaaca ggtacatgtt   5880
ccaaggcagg tggctgtgaa cttcctctga gtgaaggcat cccctccagc acctttcagc   5940
ctgctagtta ggacgacccg ccgccaccct ccaggacctc cagccctgca ctgcctttcc   6000
tctcttttaa ataattcttc attgagttct aatatgtaaa aaaaaaaagt ttactgtaaa   6060
gtttgcaaat aaggaaattt tttttaaaag tcctcagtaa tcttaccagt aacaattgtt   6120
atgggcacat ttgcttttgg aagatttctt ttgtatgcat gggataagta catttttaaa   6180
caaaaatggg attatgccat aaattctatt ttgtgacttt aatatatagt gaacaccttt   6240
tttaatgatg acaggatgtt cccttgcatg gctgtatcaa tttaaacaat cttgtttcaa   6300
tgggcataca gggtattttc tagttttttt ttcctcttag aaaataatac ttgcgatgac   6360
tttccttgta gctcagactt tttcacgtct gttgttatct ctttgggaat gctgaataca   6420
tacatttcga gaaggaaatg actgttaaac tcttaagact tcaggttcat attgctaaac   6480
tgcccagcag ggagggattt tttcaattag tgttctcact ggtgaggcaa acctgatgcc   6540
ttcccctctt cctcagaacc ggctttatca cattgaaaac ctttgctcct ccgacggatc   6600
gagtctgctt tccctctgga tgtgagcatt gctttgtctg ctggtgactg aacatctcta   6660
ccttgtgtca attggccatt tgtggtgtgt gtgtgtgtgc gtgtgtgtgt gtgtgtgtgt   6720
gtatgatttt ctaattccta gtcatttttc tattgattgt tttgcaaaag ccatttacat   6780
cttaaggata ttgataatct tttgttatat ttgatgcaaa tatttttttc cagtttatag   6840
gttgcctttt aattttgtgt ttcaggtaga taaaagttaa acgattttct taggttagtt   6900
tatcactgtg gtttctgaac ttgttatgtg tagatctttt ccaccccaag agtacataaa   6960
tattaatcca tactttctta tggaacttgt atggtttcgt tttttacatt taaaccttct   7020
```

tccccgtggt gtgtgttgtg gaatctgtgt ttgtgtgagg aggggcatgg tgctctcaga 7080
acccacctcc tgtggccaga gagccctgtc ctgtgagggt ggttgtcaca gtggcagggt 7140
tcaattcaga agaccttgag ggcaggctga tgtttcctga atgggcccct ggttgttgct 7200
tgtccctgac tctccatttc cccatctgag tggatttgga cctaataggg cactggagct 7260
ggttcgaatc ctgactggac tacttggcaa ctttatgtct gggagcaagt tacttaacct 7320
ccccaagcct gtgtctgtga aatgcgggta aatgaatgta gatgtttggc agcagctact 7380
ccttgttgag ctctcacagt gaactctcct gcctctgccc tccttccccg cctcccctgg 7440
tgcctagcgt caggtctagc cacttcctcc tgggcccctc tcccttttct gtggctggct 7500
gcctgcccgc ctggcgctgg acctttcatg taacgggaat cagcatgtat attctggtct 7560
ggtctgtttc tacacttaat tttgtttcca gtagtatttc cctgtaccgg cagagttcac 7620
aaacacattt gaagaggctt tttctcagga ttcttaacct tcccaaagga agtcccatgg 7680
atgggtttct agaagtctat aaatgctctg aaattgtatt tttctgtgga aagcataact 7740
ttcatctgct tgttcgtgct caaaaaagat catgaatgaa tgattgcatg attttatgcc 7800
attgtgctta tactaaagga tatgtagccc atctcttgag ctgttaaact gttttgacta 7860
ctttaaatcg tgcagctgtg agcatctctg taaatttagt gtacacatgt atcccctgga 7920
gtggcattgc ctcggcagtg agcacttatg gttttataac tctcttcaca gactcaaatg 7980
actccagaaa gctacacttc ctgttgtgag tatatgatat ccatttccct acatagccac 8040
taacatcagg tttttacaat tttatttatt tcttgctact ttaagaaatt tttgtggtga 8100
aatacatata atagaagttg actatctgaa tcatttttaa gtatacattc agtagtgtta 8160
agtatgtcgc cattgttgta caaccaatct ccagaacttt ttcatcttgc aaaacaaact 8220
ctgtacccat taaataacat taaacattcc attccctcca gcctcagcaa ccccattcta 8280
ctttctgttt ctgtgagttt gactattcca agcacttcat atcagttaaa tcatgaagta 8340
tttgtctgtc tgtgactggc ttatttctct gagcacagtg tcctcgagat gcgtctatgt 8400
tgtagcatat gtcagaattt ccttcctttt taaaagatcc aaataatatt cttattttat 8460
atcttttttt tatccattca tccattagtg gacacttggg ttgcttttgg ctattgtaaa 8520
taatggtgct atgtacaaat atctatatta ttgtatttac aagtataatg ctgtaatgta 8580
cacacatctt tttgagatcc taccttcagt tcttttgagt atatagccag aagtggtatt 8640
actaaatctt acgatatttc tatttttaat ttattgagga accactgtag tttttcatag 8700
caactgcacc attttacgtt ctcaccaaga gtgcacaagg gttccgaggt tcccacatcc 8760
tccccaacac ttgttatttt ctgctttttt tagattgcag ccatcatagt gggtgtgagg 8820
tgacatttca ttgtggtttt gatttgcatt tccctaatga ggagtgatgc tgagcatctt 8880
ttcatatgct tactggtcat ttgtatgttg tctttggaaa aatgtctatt caagtccttt 8940
gactatttta aaaattgggt tattagagtt atcgttgttg ttgacttgta ggagtttctt 9000
tctatattct ggatattaat cccctatcag atatatgatt tgcaaatatc ttctcttatt 9060
ccataaggtt actttttcac tttgttgatt gtgttctttg atgtatagaa gtttttagtt 9120
ttgaaatagt ctaatttatc tgtttttact tttgtggtct gtgcttttgg tgtcatatcc 9180
aagaaatcct tgccaaatcc aacgttataa ggtactttta aggtatttta gttgtcttag 9240
tctatatttc tgtactcacc tttctttatc cactcatcag ttgatgggca tgtaggttgg 9300
ttccatatct ttgcaattct gaattgtgct atgatcaggt gtctttttag tataatgatt 9360

```
tactctcctt tgggtagata cccagtagtg ggattgctgg atcgaatggt ttttataatt   9420
ttctatttta ccacagtttc tctctgcatt tttcctcttt gaccactaac catgtgaaat   9480
tctcatattg acctttataa tgatcatgaa ctcttagtat cattgggaag gccacatttg   9540
ccacttatga ttgtaaacct tatcctccat ttttcctgtt attgttggtg caaaaagcac   9600
ctattatacc aggactttaa aaatcagtct gataagtctt tgataagtct aataataata   9660
actgataagt ccattgaatt tgcttctgat tactttttct ttagtagcta aacatgtatg   9720
tactcctatg attacaatga acactcctct ccatttaaat taattattta cattgatgaa   9780
atagcaaaat gttaatgact aaatactgtc ttggtttttt cgttccaggt cagtcaatat   9840
taacttctta taattttctt ttttttcttt atgtgtgtgt gtgtgtgtat tttttttttt   9900
ttaatttcaa tggcttttgg ggtacaaatg gcttttggtc atatagatga attctacagt   9960
agtgaagtct gagattttac tgcaccggtc acctgagtag tgtacattgt acccaatatg  10020
tggtttttta taccttgccc ccctcttacc ctccccactt tgagtctcta gtgtccatta  10080
tgtcactctg tatacctttt tgtacccata agttagctct cacttataag tgagaacaca  10140
cagtatttgg ttttccattc ctgagttgct tcacttagaa taatatcctc cagctccatc  10200
caaaattgct gcaaaaaaaa aaaaaaccac aaacattatt ttgttctttt ttattgctaa  10260
gtcatattcc atggtgtaga gataccacat tttatttatc cactcactgg ttgatgggtt  10320
ggttccacat ctttgcaatt gtgacttgta ctgccatcaa gtgtctttct ggtataatga  10380
cttcttttcc tttgggtaga tacccaggag tgggattgct agatcaaatg gttcttaaca  10440
ttttctctct ggatctattt ctggaaattt taggctccag tttttgttgt tgttgttaat  10500
aaaatgcaat ggaatgtaat gatcatcact tttcattatg ctttaaaatc tggtaaatgg  10560
aggctagaac actcctgtaa ggcaagaata ttctctctgt tggaactcaa atacacagaa  10620
ctgggtaaat ctcaatctta atctttgatt caggacacaa catggctctc ttttacttgc  10680
tttctttaat tgttttttaa taatgtggta agcatttctg aatctcctat ccaatacaaa  10740
aactaggaca atacagacag taactcctat ggttacaatg aacactcctc tccacttaaa  10800
ttaattattt acactgatga aattgaaata gcaaaatttt aatgactaaa tactgtcttt  10860
gatttttgt tccaggtctg tcaatattaa cttcttataa ttttcttttt ttttctttat  10920
gtgtgtgtgt gtgtgtgtat atatatatat ttaatttcaa tggcttttgg ggtacaaatg  10980
gcttttggtc atatatatga gttctacagt agtgaagtct gagattttac tacaccttcc  11040
acttatgtgg tcccacacca cccgcctccc ctgccgcctc ctgccacccc ctaggccaag  11100
gtaataatca tcctgaatcc tgggtttatc tctcacttgc tttcttttca tataattttg  11160
caaaagaatc tgatctaaat gtgtttttca gagtatatat ttatatttta gctgttctta  11220
gagaaaattt attattttgc atgtaatctt atggaacatt ctcatttaat accatggtaa  11280
gattcagccc ttgcccaggg gatagttcat ttagtttgtt tactggatag agctcatcat  11340
gtgactatac ctcagttagt ttatcagttc tcccatccat ggtgactagg ttgcctctca  11400
gcctctcaac aacactgttt ctcagtgtcc ttgtagaagt gatatgtggg tgttttctcc  11460
ttacacagag ttgaaaggtg acgacaacaa cgttggcact accaatcccc caccctccag  11520
aggggtaacc agtgttacca gtttgctgtg tttcctgcta cacctcgcct tattcacttc  11580
catttgtatc tgaaaaacgt gttgcatggt ttcttttcta tagaagtggt aaaatgctat  11640
tgtgtcctgt acattattga ttactttttt tcatttaaca gtagggagat gcctgggagt  11700
acacagagaa ctgccctcat tgttttcaac ttctgcactg tatgtctgtg agtttagcca  11760
```

ttctgctgtt aatggaaatt tacagtattc taatcttttg atattacaaa cagttctgtg 11820
cgatcatcgt catacacaac cccttgtgca caatgcatga gtgtttctca gggtaggtac 11880
caagaagtga aattcctggg tcatagggcg tgagtccgac atttttctcc attctgccct 11940
gttgccctcc agagtgggtg tccagctttg catacctaag tatgagagta tctgttgttc 12000
atatcctcta cgacgctcca tatatgaaac ttaagtttct gctagttgcc atctttgatc 12060
tatcatgtat gcagtgacct actaagactg taattggtac agtagattct tgtcatctgt 12120
gtgtgaattt agcattcatg ggcttaatgc tgacaaggcc cccagggtcc aagacatata 12180
atcatgtata attttgtcaa ggtataattt tttaaattgc ttttgtcatg tgtctgctgg 12240
tgatgcccaa cccagtgctc tgcacccagg tcacactgtg gctttgtcct ctgcttatgc 12300
ctgcattgca gcaactgtcc tgaagagacc aaaattatgc agatttaggt aagtccatgg 12360
ctaatgttat tatattatgt gctattgtaa tggatggggc tgtggagtgt atgaatttat 12420
aaatcactgg tcttgtaatt aaaattcaaa cactatagaa aaaggccatg tagaagataa 12480
aagttcctct ataatcccgg accccctaaga taactactaa tgacaacttc atttatattc 12540
cttcagacat tttctggctg tggatgtact aaaatgtatc ctattattct ctgccctaaa 12600
atggaatcat acaaggtgta ctgttatttt tatggctcta taacatgtca tattgtacgt 12660
gttggtatgg tcattttaac catttttcta gtgatggctt tgaggttatt tgcagtttcc 12720
tagccatctc aaagtgtgct gcggggatct cttttgcatc cctctgggtg cagagctgag 12780
gcacccagag gcagtgtcca gaggaggcag catctgtagg tgtcttcacc tgctctggct 12840
cttggcacat ctggttggtg acactgtttt gtgagatggg ttgaaagcac gtgctgccaa 12900
aatagaataa tgttggtcct ctcctcatgt gccgtggaac tggggtaaaa ctgcgtagtg 12960
gctgcagctg cctgtccata ccggaatcga gtataacacg gtgcctggct tagcacaaaa 13020
cagtagtggg tcctgcaggc cccagagtct aattcctggt attctttccc ctacacagat 13080
taaataaacc aaaaacaaac tattctagga aagcgtctgt gacatttgta aaaagtggta 13140
tttaatgatc ttttattcac ttgtctgttt agtttgttga aatcttaagt ggcatcctgg 13200
tctgggaagg agtgctgtct gcgcctgccc tccgctgggc acagcgtggc tgcttcaggg 13260
gctaagcaca cactttctgt cttctaaagg gccgccacat gccaggagct caggtgtgag 13320
cccggctctg gctcttacct catagggtca ctcatagggg cacagggagc agaacattgt 13380
acacagcgag gcaccacccg gcttggcatc tgcctcggtg gacttactac ctctagaagg 13440
aaatacctga gttcctctgg cctcagctcc tagagtgact ggtgtgctgt ccctgttact 13500
cttctgtcaa ggtgacaact gtgtgaccca tcatctgtgt gtcaaagcaa ggccctgcct 13560
gggcctctgc tcctgtgctg accccaaagg caaatgcttt gctagtttcc ttccagttaa 13620
tttcacctat gaatagatgt gtgaaaactg ttcaaagcca tacctgcaca tgtttgaact 13680
tcaaaccctg tgggtgattc agtggcatct ttctctaacc cccagcctcc cttcccacag 13740
aggccaccgt catggccagt tgctgcagtt tctttccaga gaacctgtgt atgtgtaaag 13800
ctgtacaggc gtgggtacac cacacagcct gtcttgcact gtggactgtt gagttactag 13860
tacatctagg taagcaccgc atatctgtat tcatgtctgc cttggtcttt tcaacatctg 13920
tgtggtagcc gtgtttgaat tacccattcc ctttttgggg aaccattaag ttgtttcagc 13980
aatttttact gtagataagg ctataccgca tatctgtgta catgggtttt tatgtacatg 14040
ggcaagtata tctgtgagag aaaagtttcc tcaggaggaa ttctgggcac agcatgtgta 14100

```
aatttctaaa tatgatggac acccccagct tccacctcaa ggaggttggt cccattgaca  14160
tttccccaca ccttcaccca ggctgtgccc ttaaacttgg ttatttgtca atgtgagaag  14220
tggaaaatag tatttaattg tagtttggat ttgtatttct attgggttgt atacttactg  14280
attaataata agagctcttt acatattaag gaaattaacc cttttcaaat acattcctat  14340
ttctcactaa tctttaagtt ttattgtaat attttgctct ttagtttata tatatatgta  14400
tatatatata tatgtatata tatatatata catatatata tacatatata tatactaatt  14460
ttcttttatg gttcctggat tttgtgagta gtttgaaaag gctaatccag ctgaagattt  14520
tgttgttgtt gttaaacccc atgttttctc ctaactcttt ttatttttat tttggaggac  14580
tctatctaga cttaatttta gcataacaag tgacagggtt agttagcctg ttgtccttac  14640
accattttct ggctaataca gctattaact attgatctgt ctattcacgt gccagttcct  14700
aatggtttta catagtgtaa tctgcacttc aaaatagcga agggaagccc tacctcatta  14760
ttctactttt ccagaattct cctggctatt ccaggctgca tgtttacctt aaccttccct  14820
gtgatgtctt catgccgttg tcttcttatg caagaataag gtacgtcttt ccatccactc  14880
acgtctattt aatttgactt tgcattacac agaaagctgg tcttggtctg tctacctcgg  14940
catctagttg tcctcactgc cccctagccg accccacccc atctgactga ctaccccatc  15000
acagagtact tttatttacg ttttgctctg cctaatggtt acttgatact gtcacgccga  15060
cagtgtccag ttcagtggtc tttgcagttg aaatgctccc gtacacactg tcttgttaaa  15120
aatgccagta agttcataca aacccagctt gcacccaagg tcacattcag agagcgtagg  15180
gctgggatgg gttgttttcc aagcttctgc cactgtgtgg ctagctcttc ccactgggaa  15240
gttctgtgta cccggaatgt cggagtggag tcctgttcta gtgtccagca cctgaccctg  15300
tgcccaaccc ctcaacagcc tattcctgct gtccacagcc tgctggaact ttttacaaaa  15360
tatgttgcca tgctggaccc tgggcactgg acataagccc cctggcagcc tttttcatgt  15420
cacccaaagg ggtaattgtc ctactggtgg tctgtaagat gagttagggt gacttgctaa  15480
tagacattgt aaatcttaat atttatgtat gtattttatt attaccggtt ttccatttat  15540
gatggtaata ttgtttcttc taagaatatt tatttttcct tctaaatatt gagataaaat  15600
tcatgctttt gaaatgttct attcagtggc ttttagtata tttgctatgt tgtgcaacca  15660
tcgacactat ccatttctag aactttttcg tcatcccaaa cagacgctct gtattcataa  15720
aaaaataact tcctacctgt ctctcccccct agtctttggt aacctttgtt atactggtaa  15780
actttgttgt gctctctgtc tgtgtgaatt tgcctattct aggggcctca tataagtgta  15840
atcatacagt atttgtcttt ttgggtctgt ctgatttcac ttagcgggtt ttcagggttc  15900
attcatgttg cagcatataa cagtactgcg ttcctttttc tggctgaata atattccact  15960
gtatggatag accccatttt gtttattcac acatcatttg gacatttgga ttatttctgg  16020
tttttggcta ttatgaacaa tggtgctatg aacagttgcg tacaagtttt tgtgtgaaca  16080
tatgttttca attctctcat tatataccta ggagtagaat tactgggtca tatggtaact  16140
gtatattttt gaggaactgc caaactattt tcccacgtcc atgcaccatt tcacattccc  16200
accagtaagt aagagggttc caatttctgc gcattcttgc caacactagt tattatctga  16260
ctttctggtt ataatcattc taatgagtgt gaagtagcct ctggtgtcat ttggatttgc  16320
atttctctga tgagtgatgc tatcaagcac ctttgctggt gctgttggcc atatgtgtat  16380
gttccctgga gaagtgtctg tgctgagcct tggcccactt tttaattagg cgtttgtctt  16440
tttattactg agttgtaaga gttctttata tattctggat tctagaccct tatcagatac  16500
```

-continued

```
atggtttgca aatattttct cccattctgt gggttgtgtt ttcactttat cgataatgtc  16560
cttagacata taataaattt gtattttaaa agtgacttga tttggctgtg caaggtggct  16620
cacgcttgta atcccagcac tttgggagac tgaggtgggt ggatcatatg aggaggctag  16680
gagttcgagg tcagcctggc cagcatagcg aaaacttgtc tctactaaaa atacaaaaat  16740
tagtcaggca tggtggtgca cgtctgtaat accagcttct caggaggctg aggcacgagg  16800
atcacttgaa cccaggagga ggaggttgca gtgagctgag atcatgccag ggcaacagaa  16860
tgagactttg tttaaaaaaa aaaaaaagtg acttgattta agggaaaaaa tgactggcta  16920
tattcagtca gatatggcaa aaagtctcaa ggtgttaatg tgaatgatta aggtcttggg  16980
gggggtgtcc cctatcagac tacaggtgtt tagaggcaca gaaaaaggtg cagttgggtt  17040
cttaatgtga aatgatgaga agcacaactc cagtgtgtct ctttgtgtag aatgtcagca  17100
gacaccccct gctagatgtg ctggatcatg ggaaagcatt tccatttgtt actagattgt  17160
tcagaagttt taatttatga tgggtgtggt ggctcatgcc tgtagtccca gcactgtggg  17220
aggctgaggc aggaggatca tctgaggcca agagttcaag atcagcctgg gcaacatagt  17280
gataccctat ctcttaaaaa agaagaagtt tttaaatttg aaataataat aggtactgga  17340
tttatgcaaa tgtcttttct gcgtcttttg agatgagtat caggtttttt tttttccttt  17400
tatcatctga tgatgaactt aatgtttcca tttgtattaa tggaatacta agtccctctg  17460
tgatttctga accaagctat tcctaggcct gagttttatt ttgttgacac agaaataaat  17520
tagaaggcca agcgtggtgg catgtgcctg tagtcctagt tgctgaggta agaggattgc  17580
ttgagcccag gagttcaagg ctgcagcaag ctttgattgc gccactgcac tccagccttg  17640
gcgacagact aagacgctgt ctcaaaaaaa aacaaaaacg acaaaaaaaa aacaaaacag  17700
aaaaaataaa ctaaggcaat gacagtccct ggcaaatgct gggagggagg cagcagtggt  17760
cagggaaggt aaccctgaag caggacttgt aaagcaaata agattgggag gccaaggtgg  17820
gtggatcacg aggtcaggag ttcgagacca gcctggccaa catagtgaaa ccccgtcttt  17880
actaaaaata caaaaaaatt agccaggtgt ggtggtgggt gcctgtagtc ccagctactt  17940
gggaggctga ggcaggagaa tctcgaaccc aggaggcgga ggttacagtc agctgagacc  18000
gcaccattgc actccagcct gggtgacaga gcaagattcc gtctcaaaaa aaaaaaaaaa  18060
aaaaaaacca agaagaaaag gaatgaatta gaacttcttc tgcttggact taagggcatc  18120
atcaggcagg ttttgggtag gatagcaggg gaggcagaga catagtcggg gtcagtggtc  18180
atgagtgtgg ctttgagccc aaaaacttgg tttctgttcc ctactttgcc actcagtagt  18240
gcatgacttt ggccaaattt cttaaattca tgaagcaagt ttccgggtga atgaaatggg  18300
gataaaaata gtgttcaaac ctatccgttg gtttgtgtga aactgaaatg aatagtatcg  18360
tgcaggtact tgtgagcaag gggagctgct gtttcctgtc cctttatgat gggaaatatc  18420
tagacaagtt cccaaccctc tgcactgcag gctgcatggc acggagggtc ttgtaacacc  18480
agctggggct ggccttcttt taggagcttc agtggttctg aaaactttta tttgtttgtt  18540
tgttttagta gatgtggggt ctttctgtgt tgcccggact ggtctcaaac ttctggactc  18600
aagtgatcct cccccgctca acctcccaaa gtgttgggat tacaggtgtg agccactgtg  18660
cccagccttg aaaacttttt caggttcttc cagggttact gggctattaa atatttctat  18720
ttcattataa gtcagttttt caaagttata ttatcttaat taccttttttt atatgtatta  18780
gtgtagagta gcattttata ttttgatatc ctccttatgc atagtttttc actttttatt  18840
```

```
cctagttttt cgtttttaat aagactttca agaaatttat tttattggcc ttttgaaaaa  18900
agcagcttta gataaagtaa gcagttctgc tttcatttta taatttattt ctacttttgt  18960
ttcattaatc ttttcctccg gcatgccttg gattttgttg tgttactctt tttctagagg  19020
ctcgcattgt gtgtctggtt cacttatgat cacgcttgcc tacttttaag aatggaagag  19080
gggaggtgga gggtggctgc acagtcgagg gtgtgaggca gtcttgctct agccccacca  19140
tgccctcagc ccgctgtggc cacgctggtt cctcaattgc tggggcgtgc agtgtctgta  19200
agggaggcta ctgatgccat ccgaggaaga tgtaaggttt cgtgtgggca gcgagagcct  19260
agcaggcatg tggggtgccc agcaaagggt aacagtggac agttgttgcc tcattccaca  19320
gagttttgat tttttttttt tttttaatgg tcactccatc aacatccccc atggccagag  19380
cctgagctgg tccccagaga cacaggcatt cagctgacag cctcgccttc acgctgctgc  19440
tgttctcatg gggggacaggc ctcaggtggc aatgcacaaa tcattagtta agggcagttg  19500
tgacagttac caaggagtgt agtcccccgc cccccgccca gtgaaaacag ccctaaccag  19560
gggtggggac ctttgggctc tgacccgaag ggtaggagaa gctggaagga cagcattcct  19620
gtctgcgaag gcaggagcaa agctgccagg ctatgaagga aatggctgga gcctgaagtc  19680
atgcaagctg gggctggcag ggacagggcc aacttccagg cctgggggcc accatgagga  19740
ttcaggacgt gacccccagg gcacatgaag gccttccatc tgtatttaag aaaagacttt  19800
atcagacgag tatggtggct cacgcctgaa tcttagcact ttgggaggct gaggcaggtg  19860
gatcacgagg tcaggagttc aataccagcc tggccaatat ggtaaaaccc catctctact  19920
aaaactacaa aaattagcca ggcatggtgg cgcacgcctg tagtcccagc tactcgggag  19980
gctgaggcag aagaatcact tgaacccggg aggtggaggt tacagtgagc caagatcgcg  20040
ccactacact ccagcctggg tgacagagtg agactccgtc tcaaaaaaac caaaagactt  20100
tatcttattt cctatatgtt tgtggtttca gtcctgatgt ataatttgac cctagttaga  20160
atggttatct gaggaagtgg cctgtacgat ttctgctttt ttaaatgtgt ggctcccttt  20220
cttcattgat taacgtatga ttatttttat aaatgttcca tggcagtggg aagggattct  20280
ctgtcacatt ccacatctgg atcagttcct ccccattttg ttggtcaaat ccgatctgcc  20340
atatcctgtg taatgacaag tgagttgcat tctcaccgtc actcctgggg tctctccgct  20400
tcccctgagc tggctcagca gtctgctcca tgtgttttga tgcagggtga cccattggta  20460
ttcccgacac taacgccccc gtctgtggac tgcttgctgc ttgggcttca ctgtgtctgg  20520
tgttgacagt gcagacctaa aggtgtgcac acatgtgcac acacactccg ctgtcttctt  20580
gtttgcactg gacttaaata tctatgaggg ttattttcaa ctgctgaatt tggaatgatt  20640
tttatatctt ttctgctttc tgcccatgta catgtgttta ttttacactg ttgtgattgg  20700
tagttactat gtggggacac aattacttgg gctgaaataa tccacctgtt gtggttgggg  20760
tcctctgggg cattccaggg tgagaggttg tcactgccac ctgggccatg tgggccggca  20820
ccagcatttt gtggttacga attctacagt cacaaatatc tttgggcaaa tccccttcta  20880
tacctcaagg cagcttttgg tttgcaaccc cactggccag agggaagggc cagtcacttg  20940
gctctctcac tgccctgcgc cccagatggt tctagggctg ctgttttccc ttggccctgc  21000
caacaccact gtttttactt ctgctcattg gctgagtgca gtggttcctg gaagccagtg  21060
gcacgtttcc ccgcgtagct cgcttatccc acagcacaca cccaagggtt ctgttgctaa  21120
cacgctgaat taattctttg ctcatcttac agagtgtgtt ttgactgccc ccatttctga  21180
ggccttgtaa ggccagagct ttgttgcttc atcggcaggt tgggacttag atggccgtga  21240
```

atgtttcctc tctgctgctg cagtaagtaa gtgcccgcac catagtgtgt ttggaggctg 21300
aagttgaagc gaggctgtga ggggagatgg acgtgtgagg agggatgatg gggcttgagc 21360
aaagtggggg agggggcaaa ggcagttggc ccaacacatt ccccacccct ttgagaggtc 21420
tgaggcctgc agacctggct cggagcccac ctggtagtcc tcagactgtg tgtgtgtgtg 21480
tgtgtgtgtg tgtgtgtgtg tgtgtgtgtg tgtgtgtgtg tgtgtaaaag agagaagttg 21540
tggagaaatg gggggctgat tctgctcaga ttcatcagga tgagtagaag gcacccagct 21600
ctcaccctgg cctgacatgt gtgtccctga gcaggttaca gtcctctctg agcctctgct 21660
tcccatctgg accctgctgg gcagggcttc tgagctcctt agcactagca ggaggggctc 21720
caggggccct ccctccatgg cagccaggac aggactctca aatgaggaca gcagagctcg 21780
tggggggctc ccacggaccc gccgtgggcc caggggaggc agagcctgag ccaacagcag 21840
tggtgctgtg gaccgtggat cctgagggtg gcctggggca agtaccggct gagggtccag 21900
gtgggctttg tgtacctttg ggtcctgggg ccctggtgac ttggactcca ggttagagtc 21960
aagtgacagg agaaaggctg gtggggccct gtgcttccga cttcatttcg agtgatggca 22020
gttcccagga aggaatccac agctgacggt ggctgacaga tcagagaatg gaaggcgagg 22080
caggcgggcg tctgcgtgac ctcaggtgct tggggcccag cagacccaga gaaccatttc 22140
cactaggcca gggtgccgga agtgtccaca ggtcttagat tccctgttca gatgaaaaga 22200
tttgtgcctt taatgataaa agtgatctgc atagagtcaa aaattcaagc catgggtata 22260
aaatgcaagt aaaatccctg ccctcaccta tcccacccta ctacacagag atgtcctctc 22320
gagtttccta gactcactct ggaaatttct gtatacacac agaagcttgt gcctctgctc 22380
gtgaaggcag agggagggag agctgaaggg ccagcacctt ctcacctgtg ggccccctca 22440
gtgctcggtc ccagagcatg caggactgtg cctcgtgttc agtttgctgg tctgacttca 22500
tgctccttgg gcaggatatg catgtgccat gctaggagac atgtggatgt gaagctgggg 22560
gacaatgtcc cctggctatg cctttacaag ggaagtaagg aaggtaggag gtgagcctgg 22620
gagggaggga gggaggcgcg gagccgccgc aggtgtttct tttactgagt gcagcccatg 22680
gccgcactca ggttttgctt ttcaccttcc catctgtgaa agagtgagca ggaaaaagca 22740
aaa 22743

<210> SEQ ID NO 9
<211> LENGTH: 58
<212> TYPE: DNA
<213> ORGANISM: Homo sapiens

<400> SEQUENCE: 9
gatgctggtg gttggcactc ctggtttcca ggacggggtt caaatccctg cggcgtct 58

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
agatctcgtt gcgatattat 20

<210> SEQ ID NO 11
<211> LENGTH: 27
<212> TYPE: DNA

<213> ORGANISM: Artificial Sequence
<220> FEATURE:
<223> OTHER INFORMATION: Synthetic Construct

<400> SEQUENCE: 11
gagaacatta ttatagcgtt gctcgag 27

<210> SEQ ID NO 12
<211> LENGTH: 59
<212> TYPE: DNA
<213> ORGANISM: Artificial Sequence
<220> FEATURE:
<223> OTHER INFORMATION: Synthetic Construct

<400> SEQUENCE: 12
aaaggttttt cttttcctga gaaatttctc aggttttgct ttttaaaaaa aaagcaaaa 59

<210> SEQ ID NO 13
<211> LENGTH: 65
<212> TYPE: RNA
<213> ORGANISM: Artificial Sequence
<220> FEATURE:
<223> OTHER INFORMATION: Synthetic Construct

<400> SEQUENCE: 13
gcuggguuuu uccuuguucg caccggacac cuccagugac cagacggcaa gguuuuuauc 60
ccagu 65

<210> SEQ ID NO 14
<211> LENGTH: 51
<212> TYPE: RNA
<213> ORGANISM: Artificial Sequence
<220> FEATURE:
<223> OTHER INFORMATION: Synthetic Construct

<400> SEQUENCE: 14
uuuuuccuug uucgcaccgg acaccuccag ugaccagacg gcaagguuuu u 51

<210> SEQ ID NO 15
<211> LENGTH: 93
<212> TYPE: RNA
<213> ORGANISM: Artificial Sequence
<220> FEATURE:
<223> OTHER INFORMATION: Synthetic Construct

<400> SEQUENCE: 15
gaagguuuuu cuuuuccuga gaaaacaaca cguauuguuu ucucagguuu ugcuuuuugg 60
ccuuuuucua gcuuaaaaaa aaaaaaagca aaa 93

<210> SEQ ID NO 16
<211> LENGTH: 53
<212> TYPE: RNA
<213> ORGANISM: Artificial Sequence
<220> FEATURE:
<223> OTHER INFORMATION: Synthetic Construct

<400> SEQUENCE: 16
uuuuucuuuu ccugagaaaa caacacguau uguuuucuca gguuuugcuu uuu 53

<210> SEQ ID NO 17
<211> LENGTH: 75
<212> TYPE: RNA
<213> ORGANISM: Artificial Sequence
<220> FEATURE:
<223> OTHER INFORMATION: Synthetic Construct

<400> SEQUENCE: 17
gaagguuuuu cuuuuccuga ggcgaaaguc ucagguuuug cuuuuuggcc uuucuuaaaa 60
aaaaaaaaag caaaa 75

<210> SEQ ID NO 18
<211> LENGTH: 10
<212> TYPE: RNA
<213> ORGANISM: Artificial Sequence
<220> FEATURE:
<223> OTHER INFORMATION: Synthetic Construct

<400> SEQUENCE: 18
uuuuucuuuu 10

<210> SEQ ID NO 19
<211> LENGTH: 11
<212> TYPE: RNA
<213> ORGANISM: Artificial Sequence
<220> FEATURE:
<223> OTHER INFORMATION: Synthetic Construct

<400> SEQUENCE: 19
uuuugcuuuu u 11

<210> SEQ ID NO 20
<211> LENGTH: 19
<212> TYPE: RNA
<213> ORGANISM: Artificial Sequence
<220> FEATURE:
<223> OTHER INFORMATION: Synthetic Construct

<400> SEQUENCE: 20
aaaaaaaaaa aaagcaaaa 19

<210> SEQ ID NO 21
<211> LENGTH: 21
<212> TYPE: RNA
<213> ORGANISM: Artificial Sequence
<220> FEATURE:
<223> OTHER INFORMATION: Synthetic Construct

<400> SEQUENCE: 21
gaagguuuuu cuuuuccuga g 21

<210> SEQ ID NO 22
<211> LENGTH: 28
<212> TYPE: RNA
<213> ORGANISM: Artificial Sequence
<220> FEATURE:
<223> OTHER INFORMATION: Synthetic Construct

<400> SEQUENCE: 22
ucucagguuu ugcuuuuugg ccuuucuu 28

<210> SEQ ID NO 23
<211> LENGTH: 8
<212> TYPE: RNA
<213> ORGANISM: Artificial Sequence
<220> FEATURE:
<223> OTHER INFORMATION: Synthetic Construct

<400> SEQUENCE: 23 uuucuuuu 8

<210> SEQ ID NO 24
<211> LENGTH: 9
<212> TYPE: RNA
<213> ORGANISM: Artificial Sequence
<220> FEATURE:
<223> OTHER INFORMATION: Synthetic Construct

<400> SEQUENCE: 24 uuuugcuuu 9

<210> SEQ ID NO 25
<211> LENGTH: 11
<212> TYPE: RNA
<213> ORGANISM: Artificial Sequence
<220> FEATURE:
<223> OTHER INFORMATION: Synthetic Construct

<400> SEQUENCE: 25
aaaaagcaaa a 11

<210> SEQ ID NO 26
<211> LENGTH: 61
<212> TYPE: RNA
<213> ORGANISM: Artificial Sequence
<220> FEATURE:
<223> OTHER INFORMATION: Synthetic Construct

<400> SEQUENCE: 26
ggagguguuu cuuuuacuga gugcagccca uggccgcacu cagguuuugc uuuucaccuu 60
c 61

<210> SEQ ID NO 27
<211> LENGTH: 47
<212> TYPE: RNA
<213> ORGANISM: Artificial Sequence
<220> FEATURE:
<223> OTHER INFORMATION: Synthetic Construct

<400> SEQUENCE: 27
uuucuuuuac ugagugcagc ccauggccgc acucagguuu ugcuuuu 47

<210> SEQ ID NO 28
<211> LENGTH: 6788
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (34)..(602)
<223> OTHER INFORMATION: enhancer/promoter
<220> FEATURE:
<221> NAME/KEY: misc_feature
<222> LOCATION: (741)..(791)
<223> OTHER INFORMATION: codon optimized ABCA4 ORF
<220> FEATURE:
<221> NAME/KEY: misc_feature
<222> LOCATION: (741)..(743)
<223> OTHER INFORMATION: ATG
<220> FEATURE:
<221> NAME/KEY: misc_feature
<222> LOCATION: (744)..(785)
<223> OTHER INFORMATION: V5 eptiope tag
<220> FEATURE:
<221> NAME/KEY: misc_feature
<222> LOCATION: (4520)..(4578)
<223> OTHER INFORMATION: hhRz

<400> SEQUENCE: 28

```
aatattattg aagcatttat cagggttact agcctagtta ttaatagtaa tcaattacgg     60
ggtcattagt tcatagccca tatatggagt tccgcgttac ataacttacg gtaaatggcc    120
cgcctggctg accgcccaac gacccccgcc cattgacgtc aataatgacg tatgttccca    180
tagtaacgcc aatagggact ttccattgac gtcaatgggt ggagtattta cggtaaactg    240
cccacttggc agtacatcaa gtgtatcata tgccaagtac gccccctatt gacgtcaatg    300
acggtaaatg gcccgcctgg cattatgccc agtacatgac cttatgggac tttcctactt    360
ggcagtacat ctacgtatta gtcatcgcta ttaccatggt gatgcggttt tggcagtaca    420
tcaatgggcg tggatagcgg tttgactcac ggggatttcc aagtctccac cccattgacg    480
tcaatgggag tttgttttgg caccaaaatc aacgggactt tccaaaatgt cgtaacaact    540
ccgccccatt gacgcaaatg ggcggtaggc gtgtacggtg ggaggtctat ataagcagag    600
ctctctggct aactagagaa cccactgctt actggcttat cgaaattaat acgactcact    660
atagggagac ccaagctggc tagcgtttaa acgggccctc tagactcgag cggccgccac    720
tgtgctggat aaacgccacc atgggtaagc ctatccctaa ccctctcctc ggtctcgatt    780
ctacgggccg cggctttgtg cgacagattc agctgctgct gtggaagaac tggaccctgc    840
ggaagcggca gaaaatcaga ttcgtggtgg aactcgtgtg gcccctgagc ctgtttctgg    900
tgctgatctg gctgcggaac gccaatcctc tgtacagcca ccacgagtgt cacttcccca    960
acaaggccat gccttctgcc ggaatgctgc cttggctgca gggcatcttc tgcaacgtga   1020
acaacccctg ctttcagagc ccccacacctg gcgaaagccc tggcatcgtg tccaactaca   1080
acaacagcat cctggccaga gtgtaccggg acttccaaga gctgctgatg aacgcccctg   1140
agtctcagca cctgggcaga atctggaccg agctgcacat cctgagccag ttcatggaca   1200
ccctgagaac acaccccgag agaatcgccg gcaggggcat cagaatccgg gacatcctga   1260
aggacgagga aaccctgaca ctgttcctca tcaagaacat cggcctgagc gacagcgtgg   1320
tgtacctgct gatcaacagc caagtgcggc ccgagcagtt tgctcatggc gtgccggatc   1380
tcgccctgaa ggatatcgcc tgttctgagg ccctgctgga acggttcatc atcttcagcc   1440
agcggagagg cgccaagacc gtcagatatg ccctgtgcag tctgagccag ggaaccctgc   1500
agtggatcga ggataccctg tacgccaacg tggacttctt caagctgttc cgggtgctgc   1560
ccacactgct ggattctaga tcccagggca tcaacctgag aagctggggc ggcatcctgt   1620
ccgacatgag cccaagaatc caagagttca tccaccggcc tagcatgcag gacctgctgt   1680
gggttaccag acctctgatg cagaacggcg gacccgagac attcaccaag ctgatgggca   1740
ttctgagcga tctgctgtgc ggctaccctg aaggcggagg atctagagtg ctgagcttca   1800
attggtacga ggacaacaac tacaaggcct tcctgggcat cgactccacc agaaaggacc   1860
ccatctacag ctacgaccgg cggacaacca gcttctgcaa tgccctgatc cagagcctgg   1920
aaagcaaccc tctgaccaag atcgcttgga gggccgccaa acctctgctg atgggaaaga   1980
tcctgtacac ccctgacagc cctgccgcca gaagaatcct gaagaacgcc aacagcacct   2040
tcgaggaact ggaacacgtg cgcaagctgg tcaaggcctg ggaagaagtg ggacctcaga   2100
tttggtactt cttcgacaat agcacccaga tgaacatgat cagagacacc ctgggcaacc   2160
ctaccgtgaa ggacttcctg aacagacagc tgggcgaaga gggcattacc gccgaggcca   2220
tcctgaactt tctgtacaag ggccccagag agtcccaggc cgacgacatg gccaacttcg   2280
attggcggga catcttcaac atcaccgaca gaaccctgcg gctggtcaac cagtacctgg   2340
```

```
aatgcctggt gctggacaag ttcgagagct acaacgacga gacacagctg acccagagag   2400
ccctgtctct gctggaagag aatatgttct gggctggcgt ggtgttcccc gacatgtacc   2460
cttggacaag cagcctgcct cctcacgtga agtacaagat ccggatggac atcgacgtgg   2520
tcgaaaagac caacaagatc aaggaccggt actgggacag cggccctaga gctgatcccg   2580
tggaagattt tcggtacatc tggggcggat tcgcatacct gcaggacatg gtggaacagg   2640
gaatcacacg gtcccaggtg caggctgaag ctcctgtggg aatctacctg cagcagatgc   2700
cttatccttg cttcgtggac gacagcttca tgatcatcct gaatcggtgc ttccccatct   2760
tcatggtgct ggcctggatc tactccgtgt ctatgaccgt gaagtccatc gtgctggaaa   2820
aagagctgcg gctgaaagag acactgaaga accagggcgt gtccaatgcc gtgatctggt   2880
gcacctggtt tctggacagc ttctccatta tgagcatgag catctttctg ctgacgatct   2940
tcatcatgca cggccgaatc ctgcactaca gcgacccctt tatcctcttc ctgttcctgc   3000
tggccttcag caccgctaca atcatgctgt gttttctgct gtccaccttc ttcagcaagg   3060
cctctctggc cgctgcttgt agcggcgtga tctacttcac cctgtacctg cctcacatcc   3120
tgtgcttcgc atggcaggac agaatgaccg ccgagctgaa gaaagctgtg tccctgctga   3180
gccctgtggc ctttggcttt ggcaccgagt acctcgtcag atttgaggaa caaggactgg   3240
gactgcagtg gtccaacatc ggcaatagcc ctacagaggg cgacgagttc agcttcctgc   3300
tgtctatgca gatgatgctg ctggacgccg ccgtgtatgg actgctggct tggtatctgg   3360
accaggtgtt cccaggcgat tacggcactc ctctgccttg gtatttcctg ctgcaagaga   3420
gctactggct cggcggcgag ggatgtagca ccagagaaga aagagccctg gaaaagaccg   3480
agcctctgac cgaggaaaca gaggaccctg aacacccaga gggcatccac gatagctttt   3540
tcgagagaga acaccccggc tgggtgccag gcgtgtgtgt gaagaatctg gtcaagattt   3600
tcgagccctg cggcagacct gccgtggaca gactgaacat caccttctac gagaaccaga   3660
ttaccgcctt tctgggccac aacggcgctg gcaagacaac cacattgagc atcctcacag   3720
gcctgctgcc tccaacaagc ggcacagttc tcgttggcgg cagagacatc gagacaagcc   3780
tggatgccgt cagacagtcc ctgggcatgt gccctcagca caacatcctg tttcaccacc   3840
tgaccgtggc cgagcacatg ctgtttttatg cccagctgaa gggcaagagc caagaagagg   3900
ctcagctgga aatggaagcc atgttggagg acaccggcct gcaccacaag agaaatgagg   3960
aagcccagga tctgagcggc ggcatgcaga gaaaactgag cgtggccatt gccttcgtgg   4020
gcgacgccaa ggttgtgatc ctggatgagc ctacaagcgg cgtggaccct tacagcagaa   4080
gatccatctg ggatctgctg ctgaagtaca gatcaggccg gaccatcatc atgagcaccc   4140
accacatgga cgaggccgat ctgctcggag acagaatcgc catcattgct cagggcagac   4200
tgtactgcag cggcacccca ctgtttctga agaactgttt cggcaccgga ctgtatctga   4260
ccctcgtgcg gaagatgaag aacatccagt ctcagcggaa gggcagcgag gtaagtccga   4320
atacgacacg tagcaagatc ttcactgttt aatctgttaa ttcatctgag cattttgagg   4380
gtgtagtcgc ttgattttat cctagagagt gtgtgagtca cacacagaga ggagcagaac   4440
ctccaagggt ccctttggct tgtcatcaat tatgtggcag ctgtaggttc tgcggccgca   4500
gcaaaccaaa caaacaaagg cgcgtcctgg attccacggt acatccagct gatgagtccc   4560
aaataggacg aaacgcgctc aaacaaacaa aagtaggata agtaagtaat attaaggtac   4620
gggaggtatt ggacaggccg caataaaata tctttatttt cattacatct gtgtgttggt   4680
tttttgtgtg aatcgatagt actaacatac gctctccatc aaaacaaaac gaaacaaaac   4740
```

aaactagcaa aataggctgt ccccagtgca agtgcaggtg ccagaacatt tctctggcct 4800
aactggccgc gtcgaccgat gcccttgaga gccttcaacc cagtcagctc cttccggtgg 4860
gcgcggggca tgactatcgt cgccgcactt atgactgtct tctttatcat gcaactcgta 4920
ggacaggtgc cggcagcgct cttccgcttc ctcgctcact gactcgctgc gctcggtcgt 4980
tcggctgcgg cgagcggtat cagctcactc aaaggcggta atacggttat ccacagaatc 5040
aggggataac gcaggaaaga acatgtgagc aaaaggccag caaaaggcca ggaaccgtaa 5100
aaaggccgcg ttgctggcgt ttttccatag gctccgcccc cctgacgagc atcacaaaaa 5160
tcgacgctca agtcagaggt ggcgaaaccc gacaggacta taaagatacc aggcgtttcc 5220
ccctggaagc tccctcgtgc gctctcctgt tccgaccctg ccgcttaccg gatacctgtc 5280
cgcctttctc ccttcgggaa gcgtggcgct ttctcatagc tcacgctgta ggtatctcag 5340
ttcggtgtag gtcgttcgct ccaagctggg ctgtgtgcac gaaccccccg ttcagcccga 5400
ccgctgcgcc ttatccggta actatcgtct tgagtccaac ccggtaagac acgacttatc 5460
gccactggca gcagccactg gtaacaggat tagcagagcg aggtatgtag gcggtgctac 5520
agagttcttg aagtggtggc ctaactacgg ctacactaga agaacagtat ttggtatctg 5580
cgctctgctg aagccagtta ccttcggaaa aagagttggt agctcttgat ccggcaaaca 5640
aaccaccgct ggtagcggtg gtttttttgt ttgcaagcag cagattacgc gcagaaaaaa 5700
aggatctcaa gaagatcctt tgatcttttc tacggggtct gacgctcagt ggaacgaaaa 5760
ctcacgttaa gggattttgg tcatgagatt atcaaaaagg atcttcacct agatcctttt 5820
aaattaaaaa tgaagtttta aatcaatcta aagtatatat gagtaaactt ggtctgacag 5880
cggccggccg caaatgctaa accactgcag tggttaccag tgcttgatca gtgaggcacc 5940
gatctcagcg atctgcctat ttcgttcgtc catagtggcc tgactccccg tcgtgtagat 6000
cactacgatt cgtgagggct taccatcagg ccccagcgca gcaatgatgc cgcgagagcc 6060
gcgttcaccg gcccccgatt tgtcagcaat gaaccagcca gcagggaggg ccgagcgaag 6120
aagtggtcct gctactttgt ccgcctccat ccagtctatg agctgctgtc gtgatgctag 6180
agtaagaagt tcgccagtga gtagtttccg aagagttgtg gccattgcta ctggcatcgt 6240
ggtatcacgc tcgtcgttcg gtatggcttc gttcaactct ggttcccagc ggtcaagccg 6300
ggtcacatga tcacccatat tatgaagaaa tgcagtcagc tccttagggc ctccgatcgt 6360
tgtcagaagt aagttggccg cggtgttgtc gctcatggta atggcagcac tacacaattc 6420
tcttaccgtc atgccatccg taagatgctt ttccgtgacc ggcgagtact caaccaagtc 6480
gttttgtgag tagtgtatac ggcgaccaag ctgctcttgc ccggcgtcta tacgggacaa 6540
caccgcgcca catagcagta ctttgaaagt gctcatcatc gggaatcgtt cttcggggcg 6600
gaaagactca aggatcttgc cgctattgag atccagttcg atatagccca ctcttgcacc 6660
cagttgatct tcagcatctt ttactttcac cagcgtttcg ggtgtgcaa aaacaggcaa 6720 gcaaaatgcc gcaaagaagg gaatgagtgc gacacgaaaa tgttggatgc tcatactcgt 6780
cctttttc 6788

<210> SEQ ID NO 29
<211> LENGTH: 6598
<212> TYPE: DNA
<213> ORGANISM: Artificial Sequence
<220> FEATURE:
<223> OTHER INFORMATION: Synthetic Construct

<400> SEQUENCE: 29

```
aatattattg aagcatttat cagggttact agcctagtta ttaatagtaa tcaattacgg     60
ggtcattagt tcatagccca tatatggagt tccgcgttac ataacttacg gtaaatggcc    120
cgcctggctg accgcccaac gacccccgcc cattgacgtc aataatgacg tatgttccca    180
tagtaacgcc aatagggact ttccattgac gtcaatgggt ggagtattta cggtaaactg    240
cccacttggc agtacatcaa gtgtatcata tgccaagtac gccccctatt gacgtcaatg    300
acggtaaatg gcccgcctgg cattatgccc agtacatgac cttatgggac tttcctactt    360
ggcagtacat ctacgtatta gtcatcgcta ttaccatggt gatgcggttt tggcagtaca    420
tcaatgggcg tggatagcgg tttgactcac ggggatttcc aagtctccac cccattgacg    480
tcaatgggag tttgttttgg caccaaaatc aacgggactt tccaaaatgt cgtaacaact    540
ccgccccatt gacgcaaatg ggcggtaggc gtgtacggtg ggaggtctat ataagcagag    600
ctctctggct aactagagaa cccactgctt actggcttat cgaaattaat acgactcact    660
atagggagac ccaagctggc tagcgtttaa acgggccctc tagactcgag cggccgccac    720
tgtgctggat aaacgccacc atgggtaagc ctatccctaa ccctctcctc ggtctcgatt    780
ctacgggccg cggctttgtg cgacagattc agctgctgct gtggaagaac tggaccctgc    840
ggaagcggca gaaaatcaga ttcgtggtgg aactcgtgtg gcccctgagc ctgtttctgg    900
tgctgatctg gctgcggaac gccaatcctc tgtacagcca ccacgagtgt cacttcccca    960
acaaggccat gccttctgcc ggaatgctgc cttggctgca gggcatcttc tgcaacgtga   1020
acaacccctg ctttcagagc cccacacctg gcgaaagccc tggcatcgtg tccaactaca   1080
acaacagcat cctggccaga gtgtaccggg acttccaaga gctgctgatg aacgcccctg   1140
agtctcagca cctgggcaga atctggaccg agctgcacat cctgagccag ttcatggaca   1200
ccctgagaac acaccccgag agaatcgccg gcaggggcat cagaatccgg gacatcctga   1260
aggacgagga aaccctgaca ctgttcctca tcaagaacat cggcctgagc gacagcgtgg   1320
tgtacctgct gatcaacagc caagtgcggc ccgagcagtt tgctcatggc gtgccggatc   1380
tcgccctgaa ggatatcgcc tgttctgagg ccctgctgga acggttcatc atcttcagcc   1440
agcggagagg cgccaagacc gtcagatatg ccctgtgcag tctgagccag ggaaccctgc   1500
agtggatcga ggataccctg tacgccaacg tggacttctt caagctgttc cgggtgctgc   1560
ccacactgct ggattctaga tcccagggca tcaacctgag aagctggggc ggcatcctgt   1620
ccgacatgag cccaagaatc caagagttca tccaccggcc tagcatgcag gacctgctgt   1680
gggttaccag acctctgatg cagaacggcg gacccgagac attcaccaag ctgatgggca   1740
ttctgagcga tctgctgtgc ggctaccctg aaggcggagg atctagagtg ctgagcttca   1800
attggtacga ggacaacaac tacaaggcct tcctgggcat cgactccacc agaaaggacc   1860
ccatctacag ctacgaccgg cggacaacca gcttctgcaa tgccctgatc cagagcctgg   1920
aaagcaaccc tctgaccaag atcgcttgga gggccgccaa acctctgctg atgggaaaga   1980
tcctgtacac ccctgacagc cctgccgcca gaagaatcct gaagaacgcc aacagcacct   2040
tcgaggaact ggaacacgtg cgcaagctgg tcaaggcctg ggaagaagtg ggacctcaga   2100
tttggtactt cttcgacaat agcacccaga tgaacatgat cagagacacc ctgggcaacc   2160
ctaccgtgaa ggacttcctg aacagacagc tgggcgaaga gggcattacc gccgaggcca   2220
tcctgaactt tctgtacaag ggccccagag agtcccaggc cgacgacatg gccaacttcg   2280
attggcggga catcttcaac atcaccgaca gaaccctgcg gctggtcaac cagtacctgg   2340
```

```
aatgcctggt gctggacaag ttcgagagct acaacgacga gacacagctg acccagagag   2400
ccctgtctct gctggaagag aatatgttct gggctggcgt ggtgttcccc gacatgtacc   2460
cttggacaag cagcctgcct cctcacgtga agtacaagat ccggatggac atcgacgtgg   2520
tcgaaaagac caacaagatc aaggaccggt actgggacag cggccctaga gctgatcccg   2580
tggaagattt tcggtacatc tggggcggat tcgcatacct gcaggacatg gtggaacagg   2640
gaatcacacg gtcccaggtg caggctgaag ctcctgtggg aatctacctg cagcagatgc   2700
cttatccttg cttcgtggac gacagcttca tgatcatcct gaatcggtgc ttccccatct   2760
tcatggtgct ggcctggatc tactccgtgt ctatgaccgt gaagtccatc gtgctggaaa   2820
aagagctgcg gctgaaagag acactgaaga accagggcgt gtccaatgcc gtgatctggt   2880
gcacctggtt tctggacagc ttctccatta tgagcatgag catctttctg ctgacgatct   2940
tcatcatgca cggccgaatc ctgcactaca gcgacccctt tatcctcttc ctgttcctgc   3000
tggccttcag caccgctaca atcatgctgt gttttctgct gtccaccttc ttcagcaagg   3060
cctctctggc cgctgcttgt agcggcgtga tctacttcac cctgtacctg cctcacatcc   3120
tgtgcttcgc atggcaggac agaatgaccg ccgagctgaa gaaagctgtg tccctgctga   3180
gccctgtggc ctttggcttt ggcaccgagt acctcgtcag atttgaggaa caaggactgg   3240
gactgcagtg gtccaacatc ggcaatagcc ctacagaggg cgacgagttc agcttcctgc   3300
tgtctatgca gatgatgctg ctggacgccg ccgtgtatgg actgctggct tggtatctgg   3360
accaggtgtt cccaggcgat tacggcactc ctctgccttg gtatttcctg ctgcaagaga   3420
gctactggct cggcggcgag ggatgtagca ccagagaaga aagagccctg gaaaagaccg   3480
agcctctgac cgaggaaaca gaggaccctg aacacccaga gggcatccac gatagctttt   3540
tcgagagaga acaccccggc tgggtgccag gcgtgtgtgt gaagaatctg gtcaagattt   3600
tcgagccctg cggcagacct gccgtggaca gactgaacat caccttctac gagaaccaga   3660
ttaccgcctt tctgggccac aacggcgctg gcaagacaac cacattgagc atcctcacag   3720
gcctgctgcc tccaacaagc ggcacagttc tcgttggcgg cagagacatc gagacaagcc   3780
tggatgccgt cagacagtcc ctgggcatgt gccctcagca caacatcctg tttcaccacc   3840
tgaccgtggc cgagcacatg ctgttttatg cccagctgaa gggcaagagc caagaagagg   3900
ctcagctgga aatggaagcc atgttggagg acaccggcct gcaccacaag agaaatgagg   3960
aagcccagga tctgagcggc ggcatgcaga gaaaactgag cgtggccatt gccttcgtgg   4020
gcgacgccaa ggttgtgatc ctggatgagc ctacaagcgg cgtggaccct tacagcagaa   4080
gatccatctg ggatctgctg ctgaagtaca gatcaggccg gaccatcatc atgagcaccc   4140
accacatgga cgaggccgat ctgctcggag acagaatcgc catcattgct cagggcagac   4200
tgtactgcag cggcacccca ctgtttctga agaactgttt cggcaccgga ctgtatctga   4260
ccctcgtgcg gaagatgaag aacatccagt ctcagcggaa gggcagcgag gtaagtccga   4320
atacgacacg tagcaagatc ttcactgttt aatctgttaa ttcatctgag cattttgagg   4380
gtgtagtcgc ttgattttat cctagagagt gtgtgagtca cacacagaga ggagcagaac   4440
ctccaagggt ccctttggct tgtcatcaat tatgtggcag ctgtaggttc tcaaacaaac   4500
aaaaaaggtt tttcttttcc tgagaaattt ctcaggtttt gctttttaaa aaaaaagcaa   4560
aagatgctgg tggttggcac tcctggtttc caggacgggg ttcaaatccc tgcggcgtct   4620
gtcgaccgat gcccttgaga gccttcaacc cagtcagctc cttccggtgg gcgcggggca   4680
```

```
tgactatcgt cgccgcactt atgactgtct tctttatcat gcaactcgta ggacaggtgc   4740

cggcagcgct cttccgcttc ctcgctcact gactcgctgc gctcggtcgt tcggctgcgg   4800

cgagcggtat cagctcactc aaaggcggta atacggttat ccacagaatc aggggataac   4860

gcaggaaaga acatgtgagc aaaaggccag caaaaggcca ggaaccgtaa aaaggccgcg   4920

ttgctggcgt ttttccatag gctccgcccc cctgacgagc atcacaaaaa tcgacgctca   4980

agtcagaggt ggcgaaaccc gacaggacta taaagatacc aggcgtttcc ccctggaagc   5040

tccctcgtgc gctctcctgt tccgaccctg ccgcttaccg gatacctgtc cgcctttctc   5100

ccttcgggaa gcgtggcgct ttctcatagc tcacgctgta ggtatctcag ttcggtgtag   5160

gtcgttcgct ccaagctggg ctgtgtgcac gaaccccccg ttcagcccga ccgctgcgcc   5220

ttatccggta actatcgtct tgagtccaac ccggtaagac acgacttatc gccactggca   5280

gcagccactg gtaacaggat tagcagagcg aggtatgtag gcggtgctac agagttcttg   5340

aagtggtggc ctaactacgg ctacactaga agaacagtat ttggtatctg cgctctgctg   5400

aagccagtta ccttcggaaa aagagttggt agctcttgat ccggcaaaca aaccaccgct   5460

ggtagcggtg gtttttttgt ttgcaagcag cagattacgc gcagaaaaaa aggatctcaa   5520

gaagatcctt tgatcttttc tacggggtct gacgctcagt ggaacgaaaa ctcacgttaa   5580

gggattttgg tcatgagatt atcaaaaagg atcttcacct agatcctttt aaattaaaaa   5640

tgaagtttta aatcaatcta aagtatatat gagtaaactt ggtctgacag cggccggccg   5700

caaatgctaa accactgcag tggttaccag tgcttgatca gtgaggcacc gatctcagcg   5760

atctgcctat ttcgttcgtc catagtggcc tgactccccg tcgtgtagat cactacgatt   5820

cgtgagggct taccatcagg ccccagcgca gcaatgatgc cgcgagagcc gcgttcaccg   5880

gcccccgatt tgtcagcaat gaaccagcca gcagggaggg ccgagcgaag aagtggtcct   5940

gctactttgt ccgcctccat ccagtctatg agctgctgtc gtgatgctag agtaagaagt   6000

tcgccagtga gtagtttccg aagagttgtg gccattgcta ctggcatcgt ggtatcacgc   6060

tcgtcgttcg gtatggcttc gttcaactct ggttcccagc ggtcaagccg ggtcacatga   6120

tcacccatat tatgaagaaa tgcagtcagc tccttagggc ctccgatcgt tgtcagaagt   6180

aagttggccg cggtgttgtc gctcatggta atggcagcac tacacaattc tcttaccgtc   6240

atgccatccg taagatgctt ttccgtgacc ggcgagtact caaccaagtc gttttgtgag   6300

tagtgtatac ggcgaccaag ctgctcttgc ccggcgtcta tacgggacaa caccgcgcca   6360

catagcagta ctttgaaagt gctcatcatc gggaatcgtt cttcggggcg gaaagactca   6420

aggatcttgc cgctattgag atccagttcg atatagccca ctcttgcacc cagttgatct   6480

tcagcatctt ttactttcac cagcgtttcg ggtgtgcaa aaacaggcaa gcaaaatgcc   6540

gcaaagaagg gaatgagtgc gacacgaaaa tgttggatgc tcatactcgt cctttttc     6598
```

```
<210> SEQ ID NO 30
<211> LENGTH: 6644
<212> TYPE: DNA
<213> ORGANISM: Artificial Sequence
<220> FEATURE:
<223> OTHER INFORMATION: Synthetic Construct

<400> SEQUENCE: 30

aatattattg aagcatttat cagggttact agcctagtta ttaatagtaa tcaattacgg     60

ggtcattagt tcatagccca tatatggagt tccgcgttac ataacttacg gtaaatggcc    120

cgcctggctg accgcccaac gacccccgcc cattgacgtc aataatgacg tatgttccca    180
```

-continued

```
tagtaacgcc aatagggact ttccattgac gtcaatgggt ggagtattta cggtaaactg    240
cccacttggc agtacatcaa gtgtatcata tgccaagtac gccccctatt gacgtcaatg    300
acggtaaatg gcccgcctgg cattatgccc agtacatgac cttatgggac tttcctactt    360
ggcagtacat ctacgtatta gtcatcgcta ttaccatggt gatgcggttt tggcagtaca    420
tcaatgggcg tggatagcgg tttgactcac ggggatttcc aagtctccac cccattgacg    480
tcaatgggag tttgttttgg caccaaaatc aacgggactt tccaaaatgt cgtaacaact    540
ccgccccatt gacgcaaatg ggcggtaggc gtgtacggtg ggaggtctat ataagcagag    600
ctctctggct aactagagaa cccactgctt actggcttat cgaaattaat acgactcact    660
atagggagac ccaagctggc tagcgtttaa acgggccctc tagactcgag cggccgccac    720
tgtgctggat aaacgccacc atgggtaagc ctatccctaa ccctctcctc ggtctcgatt    780
ctacgggccg cggctttgtg cgacagattc agctgctgct gtggaagaac tggaccctgc    840
ggaagcggca gaaaatcaga ttcgtggtgg aactcgtgtg gcccctgagc ctgtttctgg    900
tgctgatctg gctgcggaac gccaatcctc tgtacagcca ccacgagtgt cacttcccca    960
acaaggccat gccttctgcc ggaatgctgc cttggctgca gggcatcttc tgcaacgtga   1020
acaacccctg ctttcagagc cccacacctg gcgaaagccc tggcatcgtg tccaactaca   1080
acaacagcat cctggccaga gtgtaccggg acttccaaga gctgctgatg aacgcccctg   1140
agtctcagca cctgggcaga atctggaccg agctgcacat cctgagccag ttcatggaca   1200
ccctgagaac acaccccgag agaatcgccg gcaggggcat cagaatccgg gacatcctga   1260
aggacgagga aaccctgaca ctgttcctca tcaagaacat cggcctgagc gacagcgtgg   1320
tgtacctgct gatcaacagc caagtgcggc ccgagcagtt tgctcatggc gtgccggatc   1380
tcgccctgaa ggatatcgcc tgttctgagg ccctgctgga acggttcatc atcttcagcc   1440
agcggagagg cgccaagacc gtcagatatg ccctgtgcag tctgagccag ggaaccctgc   1500
agtggatcga ggataccctg tacgccaacg tggacttctt caagctgttc cgggtgctgc   1560
ccacactgct ggattctaga tcccagggca tcaacctgag aagctggggc ggcatcctgt   1620
ccgacatgag cccaagaatc caagagttca tccaccggcc tagcatgcag gacctgctgt   1680
gggttaccag acctctgatg cagaacggcg gacccgagac attcaccaag ctgatgggca   1740
ttctgagcga tctgctgtgc ggctaccctg aaggcggagg atctagagtg ctgagcttca   1800
attggtacga ggacaacaac tacaaggcct tcctgggcat cgactccacc agaaaggacc   1860
ccatctacag ctacgaccgg cggacaacca gcttctgcaa tgccctgatc cagagcctgg   1920
aaagcaaccc tctgaccaag atcgcttgga gggccgccaa acctctgctg atgggaaaga   1980
tcctgtacac ccctgacagc cctgccgcca gaagaatcct gaagaacgcc aacagcacct   2040
tcgaggaact ggaacacgtg cgcaagctgg tcaaggcctg ggaagaagtg ggacctcaga   2100
tttggtactt cttcgacaat agcacccaga tgaacatgat cagagacacc ctgggcaacc   2160
ctaccgtgaa ggacttcctg aacagacagc tgggcgaaga gggcattacc gccgaggcca   2220
tcctgaactt tctgtacaag ggccccagag agtcccaggc cgacgacatg gccaacttcg   2280
attggcggga catcttcaac atcaccgaca gaaccctgcg gctggtcaac cagtacctgg   2340
aatgcctggt gctggacaag ttcgagagct acaacgacga gacacagctg acccagagag   2400
ccctgtctct gctggaagag aatatgttct gggctggcgt ggtgttcccc gacatgtacc   2460
cttggacaag cagcctgcct cctcacgtga agtacaagat ccggatggac atcgacgtgg   2520
```

-continued

```
tcgaaaagac caacaagatc aaggaccggt actgggacag cggccctaga gctgatcccg   2580
tggaagattt tcggtacatc tggggcggat tcgcatacct gcaggacatg gtggaacagg   2640
gaatcacacg gtcccaggtg caggctgaag ctcctgtggg aatctacctg cagcagatgc   2700
cttatccttg cttcgtggac gacagcttca tgatcatcct gaatcggtgc ttccccatct   2760
tcatggtgct ggcctggatc tactccgtgt ctatgaccgt gaagtccatc gtgctggaaa   2820
aagagctgcg gctgaaagag acactgaaga accagggcgt gtccaatgcc gtgatctggt   2880
gcacctggtt tctggacagc ttctccatta tgagcatgag catctttctg ctgacgatct   2940
tcatcatgca cggccgaatc ctgcactaca gcgacccctt tatcctcttc ctgttcctgc   3000
tggccttcag caccgctaca atcatgctgt gttttctgct gtccaccttc ttcagcaagg   3060
cctctctggc cgctgcttgt agcggcgtga tctacttcac cctgtacctg cctcacatcc   3120
tgtgcttcgc atggcaggac agaatgaccg ccgagctgaa gaaagctgtg tccctgctga   3180
gccctgtggc ctttggcttt ggcaccgagt acctcgtcag atttgaggaa caaggactgg   3240
gactgcagtg gtccaacatc ggcaatagcc ctacagaggg cgacgagttc agcttcctgc   3300
tgtctatgca gatgatgctg ctggacgccg ccgtgtatgg actgctggct tggtatctgg   3360
accaggtgtt cccaggcgat tacggcactc ctctgccttg gtatttcctg ctgcaagaga   3420
gctactggct cggcggcgag ggatgtagca ccagagaaga aagagccctg gaaaagaccg   3480
agcctctgac cgaggaaaca gaggaccctg aacacccaga gggcatccac gatagctttt   3540
tcgagagaga acaccccggc tgggtgccag gcgtgtgtgt gaagaatctg gtcaagattt   3600
tcgagccctg cggcagacct gccgtggaca gactgaacat caccttctac gagaaccaga   3660
ttaccgcctt tctgggccac aacggcgctg gcaagacaac cacattgagc atcctcacag   3720
gcctgctgcc tccaacaagc ggcacagttc tcgttggcgg cagagacatc gagacaagcc   3780
tggatgccgt cagacagtcc ctgggcatgt gccctcagca caacatcctg tttcaccacc   3840
tgaccgtggc cgagcacatg ctgttttatg cccagctgaa gggcaagagc caagaagagg   3900
ctcagctgga aatggaagcc atgttggagg acaccggcct gcaccacaag agaaatgagg   3960
aagcccagga tctgagcggc ggcatgcaga gaaaactgag cgtggccatt gccttcgtgg   4020
gcgacgccaa ggttgtgatc ctggatgagc ctacaagcgg cgtggaccct tacagcagaa   4080
gatccatctg ggatctgctg ctgaagtaca gatcaggccg gaccatcatc atgagcaccc   4140
accacatgga cgaggccgat ctgctcggag acagaatcgc catcattgct cagggcagac   4200
tgtactgcag cggcacccca ctgtttctga agaactgttt cggcaccgga ctgtatctga   4260
ccctcgtgcg gaagatgaag aacatccagt ctcagcggaa gggcagcgag gtaagtccga   4320
atacgacacg tagcaagatc ttcactgttt aatctgttaa ttcatctgag cattttgagg   4380
gtgtagtcgc ttgattttat cctagagagt gtgtgagtca cacacagaga ggagcagaac   4440
ctccaagggt ccctttggct tgtcatcaat tatgtggcag ctgtaggttc tcagtagggt   4500
catgaaggtt tttcttttcc tgagaaaaca acacgtattg ttttctcagg ttttgctttt   4560
tggccttttt ctagcttaaa aaaaaaaaaa gcaaaagatg ctggtggttg gcactcctgg   4620
tttccaggac ggggttcaaa tccctgcggc gtctttgctt tgactagtcg accgatgccc   4680
ttgagagcct tcaacccagt cagctccttc cggtgggcgc ggggcatgac tatcgtcgcc   4740
gcacttatga ctgtcttctt tatcatgcaa ctcgtaggac aggtgccggc agcgctcttc   4800
cgcttcctcg ctcactgact cgctgcgctc ggtcgttcgg ctgcggcgag cggtatcagc   4860
tcactcaaag gcggtaatac ggttatccac agaatcaggg gataacgcag gaaagaacat   4920
```

gtgagcaaaa ggccagcaaa aggccaggaa ccgtaaaaag gccgcgttgc tggcgttttt 4980
ccataggctc cgcccccctg acgagcatca caaaaatcga cgctcaagtc agaggtggcg 5040
aaacccgaca ggactataaa gataccaggc gtttccccct ggaagctccc tcgtgcgctc 5100
tcctgttccg accctgccgc ttaccggata cctgtccgcc tttctccctt cgggaagcgt 5160
ggcgctttct catagctcac gctgtaggta tctcagttcg gtgtaggtcg ttcgctccaa 5220
gctgggctgt gtgcacgaac cccccgttca gcccgaccgc tgcgccttat ccggtaacta 5280
tcgtcttgag tccaacccgg taagacacga cttatcgcca ctggcagcag ccactggtaa 5340
caggattagc agagcgaggt atgtaggcgg tgctacagag ttcttgaagt ggtggcctaa 5400
ctacggctac actagaagaa cagtatttgg tatctgcgct ctgctgaagc cagttacctt 5460
cggaaaaaga gttggtagct cttgatccgg caaacaaacc accgctggta gcggtggttt 5520
ttttgtttgc aagcagcaga ttacgcgcag aaaaaaagga tctcaagaag atcctttgat 5580
cttttctacg gggtctgacg ctcagtggaa cgaaaactca cgttaaggga ttttggtcat 5640
gagattatca aaaaggatct tcacctagat ccttttaaat taaaaatgaa gttttaaatc 5700
aatctaaagt atatatgagt aaacttggtc tgacagcggc cggccgcaaa tgctaaacca 5760
ctgcagtggt taccagtgct tgatcagtga ggcaccgatc tcagcgatct gcctatttcg 5820
ttcgtccata gtggcctgac tccccgtcgt gtagatcact acgattcgtg agggcttacc 5880
atcaggcccc agcgcagcaa tgatgccgcg agagccgcgt tcaccggccc ccgatttgtc 5940
agcaatgaac cagccagcag ggagggccga gcgaagaagt ggtcctgcta ctttgtccgc 6000
ctccatccag tctatgagct gctgtcgtga tgctagagta agaagttcgc cagtgagtag 6060
tttccgaaga gttgtggcca ttgctactgg catcgtggta tcacgctcgt cgttcggtat 6120
ggcttcgttc aactctggtt cccagcggtc aagccgggtc acatgatcac ccatattatg 6180
aagaaatgca gtcagctcct tagggcctcc gatcgttgtc agaagtaagt tggccgcggt 6240
gttgtcgctc atggtaatgg cagcactaca caattctctt accgtcatgc catccgtaag 6300
atgcttttcc gtgaccggcg agtactcaac caagtcgttt tgtgagtagt gtatacggcg 6360
accaagctgc tcttgcccgg cgtctatacg ggacaacacc gcgccacata gcagtacttt 6420
gaaagtgctc atcatcggga atcgttcttc ggggcggaaa gactcaagga tcttgccgct 6480
attgagatcc agttcgatat agcccactct tgcacccagt tgatcttcag catcttttac 6540
tttcaccagc gtttcggggt gtgcaaaaac aggcaagcaa aatgccgcaa agaagggaat 6600
gagtgcgaca cgaaaatgtt ggatgctcat actcgtcctt tttc 6644

<210> SEQ ID NO 31
<211> LENGTH: 10575
<212> TYPE: DNA
<213> ORGANISM: Artificial Sequence
<220> FEATURE:
<223> OTHER INFORMATION: Synthetic Construct

<400> SEQUENCE: 31
gtcgacttaa ttaaggctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttccttgta gttaatgatt aacccgccat gctacttatc 180
tacgtagcaa gctagcctag ttattaatag taatcaatta cggggtcatt agttcatagc 240
ccatatatgg agttccgcgt tacataactt acggtaaatg gcccgcctgg ctgaccgccc 300

-continued

```
aacgaccccc gcccattgac gtcaataatg acgtatgttc ccatagtaac gccaataggg    360
actttccatt gacgtcaatg ggtggagtat ttacggtaaa ctgcccactt ggcagtacat    420
caagtgtatc atatgccaag tacgccccct attgacgtca atgacggtaa atggcccgcc    480
tggcattatg cccagtacat gaccttatgg gactttccta cttggcagta catctacgta    540
ttagtcatcg ctattaccat ggtgatgcgg ttttggcagt acaccaatgg gcgtggatag    600
cggtttgact cacggggatt tccaagtctc caccccattg acgtcaatgg gagtttgttt    660
tggcaccaaa atcaacggga ctttccaaaa tgtcgtaaca actccgcccc gttgacgcaa    720
atgggcggta ggcgtgtacg gtgggaggtc tatataagca gagctcgttt agtgaaccgt    780
cagatcgccg ccaccatgga agatgccaaa aacattaaga agggcccagc gccattctac    840
ccactcgaag acgggaccgc cggcgagcag ctgcacaaag ccatgaagcg ctacgccctg    900
gtgcccggca ccatcgcctt taccgacgca catatcgagg tggacattac ctacgccgaa    960
tacttcgaga tgagcgttcg gctggcagaa gctatgaagc gctatgggct gaatacaaac   1020
catcggatcg tggtgtgcag cgagaatagc ttgcagttct tcatgcccgt gttgggtgcc   1080
ctgttcatcg gtgtggctgt ggccccagct aacgacatct acaacgagcg cgagctgctg   1140
aacagcatgg gcatcagcca gcccaccgtc gtattcgtga gcaagaaagg gctgcaaaag   1200
atcctcaacg tgcaaaagaa gctaccgatc atacaaaaga tcatcatcat ggatagcaag   1260
accgactacc agggcttcca aagcatgtac accttcgtga cttcccattt gccacccggc   1320
ttcaacgagt acgacttcgt gcccgagagc ttcgaccggg acaaaaccat cgccctgatc   1380
atgaacagta gtggcagtac cggattgccc aagggcgtag ccctaccgca ccgcaccgct   1440
tgtgtccgat tcagtcatgc ccgcgacccc atcttcggca accagatcat ccccgacacc   1500
gctatcctca gcgtggtgcc atttcaccac ggcttcggca tgttcaccac gctgggctac   1560
ttgatctgcg gctttcgggt cgtgctcatg taccgcttcg aggaggagct attcttgcgc   1620
agcttgcaag actataagat tcaatctgcc ctgctggtgc ccacactatt tagcttcttc   1680
gctaagagca ctctcatcga caagtacgac ctaagcaact tgcacgagat cgccagcggc   1740
ggagcgccgc tcagcaagga ggtaggtgag gccgtggcca aacgcttcca cctaccaggc   1800
atccgccagg gctacggcct gacagaaaca accagcgcca ttctgatcac ccccgaaggg   1860
gacgacaagc ctggcgcagt aggcaaggtg gtgcccttct tcgaggctaa ggtggtggac   1920
ttggacaccg gtaagacact gggtgtgaac cagcgcggcg agctgtgcgt ccgtggcccc   1980
atgatcatga gcggctacgt taacaacccc gaggctacaa acgctctcat cgacaaggac   2040
ggctggctgc acagcggcga catcgcctac tgggacgagg acgagcactt cttcatcgtg   2100
gaccggctga agagcctgat caaatacaag ggctaccagg taagtccgaa tacgacacgt   2160
agcaagatct ggtgggaggt aattgaatcg tgggggtggt ttcccccacg ctattctcat   2220
aatagtaagt tctcacgatg tctgatggtt ttataagggg ctttcccctt tgctcggctc   2280
acattcttct aattccggcc accatgtgaa gaaaaatgtg gcggccgcgt ttacttaaga   2340
catgataaga tacattgatg agtttggaca aaccacaact agaatgcagt gaaaaaaatg   2400
ctttatttgt gaaatttgtg atgctattgc tttatttgta accattataa gctgcaataa   2460
acaagttaac aacaacaatt gcattcattt tatgtttcag gttcaggggg agatgtggga   2520
ggttttttaa agcaagtaaa acctctacaa atgtggtaaa ctcgagttct acgtagataa   2580
gtagcatggc gggttaatca ttaactacaa ggaaccccta gtgatggagt tggccactcc   2640
ctctctgcgc gctcgctcgc tcactgaggc cgggcgacca aaggtcgccc gacgcccggg   2700
```

ctttgcccgg gcggcctcag tgagcgagcg agcgcgcagc cttaattaac ctaaggaaaa 2760
tgaagtgaag ttcctatact ttctagagaa taggaacttc tatagtgagt cgaataaggg 2820
cgacacaaaa tttattctaa atgcataata aatactgata acatcttata gtttgtatta 2880
tattttgtat tatcgttgac atgtataatt ttgatatcaa aaactgattt tccctttatt 2940
attttcgaga tttattttct taattctctt taacaaacta gaaatattgt atatacaaaa 3000
aatcataaat aatagatgaa tagtttaatt ataggtgttc atcaatcgaa aaagcaacgt 3060
atcttattta aagtgcgttg ctttttttctc atttataagg ttaaataatt ctcatatatc 3120
aagcaaagtg acaggcgccc ttaaatattc tgacaaatgc tctttcccta aactcccccc 3180
ataaaaaaac ccgccgaagc gggtttttac gttatttgcg gattaacgat tactcgttat 3240
cagaaccgcc cagggggccc gagcttaacc tttttatttg gggagagggg aagtcatgaa 3300
aaaactaacc tttgaaattc gatctccagc acatcagcaa aacgctattc acgcagtaca 3360
gcaaatcctt ccagacccaa ccaaaccaat cgtagtaacc attcaggaac gcaaccgcag 3420
cttagaccaa aacaggaagc tatgggcctg cttaggtgac gtctctcgtc aggttgaatg 3480
gcatggtcgc tggctggatg cagaaagctg gaagtgtgtg tttaccgcag cattaaagca 3540
gcaggatgtt gttcctaacc ttgccgggaa tggctttgtg gtaataggcc agtcaaccag 3600
caggatgcgt gtaggcgaat ttgcggagct attagagctt atacaggcat tcggtacaga 3660
gcgtggcgtt aagtggtcag acgaagcgag actggctctg gagtggaaag cgagatgggg 3720
agacagggct gcatgataaa tgtcgttagt ttctccggtg gcaggacgtc agcatatttg 3780
ctctggctaa tggagcaaaa gcgacgggca ggtaaagacg tgcattacgt tttcatggat 3840
acaggttgtg aacatccaat gacatatcgg tttgtcaggg aagttgtgaa gttctgggat 3900
ataccgctca ccgtattgca ggttgatatc aacccggagc ttggacagcc aaatggttat 3960
acggtatggg aaccaaagga tattcagacg cgaatgcctg ttctgaagcc atttatcgat 4020
atggtaaaga aatatggcac tccatacgtc ggcggcgcgt tctgcactga cagattaaaa 4080
ctcgttccct tcaccaaata ctgtgatgac catttcgggc gagggaatta caccacgtgg 4140
attggcatca gagctgatga accgaagcgg ctaaagccaa agcctggaat cagatatctt 4200
gctgaactgt cagactttga gaaggaagat atcctcgcat ggtggaagca acaaccattc 4260
gatttgcaaa taccggaaca tctcggtaac tgcatattct gcattaaaaa atcaacgcaa 4320
aaaatcggac ttgcctgcaa agatgaggag ggattgcagc gtgtttttaa tgaggtcatc 4380
acgggatccc atgtgcgtga cggacatcgg gaaacgccaa aggagattat gtaccgagga 4440
agaatgtcgc tggacggtat cgcgaaaatg tattcagaaa atgattatca agccctgtat 4500
caggacatgg tacgagctaa aagattcgat accggctctt gttctgagtc atgcgaaata 4560
tttggagggc agcttgattt cgacttcggg agggaagctg catgatgcga tgttatcggt 4620
gcggtgaatg caaagaagat aaccgcttcc gaccaaatca accttactgg aatcgatggt 4680
gtctccggtg tgaaagaaca ccaacagggg tgttaccact accgcaggaa aaggaggacg 4740
tgtggcgaga cagcgacgaa gtatcaccga cataatctgc gaaaactgca aataccttcc 4800
aacgaaacgc accagaaata aacccaagcc aatcccaaaa gaatctgacg taaaaacctt 4860
caactacacg gctcacctgt gggatatccg gtggctaaga cgtcgtgcga ggaaaacaag 4920
gtgattgacc aaaatcgaag ttacgaacaa gaaagcgtcg agcgagcttt aacgtgcgct 4980
aactgcggtc agaagctgca tgtgctggaa gttcacgtgt gtgagcactg ctgcgcagaa 5040

```
ctgatgagcg atccgaatag ctcgatgcac gaggaagaag atgatggcta aaccagcgcg   5100
aagacgatgt aaaaacgatg aatgccggga atggtttcac cctgcattcg ctaatcagtg   5160
gtggtgctct ccagagtgtg gaaccaagat agcactcgaa cgacgaagta aagaacgcga   5220
aaaagcggaa aaagcagcag agaagaaacg acgacgagag gagcagaaac agaaagataa   5280
acttaagatt cgaaaactcg ccttaaagcc ccgcagttac tggattaaac aagcccaaca   5340
agccgtaaac gccttcatca gagaaagaga ccgcgactta ccatgtatct cgtgcggaac   5400
gctcacgtct gctcagtggg atgccggaca ttaccggaca actgctgcgg cacctcaact   5460
ccgatttaat gaacgcaata ttcacaagca atgcgtggtg tgcaaccagc acaaaagcgg   5520
aaatctcgtt ccgtatcgcg tcgaactgat tagccgcatc gggcaggaag cagtagacga   5580
aatcgaatca aaccataacc gccatcgctg gactatcgaa gagtgcaagg cgatcaaggc   5640
agagtaccaa cagaaactca aagacctgcg aaatagcaga agtgaggccg catgacgttc   5700
tcagtaaaaa ccattccaga catgctcgtt gaagcatacg gaaatcagac agaagtagca   5760
cgcagactga aatgtagtcg cggtacggtc agaaaatacg ttgatgataa agacgggaaa   5820
atgcacgcca tcgtcaacga cgttctcatg gttcatcgcg gatggagtga aagagatgcg   5880
ctattacgaa aaaattgatg gcagcaaata ccgaaatatt tgggtagttg gcgatctgca   5940
cggatgctac acgaacctga tgaacaaact ggatacgatt ggattcgaca acaaaaaaga   6000
cctgcttatc tcggtgggcg atttggttga tcgtggtgca gagaacgttg aatgcctgga   6060
attaatcaca ttcccctggt tcagagctgt acgtggaaac catgagcaaa tgatgattga   6120
tggcttatca gagcgtggaa acgttaatca ctggctgctt aatggcggtg gctggttctt   6180
taatctcgat tacgacaaag aaattctggc taaagctctt gcccataaag cagatgaact   6240
tccgttaatc atcgaactgg tgagcaaaga taaaaaatat gttatctgcc acgccgatta   6300
tccctttgac gaatacgagt ttggaaagcc agttgatcat cagcaggtaa tctggaaccg   6360
cgaacgaatc agcaactcac aaaacgggat cgtgaaagaa atcaaaggcg cggacacgtt   6420
catctttggt catacgccag cagtgaaacc actcaagttt gccaaccaaa tgtatatcga   6480
taccggcgca gtgttctgcg gaaacctaac attgattcag gtacagggag aaggcgcatg   6540
agactcgaaa gcgtagctaa atttcattcg ccaaaaagcc cgatgatgag cgactcacca   6600
cgggccacgg cttctgactc tctttccggt actgatgtga tggctgctat ggggatggcg   6660
caatcacaag ccggattcgg tatggctgca ttctgcggta agcacgaact cagccagaac   6720
gacaaacaaa aggctatcaa ctatctgatg caatttgcac acaaggtatc ggggaaatac   6780
cgtggtgtgg caaagcttga aggaaatact aaggcaaagg tactgcaagt gctcgcaaca   6840
ttcgcttatg cggattattg ccgtagtgcc gcgacgccgg gggcaagatg cagagattgc   6900
catggtacag gccgtgcggt tgatattgcc aaaacagagc tgtgggggag agttgtcgag   6960
aaagagtgcg gaagatgcaa aggcgtcggc tattcaagga tgccagcaag cgcagcatat   7020
cgcgctgtga cgatgctaat cccaaacctt acccaaccca cctggtcacg cactgttaag   7080
ccgctgtatg acgctctggt ggtgcaatgc cacaaagaag agtcaatcgc agacaacatt   7140
ttgaatgcgg tcacacgtta gcagcatgat tgccacggat ggcaacatat taacggcatg   7200
atattgactt attgaataaa attgggtaaa tttgactcaa cgatgggtta attcgctcgt   7260
tgtggtagtg agatgaaaag aggcggcgct tactaccgat tccgcctagt tggtcacttc   7320
gacgtatcgt ctggaactcc aaccatcgca ggcagagagg tctgcaaaat gcaatcccga   7380
aacagttcgc aggtaatagt tagagcctgc ataacggttt cgggattttt tatatctgca   7440
```

```
caacaggtaa gagcattgag tcgataatcg tgaagagtcg gcgagcctgg ttagccagtg   7500
ctctttccgt tgtgctgaat taagcgaata ccggaagcag aaccggatca ccaaatgcgt   7560
acaggcgtca tcgccgccca gcaacagcac aacccaaact gagccgtagc cactgtctgt   7620
cctgaattca ttagtaatag ttacgctgcg gccttttaca catgaccttc gtgaaagcgg   7680
gtggcaggag gtcgcgctaa caacctcctg ccgttttgcc cgtgcatatc ggtcacgaac   7740
aaatctgatt actaaacaca gtagcctgga tttgttctat cagtaatcga ccttattcct   7800
aattaaatag agcaaatccc cttattgggg gtaagacatg aagatgccag aaaaacatga   7860
cctgttggcc gccattctcg cggcaaagga acaaggcatc ggggcaatcc ttgcgtttgc   7920
aatggcgtac cttcgcggca gatataatgg cggtgcgttt acaaaaacag taatcgacgc   7980
aacgatgtgc gccattatcg cctggttcat tcgtgacctt ctcgacttcg ccggactaag   8040
tagcaatctc gcttatataa cgagcgtgtt tatcggctac atcggtactg actcgattgg   8100
ttcgcttatc aaacgcttcg ctgctaaaaa agccggagta gaagatggta gaaatcaata   8160
atcaacgtaa ggcgttcctc gatatgctgg cgtggtcgga gggaactgat aacggacgtc   8220
agaaaaccag aaatcatggt tatgacgtca ttgtaggcgg agagctattt actgattact   8280
ccgatcaccc tcgcaaactt gtcacgctaa acccaaaact caaatcaaca ggcgcttaag   8340
actggccgtc gttttacaac acagaaagag tttgtagaaa cgcaaaaagg ccatccgtca   8400
ggggccttct gcttagtttg atgcctggca gttccctact ctcgccttcc gcttcctcgc   8460
tcactgactc gctgcgctcg gtcgttcggc tgcggcgagc ggtatcagct cactcaaagg   8520
cggtaatacg gttatccaca gaatcagggg ataacgcagg aaagaacatg tgagcaaaag   8580
gccagcaaaa ggccaggaac cgtaaaaagg ccgcgttgct ggcgtttttc cataggctcc   8640
gcccccctga cgagcatcac aaaaatcgac gctcaagtca gaggtggcga aacccgacag   8700
gactataaag ataccaggcg tttccccctg gaagctccct cgtgcgctct cctgttccga   8760
ccctgccgct taccggatac ctgtccgcct ttctcccttc gggaagcgtg gcgctttctc   8820
atagctcacg ctgtaggtat ctcagttcgg tgtaggtcgt tcgctccaag ctgggctgtg   8880
tgcacgaacc ccccgttcag cccgaccgct gcgccttatc cggtaactat cgtcttgagt   8940
ccaacccggt aagacacgac ttatcgccac tggcagcagc cactggtaac aggattagca   9000
gagcgaggta tgtaggcggt gctacagagt tcttgaagtg gtggcctaac tacggctaca   9060
ctagaagaac agtatttggt atctgcgctc tgctgaagcc agttaccttc ggaaaaagag   9120
ttggtagctc ttgatccggc aaacaaacca ccgctggtag cggtggtttt tttgtttgca   9180
agcagcagat tacgcgcaga aaaaaaggat ctcaagaaga tcctttgatc ttttctacgg   9240
ggtctgacgc tcagtggaac gacgcgcgcg taactcacgt taagggattt tggtcatgag   9300
cttgcgccgt cccgtcaagt cagcgtaatg ctctgctttt agaaaaactc atcgagcatc   9360
aaatgaaact gcaatttatt catatcagga ttatcaatac catatttttg aaaaagccgt   9420
ttctgtaatg aaggagaaaa ctcaccgagg cagttccata ggatggcaag atcctggtat   9480
cggtctgcga ttccgactcg tccaacatca atacaaccta ttaatttccc ctcgtcaaaa   9540
ataaggttat caagtgagaa atcaccatga gtgacgactg aatccggtga gaatggcaaa   9600
agtttatgca tttctttcca gacttgttca acaggccagc cattacgctc gtcatcaaaa   9660
tcactcgcat caaccaaacc gttattcatt cgtgattgcg cctgagcgag gcgaaatacg   9720
cgatcgctgt taaaaggaca attacaaaca ggaatcgagt gcaaccggcg caggaacact   9780
```

```
gccagcgcat caacaatatt ttcacctgaa tcaggatatt cttctaatac ctggaacgct   9840

gtttttccgg ggatcgcagt ggtgagtaac catgcatcat caggagtacg gataaaatgc   9900

ttgatggtcg gaagtggcat aaattccgtc agccagttta gtctgaccat ctcatctgta   9960

acatcattgg caacgctacc tttgccatgt ttcagaaaca actctggcgc atcgggcttc  10020

ccatacaagc gatagattgt cgcacctgat tgcccgacat tatcgcgagc ccatttatac  10080

ccatataaat cagcatccat gttggaattt aatcgcggcc tcgacgtttc ccgttgaata  10140

tggctcatat tcttcctttt tcaatattat tgaagcattt atcagggtta ttgtctcatg  10200

agcggataca tatttgaatg tatttagaaa aataaacaaa taggggtcag tgttacaacc  10260

aattaaccaa ttctgaacat tatcgcgagc ccatttatac ctgaatatgg ctcataacac  10320

cccttgtttg cctggcggca gtagcgcggt ggtcccacct gaccccatgc cgaactcaga  10380

agtgaaacgc cgtagcgccg atggtagtgt ggggactccc catgcgagag tagggaactg  10440

ccaggcatca aataaaacga aaggctcagt cgaaagactg ggcctttcgc ccgggctaat  10500

tagggggtgt cgcccttatt cgactctata gtgaagttcc tattctctag aaagtatagg  10560

aacttctgaa gtggg                                                   10575
```

<210> SEQ ID NO 32
<211> LENGTH: 10667
<212> TYPE: DNA
<213> ORGANISM: Artificial Sequence
<220> FEATURE:
<223> OTHER INFORMATION: Synthetic Construct

<400> SEQUENCE: 32

```
gtcgacttaa ttaaggctgc gcgctcgctc gctcactgag gccgcccggg caaagcccgg     60

gcgtcgggcg acctttggtc gcccggcctc agtgagcgag cgagcgcgca gagagggagt    120

ggccaactcc atcactaggg gttccttgta gttaatgatt aacccgccat gctacttatc    180

tacgtagcaa gctagcctag ttattaatag taatcaatta cggggtcatt agttcatagc    240

ccatatatgg agttccgcgt tacataactt acggtaaatg gcccgcctgg ctgaccgccc    300

aacgaccccc gcccattgac gtcaataatg acgtatgttc ccatagtaac gccaataggg    360

actttccatt gacgtcaatg ggtggagtat ttacggtaaa ctgcccactt ggcagtacat    420

caagtgtatc atatgccaag tacgccccct attgacgtca atgacggtaa atggcccgcc    480

tggcattatg cccagtacat gaccttatgg gactttccta cttggcagta catctacgta    540

ttagtcatcg ctattaccat ggtgatgcgg ttttggcagt acaccaatgg gcgtggatag    600

cggtttgact cacggggatt tccaagtctc caccccattg acgtcaatgg gagtttgttt    660

tggcaccaaa atcaacggga ctttccaaaa tgtcgtaaca actccgcccc gttgacgcaa    720

atgggcggta ggcgtgtacg gtgggaggtc tatataagca gagctcgttt agtgaaccgt    780

cagatcgccg ccaccatgga agatgccaaa aacattaaga agggcccagc gccattctac    840

ccactcgaag acgggaccgc cggcgagcag ctgcacaaag ccatgaagcg ctacgccctg    900

gtgcccggca ccatcgcctt taccgacgca catatcgagg tggacattac ctacgccgaa    960

tacttcgaga tgagcgttcg gctggcagaa gctatgaagc gctatgggct gaatacaaac   1020

catcggatcg tggtgtgcag cgagaatagc ttgcagttct tcatgcccgt gttgggtgcc   1080

ctgttcatcg gtgtggctgt ggccccagct aacgacatct acaacgagcg cgagctgctg   1140

aacagcatgg gcatcagcca gcccaccgtc gtattcgtga gcaagaaagg gctgcaaaag   1200

atcctcaacg tgcaaaagaa gctaccgatc atacaaaaga tcatcatcat ggatagcaag   1260
```

```
accgactacc agggcttcca aagcatgtac accttcgtga cttcccattt gccacccggc   1320
ttcaacgagt acgacttcgt gcccgagagc ttcgaccggg acaaaaccat cgccctgatc   1380
atgaacagta gtggcagtac cggattgccc aagggcgtag ccctaccgca ccgcaccgct   1440
tgtgtccgat tcagtcatgc ccgcgacccc atcttcggca accagatcat ccccgacacc   1500
gctatcctca gcgtggtgcc atttcaccac ggcttcggca tgttcaccac gctgggctac   1560
ttgatctgcg gctttcgggt cgtgctcatg taccgcttcg aggaggagct attcttgcgc   1620
agcttgcaag actataagat tcaatctgcc ctgctggtgc ccacactatt tagcttcttc   1680
gctaagagca ctctcatcga caagtacgac ctaagcaact tgcacgagat cgccagcggc   1740
ggagcgccgc tcagcaagga ggtaggtgag gccgtggcca aacgcttcca cctaccaggc   1800
atccgccagg gctacggcct gacagaaaca accagcgcca ttctgatcac ccccgaaggg   1860
gacgacaagc ctggcgcagt aggcaaggtg gtgcccttct tcgaggctaa ggtggtggac   1920
ttggacaccg gtaagacact gggtgtgaac cagcgcggcg agctgtgcgt ccgtggcccc   1980
atgatcatga gcggctacgt taacaacccc gaggctacaa acgctctcat cgacaaggac   2040
ggctggctgc acagcggcga catcgcctac tgggacgagg acgagcactt cttcatcgtg   2100
gaccggctga agagcctgat caaatacaag ggctaccagg taagtccgaa tacgacacgt   2160
agcaagatct ggtgggaggt aattgaatcg tgggggtggt ttcccccacg ctattctcat   2220
aatagtaagt tctcacgatg tctgatggtt ttataagggg ctttcccctt tgctcggctc   2280
acattcttct aattccggcc accatgtgaa gaaaaatgtg gcggccgcgt ttaaaccaaa   2340
caaacaaagg cgcgtcctgg attccacggt acatccagct gatgagtccc aaataggacg   2400
aaacgcgctc aaacaaacaa aagtacttaa gacatgataa gatacattga tgagtttgga   2460
caaaccacaa ctagaatgca gtgaaaaaaa tgctttattt gtgaaatttg tgatgctatt   2520
gctttatttg taaccattat aagctgcaat aaacaagtta acaacaacaa ttgcattcat   2580
tttatgtttc aggttcaggg ggagatgtgg gaggtttttt aaagcaagta aaacctctac   2640
aaatgtggta aactcgagtt ctacgtagat aagtagcatg gcgggttaat cattaactac   2700
aaggaacccc tagtgatgga gttggccact ccctctctgc gcgctcgctc gctcactgag   2760
gccgggcgac caaaggtcgc ccgacgcccg ggctttgccc gggcggcctc agtgagcgag   2820
cgagcgcgca gccttaatta acctaaggaa aatgaagtga agttcctata ctttctagag   2880
aataggaact tctatagtga gtcgaataag ggcgacacaa aatttattct aaatgcataa   2940
taaatactga taacatctta tagtttgtat tatattttgt attatcgttg acatgtataa   3000
ttttgatatc aaaaactgat tttcccttta ttattttcga gatttatttt cttaattctc   3060
tttaacaaac tagaaatatt gtatatacaa aaaatcataa ataatagatg aatagtttaa   3120
ttataggtgt tcatcaatcg aaaaagcaac gtatcttatt taaagtgcgt tgcttttttc   3180
tcatttataa ggttaaataa ttctcatata tcaagcaaag tgacaggcgc ccttaaatat   3240
tctgacaaat gctctttccc taaactcccc ccataaaaaa acccgccgaa gcgggttttt   3300
acgttatttg cggattaacg attactcgtt atcagaaccg cccagggggc ccgagcttaa   3360
ccttttttatt tgggggagag ggaagtcatg aaaaaactaa cctttgaaat tcgatctcca   3420
gcacatcagc aaaacgctat tcacgcagta cagcaaatcc ttccagaccc aaccaaacca   3480
atcgtagtaa ccattcagga acgcaaccgc agcttagacc aaaacaggaa gctatgggcc   3540
tgcttaggtg acgtctctcg tcaggttgaa tggcatggtc gctggctgga tgcagaaagc   3600
```

-continued

```
tggaagtgtg tgtttaccgc agcattaaag cagcaggatg ttgttcctaa ccttgccggg   3660
aatggctttg tggtaatagg ccagtcaacc agcaggatgc gtgtaggcga atttgcggag   3720
ctattagagc ttatacaggc attcggtaca gagcgtggcg ttaagtggtc agacgaagcg   3780
agactggctc tggagtggaa agcgagatgg ggagacaggg ctgcatgata aatgtcgtta   3840
gtttctccgg tggcaggacg tcagcatatt tgctctggct aatggagcaa aagcgacggg   3900
caggtaaaga cgtgcattac gttttcatgg atacaggttg tgaacatcca atgacatatc   3960
ggtttgtcag ggaagttgtg aagttctggg atataccgct caccgtattg caggttgata   4020
tcaacccgga gcttggacag ccaaatggtt atacggtatg ggaaccaaag gatattcaga   4080
cgcgaatgcc tgttctgaag ccatttatcg atatggtaaa gaaatatggc actccatacg   4140
tcggcggcgc gttctgcact gacagattaa aactcgttcc cttcaccaaa tactgtgatg   4200
accatttcgg gcgagggaat tacaccacgt ggattggcat cagagctgat gaaccgaagc   4260
ggctaaagcc aaagcctgga atcagatatc ttgctgaact gtcagacttt gagaaggaag   4320
atatcctcgc atggtggaag caacaaccat tcgatttgca aataccggaa catctcggta   4380
actgcatatt ctgcattaaa aaatcaacgc aaaaaatcgg acttgcctgc aaagatgagg   4440
agggattgca gcgtgttttt aatgaggtca tcacgggatc ccatgtgcgt gacggacatc   4500
gggaaacgcc aaaggagatt atgtaccgag gaagaatgtc gctggacggt atcgcgaaaa   4560
tgtattcaga aaatgattat caagccctgt atcaggacat ggtacgagct aaaagattcg   4620
ataccggctc ttgttctgag tcatgcgaaa tatttggagg gcagcttgat ttcgacttcg   4680
ggagggaagc tgcatgatgc gatgttatcg gtgcggtgaa tgcaaagaag ataaccgctt   4740
ccgaccaaat caaccttact ggaatcgatg gtgtctccgg tgtgaaagaa caccaacagg   4800
ggtgttacca ctaccgcagg aaaaggagga cgtgtggcga gacagcgacg aagtatcacc   4860
gacataatct gcgaaaactg caaatacctt ccaacgaaac gcaccagaaa taaacccaag   4920
ccaatcccaa aagaatctga cgtaaaaacc ttcaactaca cggctcacct gtgggatatc   4980
cggtggctaa gacgtcgtgc gaggaaaaca aggtgattga ccaaaatcga agttacgaac   5040
aagaaagcgt cgagcgagct ttaacgtgcg ctaactgcgg tcagaagctg catgtgctgg   5100
aagttcacgt gtgtgagcac tgctgcgcag aactgatgag cgatccgaat agctcgatgc   5160
acgaggaaga agatgatggc taaaccagcg cgaagacgat gtaaaaacga tgaatgccgg   5220
gaatggtttc accctgcatt cgctaatcag tggtggtgct ctccagagtg tggaaccaag   5280
atagcactcg aacgacgaag taaagaacgc gaaaaagcgg aaaaagcagc agagaagaaa   5340
cgacgacgag aggagcagaa acagaaagat aaacttaaga ttcgaaaact cgccttaaag   5400
ccccgcagtt actggattaa acaagcccaa caagccgtaa acgccttcat cagagaaaga   5460
gaccgcgact taccatgtat ctcgtgcgga acgctcacgt ctgctcagtg ggatgccgga   5520
cattaccgga caactgctgc ggcacctcaa ctccgattta atgaacgcaa tattcacaag   5580
caatgcgtgg tgtgcaacca gcacaaaagc ggaaatctcg ttccgtatcg cgtcgaactg   5640
attagccgca tcgggcagga agcagtagac gaaatcgaat caaaccataa ccgccatcgc   5700
tggactatcg aagagtgcaa ggcgatcaag gcagagtacc aacagaaact caaagacctg   5760
cgaaatagca gaagtgaggc cgcatgacgt tctcagtaaa aaccattcca gacatgctcg   5820
ttgaagcata cggaaatcag acagaagtag cacgcagact gaaatgtagt cgcggtacgg   5880
tcagaaaata cgttgatgat aaagacggga aaatgcacgc catcgtcaac gacgttctca   5940
tggttcatcg cggatggagt gaaagagatg cgctattacg aaaaaattga tggcagcaaa   6000
```

```
taccgaaata tttgggtagt tggcgatctg cacggatgct acacgaacct gatgaacaaa   6060
ctggatacga ttggattcga caacaaaaaa gacctgctta tctcggtggg cgatttggtt   6120
gatcgtggtg cagagaacgt tgaatgcctg gaattaatca cattcccctg gttcagagct   6180
gtacgtggaa accatgagca aatgatgatt gatggcttat cagagcgtgg aaacgttaat   6240
cactggctgc ttaatggcgg tggctggttc tttaatctcg attacgacaa agaaattctg   6300
gctaaagctc ttgcccataa agcagatgaa cttccgttaa tcatcgaact ggtgagcaaa   6360
gataaaaaat atgttatctg ccacgccgat tatccctttg acgaatacga gtttggaaag   6420
ccagttgatc atcagcaggt aatctggaac cgcgaacgaa tcagcaactc acaaaacggg   6480
atcgtgaaag aaatcaaagg cgcggacacg ttcatctttg gtcatacgcc agcagtgaaa   6540
ccactcaagt ttgccaacca aatgtatatc gataccggcg cagtgttctg cggaaaccta   6600
acattgattc aggtacaggg agaaggcgca tgagactcga aagcgtagct aaatttcatt   6660
cgccaaaaag cccgatgatg agcgactcac cacgggccac ggcttctgac tctctttccg   6720
gtactgatgt gatggctgct atggggatgg cgcaatcaca agccggattc ggtatggctg   6780
cattctgcgg taagcacgaa ctcagccaga acgacaaaca aaaggctatc aactatctga   6840
tgcaatttgc acacaaggta tcggggaaat accgtggtgt ggcaaagctt gaaggaaata   6900
ctaaggcaaa ggtactgcaa gtgctcgcaa cattcgctta tgcggattat tgccgtagtg   6960
ccgcgacgcc gggggcaaga tgcagagatt gccatggtac aggccgtgcg gttgatattg   7020
ccaaaacaga gctgtggggg agagttgtcg agaaagagtg cggaagatgc aaaggcgtcg   7080
gctattcaag gatgccagca agcgcagcat atcgcgctgt gacgatgcta atcccaaacc   7140
ttacccaacc cacctggtca cgcactgtta agccgctgta tgacgctctg gtggtgcaat   7200
gccacaaaga agagtcaatc gcagacaaca ttttgaatgc ggtcacacgt tagcagcatg   7260
attgccacgg atggcaacat attaacggca tgatattgac ttattgaata aaattgggta   7320
aatttgactc aacgatgggt taattcgctc gttgtggtag tgagatgaaa agaggcggcg   7380
cttactaccg attccgccta gttggtcact tcgacgtatc gtctggaact ccaaccatcg   7440
caggcagaga ggtctgcaaa atgcaatccc gaaacagttc gcaggtaata gttagagcct   7500
gcataacggt ttcgggattt tttatatctg cacaacaggt aagagcattg agtcgataat   7560
cgtgaagagt cggcgagcct ggttagccag tgctctttcc gttgtgctga attaagcgaa   7620
taccggaagc agaaccggat caccaaatgc gtacaggcgt catcgccgcc cagcaacagc   7680
acaacccaaa ctgagccgta gccactgtct gtcctgaatt cattagtaat agttacgctg   7740
cggcctttta cacatgacct tcgtgaaagc gggtggcagg aggtcgcgct aacaacctcc   7800
tgccgttttg cccgtgcata tcggtcacga acaaatctga ttactaaaca cagtagcctg   7860
gatttgttct atcagtaatc gaccttattc ctaattaaat agagcaaatc cccttattgg   7920
gggtaagaca tgaagatgcc agaaaaacat gacctgttgg ccgccattct cgcggcaaag   7980
gaacaaggca tcggggcaat ccttgcgttt gcaatggcgt accttcgcgg cagatataat   8040
ggcggtgcgt ttacaaaaac agtaatcgac gcaacgatgt gcgccattat cgcctggttc   8100
attcgtgacc ttctcgactt cgccggacta agtagcaatc tcgcttatat aacgagcgtg   8160
tttatcggct acatcggtac tgactcgatt ggttcgctta tcaaacgctt cgctgctaaa   8220
aaagccggag tagaagatgg tagaaatcaa taatcaacgt aaggcgttcc tcgatatgct   8280
ggcgtggtcg gagggaactg ataacggacg tcagaaaacc agaaatcatg gttatgacgt   8340
```

```
cattgtaggc ggagagctat ttactgatta ctccgatcac cctcgcaaac ttgtcacgct   8400
aaacccaaaa ctcaaatcaa caggcgctta agactggccg tcgttttaca acacagaaag   8460
agtttgtaga aacgcaaaaa ggccatccgt caggggcctt ctgcttagtt tgatgcctgg   8520
cagttcccta ctctcgcctt ccgcttcctc gctcactgac tcgctgcgct cggtcgttcg   8580
gctgcggcga gcggtatcag ctcactcaaa ggcggtaata cggttatcca cagaatcagg   8640
ggataacgca ggaaagaaca tgtgagcaaa aggccagcaa aaggccagga accgtaaaaa   8700
ggccgcgttg ctggcgtttt tccataggct ccgcccccct gacgagcatc acaaaaatcg   8760
acgctcaagt cagaggtggc gaaacccgac aggactataa agataccagg cgtttccccc   8820
tggaagctcc ctcgtgcgct ctcctgttcc gaccctgccg cttaccggat acctgtccgc   8880
ctttctccct tcgggaagcg tggcgctttc tcatagctca cgctgtaggt atctcagttc   8940
ggtgtaggtc gttcgctcca agctgggctg tgtgcacgaa ccccccgttc agcccgaccg   9000
ctgcgcctta tccggtaact atcgtcttga gtccaacccg gtaagacacg acttatcgcc   9060
actggcagca gccactggta acaggattag cagagcgagg tatgtaggcg gtgctacaga   9120
gttcttgaag tggtgggcta actacggcta cactagaaga acagtatttg gtatctgcgc   9180
tctgctgaag ccagttacct tcggaaaaag agttggtagc tcttgatccg gcaaacaaac   9240
caccgctggt agcggtggtt tttttgtttg caagcagcag attacgcgca gaaaaaaagg   9300
atctcaagaa gatcctttga tcttttctac ggggtctgac gctcagtgga acgacgcgcg   9360
cgtaactcac gttaagggat tttggtcatg agcttgcgcc gtcccgtcaa gtcagcgtaa   9420
tgctctgctt ttagaaaaac tcatcgagca tcaaatgaaa ctgcaattta ttcatatcag   9480
gattatcaat accatatttt tgaaaaagcc gtttctgtaa tgaaggagaa aactcaccga   9540
ggcagttcca taggatggca agatcctggt atcggtctgc gattccgact cgtccaacat   9600
caatacaacc tattaatttc ccctcgtcaa aaataaggtt atcaagtgag aaatcaccat   9660
gagtgacgac tgaatccggt gagaatggca aaagtttatg catttctttc cagacttgtt   9720
caacaggcca gccattacgc tcgtcatcaa aatcactcgc atcaaccaaa ccgttattca   9780
ttcgtgattg cgcctgagcg aggcgaaata cgcgatcgct gttaaaagga caattacaaa   9840
caggaatcga gtgcaaccgg cgcaggaaca ctgccagcgc atcaacaata ttttcacctg   9900
aatcaggata ttcttctaat acctggaacg ctgtttttcc ggggatcgca gtggtgagta   9960
accatgcatc atcaggagta cggataaaat gcttgatggt cggaagtggc ataaattccg  10020
tcagccagtt tagtctgacc atctcatctg taacatcatt ggcaacgcta cctttgccat  10080
gtttcagaaa caactctggc gcatcgggct tcccatacaa gcgatagatt gtcgcacctg  10140
attgcccgac attatcgcga gcccatttat acccatataa atcagcatcc atgttggaat  10200
ttaatcgcgg cctcgacgtt tcccgttgaa tatggctcat attcttcctt tttcaatatt  10260
attgaagcat ttatcagggt tattgtctca tgagcggata catatttgaa tgtatttaga  10320
aaaataaaca aataggggtc agtgttacaa ccaattaacc aattctgaac attatcgcga  10380
gcccatttat acctgaatat ggctcataac accccttgtt tgcctggcgg cagtagcgcg  10440
gtggtcccac ctgaccccat gccgaactca gaagtgaaac gccgtagcgc cgatggtagt  10500
gtggggactc cccatgcgag agtagggaac tgccaggcat caaataaaac gaaaggctca  10560
gtcgaaagac tgggcctttc gcccgggcta attagggggt gtcgccctta ttcgactcta  10620
tagtgaagtt cctattctct agaaagtata ggaacttctg aagtggg                10667
```

<210> SEQ ID NO 33
<211> LENGTH: 10446
<212> TYPE: DNA
<213> ORGANISM: Artificial Sequence
<220> FEATURE:
<223> OTHER INFORMATION: Synthetic Construct

<400> SEQUENCE: 33
gtcgacttaa ttaaggctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttccttgta gttaatgatt aacccgccat gctacttatc 180
tacgtagcaa gctagcctag ttattaatag taatcaatta cggggtcatt agttcatagc 240
ccatatatgg agttccgcgt tacataactt acggtaaatg gcccgcctgg ctgaccgccc 300
aacgaccccc gcccattgac gtcaataatg acgtatgttc ccatagtaac gccaataggg 360
actttccatt gacgtcaatg ggtggagtat ttacggtaaa ctgcccactt ggcagtacat 420
caagtgtatc atatgccaag tacgccccct attgacgtca atgacggtaa atggcccgcc 480
tggcattatg cccagtacat gaccttatgg gactttccta cttggcagta catctacgta 540
ttagtcatcg ctattaccat ggtgatgcgg ttttggcagt acaccaatgg gcgtggatag 600
cggtttgact cacggggatt tccaagtctc caccccattg acgtcaatgg gagtttgttt 660
tggcaccaaa atcaacggga ctttccaaaa tgtcgtaaca actccgcccc gttgacgcaa 720
atgggcggta ggcgtgtacg gtgggaggtc tatataagca gagctcgttt agtgaaccgt 780
cagatcgccg ccaccatgga agatgccaaa aacattaaga agggcccagc gccattctac 840
ccactcgaag acgggaccgc cggcgagcag ctgcacaaag ccatgaagcg ctacgccctg 900
gtgcccggca ccatcgcctt taccgacgca catatcgagg tggacattac ctacgccgaa 960
tacttcgaga tgagcgttcg gctggcagaa gctatgaagc gctatgggct gaatacaaac 1020
catcggatcg tggtgtgcag cgagaatagc ttgcagttct tcatgcccgt gttgggtgcc 1080
ctgttcatcg gtgtggctgt ggccccagct aacgacatct acaacgagcg cgagctgctg 1140
aacagcatgg gcatcagcca gcccaccgtc gtattcgtga gcaagaaagg gctgcaaaag 1200
atcctcaacg tgcaaaagaa gctaccgatc atacaaaaga tcatcatcat ggatagcaag 1260
accgactacc agggcttcca aagcatgtac accttcgtga cttcccattt gccacccggc 1320
ttcaacgagt acgacttcgt gcccgagagc ttcgaccggg acaaaaccat cgccctgatc 1380
atgaacagta gtggcagtac cggattgccc aagggcgtag ccctaccgca ccgcaccgct 1440
tgtgtccgat tcagtcatgc ccgcgacccc atcttcggca accagatcat ccccgacacc 1500
gctatcctca gcgtggtgcc atttcaccac ggcttcggca tgttcaccac gctgggctac 1560
ttgatctgcg gctttcgggt cgtgctcatg taccgcttcg aggaggagct attcttgcgc 1620
agcttgcaag actataagat tcaatctgcc ctgctggtgc ccacactatt tagcttcttc 1680
gctaagagca ctctcatcga caagtacgac ctaagcaact tgcacgagat cgccagcggc 1740
ggagcgccgc tcagcaagga ggtaggtgag gccgtggcca aacgcttcca cctaccaggc 1800
atccgccagg gctacggcct gacagaaaca accagcgcca ttctgatcac ccccgaaggg 1860
gacgacaagc ctggcgcagt aggcaaggtg gtgcccttct tcgaggctaa ggtggtggac 1920
ttggacaccg gtaagacact gggtgtgaac cagcgcggcg agctgtgcgt ccgtggcccc 1980
atgatcatga gcggctacgt taacaacccc gaggctacaa acgctctcat cgacaaggac 2040
ggctggctgc acagcggcga catcgcctac tgggacgagg acgagcactt cttcatcgtg 2100
gaccggctga agagcctgat caaatacaag ggctaccagg taagtccgaa tacgatactc 2160
agcaggtggg aggtaattga atcgtggggg tggtttcccc cacgctattc tcataatagt 2220
aagttctcac gatgtctgat ggttttataa ggggctttcc cctttgctcg gctcacattc 2280
ttctaattcc ggccaccatg tgaagaaaaa tgtgaaaggt ttttcttttc ctgagaaatt 2340
tctcaggttt tgctttttaa aaaaaaagca aaagatgctg gtggttggca ctcctggttt 2400
ccaggacggg gttcaaatcc ctgcggcgtc tctcgagttc tacgtagata agtagcatgg 2460
cgggttaatc attaactaca aggaacccct agtgatggag ttggccactc cctctctgcg 2520
cgctcgctcg ctcactgagg ccgggcgacc aaaggtcgcc cgacgcccgg gctttgcccg 2580
ggcggcctca gtgagcgagc gagcgcgcag ccttaattaa cctaaggaaa atgaagtgaa 2640
gttcctatac tttctagaga ataggaactt ctatagtgag tcgaataagg gcgacacaaa 2700
atttattcta aatgcataat aaatactgat aacatcttat agtttgtatt atattttgta 2760
ttatcgttga catgtataat tttgatatca aaaactgatt ttccctttat tattttcgag 2820
atttattttc ttaattctct ttaacaaact agaaatattg tatatacaaa aaatcataaa 2880
taatagatga atagtttaat tataggtgtt catcaatcga aaaagcaacg tatcttattt 2940
aaagtgcgtt gctttttct catttataag gttaaataat tctcatatat caagcaaagt 3000
gacaggcgcc cttaaatatt ctgacaaatg ctctttccct aaactccccc cataaaaaaa 3060
cccgccgaag cgggttttta cgttatttgc ggattaacga ttactcgtta tcagaaccgc 3120
ccagggggcc cgagcttaac ctttttattt gggggagagg gaagtcatga aaaaactaac 3180
ctttgaaatt cgatctccag cacatcagca aaacgctatt cacgcagtac agcaaatcct 3240
tccagaccca accaaaccaa tcgtagtaac cattcaggaa cgcaaccgca gcttagacca 3300
aaacaggaag ctatgggcct gcttaggtga cgtctctcgt caggttgaat ggcatggtcg 3360
ctggctggat gcagaaagct ggaagtgtgt gtttaccgca gcattaaagc agcaggatgt 3420
tgttcctaac cttgccggga atggctttgt ggtaataggc cagtcaacca gcaggatgcg 3480
tgtaggcgaa tttgcggagc tattagagct tatacaggca ttcggtacag agcgtggcgt 3540
taagtggtca gacgaagcga gactggctct ggagtggaaa gcgagatggg gagacagggc 3600
tgcatgataa atgtcgttag tttctccggt ggcaggacgt cagcatattt gctctggcta 3660
atggagcaaa agcgacgggc aggtaaagac gtgcattacg ttttcatgga tacaggttgt 3720
gaacatccaa tgacatatcg gtttgtcagg gaagttgtga agttctggga tataccgctc 3780
accgtattgc aggttgatat caacccggag cttggacagc caaatggtta tacggtatgg 3840
gaaccaaagg atattcagac gcgaatgcct gttctgaagc catttatcga tatggtaaag 3900
aaatatggca ctccatacgt cggcggcgcg ttctgcactg acagattaaa actcgttccc 3960
ttcaccaaat actgtgatga ccatttcggg cgagggaatt acaccacgtg gattggcatc 4020
agagctgatg aaccgaagcg gctaaagcca aagcctggaa tcagatatct tgctgaactg 4080
tcagactttg agaaggaaga tatcctcgca tggtggaagc aacaaccatt cgatttgcaa 4140
ataccggaac atctcggtaa ctgcatattc tgcattaaaa aatcaacgca aaaaatcgga 4200
cttgcctgca aagatgagga gggattgcag cgtgttttta atgaggtcat cacgggatcc 4260
catgtgcgtg acggacatcg ggaaacgcca aaggagatta tgtaccgagg aagaatgtcg 4320
ctggacggta tcgcgaaaat gtattcagaa aatgattatc aagccctgta tcaggacatg 4380
gtacgagcta aaagattcga taccggctct tgttctgagt catgcgaaat atttggaggg 4440
cagcttgatt tcgacttcgg gagggaagct gcatgatgcg atgttatcgg tgcggtgaat 4500
gcaaagaaga taaccgcttc cgaccaaatc aaccttactg gaatcgatgg tgtctccggt 4560
gtgaaagaac accaacaggg gtgttaccac taccgcagga aaggaggac gtgtggcgag 4620 acagcgacga agtatcaccg acataatctg cgaaaactgc aaataccttc caacgaaacg 4680
caccagaaat aaacccaagc caatcccaaa agaatctgac gtaaaaacct tcaactacac 4740
ggctcacctg tgggatatcc ggtggctaag acgtcgtgcg aggaaaacaa ggtgattgac 4800
caaaatcgaa gttacgaaca agaaagcgtc gagcgagctt taacgtgcgc taactgcggt 4860
cagaagctgc atgtgctgga agttcacgtg tgtgagcact gctgcgcaga actgatgagc 4920
gatccgaata gctcgatgca cgaggaagaa gatgatggct aaaccagcgc gaagacgatg 4980
taaaaacgat gaatgccggg aatggtttca ccctgcattc gctaatcagt ggtggtgctc 5040
tccagagtgt ggaaccaaga tagcactcga acgacgaagt aaagaacgcg aaaaagcgga 5100
aaaagcagca gagaagaaac gacgacgaga ggagcagaaa cagaaagata aacttaagat 5160
tcgaaaactc gccttaaagc cccgcagtta ctggattaaa caagcccaac aagccgtaaa 5220
cgccttcatc agagaaagag accgcgactt accatgtatc tcgtgcggaa cgctcacgtc 5280
tgctcagtgg gatgccggac attaccggac aactgctgcg gcacctcaac tccgatttaa 5340
tgaacgcaat attcacaagc aatgcgtggt gtgcaaccag cacaaaagcg gaaatctcgt 5400
tccgtatcgc gtcgaactga ttagccgcat cgggcaggaa gcagtagacg aaatcgaatc 5460
aaaccataac cgccatcgct ggactatcga agagtgcaag gcgatcaagg cagagtacca 5520
acagaaactc aaagacctgc gaaatagcag aagtgaggcc gcatgacgtt ctcagtaaaa 5580
accattccag acatgctcgt tgaagcatac ggaaatcaga cagaagtagc acgcagactg 5640
aaatgtagtc gcggtacggt cagaaaatac gttgatgata aagacgggaa aatgcacgcc 5700
atcgtcaacg acgttctcat ggttcatcgc ggatggagtg aaagagatgc gctattacga 5760
aaaaattgat ggcagcaaat accgaaatat ttgggtagtt ggcgatctgc acggatgcta 5820
cacgaacctg atgaacaaac tggatacgat tggattcgac aacaaaaaag acctgcttat 5880
ctcggtgggc gatttggttg atcgtggtgc agagaacgtt gaatgcctgg aattaatcac 5940
attcccctgg ttcagagctg tacgtggaaa ccatgagcaa atgatgattg atggcttatc 6000
agagcgtgga aacgttaatc actggctgct taatggcggt ggctggttct ttaatctcga 6060
ttacgacaaa gaaattctgg ctaaagctct tgcccataaa gcagatgaac ttccgttaat 6120
catcgaactg gtgagcaaag ataaaaaata tgttatctgc cacgccgatt atccctttga 6180
cgaatacgag tttggaaagc cagttgatca tcagcaggta atctggaacc gcgaacgaat 6240
cagcaactca caaaacggga tcgtgaaaga aatcaaaggc gcggacacgt tcatctttgg 6300
tcatacgcca gcagtgaaac cactcaagtt tgccaaccaa atgtatatcg ataccggcgc 6360
agtgttctgc ggaaacctaa cattgattca ggtacaggga gaaggcgcat gagactcgaa 6420
agcgtagcta aatttcattc gccaaaaagc ccgatgatga gcgactcacc acgggccacg 6480
gcttctgact ctctttccgg tactgatgtg atggctgcta tggggatggc gcaatcacaa 6540
gccggattcg gtatggctgc attctgcggt aagcacgaac tcagccagaa cgacaaacaa 6600
aaggctatca actatctgat gcaatttgca cacaaggtat cggggaaata ccgtggtgtg 6660
gcaaagcttg aaggaaatac taaggcaaag gtactgcaag tgctcgcaac attcgcttat 6720
gcggattatt gccgtagtgc cgcgacgccg gggcaagat gcagagattg ccatggtaca 6780
ggccgtgcgg ttgatattgc caaaacagag ctgtggggga gagttgtcga gaaagagtgc 6840

```
ggaagatgca aaggcgtcgg ctattcaagg atgccagcaa gcgcagcata tcgcgctgtg   6900
acgatgctaa tcccaaacct tacccaaccc acctggtcac gcactgttaa gccgctgtat   6960
gacgctctgg tggtgcaatg ccacaaagaa gagtcaatcg cagacaacat tttgaatgcg   7020
gtcacacgtt agcagcatga ttgccacgga tggcaacata ttaacggcat gatattgact   7080
tattgaataa aattgggtaa atttgactca acgatgggtt aattcgctcg ttgtggtagt   7140
gagatgaaaa gaggcggcgc ttactaccga ttccgcctag ttggtcactt cgacgtatcg   7200
tctggaactc caaccatcgc aggcagagag gtctgcaaaa tgcaatcccg aaacagttcg   7260
caggtaatag ttagagcctg cataacggtt tcgggatttt ttatatctgc acaacaggta   7320
agagcattga gtcgataatc gtgaagagtc ggcgagcctg gttagccagt gctctttccg   7380
ttgtgctgaa ttaagcgaat accggaagca gaaccggatc accaaatgcg tacaggcgtc   7440
atcgccgccc agcaacagca caacccaaac tgagccgtag ccactgtctg tcctgaattc   7500
attagtaata gttacgctgc ggccttttac acatgacctt cgtgaaagcg ggtggcagga   7560
ggtcgcgcta acaacctcct gccgttttgc ccgtgcatat cggtcacgaa caaatctgat   7620
tactaaacac agtagcctgg atttgttcta tcagtaatcg accttattcc taattaaata   7680
gagcaaatcc ccttattggg ggtaagacat gaagatgcca gaaaaacatg acctgttggc   7740
cgccattctc gcggcaaagg aacaaggcat cggggcaatc cttgcgtttg caatggcgta   7800
ccttcgcggc agatataatg gcggtgcgtt tacaaaaaca gtaatcgacg caacgatgtg   7860
cgccattatc gcctggttca ttcgtgacct tctcgacttc gccggactaa gtagcaatct   7920
cgcttatata acgagcgtgt ttatcggcta catcggtact gactcgattg gttcgcttat   7980
caaacgcttc gctgctaaaa aagccggagt agaagatggt agaaatcaat aatcaacgta   8040
aggcgttcct cgatatgctg gcgtggtcgg agggaactga taacggacgt cagaaaacca   8100
gaaatcatgg ttatgacgtc attgtaggcg gagagctatt tactgattac tccgatcacc   8160
ctcgcaaact tgtcacgcta aacccaaaac tcaaatcaac aggcgcttaa gactggccgt   8220
cgttttacaa cacagaaaga gtttgtagaa acgcaaaaag gccatccgtc aggggccttc   8280
tgcttagttt gatgcctggc agttccctac tctcgccttc cgcttcctcg ctcactgact   8340
cgctgcgctc ggtcgttcgg ctgcggcgag cggtatcagc tcactcaaag gcggtaatac   8400
ggttatccac agaatcaggg gataacgcag gaaagaacat gtgagcaaaa ggccagcaaa   8460
aggccaggaa ccgtaaaaag gccgcgttgc tggcgttttt ccataggctc cgcccccctg   8520
acgagcatca caaaaatcga cgctcaagtc agaggtggcg aaacccgaca ggactataaa   8580
gataccaggc gtttccccct ggaagctccc tcgtgcgctc tcctgttccg accctgccgc   8640
ttaccggata cctgtccgcc tttctccctt cgggaagcgt ggcgctttct catagctcac   8700
gctgtaggta tctcagttcg gtgtaggtcg ttcgctccaa gctgggctgt gtgcacgaac   8760
cccccgttca gcccgaccgc tgcgccttat ccggtaacta tcgtcttgag tccaacccgg   8820
taagacacga cttatcgcca ctggcagcag ccactggtaa caggattagc agagcgaggt   8880
atgtaggcgg tgctacagag ttcttgaagt ggtgggctaa ctacggctac actagaagaa   8940
cagtatttgg tatctgcgct ctgctgaagc cagttacctt cggaaaaaga gttggtagct   9000
cttgatccgg caaacaaacc accgctggta gcggtggttt ttttgtttgc aagcagcaga   9060
ttacgcgcag aaaaaaagga tctcaagaag atcctttgat cttttctacg gggtctgacg   9120
ctcagtggaa cgacgcgcgc gtaactcacg ttaagggatt ttggtcatga gcttgcgccg   9180
tcccgtcaag tcagcgtaat gctctgcttt tagaaaaact catcgagcat caaatgaaac   9240
```

```
tgcaatttat tcatatcagg attatcaata ccatattttt gaaaaagccg tttctgtaat   9300

gaaggagaaa actcaccgag gcagttccat aggatggcaa gatcctggta tcggtctgcg   9360

attccgactc gtccaacatc aatacaacct attaatttcc cctcgtcaaa aataaggtta   9420

tcaagtgaga aatcaccatg agtgacgact gaatccggtg agaatggcaa aagtttatgc   9480

atttctttcc agacttgttc aacaggccag ccattacgct cgtcatcaaa atcactcgca   9540

tcaaccaaac cgttattcat tcgtgattgc gcctgagcga ggcgaaatac gcgatcgctg   9600

ttaaaaggac aattacaaac aggaatcgag tgcaaccggc gcaggaacac tgccagcgca   9660

tcaacaatat tttcacctga atcaggatat tcttctaata cctggaacgc tgtttttccg   9720

gggatcgcag tggtgagtaa ccatgcatca tcaggagtac ggataaaatg cttgatggtc   9780

ggaagtggca taaattccgt cagccagttt agtctgacca tctcatctgt aacatcattg   9840

gcaacgctac ctttgccatg tttcagaaac aactctggcg catcgggctt cccatacaag   9900

cgatagattg tcgcacctga ttgcccgaca ttatcgcgag cccatttata cccatataaa   9960

tcagcatcca tgttggaatt taatcgcggc ctcgacgttt cccgttgaat atggctcata  10020

ttcttccttt ttcaatatta ttgaagcatt tatcagggtt attgtctcat gagcggatac  10080

atatttgaat gtatttagaa aaataaacaa ataggggtca gtgttacaac caattaacca  10140

attctgaaca ttatcgcgag cccatttata cctgaatatg gctcataaca ccccttgttt  10200

gcctggcggc agtagcgcgg tggtcccacc tgaccccatg ccgaactcag aagtgaaacg  10260

ccgtagcgcc gatggtagtg tggggactcc ccatgcgaga gtagggaact gccaggcatc  10320

aaataaaacg aaaggctcag tcgaaagact gggcctttcg cccgggctaa ttagggggtg  10380

tcgcccttat tcgactctat agtgaagttc ctattctcta gaaagtatag gaacttctga  10440

agtggg                                                             10446
```

<210> SEQ ID NO 34
<211> LENGTH: 10465
<212> TYPE: DNA
<213> ORGANISM: Artificial Sequence
<220> FEATURE:
<223> OTHER INFORMATION: Synthetic Construct

<400> SEQUENCE: 34

```
gtcgacttaa ttaaggctgc gcgctcgctc gctcactgag gccgcccggg caaagcccgg     60

gcgtcgggcg acctttggtc gcccggcctc agtgagcgag cgagcgcgca gagagggagt    120

ggccaactcc atcactaggg gttccttgta gttaatgatt aacccgccat gctacttatc    180

tacgtagcaa gctagcctag ttattaatag taatcaatta cggggtcatt agttcatagc    240

ccatatatgg agttccgcgt tacataactt acggtaaatg gcccgcctgg ctgaccgccc    300

aacgaccccc gcccattgac gtcaataatg acgtatgttc ccatagtaac gccaataggg    360

actttccatt gacgtcaatg ggtggagtat ttacggtaaa ctgcccactt ggcagtacat    420

caagtgtatc atatgccaag tacgccccct attgacgtca atgacggtaa atggcccgcc    480

tggcattatg cccagtacat gaccttatgg gactttccta cttggcagta catctacgta    540

ttagtcatcg ctattaccat ggtgatgcgg ttttggcagt acaccaatgg gcgtggatag    600

cggtttgact cacggggatt tccaagtctc caccccattg acgtcaatgg gagtttgttt    660

tggcaccaaa atcaacggga ctttccaaaa tgtcgtaaca actccgcccc gttgacgcaa    720

atgggcggta ggcgtgtacg gtgggaggtc tatataagca gagctcgttt agtgaaccgt    780
```

```
cagatcgccg ccaccatgga agatgccaaa aacattaaga agggcccagc gccattctac    840
ccactcgaag acgggaccgc cggcgagcag ctgcacaaag ccatgaagcg ctacgccctg    900
gtgcccggca ccatcgcctt taccgacgca catatcgagg tggacattac ctacgccgaa    960
tacttcgaga tgagcgttcg gctggcagaa gctatgaagc gctatgggct gaatacaaac   1020
catcggatcg tggtgtgcag cgagaatagc ttgcagttct tcatgcccgt gttgggtgcc   1080
ctgttcatcg gtgtggctgt ggccccagct aacgacatct acaacgagcg cgagctgctg   1140
aacagcatgg gcatcagcca gcccaccgtc gtattcgtga gcaagaaagg gctgcaaaag   1200
atcctcaacg tgcaaaagaa gctaccgatc atacaaaaga tcatcatcat ggatagcaag   1260
accgactacc agggcttcca aagcatgtac accttcgtga cttcccattt gccacccggc   1320
ttcaacgagt acgacttcgt gcccgagagc ttcgaccggg acaaaaccat cgccctgatc   1380
atgaacagta gtggcagtac cggattgccc aagggcgtag ccctaccgca ccgcaccgct   1440
tgtgtccgat tcagtcatgc ccgcgacccc atcttcggca accagatcat ccccgacacc   1500
gctatcctca gcgtggtgcc atttcaccac ggcttcggca tgttcaccac gctgggctac   1560
ttgatctgcg gctttcgggt cgtgctcatg taccgcttcg aggaggagct attcttgcgc   1620
agcttgcaag actataagat tcaatctgcc ctgctggtgc ccacactatt tagcttcttc   1680
gctaagagca ctctcatcga caagtacgac ctaagcaact tgcacgagat cgccagcggc   1740
ggagcgccgc tcagcaagga ggtaggtgag gccgtggcca aacgcttcca cctaccaggc   1800
atccgccagg gctacggcct gacagaaaca accagcgcca ttctgatcac ccccgaaggg   1860
gacgacaagc ctggcgcagt aggcaaggtg gtgcccttct tcgaggctaa ggtggtggac   1920
ttggacaccg gtaagacact gggtgtgaac cagcgcggcg agctgtgcgt ccgtggcccc   1980
atgatcatga gcggctacgt taacaacccc gaggctacaa acgctctcat cgacaaggac   2040
ggctggctgc acagcggcga catcgcctac tgggacgagg acgagcactt cttcatcgtg   2100
gaccggctga agagcctgat caaatacaag ggctaccagg taagtccgaa tacgatactc   2160
agcaggtggg aggtaattga atcgtggggg tggtttcccc cacgctattc tcataatagt   2220
aagttctcac gatgtctgat ggttttataa ggggctttcc cctttgctcg gctcacattc   2280
ttctaattcc ggccaccatg tgaagaaaaa tgtggattcg tcagtagggt tgtaaaggtt   2340
tttcttttcc tgagaaattt ctcaggtttt gctttttaaa aaaaaagcaa aagatgctgg   2400
tggttggcac tcctggtttc caggacgggg ttcaaatccc tgcggcgtct ctcgagttct   2460
acgtagataa gtagcatggc gggttaatca ttaactacaa ggaaccccta gtgatggagt   2520
tggccactcc ctctctgcgc gctcgctcgc tcactgaggc cgggcgacca aaggtcgccc   2580
gacgcccggg ctttgcccgg gcggcctcag tgagcgagcg agcgcgcagc cttaattaac   2640
ctaaggaaaa tgaagtgaag ttcctatact ttctagagaa taggaacttc tatagtgagt   2700
cgaataaggg cgacacaaaa tttattctaa atgcataata aatactgata acatcttata   2760
gtttgtatta tattttgtat tatcgttgac atgtataatt ttgatatcaa aaactgattt   2820
tccctttatt attttcgaga tttattttct taattctctt taacaaacta gaaatattgt   2880
atatacaaaa aatcataaat aatagatgaa tagtttaatt ataggtgttc atcaatcgaa   2940
aaagcaacgt atcttattta aagtgcgttg ctttttttctc atttataagg ttaaataatt   3000
ctcatatatc aagcaaagtg acaggcgccc ttaaatattc tgacaaatgc tctttcccta   3060
aactcccccc ataaaaaaac ccgccgaagc gggtttttac gttatttgcg gattaacgat   3120
tactcgttat cagaaccgcc caggggggccc gagcttaacc tttttatttg gggagaggg    3180
```

```
aagtcatgaa aaaactaacc tttgaaattc gatctccagc acatcagcaa aacgctattc   3240
acgcagtaca gcaaatcctt ccagacccaa ccaaaccaat cgtagtaacc attcaggaac   3300
gcaaccgcag cttagaccaa aacaggaagc tatgggcctg cttaggtgac gtctctcgtc   3360
aggttgaatg gcatggtcgc tggctggatg cagaaagctg gaagtgtgtg tttaccgcag   3420
cattaaagca gcaggatgtt gttcctaacc ttgccgggaa tggctttgtg gtaataggcc   3480
agtcaaccag caggatgcgt gtaggcgaat ttgcggagct attagagctt atacaggcat   3540
tcggtacaga gcgtggcgtt aagtggtcag acgaagcgag actggctctg gagtggaaag   3600
cgagatgggg agacagggct gcatgataaa tgtcgttagt ttctccggtg gcaggacgtc   3660
agcatatttg ctctggctaa tggagcaaaa gcgacgggca ggtaaagacg tgcattacgt   3720
tttcatggat acaggttgtg aacatccaat gacatatcgg tttgtcaggg aagttgtgaa   3780
gttctgggat ataccgctca ccgtattgca ggttgatatc aacccggagc ttggacagcc   3840
aaatggttat acggtatggg aaccaaagga tattcagacg cgaatgcctg ttctgaagcc   3900
atttatcgat atggtaaaga aatatggcac tccatacgtc ggcggcgcgt tctgcactga   3960
cagattaaaa ctcgttccct tcaccaaata ctgtgatgac catttcgggc gagggaatta   4020
caccacgtgg attggcatca gagctgatga accgaagcgg ctaaagccaa agcctggaat   4080
cagatatctt gctgaactgt cagactttga gaaggaagat atcctcgcat ggtggaagca   4140
acaaccattc gatttgcaaa taccggaaca tctcggtaac tgcatattct gcattaaaaa   4200
atcaacgcaa aaaatcggac ttgcctgcaa agatgaggag ggattgcagc gtgtttttaa   4260
tgaggtcatc acgggatccc atgtgcgtga cggacatcgg gaaacgccaa aggagattat   4320
gtaccgagga agaatgtcgc tggacggtat cgcgaaaatg tattcagaaa atgattatca   4380
agccctgtat caggacatgg tacgagctaa aagattcgat accggctctt gttctgagtc   4440
atgcgaaata tttggagggc agcttgattt cgacttcggg agggaagctg catgatgcga   4500
tgttatcggt gcggtgaatg caaagaagat aaccgcttcc gaccaaatca accttactgg   4560
aatcgatggt gtctccggtg tgaaagaaca ccaacagggg tgttaccact accgcaggaa   4620
aaggaggacg tgtggcgaga cagcgacgaa gtatcaccga cataatctgc gaaaactgca   4680
aataccttcc aacgaaacgc accagaaata aacccaagcc aatcccaaaa gaatctgacg   4740
taaaaacctt caactacacg gctcacctgt gggatatccg gtggctaaga cgtcgtgcga   4800
ggaaaacaag gtgattgacc aaaatcgaag ttacgaacaa gaaagcgtcg agcgagcttt   4860
aacgtgcgct aactgcggtc agaagctgca tgtgctggaa gttcacgtgt gtgagcactg   4920
ctgcgcagaa ctgatgagcg atccgaatag ctcgatgcac gaggaagaag atgatggcta   4980
aaccagcgcg aagacgatgt aaaaacgatg aatgccggga atggtttcac cctgcattcg   5040
ctaatcagtg gtggtgctct ccagagtgtg gaaccaagat agcactcgaa cgacgaagta   5100
aagaacgcga aaaagcggaa aaagcagcag agaagaaacg acgacgagag gagcagaaac   5160
agaaagataa acttaagatt cgaaaactcg ccttaaagcc ccgcagttac tggattaaac   5220
aagcccaaca agccgtaaac gccttcatca gagaaagaga ccgcgactta ccatgtatct   5280
cgtgcggaac gctcacgtct gctcagtggg atgccggaca ttaccggaca actgctgcgg   5340
cacctcaact ccgatttaat gaacgcaata ttcacaagca atgcgtggtg tgcaaccagc   5400
acaaaagcgg aaatctcgtt ccgtatcgcg tcgaactgat tagccgcatc gggcaggaag   5460
cagtagacga aatcgaatca aaccataacc gccatcgctg gactatcgaa gagtgcaagg   5520
```

```
cgatcaaggc agagtaccaa cagaaactca aagacctgcg aaatagcaga agtgaggccg   5580
catgacgttc tcagtaaaaa ccattccaga catgctcgtt gaagcatacg gaaatcagac   5640
agaagtagca cgcagactga aatgtagtcg cggtacggtc agaaaatacg ttgatgataa   5700
agacgggaaa atgcacgcca tcgtcaacga cgttctcatg gttcatcgcg gatggagtga   5760
aagagatgcg ctattacgaa aaaattgatg gcagcaaata ccgaaatatt tgggtagttg   5820
gcgatctgca cggatgctac acgaacctga tgaacaaact ggatacgatt ggattcgaca   5880
acaaaaaaga cctgcttatc tcggtgggcg atttggttga tcgtggtgca gagaacgttg   5940
aatgcctgga attaatcaca ttcccctggt tcagagctgt acgtggaaac catgagcaaa   6000
tgatgattga tggcttatca gagcgtggaa acgttaatca ctggctgctt aatggcggtg   6060
gctggttctt taatctcgat tacgacaaag aaattctggc taaagctctt gcccataaag   6120
cagatgaact tccgttaatc atcgaactgg tgagcaaaga taaaaaatat gttatctgcc   6180
acgccgatta tccctttgac gaatacgagt ttggaaagcc agttgatcat cagcaggtaa   6240
tctggaaccg cgaacgaatc agcaactcac aaaacgggat cgtgaaagaa atcaaaggcg   6300
cggacacgtt catctttggt catacgccag cagtgaaacc actcaagttt gccaaccaaa   6360
tgtatatcga taccggcgca gtgttctgcg gaaacctaac attgattcag gtacagggag   6420
aaggcgcatg agactcgaaa gcgtagctaa atttcattcg ccaaaaagcc cgatgatgag   6480
cgactcacca cgggccacgg cttctgactc tctttccggt actgatgtga tggctgctat   6540
ggggatggcg caatcacaag ccggattcgg tatggctgca ttctgcggta agcacgaact   6600
cagccagaac gacaaacaaa aggctatcaa ctatctgatg caatttgcac acaaggtatc   6660
ggggaaatac cgtggtgtgg caaagcttga aggaaatact aaggcaaagg tactgcaagt   6720
gctcgcaaca ttcgcttatg cggattattg ccgtagtgcc gcgacgccgg gggcaagatg   6780
cagagattgc catggtacag gccgtgcggt tgatattgcc aaaacagagc tgtgggggag   6840
agttgtcgag aaagagtgcg gaagatgcaa aggcgtcggc tattcaagga tgccagcaag   6900
cgcagcatat cgcgctgtga cgatgctaat cccaaacctt acccaaccca cctggtcacg   6960
cactgttaag ccgctgtatg acgctctggt ggtgcaatgc cacaaagaag agtcaatcgc   7020
agacaacatt ttgaatgcgg tcacacgtta gcagcatgat tgccacggat ggcaacatat   7080
taacggcatg atattgactt attgaataaa attgggtaaa tttgactcaa cgatgggtta   7140
attcgctcgt tgtggtagtg agatgaaaag aggcggcgct tactaccgat tccgcctagt   7200
tggtcacttc gacgtatcgt ctggaactcc aaccatcgca ggcagagagg tctgcaaaat   7260
gcaatcccga aacagttcgc aggtaatagt tagagcctgc ataacggttt cgggattttt   7320
tatatctgca caacaggtaa gagcattgag tcgataatcg tgaagagtcg gcgagcctgg   7380
ttagccagtg ctctttccgt tgtgctgaat taagcgaata ccggaagcag aaccggatca   7440
ccaaatgcgt acaggcgtca tcgccgccca gcaacagcac aacccaaact gagccgtagc   7500
cactgtctgt cctgaattca ttagtaatag ttacgctgcg gccttttaca catgaccttc   7560
gtgaaagcgg gtggcaggag gtcgcgctaa caacctcctg ccgttttgcc cgtgcatatc   7620
ggtcacgaac aaatctgatt actaaacaca gtagcctgga tttgttctat cagtaatcga   7680
ccttattcct aattaaatag agcaaatccc cttattgggg gtaagacatg aagatgccag   7740
aaaaacatga cctgttggcc gccattctcg cggcaaagga acaaggcatc ggggcaatcc   7800
ttgcgtttgc aatggcgtac cttcgcggca gatataatgg cggtgcgttt acaaaaacag   7860
taatcgacgc aacgatgtgc gccattatcg cctggttcat tcgtgacctt ctcgacttcg   7920
```

ccggactaag tagcaatctc gcttatataa cgagcgtgtt tatcggctac atcggtactg 7980
actcgattgg ttcgcttatc aaacgcttcg ctgctaaaaa agccggagta gaagatggta 8040
gaaatcaata atcaacgtaa ggcgttcctc gatatgctgg cgtggtcgga gggaactgat 8100
aacggacgtc agaaaaccag aaatcatggt tatgacgtca ttgtaggcgg agagctattt 8160
actgattact ccgatcaccc tcgcaaactt gtcacgctaa acccaaaact caaatcaaca 8220
ggcgcttaag actggccgtc gttttacaac acagaaagag tttgtagaaa cgcaaaaagg 8280
ccatccgtca ggggccttct gcttagtttg atgcctggca gttccctact ctcgccttcc 8340
gcttcctcgc tcactgactc gctgcgctcg gtcgttcggc tgcggcgagc ggtatcagct 8400
cactcaaagg cggtaatacg gttatccaca gaatcagggg ataacgcagg aaagaacatg 8460
tgagcaaaag gccagcaaaa ggccaggaac cgtaaaaagg ccgcgttgct ggcgtttttc 8520
cataggctcc gcccccctga cgagcatcac aaaaatcgac gctcaagtca gaggtggcga 8580
aacccgacag gactataaag ataccaggcg tttccccctg gaagctccct cgtgcgctct 8640
cctgttccga ccctgccgct taccggatac ctgtccgcct ttctcccttc gggaagcgtg 8700
gcgctttctc atagctcacg ctgtaggtat ctcagttcgg tgtaggtcgt tcgctccaag 8760
ctgggctgtg tgcacgaacc ccccgttcag cccgaccgct gcgccttatc cggtaactat 8820
cgtcttgagt ccaacccggt aagacacgac ttatcgccac tggcagcagc cactggtaac 8880
aggattagca gagcgaggta tgtaggcggt gctacagagt tcttgaagtg gtggcctaac 8940
tacggctaca ctagaagaac agtatttggt atctgcgctc tgctgaagcc agttaccttc 9000
ggaaaaagag ttggtagctc ttgatccggc aaacaaacca ccgctggtag cggtggtttt 9060
tttgtttgca agcagcagat tacgcgcaga aaaaaaggat ctcaagaaga tcctttgatc 9120
ttttctacgg ggtctgacgc tcagtggaac gacgcgcgcg taactcacgt taagggattt 9180
tggtcatgag cttgcgccgt cccgtcaagt cagcgtaatg ctctgctttt agaaaaactc 9240
atcgagcatc aaatgaaact gcaatttatt catatcagga ttatcaatac catatttttg 9300
aaaaagccgt ttctgtaatg aaggagaaaa ctcaccgagg cagttccata ggatggcaag 9360
atcctggtat cggtctgcga ttccgactcg tccaacatca atacaaccta ttaatttccc 9420
ctcgtcaaaa ataaggttat caagtgagaa atcaccatga gtgacgactg aatccggtga 9480
gaatggcaaa agtttatgca tttctttcca gacttgttca acaggccagc cattacgctc 9540
gtcatcaaaa tcactcgcat caaccaaacc gttattcatt cgtgattgcg cctgagcgag 9600
gcgaaatacg cgatcgctgt taaaaggaca attacaaaca ggaatcgagt gcaaccggcg 9660
caggaacact gccagcgcat caacaatatt ttcacctgaa tcaggatatt cttctaatac 9720
ctggaacgct gtttttccgg ggatcgcagt ggtgagtaac catgcatcat caggagtacg 9780
gataaaatgc ttgatggtcg gaagtggcat aaattccgtc agccagttta gtctgaccat 9840
ctcatctgta acatcattgg caacgctacc tttgccatgt ttcagaaaca actctggcgc 9900
atcgggcttc ccatacaagc gatagattgt cgcacctgat tgcccgacat tatcgcgagc 9960
ccatttatac ccatataaat cagcatccat gttggaattt aatcgcggcc tcgacgtttc 10020
ccgttgaata tggctcatat tcttcctttt tcaatattat tgaagcattt atcagggtta 10080
ttgtctcatg agcggataca tatttgaatg tatttagaaa aataaacaaa taggggtcag 10140
tgttacaacc aattaaccaa ttctgaacat tatcgcgagc ccatttatac ctgaatatgg 10200
ctcataacac cccttgtttg cctggcggca gtagcgcggt ggtcccacct gaccccatgc 10260

```
cgaactcaga agtgaaacgc cgtagcgccg atggtagtgt ggggactccc catgcgagag  10320

tagggaactg ccaggcatca aataaaacga aaggctcagt cgaaagactg ggcctttcgc  10380

ccgggctaat tagggggtgt cgcccttatt cgactctata gtgaagttcc tattctctag  10440

aaagtatagg aacttctgaa gtggg                                        10465
```

<210> SEQ ID NO 35
<211> LENGTH: 10449
<212> TYPE: DNA
<213> ORGANISM: Artificial Sequence
<220> FEATURE:
<223> OTHER INFORMATION: Synthetic Construct

<400> SEQUENCE: 35

```
gtcgacttaa ttaaggctgc gcgctcgctc gctcactgag gccgcccggg caaagcccgg     60

gcgtcgggcg acctttggtc gcccggcctc agtgagcgag cgagcgcgca gagagggagt    120

ggccaactcc atcactaggg gttccttgta gttaatgatt aacccgccat gctacttatc    180

tacgtagcaa gctagcctag ttattaatag taatcaatta cggggtcatt agttcatagc    240

ccatatatgg agttccgcgt tacataactt acggtaaatg gcccgcctgg ctgaccgccc    300

aacgaccccc gcccattgac gtcaataatg acgtatgttc ccatagtaac gccaataggg    360

actttccatt gacgtcaatg ggtggagtat ttacggtaaa ctgcccactt ggcagtacat    420

caagtgtatc atatgccaag tacgccccct attgacgtca atgacggtaa atggcccgcc    480

tggcattatg cccagtacat gaccttatgg gactttccta cttggcagta catctacgta    540

ttagtcatcg ctattaccat ggtgatgcgg ttttggcagt acaccaatgg gcgtggatag    600

cggtttgact cacggggatt tccaagtctc caccccattg acgtcaatgg gagtttgttt    660

tggcaccaaa atcaacggga ctttccaaaa tgtcgtaaca actccgcccc gttgacgcaa    720

atgggcggta ggcgtgtacg gtgggaggtc tatataagca gagctcgttt agtgaaccgt    780

cagatcgccg ccaccatgga agatgccaaa aacattaaga agggcccagc gccattctac    840

ccactcgaag acgggaccgc cggcgagcag ctgcacaaag ccatgaagcg ctacgccctg    900

gtgcccggca ccatcgcctt taccgacgca catatcgagg tggacattac ctacgccgaa    960

tacttcgaga tgagcgttcg gctggcagaa gctatgaagc gctatgggct gaatacaaac   1020

catcggatcg tggtgtgcag cgagaatagc ttgcagttct tcatgcccgt gttgggtgcc   1080

ctgttcatcg gtgtggctgt ggccccagct aacgacatct acaacgagcg cgagctgctg   1140

aacagcatgg gcatcagcca gcccaccgtc gtattcgtga gcaagaaagg gctgcaaaag   1200

atcctcaacg tgcaaaagaa gctaccgatc atacaaaaga tcatcatcat ggatagcaag   1260

accgactacc agggcttcca aagcatgtac accttcgtga cttcccattt gccacccggc   1320

ttcaacgagt acgacttcgt gcccgagagc ttcgaccggg acaaaaccat cgccctgatc   1380

atgaacagta gtggcagtac cggattgccc aagggcgtag ccctaccgca ccgcaccgct   1440

tgtgtccgat tcagtcatgc ccgcgacccc atcttcggca accagatcat ccccgacacc   1500

gctatcctca gcgtggtgcc atttcaccac ggcttcggca tgttcaccac gctgggctac   1560

ttgatctgcg gctttcgggt cgtgctcatg taccgcttcg aggaggagct attcttgcgc   1620

agcttgcaag actataagat tcaatctgcc ctgctggtgc ccacactatt tagcttcttc   1680

gctaagagca ctctcatcga caagtacgac ctaagcaact tgcacgagat cgccagcggc   1740

ggagcgccgc tcagcaagga ggtaggtgag gccgtggcca aacgcttcca cctaccaggc   1800

atccgccagg gctacggcct gacagaaaca accagcgcca ttctgatcac ccccgaaggg   1860
```

```
gacgacaagc ctggcgcagt aggcaaggtg gtgcccttct tcgaggctaa ggtggtggac   1920
ttggacaccg gtaagacact gggtgtgaac cagcgcggcg agctgtgcgt ccgtggcccc   1980
atgatcatga gcggctacgt taacaacccc gaggctacaa acgctctcat cgacaaggac   2040
ggctggctgc acagcggcga catcgcctac tgggacgagg acgagcactt cttcatcgtg   2100
gaccggctga agagcctgat caaatacaag ggctaccagg taagtccgaa tacgatactc   2160
agcaggtggg aggtaattga atcgtggggg tggtttcccc cacgctattc tcataatagt   2220
aagttctcac gatgtctgat ggttttataa ggggctttcc cctttgctcg gctcacattc   2280
ttctaattcc ggccaccatg tgaagaaaaa tgtgaaaggt ttttcttttc ctgagaaatt   2340
tctcaggttt tgctttttaa aaaaaaagca aaaggcgcgt cctggattcc acggtacatc   2400
cagctgatga gtcccaaata ggacgaaacg cgctctcgag ttctacgtag ataagtagca   2460
tggcgggtta atcattaact acaaggaacc cctagtgatg gagttggcca ctccctctct   2520
gcgcgctcgc tcgctcactg aggccgggcg accaaaggtc gcccgacgcc cgggctttgc   2580
ccgggcggcc tcagtgagcg agcgagcgcg cagccttaat taacctaagg aaaatgaagt   2640
gaagttccta tactttctag agaataggaa cttctatagt gagtcgaata agggcgacac   2700
aaaatttatt ctaaatgcat aataaatact gataacatct tatagtttgt attatatttt   2760
gtattatcgt tgacatgtat aattttgata tcaaaaactg attttccctt tattattttc   2820
gagatttatt ttcttaattc tctttaacaa actagaaata ttgtatatac aaaaaatcat   2880
aaataataga tgaatagttt aattataggt gttcatcaat cgaaaaagca acgtatctta   2940
tttaaagtgc gttgcttttt tctcatttat aaggttaaat aattctcata tatcaagcaa   3000
agtgacaggc gcccttaaat attctgacaa atgctctttc cctaaactcc ccccataaaa   3060
aaacccgccg aagcgggttt ttacgttatt tgcggattaa cgattactcg ttatcagaac   3120
cgcccagggg gcccgagctt aacctttta tttgggggag agggaagtca tgaaaaaact   3180
aacctttgaa attcgatctc cagcacatca gcaaaacgct attcacgcag tacagcaaat   3240
ccttccagac ccaaccaaac caatcgtagt aaccattcag gaacgcaacc gcagcttaga   3300
ccaaaacagg aagctatggg cctgcttagg tgacgtctct cgtcaggttg aatggcatgg   3360
tcgctggctg gatgcagaaa gctggaagtg tgtgtttacc gcagcattaa agcagcagga   3420
tgttgttcct aaccttgccg ggaatggctt tgtggtaata ggccagtcaa ccagcaggat   3480
gcgtgtaggc gaatttgcgg agctattaga gcttatacag gcattcggta cagagcgtgg   3540
cgttaagtgg tcagacgaag cgagactggc tctggagtgg aaagcgagat ggggagacag   3600
ggctgcatga taaatgtcgt tagtttctcc ggtggcagga cgtcagcata tttgctctgg   3660
ctaatggagc aaaagcgacg ggcaggtaaa gacgtgcatt acgttttcat ggatacaggt   3720
tgtgaacatc caatgacata tcggtttgtc agggaagttg tgaagttctg ggatataccg   3780
ctcaccgtat tgcaggttga tatcaacccg gagcttggac agccaaatgg ttatacggta   3840
tgggaaccaa aggatattca gacgcgaatg cctgttctga agccatttat cgatatggta   3900
aagaaatatg gcactccata cgtcggcggc gcgttctgca ctgacagatt aaaactcgtt   3960
cccttcacca aatactgtga tgaccatttc gggcgaggga attacaccac gtggattggc   4020
atcagagctg atgaaccgaa gcggctaaag ccaaagcctg gaatcagata tcttgctgaa   4080
ctgtcagact ttgagaagga agatatcctc gcatggtgga agcaacaacc attcgatttg   4140
caaataccgg aacatctcgg taactgcata ttctgcatta aaaaatcaac gcaaaaaatc   4200
```

-continued

```
ggacttgcct gcaaagatga ggagggattg cagcgtgttt ttaatgaggt catcacggga   4260
tcccatgtgc gtgacggaca tcgggaaacg ccaaaggaga ttatgtaccg aggaagaatg   4320
tcgctggacg gtatcgcgaa aatgtattca gaaaatgatt atcaagccct gtatcaggac   4380
atggtacgag ctaaaagatt cgataccggc tcttgttctg agtcatgcga aatatttgga   4440
gggcagcttg atttcgactt cgggagggaa gctgcatgat gcgatgttat cggtgcggtg   4500
aatgcaaaga agataaccgc ttccgaccaa atcaacctta ctggaatcga tggtgtctcc   4560
ggtgtgaaag aacaccaaca ggggtgttac cactaccgca ggaaaaggag gacgtgtggc   4620
gagacagcga cgaagtatca ccgacataat ctgcgaaaac tgcaaatacc ttccaacgaa   4680
acgcaccaga aataaaccca agccaatccc aaaagaatct gacgtaaaaa ccttcaacta   4740
cacggctcac ctgtgggata tccggtggct aagacgtcgt gcgaggaaaa caaggtgatt   4800
gaccaaaatc gaagttacga acaagaaagc gtcgagcgag ctttaacgtg cgctaactgc   4860
ggtcagaagc tgcatgtgct ggaagttcac gtgtgtgagc actgctgcgc agaactgatg   4920
agcgatccga atagctcgat gcacgaggaa gaagatgatg gctaaaccag cgcgaagacg   4980
atgtaaaaac gatgaatgcc gggaatggtt tcaccctgca ttcgctaatc agtggtggtg   5040
ctctccagag tgtggaacca agatagcact cgaacgacga agtaaagaac gcgaaaaagc   5100
ggaaaaagca gcagagaaga aacgacgacg agaggagcag aaacagaaag ataaacttaa   5160
gattcgaaaa ctcgccttaa agccccgcag ttactggatt aaacaagccc aacaagccgt   5220
aaacgccttc atcagagaaa gagaccgcga cttaccatgt atctcgtgcg gaacgctcac   5280
gtctgctcag tgggatgccg gacattaccg gacaactgct gcggcacctc aactccgatt   5340
taatgaacgc aatattcaca agcaatgcgt ggtgtgcaac cagcacaaaa gcggaaatct   5400
cgttccgtat cgcgtcgaac tgattagccg catcgggcag gaagcagtag acgaaatcga   5460
atcaaaccat aaccgccatc gctggactat cgaagagtgc aaggcgatca aggcagagta   5520
ccaacagaaa ctcaaagacc tgcgaaatag cagaagtgag gccgcatgac gttctcagta   5580
aaaaccattc cagacatgct cgttgaagca tacggaaatc agacagaagt agcacgcaga   5640
ctgaaatgta gtcgcggtac ggtcagaaaa tacgttgatg ataaagacgg gaaaatgcac   5700
gccatcgtca acgacgttct catggttcat cgcggatgga gtgaaagaga tgcgctatta   5760
cgaaaaaatt gatggcagca aataccgaaa tatttgggta gttggcgatc tgcacggatg   5820
ctacacgaac ctgatgaaca aactggatac gattggattc gacaacaaaa aagacctgct   5880
tatctcggtg ggcgatttgg ttgatcgtgg tgcagagaac gttgaatgcc tggaattaat   5940
cacattcccc tggttcagag ctgtacgtgg aaaccatgag caaatgatga ttgatggctt   6000
atcagagcgt ggaaacgtta atcactggct gcttaatggc ggtggctggt tctttaatct   6060
cgattacgac aaagaaattc tggctaaagc tcttgcccat aaagcagatg aacttccgtt   6120
aatcatcgaa ctggtgagca aagataaaaa atatgttatc tgccacgccg attatccctt   6180
tgacgaatac gagtttggaa agccagttga tcatcagcag gtaatctgga accgcgaacg   6240
aatcagcaac tcacaaaacg ggatcgtgaa agaaatcaaa ggcgcggaca cgttcatctt   6300
tggtcatacg ccagcagtga aaccactcaa gtttgccaac caaatgtata tcgataccgg   6360
cgcagtgttc tgcggaaacc taacattgat tcaggtacag ggagaaggcg catgagactc   6420
gaaagcgtag ctaaatttca ttcgccaaaa agcccgatga tgagcgactc accacgggcc   6480
acggcttctg actctctttc cggtactgat gtgatggctg ctatggggat ggcgcaatca   6540
caagccggat tcggtatggc tgcattctgc ggtaagcacg aactcagcca gaacgacaaa   6600
```

caaaaggcta tcaactatct gatgcaattt gcacacaagg tatcggggaa ataccgtggt 6660
gtggcaaagc ttgaaggaaa tactaaggca aaggtactgc aagtgctcgc aacattcgct 6720
tatgcggatt attgccgtag tgccgcgacg ccgggggcaa gatgcagaga ttgccatggt 6780
acaggccgtg cggttgatat tgccaaaaca gagctgtggg ggagagttgt cgagaaagag 6840
tgcggaagat gcaaaggcgt cggctattca aggatgccag caagcgcagc atatcgcgct 6900
gtgacgatgc taatcccaaa ccttacccaa cccacctggt cacgcactgt taagccgctg 6960
tatgacgctc tggtggtgca atgccacaaa gaagagtcaa tcgcagacaa cattttgaat 7020
gcggtcacac gttagcagca tgattgccac ggatggcaac atattaacgg catgatattg 7080
acttattgaa taaaattggg taaatttgac tcaacgatgg gttaattcgc tcgttgtggt 7140
agtgagatga aaagaggcgg cgcttactac cgattccgcc tagttggtca cttcgacgta 7200
tcgtctggaa ctccaaccat cgcaggcaga gaggtctgca aaatgcaatc ccgaaacagt 7260
tcgcaggtaa tagttagagc ctgcataacg gtttcgggat tttttatatc tgcacaacag 7320
gtaagagcat tgagtcgata atcgtgaaga gtcggcgagc ctggttagcc agtgctcttt 7380
ccgttgtgct gaattaagcg aataccggaa gcagaaccgg atcaccaaat gcgtacaggc 7440
gtcatcgccg cccagcaaca gcacaaccca aactgagccg tagccactgt ctgtcctgaa 7500
ttcattagta atagttacgc tgcggccttt tacacatgac cttcgtgaaa gcgggtggca 7560
ggaggtcgcg ctaacaacct cctgccgttt tgcccgtgca tatcggtcac gaacaaatct 7620
gattactaaa cacagtagcc tggatttgtt ctatcagtaa tcgaccttat tcctaattaa 7680
atagagcaaa tccccttatt gggggtaaga catgaagatg ccagaaaaac atgacctgtt 7740
ggccgccatt ctcgcggcaa aggaacaagg catcggggca atccttgcgt ttgcaatggc 7800
gtaccttcgc ggcagatata atggcggtgc gtttacaaaa acagtaatcg acgcaacgat 7860
gtgcgccatt atcgcctggt tcattcgtga ccttctcgac ttcgccggac taagtagcaa 7920
tctcgcttat ataacgagcg tgtttatcgg ctacatcggt actgactcga ttggttcgct 7980
tatcaaacgc ttcgctgcta aaaaagccgg agtagaagat ggtagaaatc aataatcaac 8040
gtaaggcgtt cctcgatatg ctggcgtggt cggagggaac tgataacgga cgtcagaaaa 8100
ccagaaatca tggttatgac gtcattgtag gcggagagct atttactgat tactccgatc 8160
accctcgcaa acttgtcacg ctaaacccaa aactcaaatc aacaggcgct taagactggc 8220
cgtcgtttta caacacagaa agagtttgta gaaacgcaaa aaggccatcc gtcaggggcc 8280
ttctgcttag tttgatgcct ggcagttccc tactctcgcc ttccgcttcc tcgctcactg 8340
actcgctgcg ctcggtcgtt cggctgcggc gagcggtatc agctcactca aaggcggtaa 8400
tacggttatc cacagaatca ggggataacg caggaaagaa catgtgagca aaaggccagc 8460
aaaaggccag gaaccgtaaa aaggccgcgt tgctggcgtt tttccatagg ctccgccccc 8520
ctgacgagca tcacaaaaat cgacgctcaa gtcagaggtg gcgaaacccg acaggactat 8580
aaagatacca ggcgtttccc cctggaagct ccctcgtgcg ctctcctgtt ccgaccctgc 8640
cgcttaccgg atacctgtcc gcctttctcc cttcgggaag cgtggcgctt tctcatagct 8700
cacgctgtag gtatctcagt tcggtgtagg tcgttcgctc caagctgggc tgtgtgcacg 8760
aaccccccgt tcagcccgac cgctgcgcct tatccggtaa ctatcgtctt gagtccaacc 8820
cggtaagaca cgacttatcg ccactggcag cagccactgg taacaggatt agcagagcga 8880
ggtatgtagg cggtgctaca gagttcttga agtggtgggc taactacggc tacactagaa 8940

```
gaacagtatt tggtatctgc gctctgctga agccagttac cttcggaaaa agagttggta   9000
gctcttgatc cggcaaacaa accaccgctg gtagcggtgg tttttttgtt tgcaagcagc   9060
agattacgcg cagaaaaaaa ggatctcaag aagatccttt gatcttttct acggggtctg   9120
acgctcagtg gaacgacgcg cgcgtaactc acgttaaggg attttggtca tgagcttgcg   9180
ccgtcccgtc aagtcagcgt aatgctctgc ttttagaaaa actcatcgag catcaaatga   9240
aactgcaatt tattcatatc aggattatca ataccatatt tttgaaaaag ccgtttctgt   9300
aatgaaggag aaaactcacc gaggcagttc cataggatgg caagatcctg gtatcggtct   9360
gcgattccga ctcgtccaac atcaatacaa cctattaatt tcccctcgtc aaaaataagg   9420
ttatcaagtg agaaatcacc atgagtgacg actgaatccg gtgagaatgg caaaagttta   9480
tgcatttctt tccagacttg ttcaacaggc cagccattac gctcgtcatc aaaatcactc   9540
gcatcaacca aaccgttatt cattcgtgat tgcgcctgag cgaggcgaaa tacgcgatcg   9600
ctgttaaaag gacaattaca aacaggaatc gagtgcaacc ggcgcaggaa cactgccagc   9660
gcatcaacaa tattttcacc tgaatcagga tattcttcta atacctggaa cgctgttttt   9720
ccggggatcg cagtggtgag taaccatgca tcatcaggag tacggataaa atgcttgatg   9780
gtcggaagtg gcataaattc cgtcagccag tttagtctga ccatctcatc tgtaacatca   9840
ttggcaacgc tacctttgcc atgtttcaga aacaactctg gcgcatcggg cttcccatac   9900
aagcgataga ttgtcgcacc tgattgcccg acattatcgc gagcccattt atacccatat   9960
aaatcagcat ccatgttgga atttaatcgc ggcctcgacg tttcccgttg aatatggctc  10020
atattcttcc tttttcaata ttattgaagc atttatcagg gttattgtct catgagcgga  10080
tacatatttg aatgtattta gaaaaataaa caaatagggg tcagtgttac aaccaattaa  10140
ccaattctga acattatcgc gagcccattt atacctgaat atggctcata acaccccttg  10200
tttgcctggc ggcagtagcg cggtggtccc acctgacccc atgccgaact cagaagtgaa  10260
acgccgtagc gccgatggta gtgtggggac tccccatgcg agagtaggga actgccaggc  10320
atcaaataaa acgaaaggct cagtcgaaag actgggcctt tcgcccgggc taattagggg  10380
gtgtcgccct tattcgactc tatagtgaag ttcctattct ctagaaagta taggaacttc  10440
tgaagtggg                                                          10449
```

<210> SEQ ID NO 36
<211> LENGTH: 11651
<212> TYPE: DNA
<213> ORGANISM: Artificial Sequence
<220> FEATURE:
<223> OTHER INFORMATION: Synthetic Construct

<400> SEQUENCE: 36

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
```

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgccacca tggaacaaaa actcatctca gaagaggatc   1020
tgaatttgct caatgctctt cagatggatt cggatgaaat gaaaaaaata cttgcagaaa   1080
atagtaggaa aattactgtt ttgcaagtga atgaaaaatc acttataagg caatatacaa   1140
ccttagtaga attggagcga caacttagaa aagaaaatga gaagcaaaag aatgaattgt   1200
tgtcaatgga ggctgaagtt tgtgaaaaaa ttgggtgttt gcaaagattt aaggaaatgg   1260
ccattttcaa gattgcagct ctccaaaaag ttgtagataa tagtgtttct ttgtctgaac   1320
tagaactggc taataaacag tacaatgaac tgactgctaa gtacagggac atcttgcaaa   1380
aagataatat gcttgttcaa agaacaagta acctcgagca tctggaggta agtttgtgtg   1440
attcttgaac cttgtgaaat tagccatttt tcttcaatat ttttgtgttt ggggggattt   1500
ggcagatttt aattaaagtt tgcctgcatt tatataaatt taacagagat ataattatcc   1560
atattattca ttcagtttag ttataaatat tttgttccca cataacacac acacacacac   1620
acaatatatt atctatttat agtggctgaa tgacttctga atgattatct agatcattct   1680
ccttaggtca cttgcatgat ttagctgaat caaacctctt ttaaccagac atctaagaga   1740
aaaaggagca tgaaacaggt agaatattgt aatcaaagga gggaagcact cattaagtgc   1800
ccatcccttt ctcttacccc tgtacccaga acaaactatt ctcccatggt ccctggcttt   1860
tgttccttgg aatggatgta gccaacagta gctgaaatat taagggctct tcctggacca   1920
tggatgcact ctgtaaattc tcatcatttt ttattgtaga ataaatgtag aattttaatg   1980
tagaataaat ttatttaatg tagaataaaa aataaaaaaa ctagagtaga atatcataag   2040
ttacaatctg tgaatatgga ccagaccctt tgtagttatc ttacagccac ttgaactcta   2100
taccttttac tgaggacaga acaagctcct gatttgttca tcttcctcat cagaaataga   2160
ggcttatgga ttttggatta ttcttatcta agatcctttc acaggagtag aataagatct   2220
aattctatta gctcaaaagc ttttgctggc tcatagagac acattcagta aatgaaaacg   2280
ttgttctgag tagctttcag gattcctact aaattatgag tcatgtttat caatattatt   2340
tagaagtaat cataatcagt ttgctttctg ctgcttttgc caaagagagg tgattatgtt   2400
actttttata gaaaattatg cctatttagt gtggtgataa tttatttttt tccattctcc   2460
atgtcctctg tcctatcctc tccagcatta gaaagtccta ggcaagagac atcttgtgga   2520
taatgtatca atgagtgatg tttaacgtta tcattttccc aaagagtatt tttcatcttt   2580
cctaaagatt tttttttttt ttttttgaga tggagtttca ttctgtcacc caggctgagt   2640
gcagtggcac gatctcggct taacgcttac tgcatcctct gcctcccaga ttcaagcagt   2700
tctcctgcct cagcctctga gtagctggga ttacaggtgt gcaccaccac accagctaat   2760
tttttttttt tttttttttt ttttgaggca gagtctcgct ctgtcaccca ggctggagtg   2820
cagtggcgcc atcttggctc actgcaagct ccacctcccg ggttcaggcc gttctcctgc   2880
```

```
ctcagcctcc tgagtagctg gtaccacagg cacccaccat catgcccggc taatttttg   2940
tatttttagt agagatgggg tttcaccttg ttagccagga tggtgtcgat ctcctgaact   3000
cgtgatccac ccgcctcggc ctcctaaagt gctgggatta cagatgtgag ccaccgcacc   3060
tggccccagt tgtaattgtg agtatctcat acctatccct attggcagtg tcttagtttt   3120
atttttatt atctttattg tggcagccat tattcctgtc tctatctcca gtcttacatc   3180
ctccttactg ccacaagaat gatcattcta aacatgaatc ctaccctgtg actcccatgt   3240
gactccccgc cttaaaaact gtcaaaagct accggttacc tgaagggtaa aagtcaagtc   3300
ccctacttac ctcatgtcat ctagagcaag agatgaacta gctgagtttt ctgaccacag   3360
tgttctttct tatgtatgtt cttttgtacg tgctcttttc tatatatagg gaaccatttc   3420
tctcttccag ttgttttgct cagtgaattt ctattcctgt ttcaaaactt gttcaggcat   3480
taccttttt ttcttaagca tacttttttt aatggaacaa agtcactcct gtctacacta   3540
gttctgcatc ttatacatag gttttgtaca tagtacatat ttatatcaca tcaaattata   3600
tgtgtttaca tatctgtctt ccttaatgga atataagtct tttgatataa ggaactattt   3660
aatttgtttc tgtgtgttga gtatctcctg tttggcacag agttcaagct aatacatgag   3720
agtgattagt ggtggagagc cacagtgcat gtggtgtcaa atatggtgct taggaaatta   3780
ttgttgcttt ttgagaggta aaggttcatg agactagagg tcacgaaaat cagatttcat   3840
gtgtgaagaa tggaatagat aataaggaaa tacaaaaact ggatgggtaa taaagcaaaa   3900
gaaaaacttg aaatttgata gtagaagaaa aaagaaatag atgtagattg aggtagaatc   3960
aagaagagga ttctttttt gttgtttttt tttttgaaac agagtctcac tgtgttgccc   4020
aggctggagt gcagtggagt gatcttggct tactgcaacc tctgcctccc aggttcaagc   4080
gattcttctg cttcagtctc ccgagtagct ggaattacag gtgcccacca gcacggccgg   4140
ctaatttagt agagacaggg ttttgccatg ttggccgggc tggtctcaaa ctttggatct   4200
caggtaatcc gccagcctca acttcccaaa gtgctgggat tacaggcatg agccactgtg   4260
cccagcctgt tttttttttt ttaaaggaga ccagtgaagt ttcaggagga gggaaagaaa   4320
atttagagtt actagggaga gagtgatgaa gataagagat gaaagtggta ataagggaaa   4380
tagcaaaata tcagggtagg tgggagaaaa agagatttgt aacaaacaat aggattatcc   4440
tgtgaaaaag gatgaaagga agaaaaaaat ggatagaaag atatttaaaa caccctcagc   4500
ctcctgtttt ccctcctgtg tattcatagt atataaaact ataattatgt actttactta   4560
aaaaatatat tattattacc ttatcgtgct tatttaatca tagcatgtcc tctttttagt   4620
ctcattaccc tgtttgtatt attcttcata acacttaata cctgacattg tattatatat   4680
tggcttattt tccaggtact ccactcaaat ataagttcta ggatataatt tatttatcac   4740
tgaaatccat tgcttagagt acctggcatg tagtaaatag gcattctgtt ttttcaaata   4800
aaaaataaag gaacttaaga tatatattta tgttatatcg ccagcctttt tcctcacagc   4860
tctattctgt tgtacagaat tacctacttt acaattcctg tgtttcaagg ggatctcaaa   4920
tttaacgtgt ccacaatgaa ctcctgattt ctgtttctct cctagtcatt cttatttcaa   4980
tatatgttca gttacctaac cagctagtca aggcagatac tttagagtta ttctgtagtc   5040
attctttttc cctaccattt ttgttttcca aatgtaattt atgtgtgtct tcttcatcct   5100
cgcagctcta acccttgtcc aaaccagcat catcactcat ctggagttcc acaatgtctt   5160
tctggctagt ttccctgatt tctctattga cccctttatt ctccacagtg cagccagaat   5220
gattgtttaa aacttcctcc ttaaaatctt taaattgttt tcttttatac gttaagttaa   5280
```

```
attccagttc cttgtcttgg catgccatgc cctgcctggt gtggcccctg atggtctctc   5340
caacttcatg ttttactact attgactctt atttttgctt actctgcttg ggtgctccag   5400
tcctccaaat catttcctgc tccaatcatt tcaatcattt tttcctctca gatcttatag   5460
tattccaaat gctttcttcc tttggagcat ctgggtttac taataaatac ttcgtacctc   5520
acagttcagc ttaaatatca attatttggt ggttaagaca tccttcaacc gctctatcta   5580
aatgttcctt tctattattc actggctcag tactctgttt ttattttctt tctaaatgtc   5640
aacttttttt tttttgagtc agggtctcac tgttgcccag gctcgagtgc agttgcacaa   5700
tcatagctca ttgcagcctt gccctcctgg gatcaagtaa ttctcccacc tcagcctcca   5760
aaatagctgg gattacaggt atgcatcacc atgctcagct aattttttgt gttttttttgt   5820
agagatgagg tctcactttg ttgcccaggc tggtctcaaa ctcctggact caagtgattc   5880
tcccacctca gcctcccaaa gtgctggggt tacaggtgtg agccactgca cctggtcgat   5940
actgactttt tttttttttt gagatggagt tttgctctgt tgcccaggct agagcgcagt   6000
ggtgtgatct cagctcactg caacctccac ctcccaggtt aaagggattc ttctgcctca   6060
gtctcctgag tagctgggat tacaggcaag tgccatcatg actggctaat ttttgtattt   6120
ttagcactat gtttagtact gtgttggcca ggcttgtctc gaactcctga cctcaagtga   6180
tccacccacc tcagcctccc aaagtgctgg gattacaggt gtgagccacc gtaatcggcc   6240
aacattgaca tttttagtag actttttgtt tgtttacttg cttattatct gctgccttcc   6300
acactctggc gaaatcctgc cacccaccca cacacacata ggcactgaat gggcagaact   6360
ctgaaggcca gaattttata tttcttttca ctgtaaacat catcatctgt cactgatggc   6420
acactaggat gctcagcaac tgtgtgcatg aaggaagtaa gcactagttt gtgaaggctg   6480
caaaactctt gagtattcta agagttttgg ccaaaatgaa tgtacagctt tagtggcaga   6540
agctaatact cagaaattga ggccgtatat tggataacac aggatttgga tgattatttt   6600
aaaataatat tttacattgt atatatgtgt gtgtgtgtgt gtgtgtgtgt gtgtatgtgt   6660
gtgtgtgtgt atatatatat gtatgtatgt gtattagtcc gttctcatgc tgctatgaag   6720
aaatacctga gactgggtaa tttataaagg aaagaggttt aattgactca cagttccaca   6780
gagctgggga ggcctcagaa aacttaacag ttatggcaga aggggaagca aacacatttt   6840
tcttcacatg gtggccggaa ttagaagaat gtgagccgag caaaggggaa agccccttat   6900
aaaaccatca gacatcgtga gaacttacta ttatgagaat agcgtggggg aaaccacccc   6960
cacgattcaa ttacctccca ccaaatccct cccatgacat atgaggatta tgggaactat   7020
gattcaagat gagatttggg tagggacaca gccaaaccat atcagtatgt atatgtatac   7080
aagtattata tatatatgta tgtgtttgta tgcatacatg tattatatat ggaggaaatt   7140
ctaattttgt aaaaaactgg attgtgagtt ttaaggagat gttatataaa gttaagacaa   7200
tgtcattttg tggtattggt ctgaattaca atgtagtttc ttagtgatat ttttccttta   7260
ttcaggtagc cccagccgaa ctggagagca tcctgctgca acaccccaac atcttcgacg   7320
ccggggtcgc cggcctgccc gacgacgatg ccggcgagct gcccgccgca gtcgtcgtgc   7380
tggaacacgg taaaaccatg accgagaagg agatcgtgga ctatgtggcc agccaggtta   7440
caaccgccaa gaagctgcgc ggtggtgttg tgttcgtgga cgaggtgcct aaaggactga   7500
ccggcaagtt ggacgcccgc aagatccgcg agattctcat taaggccaag aagggcggca   7560
agatcgccgt gtaataaggg cccgtttaaa cccgctgatc agcctcgact gtgccttcta   7620
```

-continued

```
gttgccagcc atctgttgtt tgcccctccc ccgtgccttc cttgaccctg gaaggtgcca   7680
ctcccactgt cctttcctaa taaaatgagg aaattgcatc gcattgtctg agtaggtgtc   7740
attctattct ggggggtggg gtggggcagg acagcaaggg ggaggattgg gaagacaata   7800
gcaggcatgc tggggatgcg gtgggctcta tggcttctga ggcggaaaga accagctggg   7860
gctctagggg gtatccccac gcgccctgta gcggcgcatt aagcgcggcg ggtgtggtgg   7920
ttacgcgcag cgtgaccgct acacttgcca gcgccctagc gcccgctcct ttcgctttct   7980
tcccttcctt tctcgccacg ttcgccggct ttccccgtca agctctaaat cgggggctcc   8040
ctttagggtt ccgatttagt gctttacggc acctcgaccc caaaaaactt gattagggtg   8100
atggttcacg tacctagaag ttcctattcc gaagttccta ttctctagaa agtataggaa   8160
cttccttggc caaaaagcct gaactcaccg cgacgtctgt cgagaagttt ctgatcgaaa   8220
agttcgacag cgtctccgac ctgatgcagc tctcggaggg cgaagaatct cgtgctttca   8280
gcttcgatgt aggagggcgt ggatatgtcc tgcgggtaaa tagctgcgcc gatggtttct   8340
acaaagatcg ttatgtttat cggcactttg catcggccgc gctcccgatt ccggaagtgc   8400
ttgacattgg ggaattcagc gagagcctga cctattgcat ctcccgccgt gcacagggtg   8460
tcacgttgca agacctgcct gaaaccgaac tgcccgctgt tctgcagccg gtcgcggagg   8520
ccatggatgc gatcgctgcg gccgatctta gccagacgag cgggttcggc ccattcggac   8580
cgcaaggaat cggtcaatac actacatggc gtgatttcat atgcgcgatt gctgatcccc   8640
atgtgtatca ctggcaaact gtgatggacg acaccgtcag tgcgtccgtc gcgcaggctc   8700
tcgatgagct gatgctttgg gccgaggact gccccgaagt ccggcacctc gtgcacgcgg   8760
atttcggctc caacaatgtc ctgacggaca atggccgcat aacagcggtc attgactgga   8820
gcgaggcgat gttcggggat tcccaatacg aggtcgccaa catcttcttc tggaggccgt   8880
ggttggcttg tatggagcag cagacgcgct acttcgagcg gaggcatccg gagcttgcag   8940
gatcgccgcg gctccgggcg tatatgctcc gcattggtct tgaccaactc tatcagagct   9000
tggttgacgg caatttcgat gatgcagctt gggcgcaggg tcgatgcgac gcaatcgtcc   9060
gatccggagc cgggactgtc gggcgtacac aaatcgcccg cagaagcgcg gccgtctgga   9120
ccgatggctg tgtagaagta ctcgccgata gtggaaaccg acgccccagc actcgtccga   9180
gggcaaagga atagcacgta ctacgagatt tcgattccac cgccgccttc tatgaaaggt   9240
tgggcttcgg aatcgttttc cgggacgccg gctggatgat cctccagcgc ggggatctca   9300
tgctggagtt cttcgcccac cccaacttgt ttattgcagc ttataatggt tacaaataaa   9360
gcaatagcat cacaaatttc acaaataaag catttttttc actgcattct agttgtggtt   9420
tgtccaaact catcaatgta tcttatcatg tctgtatacc gtcgacctct agctagagct   9480
tggcgtaatc atggtcatag ctgtttcctg tgtgaaattg ttatccgctc acaattccac   9540
acaacatacg agccggaagc ataaagtgta aagcctgggg tgcctaatga gtgagctaac   9600
tcacattaat tgcgttgcgc tcactgcccg ctttccagtc gggaaacctg tcgtgccagc   9660
tgcattaatg aatcggccaa cgcgcgggga gaggcggttt gcgtattggg cgctcttccg   9720
cttcctcgct cactgactcg ctgcgctcgg tcgttcggct gcggcgagcg gtatcagctc   9780
actcaaaggc ggtaatacgg ttatccacag aatcagggga taacgcagga aagaacatgt   9840
gagcaaaagg ccagcaaaag gccaggaacc gtaaaaaggc cgcgttgctg gcgtttttcc   9900
ataggctccg cccccctgac gagcatcaca aaaatcgacg ctcaagtcag aggtggcgaa   9960
acccgacagg actataaaga taccaggcgt ttccccctgg aagctccctc gtgcgctctc  10020
```

```
ctgttccgac cctgccgctt accggatacc tgtccgcctt tctcccttcg ggaagcgtgg  10080
cgctttctca tagctcacgc tgtaggtatc tcagttcggt gtaggtcgtt cgctccaagc  10140
tgggctgtgt gcacgaaccc cccgttcagc ccgaccgctg cgccttatcc ggtaactatc  10200
gtcttgagtc caacccggta agacacgact tatcgccact ggcagcagcc actggtaaca  10260
ggattagcag agcgaggtat gtaggcggtg ctacagagtt cttgaagtgg tggcctaact  10320
acggctacac tagaaggaca gtatttggta tctgcgctct gctgaagcca gttaccttcg  10380
gaaaaagagt tggtagctct tgatccggca aacaaaccac cgctggtagc ggtggttttt  10440
ttgtttgcaa gcagcagatt acgcgcagaa aaaaaggatc tcaagaagat cctttgatct  10500
tttctacggg gtctgacgct cagtggaacg aaaactcacg ttaagggatt ttggtcatga  10560
gattatcaaa aaggatcttc acctagatcc ttttaaatta aaaatgaagt tttaaatcaa  10620
tctaaagtat atatgagtaa acttggtctg acagttacca atgcttaatc agtgaggcac  10680
ctatctcagc gatctgtcta tttcgttcat ccatagttgc ctgactcccc gtcgtgtaga  10740
taactacgat acgggagggc ttaccatctg gccccagtgc tgcaatgata ccgcgagacc  10800
cacgctcacc ggctccagat ttatcagcaa taaaccagcc agccggaagg gccgagcgca  10860
gaagtggtcc tgcaacttta tccgcctcca tccagtctat taattgttgc cgggaagcta  10920
gagtaagtag ttcgccagtt aatagtttgc gcaacgttgt tgccattgct acaggcatcg  10980
tggtgtcacg ctcgtcgttt ggtatggctt cattcagctc cggttcccaa cgatcaaggc  11040
gagttacatg atcccccatg ttgtgcaaaa aagcggttag ctccttcggt cctccgatcg  11100
ttgtcagaag taagttggcc gcagtgttat cactcatggt tatggcagca ctgcataatt  11160
ctcttactgt catgccatcc gtaagatgct tttctgtgac tggtgagtac tcaaccaagt  11220
cattctgaga atagtgtatg cggcgaccga gttgctcttg cccggcgtca atacgggata  11280
ataccgcgcc acatagcaga actttaaaag tgctcatcat tggaaaacgt tcttcggggc  11340
gaaaactctc aaggatctta ccgctgttga gatccagttc gatgtaaccc actcgtgcac  11400
ccaactgatc ttcagcatct tttactttca ccagcgtttc tgggtgagca aaaacaggaa  11460
ggcaaaatgc cgcaaaaaag ggaataaggg cgacacggaa atgttgaata ctcatactct  11520
tcctttttca atattattga agcatttatc agggttattg tctcatgagc ggatacatat  11580
ttgaatgtat ttagaaaaat aaacaaatag gggttccgcg cacatttccc cgaaaagtgc  11640
cacctgacgt c                                                       11651

<210> SEQ ID NO 37
<211> LENGTH: 25
<212> TYPE: DNA
<213> ORGANISM: Artificial Sequence
<220> FEATURE:
<223> OTHER INFORMATION: Synthetic Construct

<400> SEQUENCE: 37

ccgaatacga cacgtagcaa gatct                                           25
```

TRIPLE HELIX TERMINATOR FOR EFFICIENT RNA TRANS-SPLICING

CROSS-REFERENCE TO RELATED APPLICATIONS

This is a National Stage Entry under 35 U.S.C. 371 of International Patent Application No. PCT/US2020/028797, filed Apr. 17, 2020, which claims priority under 35 USC § 119 to U.S. Provisional Patent Application No. 62/835,164, filed Apr. 17, 2019. These applications are incorporated by reference herein.

REFERENCE TO AN ELECTRONIC SEQUENCE LISTING

The electronic sequence listing filed herewith named "19-8992PCT_20200417_Sequence-Listing_ST25.txt" with size of 158,328 bytes, created on date of Apr. 17, 2020, and the contents of the electronic sequence listing (e.g., the sequences and text therein) are incorporated herein by reference in entirety.

BACKGROUND

A number of inherited retinal diseases are caused by mutations, generally multiple-mutations, located throughout portions of large ocular genes. As one example, Stargardt disease, also known as Stargardt 1 (STGD1), is an autosomal recessive form of retinal dystrophy that is usually characterized by a progressive loss of central vision. Similar retinal diseases are caused by defects in other large ocular genes, including CEP290 (7440 nucleotides) which defects or mutations cause Leber's congenital amaurosis, among other ocular disorders, and MYO7A (7465 nucleotides), which defects or mutations cause Usher's disease.

The occurrences and locations of multiple mutations in such large ocular, and other, genes have made strategies for repairing the mutations very challenging. Despite the great promise of trans-splicing technology spanning over two decades to meet this challenge, it has yet to emerge a meaningful approach for gene therapy. This is due primarily, if not exclusively, to the poor efficiency of the trans-splicing reaction. It is important to recognize that trans-splicing is unusual in higher eukaryotes, including humans. And while there are a handful of rare examples of endogenous trans-splicing, cis-splicing clearly dominates by a large margin. Simply stated, trans-splicing in humans appears to be a novel class of alternative splicing that utilizes the same cellular factors and mechanisms that mediate the traditional cis-splicing pathway.

There remains a need for effective compositions and therapeutic methods for treating such disorders.

SUMMARY

Provided herein are RNA trans-splicing molecules (RTM) useful in treatment of diseases caused by defects in one or more exons of the coding sequence. Also provided are methods and compositions utilizing these RTM.

In one aspect, the invention includes a nucleic acid trans-splicing molecule (e.g., RTM) comprising a 3' transcription terminator domain (TTD), which comprises a triple helix. In some embodiments, the triple helix comprises at least five consecutive A-U Hoogsteen base pairs (e.g., four to 20 consecutive A-U Hoogsteen base pairs, four to 18 consecutive A-U Hoogsteen base pairs, four to 15 consecutive A-U Hoogsteen base pairs, four to 12 consecutive A-U Hoogsteen base pairs, four to 11 consecutive A-U Hoogsteen base pairs, or four to 10 consecutive A-U Hoogsteen base pairs, e.g., six to eight consecutive A-U Hoogsteen base pairs, eight to 10 consecutive A-U Hoogsteen base pairs, 10 to 12 consecutive A-U Hoogsteen base pairs, 12 to 14 consecutive A-U Hoogsteen base pairs, 14 to 16 consecutive A-U Hoogsteen base pairs, 16 to 18 consecutive A-U Hoogsteen base pairs, or 18 to 20 consecutive A-U Hoogsteen base pairs).

In some embodiments, the triple helix comprises an A-rich tract of 5-30 nucleic acids (e.g., 5-10 nucleic acids, 10-20 nucleic acids, or 20-30 nucleic acids). In some embodiments, the A-rich tract is at the 3' end of the TTD (e.g., at or within a poly-A tail).

In some embodiments, the triple helix comprises a strand of 10 consecutive nucleotides, wherein 9 of the 10 consecutive nucleotides are paired via Hoogsteen base pairing. In some embodiments, the TTD comprises a stem-loop motif.

In some embodiments, the 3' TTD comprises, operatively linked in a 5'-to-3' direction, a 5' U-rich motif, a stem-loop motif, a t' U-rich motif, and an A-rich tract.

In some embodiments, 3' TTD is at least 95% homologous with SEQ ID NO: 13, SEQ ID NO: 15, SEQ ID NO: 17, or SEQ ID NO: 23 (e.g., at least 96% homologous with SEQ ID NO: 13, SEQ ID NO: 15, SEQ ID NO: 17, or SEQ ID NO: 23; at least 97% homologous with SEQ ID NO: 13, SEQ ID NO: 15, SEQ ID NO: 17, or SEQ ID NO: 23; at least 98% homologous with SEQ ID NO: 13, SEQ ID NO: 15, SEQ ID NO: 17, or SEQ ID NO: 23; at least 99% homologous with SEQ ID NO: 13, SEQ ID NO: 15, SEQ ID NO: 17, or SEQ ID NO: 23; or 100% homologous with SEQ ID NO: 13, SEQ ID NO: 15, SEQ ID NO: 17, or SEQ ID NO: 23).

In some embodiments, the 3' TTD is at least 95% homologous (e.g., at least 96%, at least 97%, at least 98%, or at least 99% homologous) with SEQ ID NO: 13, and wherein the triple helix comprises Hoogsteen base pairing of U7-U11 of SEQ ID NO: 13 with an A-rich tract. In some embodiments, the 3' TTD is the PAN ENE+A.

In some embodiments, the 3' TTD is at least 95% homologous (e.g., at least 96%, at least 97%, at least 98%, or at least 99% homologous) with SEQ ID NO: 15, and wherein the triple helix comprises Hoogsteen base pairing of U6-10, C11, and U12-15 of SEQ ID NO: 15 with an A-rich tract. In some embodiments, the 3' TTD is the MALAT1 ENE+A.

In some embodiments, the 3' TTD is at least 95% homologous (e.g., at least 96%, at least 97%, at least 98%, or at least 99% homologous) with SEQ ID NO: 17, and wherein the triple helix comprises Hoogsteen base pairing of U6-10, C11, and U12-15 of SEQ ID NO: 17 with an A-rich tract. In some embodiments, the 3' TTD is the MALAT1 core ENE+A.

In some embodiments, the 3' TTD is at least 95% homologous with SEQ ID NO: 23, and wherein the triple helix comprises Hoogsteen base pairing of U8-10, C11, and U12-15 of SEQ ID NO: 23 with an A-rich tract. In some embodiments, the 3' TTD is the MENβ ENE+A.

In one aspect, a nucleic acid trans-splicing molecule is provided. The RTM includes the following, operatively linked in a 5'-to-3' direction:

(a) a coding sequence domain (CDS) comprising one or more functional exon(s) of a selected gene;

(b) a linker sequence of varying length and/or composition that acts as a structural connection between the coding domain and the binding domain, and may contain motifs that function as splicing enhancers, or have the capacity to fold into complex secondary structures that act to minimize the translation of the coding region before the trans-splicing event occurs, or encode a degradation peptide in the event of premature RTM maturation;

(c) a spliceosome recognition motif (Splice Donor, SD, also called the 5' Splice Site (5' SS)) configured to initiate spliceosome-mediated trans-splicing;

(d) a binding domain (BD) of varying length and sequence designed to hybridize to a target intron of the selected gene, wherein said gene has at least one defect or mutation in an exon 5' to the target intron; and (e) a 3' transcription terminator domain (TTD), wherein the nucleic acid trans-splicing molecule is configured to trans-splice the coding domain to an endogenous exon of the selected gene adjacent to the target intron, thereby replacing the endogenous defective or mutated exon with the functional exon and correcting a mutation in the selected gene.

In one embodiment, the binding domain hybridizes to the target intron of the selected gene 3' to the mutation and the coding domain comprises one or more exon(s) 5' to the target intron.

In another aspect, the RTM includes the following, operatively linked in a 5'-to-3' direction:

(a) a binding domain (BD) of varying length and sequence designed to hybridize to a target intron of the selected gene, wherein said gene has at least one defect or mutation in an exon 3' to the targeted intron;

(b) a linker sequence of varying length and composition that acts as a structural connection between the binding domain the coding region, and contains motifs that function as splicing enhancers or fold into complex secondary structures that impede translation of the coding region as a competitive event for trans-splicing, or encode a degradation peptide in the event of premature RTM maturation;

(c) a 3' spliceosome recognition motif ((Splice Acceptor, SA), also called the 3' Splice Site (3' SS)) configured to mediate trans-splicing;

(d) a coding sequence domain (CDS) comprising one or more functional exon(s) of the selected gene; and (e) a 3' transcription terminator domain (TTD), wherein the nucleic acid trans-splicing molecule is configured to trans-splice the coding domain to an endogenous exon of the selected gene adjacent to the target intron, thereby replacing the endogenous defective or mutated exon with the functional exon and correcting a mutation in the selected gene. In one embodiment, the binding domain binds to the target intron of the selected gene 3' to the mutation and the coding domain comprises one or more exon 5' to the target intron.

In one embodiment, the 3' transcription terminator domain is a sequence from one or more long non-coding RNAs (lncRNA) or other nuclear RNA molecules that contain a 3' transcription terminator that condenses into a triple helix 3' blunt-ended cap.

In another aspect, a recombinant adeno-associated virus (rAAV) is provided, which includes any of the RTM described herein.

In another aspect, a method of treating a disease caused by a defect or mutation in a target gene is provided. The method includes administering to the cells of a subject having the disease a composition comprising a recombinant AAV comprising a nucleic acid trans-splicing molecule as described herein.

In yet another aspect, a pharmaceutical preparation is provided, comprising a physiologically acceptable carrier and the rAAV or RTM as described herein.

Other aspects and embodiments are described in the following detailed description.

BRIEF DESCRIPTION OF THE FIGURES

FIG. 1E (391.Comp14.hhRz) SEQ ID NO: 35 nt 2081-2470 are shown.

FIG. 1F (pcDNA_FRT. In26 target.3'Luc) SEQ ID NO: 36 nt 6761-7280 are shown.

FIG. 3A shows a portion of the sequence shown in SEQ ID NO: 28, with the 5' SS (also called SD or splicing domain) beginning at nt 4311, and the insulator ending at nt 4591. FIG. 3B shows a portion of the sequence shown in SEQ ID NO: 29, with the 5' SS (also called SD or splicing domain) beginning at nt 4311, and the mascRNA ending at nt 4620. FIG. 3C shows a portion of the sequence shown in SEQ ID NO: 30, with the 5' SS (also called SD or splicing domain) beginning at nt 4311, and the mascRNA ending at nt 4654.

FIGS. 4A and 4B are Western blots, and quantitation thereof, showing ABCA4 protein generated by RTM-mediated trans-splicing. RTMs of FIG. 3 that were tested include binding domains for ABCA4 intron23 (motifs 27 and 81) and intron22 (motifs 117 and 118). NB is a negative control Non-Binding motif.

FIG. 5A shows Western blot analysis of RTMs containing different triple helix terminators from lncRNAs. They include the wild-type sequence from MALAT1 and NEAT1 (MENβ), as well as chimeric forms where the triple helix domain from MALAT1 was fused to the tRNA-like motif from NEAT1 (called menRNA) and one where the triple helix domain from NEAT1 was fused to the mascRNA motif from MALAT1. The data suggests trans-splicing activity is highest when an RTM contains the wild-type MALAT1 terminator.

FIG. 5B shows the predicted base-pairing for triple helix terminators from three different lncRNAs, including MALAT1, MENβ (NEAT1), and PAN RNA (produced from the Kaposi's sarcoma-associated herpesvirus, KSHV). The structural similarity across distinct lncRNAs suggests a common evolutionary strategy for protecting the 3' end of the lncRNA following transcription termination. However, X-ray crystallography of the MALAT1 triple helix domain revealed it contains 10 major groove and 2 minor groove triples, the most of any known naturally occurring triple helical structure (Brown, J. A. et al. 2014). This intricate design likely confers a level of structural stability that is greater than either NEAT1 or PAN, and could explain why the MALAT1 terminator appears to better support trans-splicing. By way of protecting the RTM from degradation in the nucleus. Importantly, the blunt-ended triple helix of MALAT1 has been shown to inhibit rapid nuclear RNA decay as shown by in vivo decay assays (Brown, J. A. 2014).

DETAILED DESCRIPTION

Figure 1A:
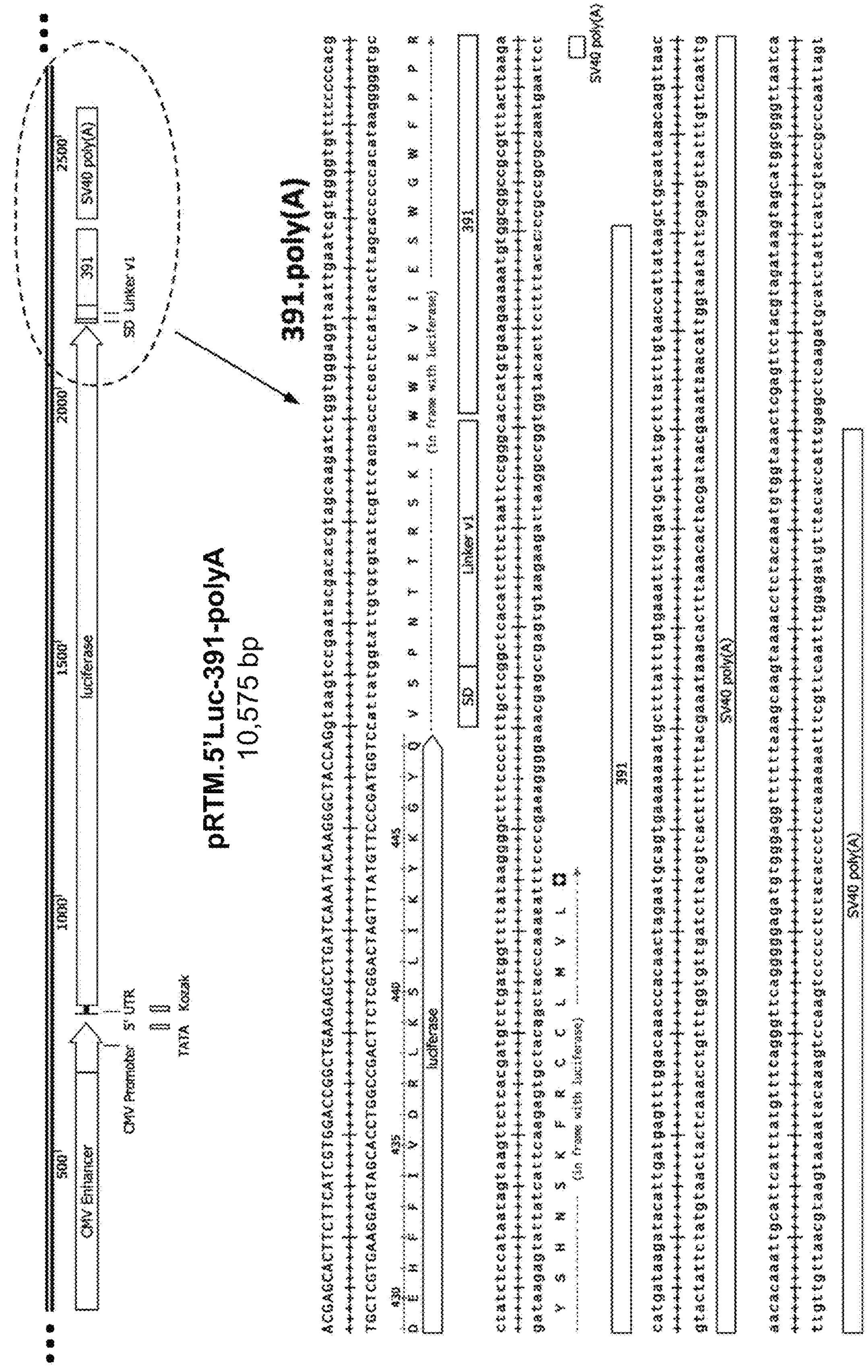
FIGS. 1A-1E shows a map and partial sequence of RTM Luciferase reporter constructs that target Intron26 from human CEP290. They encode the 5' half of the Luciferase coding sequence (CDS) along with different transcription terminator sequences: poly(A)—polyadenylation signal from SV40, which creates a 3' terminal end following cleavage at the poly(A) sisignal and addition of an untemplated poly(A) tail (FIG. 1A); hhRz-hammerhead Ribozyme, which self-cleaves to create a 3' terminal end of the RTM (FIG. 1B); Comp14—a truncated MALAT1 triple helix terminator structure, which creates a 3' terminal end of the RTM following RNase P cleavage (two versions-FIG. 1C, 1D); and a hybrid in which the mascRNA domain of Comp14 is replaced by hhRz, which creates a 3' terminal end of the RTM following ribozyme self-cleavage (FIG. 1E). For FIG. 1A (391.poly(A)), SEQ ID NO: 31 nt 2081-2600 are shown. For FIG. 1B (391.hhRz) SEQ ID NO: 32 nt 2081-2447 are shown. For FIG. 1C (391.Comp14-v1) SEQ ID NO: 33 nt 2081-2470 are shown. For FIG. 1D (391.Comp14-v2) SEQ ID NO: 34 nt 2081-2470 are shown.
Figure 1B:
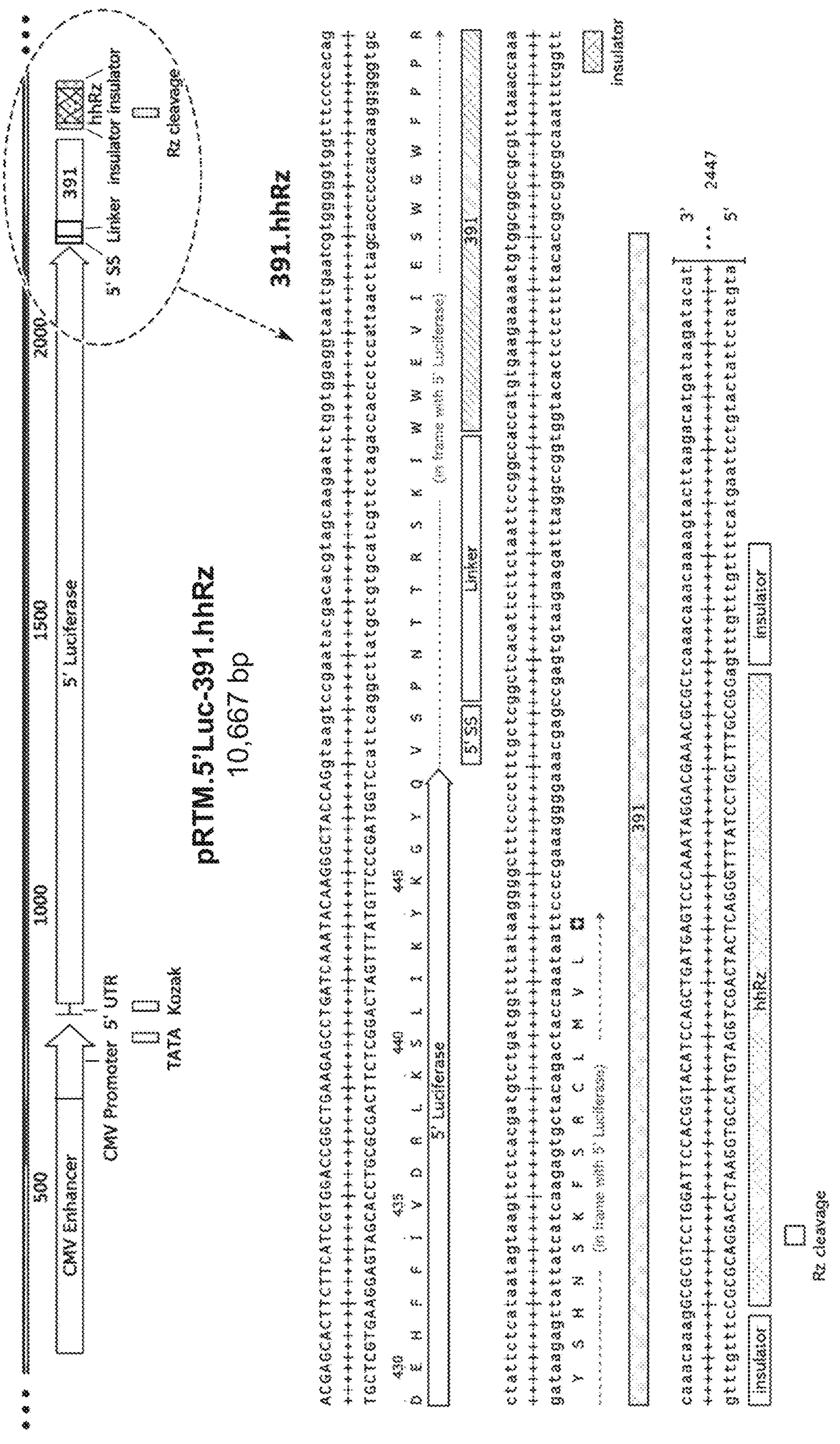
Figure 1C:
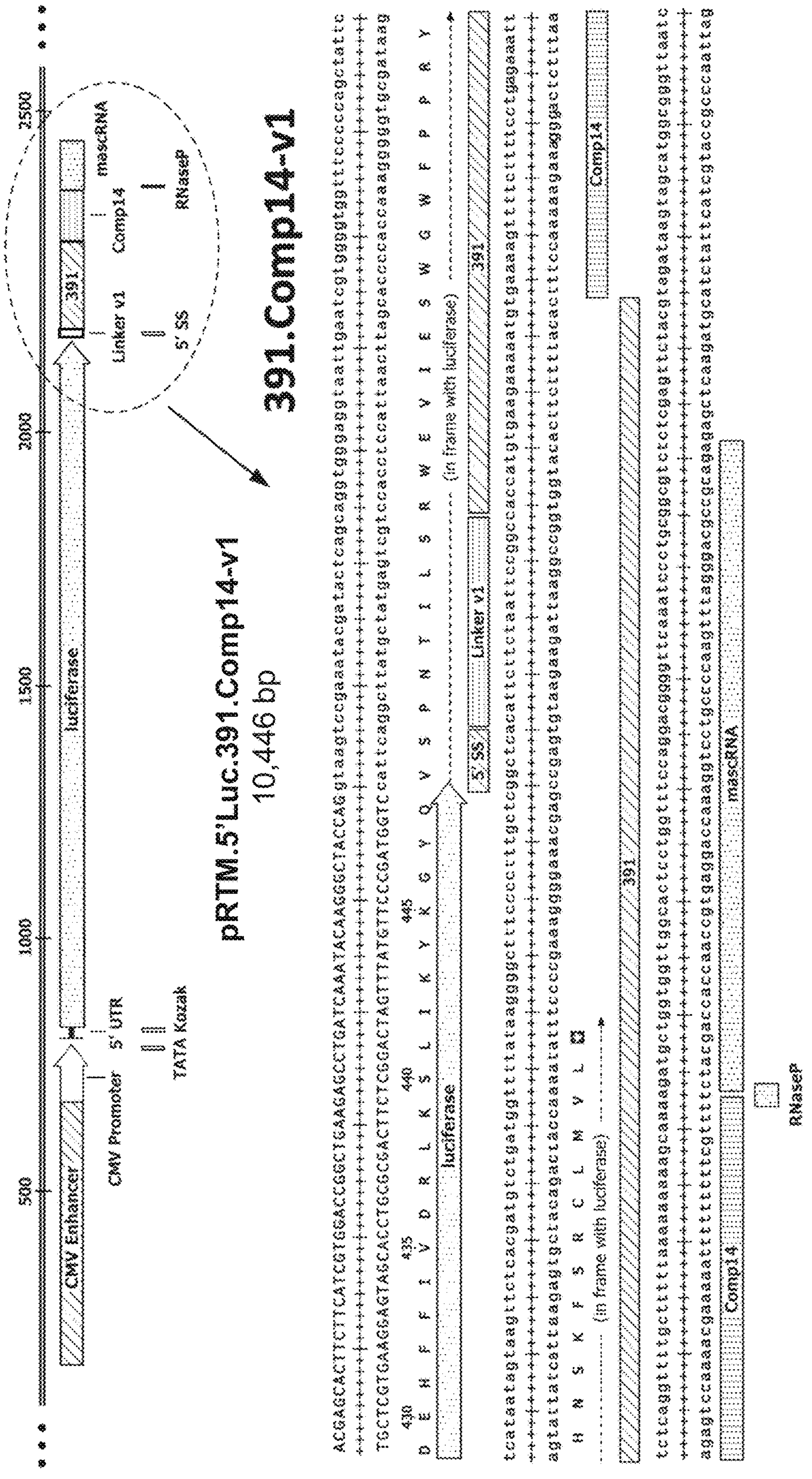
Figure 1D:
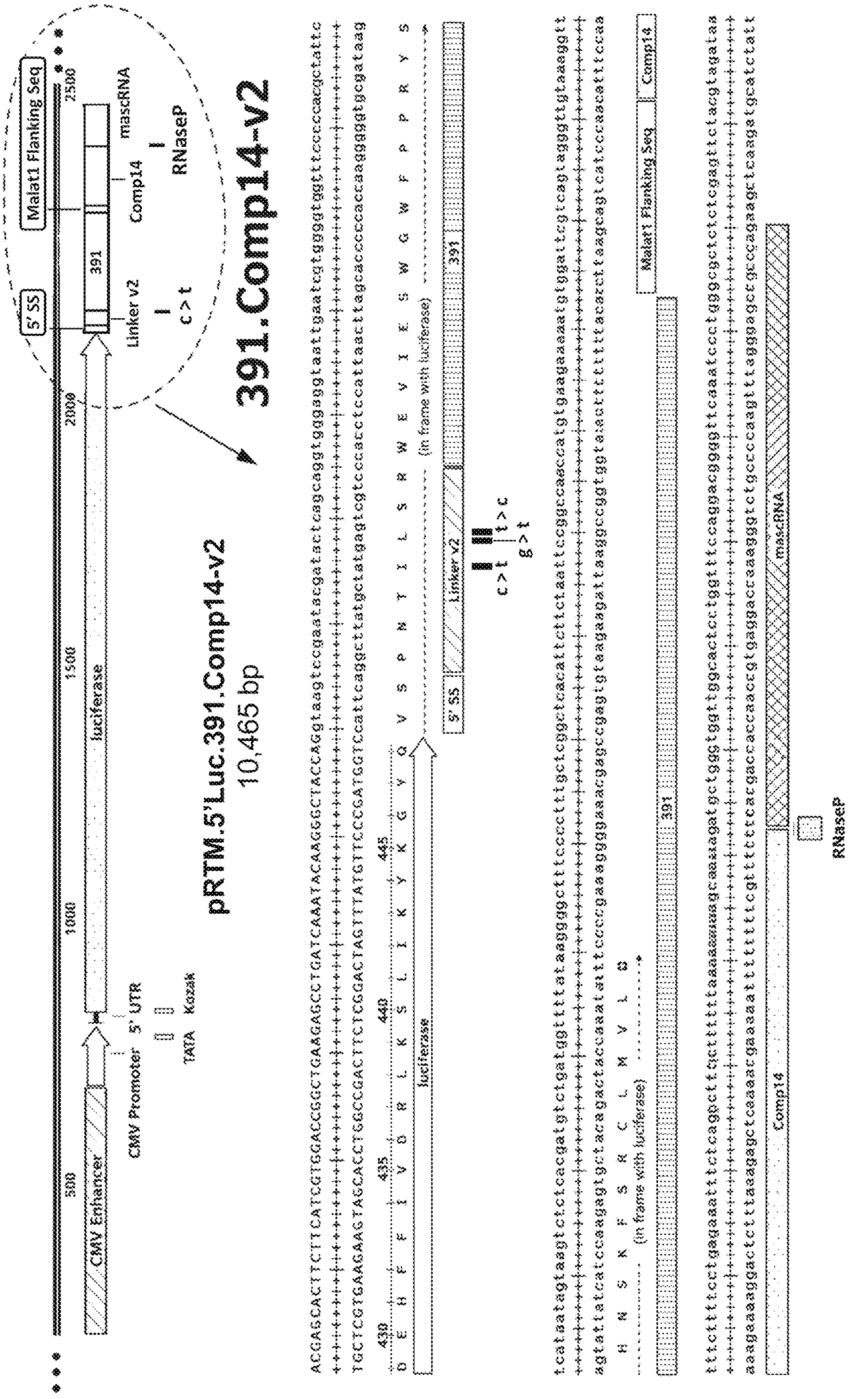
Figure 1E:
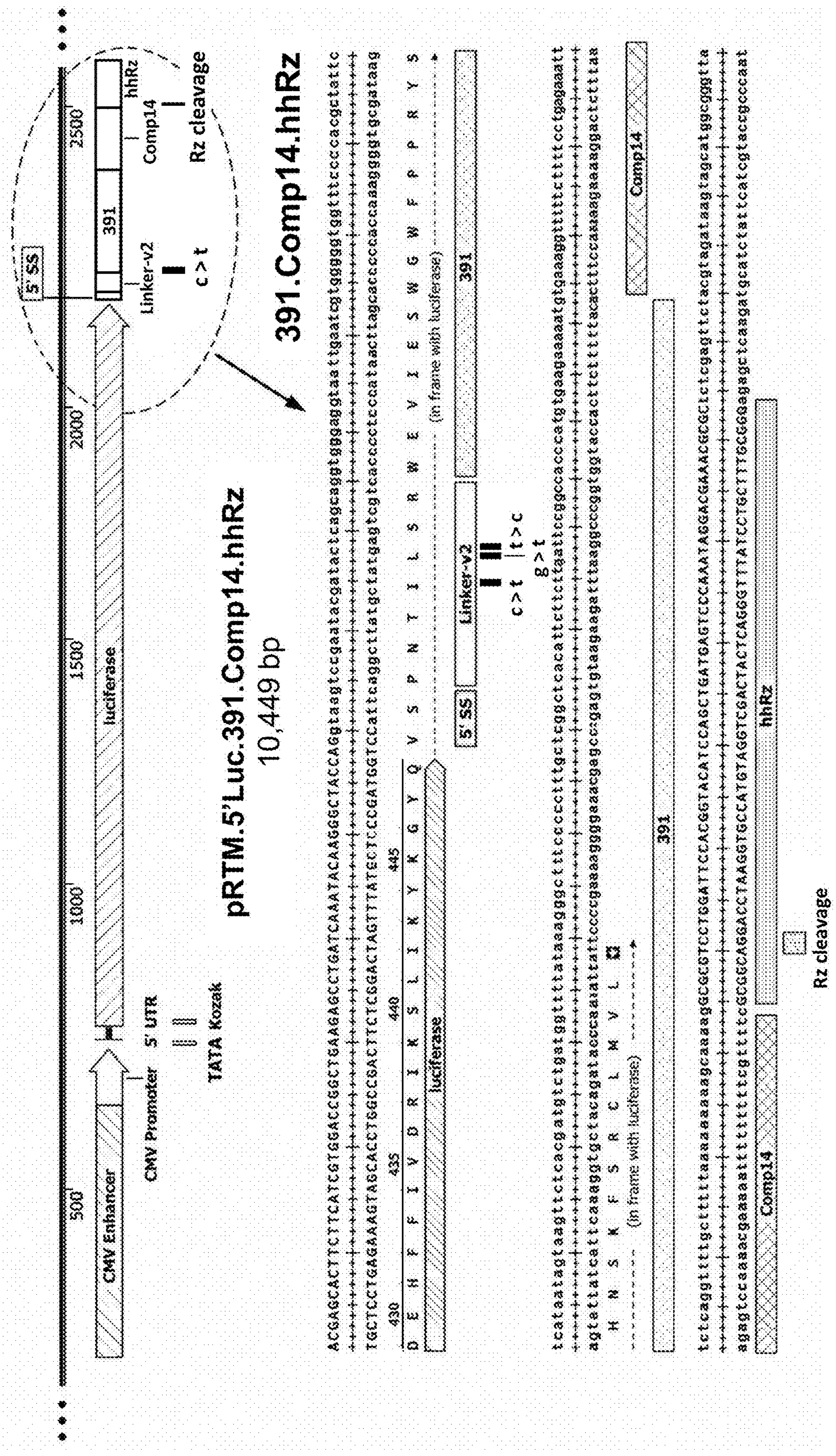

Many experimental trans-splicing studies that are reported in the literature often fall short of therapeutically meaningful endpoints. This is not to suggest these studies are not significant, as they invariably demonstrate the essential role of the RTM binding domain and splice site signals. And while these basic elements are indeed important, the complexities of RNA splicing involve an array of additional cis- and trans-acting factors for template recognition, spliceosome assembly, not to mention other non-splicing mechanisms that can directly impact the turn-over or localization of RTM molecules. Because trans-splicing is at a competitive disadvantage relative to cis-splicing, it is essential that the technical design of RNA trans-splicing molecules (RTM) includes features that increase the odds in favor of an RTM. One way to achieve that is by increasing the effective concentration of the RTM in the nucleus or by making the RTM a more attractive target to the spliceosome (via cis-acting elements or localization).

At the center of the present disclosure are RNA trans-splicing molecules (RTM) that are designed to specifically target a gene of interest and deliver its genetic payload via a trans-splicing reaction. Structurally, RTMs are organized into three core domains: 1) a protein coding region; 2) a binding domain that hybridizes to an intron within a target gene RNA transcript; and 3) a linker sequence with splicing signals (5' SS or 3'SS) that connects the coding region to the binding domain. It's important to emphasize that each of these three regions also have functional roles. Although modifications to any of these regions could theoretically impact RTM activity, the binding domain has attracted the most attention. Indeed, most reports in the literature include some degree of screening to identify the optimal binding sequence. Both the location of the target sequence and the length have shown to influence RTM activity. However, there has been no evidence of sequence specific features that might constitute consensus motifs or aid the development of binding domain design rules that might be applicable across different gene targets. As a result, binding domains are invariably determined by trial and error.

It remains unclear why some binding domains work better than others. A likely explanation involves RNA folding, and how this might influence the availability of a given target sequence for hybridization of an RTM. RNA folding can also influence the RTM binding domain itself; i.e. if the binding domain assumes a complex secondary structure it won't be available for hybridization with the target intron. Given an optimal binding domain is identified, an RTM remains subject to the same rules as other RNAs in the nucleus. And this could influence RTM activity independent of the binding reaction. Mechanistically, RTMs must have a half-life in the nucleus that is sufficiently long to allow the binding reaction to occur. If the RTM is transported out of the nucleus, or degraded by ubiquitous nuclear ribonucleases, two events that would markedly reduce the effective RTM concentration, trans-splicing efficiency will decline.

The biology of long non-coding RNAs (lncRNAs) has just recently become a topic of great interest in biomedical research and medicine. This due largely to the observation that some have been shown to be up-regulated in certain cancers. And while the relationship does not appear to be causative, understanding the role of these enigmatic RNAs could shed light on their possible role in gene regulation. Like RTMs, lncRNAs are transcribed by RNA polymerase II. And they both face the same problem; 3' end processing to ensuring precise polymerase termination and functionality of the mature transcript. For an RTM, most literature reports use a polyadenylation signal for 3' end processing. However, this approach signals the RTM to the cytoplasm, effectively reducing the nuclear copy number and allowing the RTM to express a truncated protein with unknown biological consequences. RTM expression, or sometimes referred to as RTM maturation, that generates a truncated protein is an undesirable outcome/off-target effect with unknown biological consequences. In contrast, many lncRNAs lack a polyadenylation signal and instead rely on noncanonical 3' end processing for PolII termination. Some of these assume simple stem-loop structures at the 3' end that are believed to help stabilize the mature transcript (e.g. histone mRNA). While others employ significantly more complex secondary structures.

lncRNAs have evolved a blueprint for nuclear localization that appears to include at least two features: 1) a nuclear localization signal, and 2) a mechanism for noncanonical 3' end processing to evade degradation by ribonucleases, thereby increasing their stability. A prototype lncRNA that has been shown to include both of these features is called MALAT1 (metastasis-associated lung adenocarcinoma transcript 1). Interestingly, the 3' end of MALAT1 is highly conserved across species and shown to condense into a triple helical structure following recognition and cleavage of a tRNA-like structure by RNaseP (Wilutz et al. 2012.Genes and Develop. 26:2392-2407). It is believed that this triple helix aids in stabilizing the MALAT1 transcript in the nuclease.

As described herein, the 3' terminal triple helix from human MALAT1 was added to investigational RTMs that target the primary RNA transcript encoded by a CEP290-Luciferase reporter or the primary RNA transcript encoded by the endogenous ABCA4 gene. In all instances, the presence of the 3' triple helix terminator marked enhanced trans-splicing activity. This was initially demonstrated with a 117bp truncated version of the 3' terminal triple helix (called Comp14, described in Wilutz et al. 2012) and later with the 151bp native sequence (NCBI REFSEQ: NR_002819).

In one aspect, the compositions and methods described herein employ gene therapy using adeno-associated virus (AAV) as a means for treating heritable genetic disorders. More specifically, the methods and compositions described herein employ the use of pre-mRNA trans-splicing as a gene therapy, both ex vivo and in vivo, for the treatment of diseases caused by defects in large genes. In one embodiment, these compositions and methods overcome the problem caused by the packaging limit for nucleic acids into AAV being limited to 4700 nucleotides. When including sequences necessary for producing an effective rAAV therapeutic and expressing the RNA-trans-splicing molecule (RTM), the effective size constraint for the RTM containing the ocular gene sequences is about 4000 nucleotides. These methods and compositions are particularly desirable for treatment of disorders caused by defects in genes exceeding the size necessary for incorporation and expression in an AAV, such as ABCA4, CEP290 and MYO7A, among other genes.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The definitions used herein are provided for clarity only and are not intended to limit the claimed invention.

As used here, a "3' transcription terminator domain" or "3' TTD" refers to a long noncoding RNA (lncRNA) positioned at a 3' terminus of a trans-splicing molecule. In some instances, a 3' TTD increases trans-splicing efficiency. In some instances, the transcription terminator domain includes an expression and nuclear retention element (ENE), which, when aligned with an A-rich tract (e.g., a poly-A tail), can form an ENE+A.

As used herein, a "long non-coding RNA" or "lncRNA" refers to a non-protein coding RNA transcript longer than 200 nucleotides (e.g., longer than 300 nucleotides, longer than 400 nucleotides, or longer than 500 nucleotides). In some embodiments, the lncRNA is from 200 to 300 nucleotides, from 300 to 400 nucleotides, from 400 to 500 nucleotides, or more than 500 nucleotides.

As used herein, the term "trans-splicing efficiency" refers to the number of trans-spliced RNA transcripts produced per trans-splicing molecule administered to a cell. Thus, trans-splicing efficiency reflects the stability and nuclear localization and retention of a trans-splicing molecule.

As used herein, the terms "triple helix," triple helical structure," and "triplex," and grammatical derivations thereof, are used interchangeably and refer to a region of polynucleotide (e.g., RNA) characterized by a stacked major groove triple formed by Hoogsteen base pairing. In some instances, a triple helix includes multiple (e.g., four or more) consecutive nucleotides that pair via Hoogsteen base pairing. In some embodiments, the triple helix includes four or more consecutive adenosine nucleotides, wherein each of the consecutive adenines is paired to a uracil via Hoogsteen base pairing (e.g., a poly-A tract aligns with a U-rich motif, e.g., in a stacked major groove triple).

As used herein, the term "A-rich tract" refers to a strand of consecutive nucleic acids in which at least 80% of the consecutive nucleic acids are adenine (A).

As used herein, the term "U-rich motif" refers to a strand of consecutive nucleic acids in which at least 80% of the consecutive nucleic acids are uracil (U).

A "nucleic acid trans-splicing molecule" or "trans-splicing molecule" has three main elements: (a) a binding domain that confers specificity by tethering the trans-splicing molecule to its target gene (e.g., pre-mRNA); (b) a splicing domain (e.g., a splicing domain having a 3' or 5' splice site); and (c) a coding sequence configured to be trans-spliced onto the target gene, which can replace one or more exons in the target gene (e.g., one or more mutated exons). A "pre-mRNA trans-splicing molecule" or "RTM" refers to a nucleic acid trans-splicing molecule that targets pre-mRNA. In some embodiments, a trans-splicing molecule, such as an RTM, can include cDNA, e.g., as part of a functional exon for replacement or correction of a mutated exon.

A nucleic acid is "operably linked" when it is placed into a structural or functional relationship with another nucleic acid sequence. For example, one nucleic acid sequence may be operably linked to another nucleic acid sequence if they are positioned relative to one another on the same contiguous polynucleotide and have a structural or functional relationship, such as formation of a triple helix (e.g., through Hoogsteen base pairing). In some instances, operably linked nucleic acid sequences are directly linked (i.e., the nucleic acid sequence is directly, covalently linked to another nucleic acid sequence, without intervening nucleotides). In other instances, operably linked nucleic acid sequences are not directly linked. In instances in which operably linked nucleic acid sequences are not directly linked, they can be operatively linked (indirectly) through a linker sequence. In some instances, the linker sequence can be 1-1,000 bases in length (e.g., 1-900, 1-800, 1-700, 1-600, 1-500, 1-400, 1-300, 1-250, 1-200, 1-150, 1-100, 1-90, 1-80, 1-70, 1-60, 1-50, 1-40, 1-30-, 1-20, 1-10, 1-8, 1-6, 1-5, 1-4, or 1-3 bases in length, e.g., 1-10, 10-15, 15-20, 20-30, 30-40, 40-50, 50-100, 100-150, 150-200, or 200-500 bases in length). In some instances, an A-rich tract is operatively linked 3' to a U-rich motif through a linker sequence.

As used herein, the term "mammalian subject" or "subject" includes any mammal in need of these methods of treatment or prophylaxis, including particularly humans. Other mammals in need of such treatment or prophylaxis include dogs, cats, or other domesticated animals, horses, livestock, laboratory animals, including non-human primates, etc. The subject may be male or female.

In one embodiment, the subject has, or is at risk of developing a disorder caused by a genetic mutation. In one embodiment, the subject has, or is at risk of developing an ocular disorder. In another embodiment, the subject has shown clinical signs of an ocular disorder, particular a disorder related to a defect or mutation in the genes ABCA4, CEP290, or MYO7A.

The term "ocular disorder" includes, without limitation, Stargardt disease (autosomal dominant or autosomal recessive), retinitis pigmentosa, rod-cone dystrophy, Leber's congenital amaurosis, Usher's syndrome, Bardet-Biedl Syndrome, Best disease, retinoschisis, untreated retinal detachment, pattern dystrophy, cone-rod dystrophy, achromatopsia, ocular albinism, enhanced S cone syndrome, diabetic retinopathy, age-related macular degeneration, retinopathy of prematurity, sickle cell retinopathy, Congenital Stationary Night Blindness, glaucoma, or retinal vein occlusion. In another embodiment, the subject has, or is at risk of developing glaucoma, Leber's hereditary optic neuropathy, lysosomal storage disorder, or peroxisomal disorder.

Clinical signs of ocular disease include, but are not limited to, decreased peripheral vision, decreased central (reading) vision, decreased night vision, loss of color perception, reduction in visual acuity, decreased photoreceptor function, pigmentary changes. In another embodiment, the subject has been diagnosed with STGD1. In another embodiment, the subject has been diagnosed with a juvenile onset macular degeneration, fundus flavimaculatus. In another embodiment, the subject has been diagnosed with cone-rod dystrophy. In another embodiment, the subject has been diagnosed with retinitis pigmentosa. In another embodiment, the subject has been diagnosed with age-related macular degeneration (AMD). In another embodiment, the subject has been diagnosed with LCA10. In yet another embodiment, the subject has not yet shown clinical signs of these ocular pathologies.

As used herein, the term "treatment" or "treating" is defined as one or more of reducing onset or progression of an ocular disease, preventing disease, reinducing the severity of the disease symptoms, or retarding their progression, removing the disease symptoms, delaying onset of disease or monitoring progression of disease or efficacy of therapy in a given subject.

As used herein, the term "selected cells" refers to any cell or cell type to which the RTM is delivered (i.e., targets of interest for modification using the compositions and methods provided herein). In certain embodiments, the selected cell is a prokaryotic cell. In other embodiments, the selected cell is a eukaryotic cell, non-limiting examples of which include plant cells and tissues, animal cells and tissues, and human cells and tissues. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages of the culture. Without limitation, selected cells may for instance be cancerous. In certain embodiments, the selected cell is manipulated ex vivo and then administered to the subject. In yet other embodiments, the selected cells are targeted in vivo, e.g., by delivery of an rAVV, to a subject. In some embodiments, the term "selected cells" refers to ocular cells, which are any cell associated with the function of the eye, such as photoreceptor cells. In some embodiments, the term refers to rods, cones, photosensitive ganglion cells, retinal pigment epithelium (RPE) cells, Mueller cells, bipolar cells, horizontal cells, or amacrine cells. Some genes targets are expressed in the eye as well as in other organs. For example, CEP290 is expressed in kidney epithelium and in the central nervous system and MY07A is expressed in cochlear hair cells. Thus, selected cells may also include these extra-ocular cells. In certain embodiments, the selected cells are a skeletal muscle cell, e.g., a red (slow) skeletal muscle cell, a white (fast) skeletal muscle cell, or an intermediate skeletal muscle cell. In certain embodiments, the selected cell is a cardiac muscle cell, e.g., a cardiomyocyte or a nodal cardiac muscle cell. In certain embodiments, the selected cell is a smooth muscle cell. In certain embodiments, the selected cell is a muscle satellite cell or muscle stem cell.

As used herein, the term "host cell" may refer to the packaging cell line in which the rAAV is produced from the plasmid. In the alternative, the term "host cell" may refer to the target cell in which expression of the transgene is desired.

Codon optimization refers to modifying a nucleic acid sequence to change individual nucleic acids without any resulting change in the encoded amino acid. This process may be performed on any of the sequences described in this specification to enhance expression or stability. Codon optimization may be performed in a manner such as that described in, e.g., U.S. Pat. Nos. 7,561,972; 7,561,973; and 7,888,112, incorporated herein by reference, and conversion of the sequence surrounding the translational start site to a consensus Kozak sequence. See, Kozak et al, *Nucleic Acids Res.* 15(20):8125-8148, incorporated herein by reference. In one embodiment, the coding sequences are codon optimized.

The term "homologous" refers to the degree of identity between sequences of two nucleic acid sequences. The homology of homologous sequences is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22):4673 4680 (1994). Commonly available sequence analysis software, more specifically, Vector NTI, GENETYX, BLAST or analysis tools provided by public databases may also be used.

The term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the synthetic is administered. Examples of suitable pharmaceutical carriers are described in "Remington's Pharmaceutical sciences" by E. W. Martin.

The terms "a" or "an" refers to one or more, for example, "a gene" is understood to represent one or more such genes. As such, the terms "a" (or "an"), "one or more," and "at least one" are used interchangeably herein.

As used herein, the term "about" means a variability of +0.1 to 10% from the reference given, unless otherwise specified.

With regard to the following description, it is intended that each of the compositions herein described, is useful, in another embodiment, in the methods of treatment described herein. In addition, it is also intended that each of the compositions herein described as useful in the methods, is itself an embodiment. While various embodiments in the specification are presented using "comprising" language, which is inclusive of other components or steps, under other circumstances, a related embodiment is also intended to be interpreted and described using "consisting of" or "consisting essentially of" language, which is exclusive of all or any components or steps which significantly change the embodiment.

Pre-mRNA Trans-Splicing Methods and Molecules

Within a cell, a pre-mRNA intermediate exists that includes non-coding nucleic acid sequences, i.e., introns, and nucleic acid sequences that encode the amino acids forming the gene product. The introns are interspersed between the exons of a gene in the pre-mRNA, and are ultimately excised from the pre-mRNA molecule, when the exons are joined together by a protein complex known as the spliceosome. Using spliceosome activity, one may introduce an alternative exon via the introduction of a second nucleic acid. Spliceosome mediated RNA trans-splicing (SMaRT) has been described as employing an engineered pre-mRNA trans-splicing molecule (RTM) that binds specifically to target pre-mRNA in the nucleus and triggers trans-splicing in a process mediated by the spliceosome. This methodology is described in, for example, Puttaraju M, et al 1999 Nat Biotechnol., 17:246-252; Gruber C et al, 2013 December, Mol. Oncol. 7 (6): 1056; Avale M E, 2013 July, Hum. Mol. Genet., 22(13):2603-11; Rindt H et al, 2012 December, Cell Mol. Life Sci., 69(24):4191; US Patent Application Publication Nos. 2006/0246422 and 20130059901, and U.S. Pat. Nos. 6,083,702; 6,013,487; 6,280,978; 7,399,753; and 8,053,232. These documents are incorporated herein by reference.

The nucleic acid trans-splicing molecules disclosed herein can include any of the structural or functional characteristics of nucleic acid trans-splicing molecules and related methods known in the art, for example, those described in WO 2017/087900 and WO 2019/2045114, each of which is incorporated herein by reference in its entirety.

In some embodiments, an RNA trans-splicing molecule (RTM) as described herein, has five main elements. In one embodiment, the elements include, operatively linked in a 5'-to-3' direction:

(a) a coding domain (CD) comprising one or more functional exon(s) of a selected gene;

(b) a linker domain (LD) of varying length and sequence that acts as a structural connection between the coding domain and the binding domain, and may contain motifs that function as splicing enhancers, or have the capacity to fold into complex secondary structures that act to minimize the translation of the coding region before the trans-splicing event occurs, or encode a degradation peptide in the event of premature RTM maturation;

(c) a spliceosome recognition motif (Splice Donor, SD) configured to initiate spliceosome-mediated trans-splicing;

(d) a binding domain (BD) of varying length and sequence configured to hybridize to a target intron of the selected gene, wherein said gene has at least one defect or mutation in an exon 5' to the target intron; and (e) a 3' transcription terminator domain (TTD) that increases the efficiency of trans-splicing.

The nucleic acid trans-splicing molecule is configured to trans-splice the coding domain to an endogenous exon of the selected gene adjacent to the target intron, thereby replacing the endogenous defective or mutated exon with the functional exon and correcting a mutation in the selected gene In another embodiment the elements include, operatively linked in a 5' to 3' direction:

(a) a binding domain (BD) configured to bind a target intron of a selected gene, wherein said gene has at least one defect or mutation in an exon 3' to the targeted intron;

(b) a linker sequence of varying length and composition that acts as a structural connection between the binding domain the coding region, and contains motifs that function as splicing enhancers or fold into complex secondary structures that impede translation of the coding region as a competitive event for trans-splicing, or encode a degradation peptide in the event of premature RTM maturation;

(c) a 3' spliceosome recognition motif (Splice Acceptor, SA) configured to mediate trans-splicing;

(d) a coding domain (CD) comprising one or more functional exon(s) of the selected gene; and (e) a 3' transcription terminator domain (TTD) that increases the efficiency of trans-splicing.

Coding Domain Sequence (CDS)

The coding domain of the RTMs described herein includes part of the wild-type coding sequence to be trans-spliced to the target pre-mRNA. By "wild-type coding sequence" it is meant a sequence which, when translated and assembled, provides a functional protein. The expression or function need not be to the same level as the wild-type protein. In one embodiment, the wild-type coding sequence is modified, e.g., via codon optimization.

The pre-RNA trans-splicing molecule (RTM) is configured to trans-splice the coding domain to an endogenous exon of the selected gene adjacent to the target intron, thereby replacing the endogenous defective or mutated exon with the functional exon and correcting a mutation in the selected gene. The CDS may provide some or of all of the exons of the selected gene 3' or 5' to the binding domain, depending on the configuration of the RTM. For example, for 5' trans-splicing reactions, all or some of the exons 5' to the BD are replaced. For 3' trans-splicing reactions, all or some of the exons 3' to the BD are replaced. The design of the RTM permits replacement of the defective or mutated portion of the pre-mRNA exon(s) with a nucleic acid sequence, i.e., the exon(s) having a normal sequence without the defect or mutation. The "normal" sequence can be a wild-type naturally-occurring sequence or a corrected sequence with some other modification, e.g., codon-modified, that is not disease-causing.

In one embodiment, the coding domain is a single exon of the target gene, which contains the normal wildtype sequence lacking the disease-causing mutations, e.g., Exon 22 of ABCA4. In another embodiment, the coding domain comprises multiple exons which contain multiple mutations causing disease, e.g., Exons 1-22 of ABCA4. Depending upon the location of the exon to be corrected, the RTM may contain multiple exons located at the 5' or 3' end of the target gene, or the RTM may be designed to replace an exon in the middle of the gene. For use and delivery in the rAAV, the entire coding sequence of the ocular gene is not useful as the coding domain of RTM, unless this technique is directed to a small ocular gene less than 3000 nucleotides in length. As described herein, to replace an entire large gene, two RTMs, a 3' and a 5' RTM can be employed in different rAAV particles.

RTMs described herein can comprise coding domains encoding for one or more exons identified herein and characterized by containing a gene mutation or defect relating to the associated disease, e.g., Exon 27 of ABCA4 may be the coding domain for an RTM designed for the treatment of Stargardt's disease. In TABLEs 1 to 3 herein, the names of the targeted genes and the exons containing likely mutations causing disease are identified.

In one embodiment, the coding domain of a 5' RTM is designed to replace the exons in the 5' portion of the targeted gene. In another embodiment, the coding domain of a 3' RTM is designed to replace the exons in the 3' portion of a gene. In another embodiment, the coding domain is one or a multiple exons located internally in the gene and the coding domain is located in a double trans-splicing RTMs.

Thus, for example, three possible types of RTMs are useful for treatment of disease caused by defects in e.g., ABCA4: A 5' trans-splicing RTMs which include a 5' splice site. After trans-splicing, the 5' RTM will have changed the 5' region of the target mRNA; a 3' RTM which include a 3' splice site that is used to trans-splice and replace the 3' region of the target mRNA; and a double trans-splicing RTM, which carry multiple binding domains along with a 3' and a 5' splice site. After trans-splicing, this RTM replaces an internal exon in the processed target mRNA. In other embodiments, the coding domain can include an exon that comprises naturally occurring or artificially introduced stop-codons in order to reduce gene expression; or the RTM can contain other sequences which produce an RNAi-like effect.

For use in treating Stargardt's disease, suitable coding regions of ABCA4 are Exons 1-22 or 27-50, in separate RTMs. For use in treating LCA10, suitable coding regions of CEP290 are Exons 1-26 or exons 27-54 in separate RTMs. For use in treating Usher Syndrome, suitable coding regions of MYO7A are Exons 1-18 or 33-49, in separate RTMs.

Still other coding domains can be constructed by one of skill in the art to replace the entirety of the genes in fragments provided by a 5' RTM and 3'RTM, and/or a double splicing RTM, given the teachings provided herein.

Linker Domain (LD)

The RTM described herein includes, in some embodiments, a linker domain (LD) of varying length and sequence that acts as a structural connection between the coding domain and the binding domain. In one embodiment, the LD contains one or more motifs that function as splicing enhancers. In one embodiment the LD provides one or more motifs that have the capacity to fold into complex secondary structures that act to minimize the translation of the coding region before the trans-splicing event occurs.

In one embodiment, the linker sequence is SEQ ID NO: 37: ccgaatacgacacgtagcaagatct.

Spliceosome Recognition Motif (Splice Donor (SD) and Splice Acceptor (SA))

Depending on the RTM (5'- or 3') directionality, the RTM includes a spliceosome recognition motif, which is either a splice donor (SD), splice acceptor (SA) or both.

Introns always have two distinct nucleotides at either end. At the 5' end the DNA nucleotides are GT [GU in the premessenger RNA (pre-mRNA)]; at the 3' end they are AG. These nucleotides are part of the splicing sites. The SD is the splicing site at the beginning of an intron, intron 5' left end, and is sometimes referred to as the 5' splice site or 5'SS. The SA is the splicing site at the end of an intron, intron 3' right end, and is sometimes referred to as the 3' splice site, or 3'SS.

Figure 11:
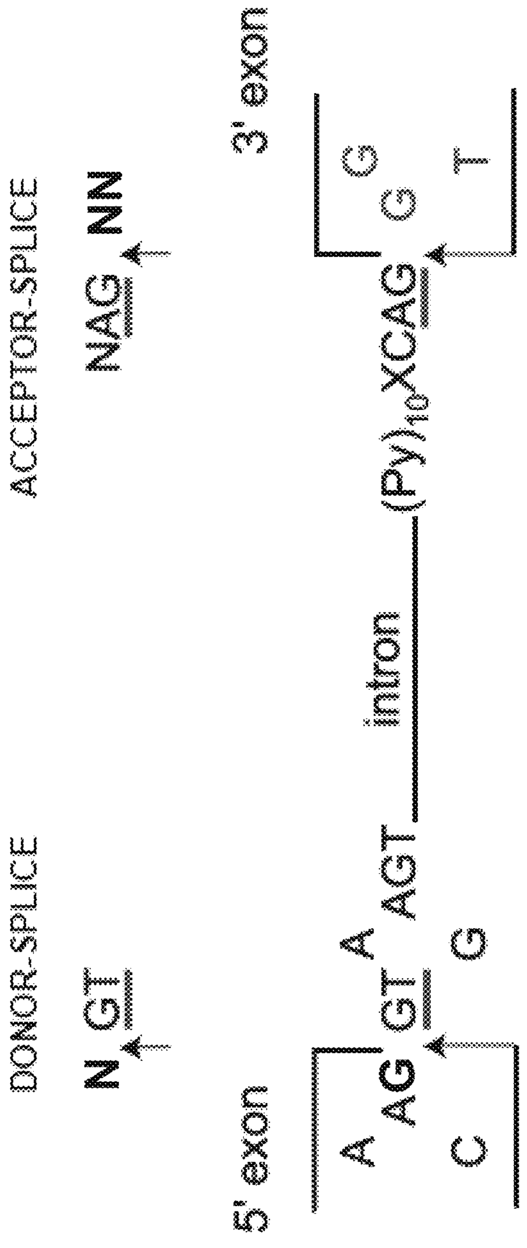
FIG. 11 is a schematic illustration of exemplary splice donor (SD) and splice acceptor (SA) recognition motifs at the 5' and 3' boundaries of an intron.

FIG. 11 schematically illustrates exemplary splice donor and splice acceptor recognition motifs at the 5' and 3' boundaries of an intron.

Briefly, the splicing domain provides essential consensus motifs that are recognized by the spliceosome. The use of BP and PPT follows consensus sequences required for performance of the two phosphoryl transfer reaction involved in cis-splicing and, presumably, also in trans-splicing. In one embodiment a branch point consensus sequence in mammals is YNYURAC (Y=pyrimidine; N=any nucleotide). The underlined A is the site of branch formation. A polypyrimidine tract is located between the branch point and the splice site acceptor and is important for different branch point utilization and 3' splice site recognition. Consensus sequences for the 5' splice donor site and the 3' splice region used in RNA splicing are well known in the art. In addition, modified consensus sequences that maintain the ability to function as 5' donor splice sites and 3' splice regions may be used. Briefly, in one embodiment, the 5' splice site consensus sequence is the nucleic acid sequence AG/GURAGU (where/indicates the splice site). In another embodiment the endogenous splice sites that correspond to the exon proximal to the splice site can be employed to maintain any splicing regulatory signals. In one embodiment, the ABCA4 5'RTM containing as a coding region the sequence encoding exon 1-22 with a binding domain complementary to a region in intron 22 uses the endogenous intron 22 5' splice site. In another embodiment, the ABCA4 3'RTM encoding exons 27-50 with a binding domain complementary to intron 26 uses the endogenous intron 26 3' splice site.

In one embodiment a suitable 5' splice site with spacer is: 5'-GTA AGA GAG CTC GTT GCG ATA TTA T-3' SEQ ID NO: 1. In one embodiment a suitable 5' splice site is AGGT.

In one embodiment, a suitable 3' RTM BP is 5'-TACTAAC-3' (SEQ ID NO: 2). In one embodiment, a suitable 3' splice site is: 5'-TAC TAA CTG GTA CCT CTT CTT TTT TTT CTG CAG-3' SEQ ID NO: 2 or 5'-CAGGT-3' (SEQ ID NO: 4). In one embodiment, a suitable 3'RTM PPT is 5'-TGG TAC CTC TTC TTT TTT TTC TG-3' SEQ ID NO: 5.

Binding Domain (BD)

The RTM includes a binding domain (BD) of varying length and sequence configured to hybridize to a target intron of the selected gene. In one embodiment, the binding domain is a nucleic acid sequence complementary to a sequence of the target pre-mRNA to suppress endogenous target cis-splicing while enhancing trans-splicing between the trans-splicing molecule and the target pre-mRNA, e.g., to create a chimeric molecule having a portion of endogenous mRNA and the coding domain having one or more functional exons. In some embodiments, the binding domain is in an antisense orientation to a sequence of the target intron.

A 5' trans-splicing molecule will generally bind the target intron 3' to the mutation, while a 3' trans-splicing molecule will generally bind the target intron 5' to the mutation. In one embodiment, the binding domain comprises a part of a sequence complementary to the target intron. In one embodiment herein, the binding domain is a nucleic acid sequence complementary to the intron closest to (i.e., adjacent to) the exon sequence that is being corrected.

In another embodiment, the binding domain is targeted to an intron sequence in close proximity to the 3' or 5' splice signals of a target intron. In still another embodiment, a binding domain sequence can bind to the target intron in addition to part of an adjacent exon.

Thus, in some instances, the binding domain binds specifically to the mutated endogenous target pre-mRNA to anchor the coding domain of the trans-splicing molecule to the pre-mRNA to permit trans-splicing to occur at the correct position in the target gene. The spliceosome processing machinery of the nucleus may then mediate successful trans-splicing of the corrected exon for the mutated exon causing the disease.

In certain embodiments, the trans-splicing molecules feature binding domains that contain sequences on the target pre-mRNA that bind in more than one place. The binding domain may contain any number of nucleotides necessary to stably bind to the target pre-mRNA to permit trans-splicing to occur with the coding domain. In one embodiment, the binding domains are selected using mFOLD structural analysis for accessible loops (Zuker, Nucleic Acids Res. 2003, 31 (13): 3406-3415).

Suitable target binding domains can be from 10 to 500 nucleotides in length. In some embodiments, the binding domain is from 20 to 400 nucleotides in length. In some embodiments, the binding domain is from 50 to 300 nucleotides in length. In some embodiments, the binding domain is from 100 to 200 nucleotides in length. In some embodiments, the binding domain is from 10-20 nucleotides in length (e.g., 10, 11, 12, 13, 14, 15, 16, 17, 18, 19, or 20 nucleotides in length), 20-30 nucleotides in length (e.g., 20, 21, 22, 23, 24, 25, 26, 27, 28, 29, or 30 nucleotides in length), 30-40 nucleotides in length (e.g., 30, 31, 32, 33, 34, 35, 36, 37, 38, 39, or 40 nucleotides in length), 40-50 nucleotides in length (e.g., 40, 41, 42, 43, 44, 45, 46, 47, 48, 49, 50 nucleotides in length), 50-60 nucleotides in length (e.g., 50, 51, 52, 53, 54, 55, 56, 57, 58, 59, or 60 nucleotides in length), 60-70 nucleotides in length (e.g., 60, 61, 62, 63, 64, 65, 66, 67, 68, 69, or 70 nucleotides in length), 70-80 nucleotides in length (e.g., 70, 71, 72, 73, 74, 75, 76, 77, 78, 79, or 80 nucleotides in length), 80-90 nucleotides in length (e.g., 80, 81, 82, 83, 84, 85, 86, 87, 88, 89, or 90 nucleotides in length), 90-100 nucleotides in length (e.g., 90, 91, 92, 93, 94, 95, 96, 97, 98, 99, or 100 nucleotides in length), 100-110 nucleotides in length (e.g., 100, 101, 102, 103, 104, 105, 106, 107, 108, 109, or 110 nucleotides in length), 110-120 nucleotides in length (e.g., 110, 111, 112, 113, 114, 115, 116, 117, 118, 119, or 120 nucleotides in length), 120-130 nucleotides in length (e.g., 120, 121, 122, 123, 124, 125, 126, 127, 128, 129, or 130 nucleotides in length), 130-140 nucleotides in length (e.g., 130, 131, 132, 133, 134, 135, 136, 137, 138, 139, or 140 nucleotides in length), 140-150 nucleotides in length (e.g., 140, 141, 142, 143, 144, 145, 146, 147, 148, 149, or 150 nucleotides in length), 150-160 nucleotides in length (e.g., 150, 151, 152, 153, 154, 155, 156, 157, 158, 159, or 160 nucleotides in length), 160-170 nucleotides in length (e.g., 160, 161, 162, 163, 164, 165, 166, 167, 168, 169, or 170 nucleotides in length), 170-180 nucleotides in length (e.g., 170, 171, 172, 173, 174, 175, 176, 177, 178, 179, or 180 nucleotides in length), 180-190 nucleotides in length (e.g., 180, 181, 182, 183, 184, 185, 186, 187, 188, 189, or 190 nucleotides in length), 190-200 nucleotides in length (e.g., 190, 191, 192, 193, 194, 195, 196, 197, 198, 199, or 200 nucleotides in length), 200-210 nucleotides in length, 210-220 nucleotides in length, 220-230 nucleotides in length, 230-240 nucleotides in length, 240-250 nucleotides in length, 250-260 nucleotides in length, 260-270 nucleotides in length, 270-280 nucleotides in length, 280-290 nucleotides in length, 290-300 nucleotides in length, 300-350 nucleotides in length, 350-400 nucleotides in length, 400-450 nucleotides in length, or 450-500 nucleotides in length. In some embodiments, the binding domain is about 150 nucleotides in length. In another embodiment, the target binding domains may include a nucleic acid sequence up to 750 nucleotides in length. In another embodiment, the target binding domains may include a nucleic acid sequence up to 1000 nucleotides in length. In another embodiment, the target binding domains may include a nucleic acid sequence up to 2000 nucleotides or more in length.

In some embodiments, the specificity of the trans-splicing molecule may be increased by increasing the length of the target binding domain. Other lengths may be used depending upon the lengths of the other components of the trans-splicing molecule.

The binding domain may be from 80% to 100% complementary to the target intron to be able to hybridize stably with the target intron. For example, in some embodiments, the binding domain is 80%, 81%, 82%, 83%, 84%, 85%, 86%, 87%, 88%, 89%, 90%, 91%, 92%, 93%, 94%, 95%, 96%, 97%, 98%, 99%, or 100% complimentary to the target intron. The degree of complementarity is selected by one of skill in the art based on the need to keep the trans-splicing molecule and the nucleic acid construct containing the necessary sequences for expression and for inclusion in the rAAV within a 3,000 or up to 4,000 nucleotide base limit. The selection of this sequence and strength of hybridization depends on the complementarity and the length of the nucleic acid.

In one embodiment, the BD targets intron 23, motif 81 of ABCA4. In one embodiment, the sequence is: SEQ ID NO: 6:

```
TCACTGTTTAATCTGTTAATTCATCTGAGCATTTTGAGGGTGTAGTCGCTT
GATTTTATCCTAGAGAGTGTGTGAGTCACACACAGAGAGGAGCAGAACCTC
CAAGGGTCCCTTTGGCTTGTCATCAATTATGTGGCAGCTGTAGGTTCT.
```

3' Transcription Terminator Domain (TTD)

The RTM as described herein, contains a 3' transcription terminator domain (TTD), e.g., a 3' TTD that increases the efficiency of trans-splicing. The TTD, in one embodiment, comprises one or more of the following sequences: a sequence that is involved in the formation of a triplex (also referred to herein as the "triple helix" or "triple helical structure"), an RNase P cleavage site, the tRNA like structure that serves as a template for RNaseP cleavage (also referred to herein as the tRNA-like domain, structure or sequence), and any flanking sequence that might facilitate folding of these domains, independently or collectively. Such flanking sequence may be an artificial linker, a linker derived from another sequence, or flanking sequences from the native lncRNA. In one embodiment, the 3' transcription terminator domain forms a triple helical structure that effectively caps the 3' end or protects the 3' end from nuclease degradation. As discussed herein, the tRNA-like domain may also include the RNase P cleavage site.

Long non-coding RNAs serve as important regulatory mediators in gene expression. Some lncRNAs have been shown to have 3' ends produced by noncanonical recognition and cleavage of a tRNA-like structure by RNase P. In some instances, it has been shown that some lncRNAs are protected from 3'-5' endonucleases by highly conserved triple helical structures. As provided herein, sequences of the 3' terminal ends of certain lncRNAs are able to be incorporated in RTM as a terminal domain (TTD) which is able to increase the efficiency of trans-splicing. In one embodiment, the TTD is a sequence from one or more long non-coding RNAs (lncRNA) or other nuclear RNA molecules that contain a 3' transcription terminator that condenses into a triple helix 3' end cap. In one embodiment, the TTD sequences are from the human long non-coding RNA MALAT1. In another embodiment, the TTD sequences are from the human lncRNA MENβ. In one embodiment, the TTD includes nucleotides 8287-8437 of human MALAT1 (SEQ ID NO: 7). In another embodiment, the TTD includes, in order from 5' to 3', a triplex forming sequence that comprises nucleotides 8287-8379 of SEQ ID NO: 7, an RNaseP cleavage site the comprises nucleotides 8379-8380 of SEQ ID NO: 7, and a tRNA-like sequence that comprises nucleotides 8380-8437 of SEQ ID NO: 7.

In some embodiments, the 3' TTD comprises, in a 5'-to-3' direction (linked directly or indirectly), a 5' U-rich motif, a stem-loop motif, a 3' U-rich motif, and an A-rich tract (e.g., a poly-A tail). In some instances, the A-rich tract is capable of Hoogsteen base pairing with the 5' U-rich motif. In some embodiments, one or both stem strands is about 8-20 base pairs in length (e.g., from 9-16, 10-14, or 11-23 base pairs in length). In some embodiments, the 5' U-rich motif and the 3' U-rich motif each comprise at least five consecutive uracils. In some embodiments, the 5' U-rich motif and the 3' U-rich motif are each 5-15 base pairs in length.

In some embodiments, the 3' TTD comprises, in a 5' to 3' direction, a 5' U-rich motif comprising five consecutive uracils, a stem-loop motif in which at least one stem strand has a length of about 16 base pairs, a 3' U-rich motif comprising five consecutive uracils, and an A-rich tract comprising at least 18 adenines. In some embodiments, the 3' TTD comprises SEQ ID NO: 14. In some embodiments, the 3' TTD comprises SEQ ID NO: 13.

In some embodiments, the 3' TTD comprises, in a 5' to 3' direction, a 5' U-rich motif comprising SEQ ID NO: 18, a stem-loop motif in which at least one stem strand has a length of about 13 nucleotides, a 3' U-rich motif comprising SEQ ID NO: 19, and an A-rich tract comprising SEQ ID NO: 20. In some embodiments, the 3' TTD comprises SEQ ID NO: 16. In some embodiments, the 3' TTD comprises SEQ ID NO: 15.

In some embodiments, the 3' TTD comprises, in a 5' to 3' direction, SEQ ID NO: 18, SEQ ID NO: 19, and SEQ ID NO: 20. In some embodiments, the 3' TTD comprises SEQ ID NO: 17.

In some embodiments, the 3' TTD comprises, in a 5' to 3' direction, a 5' U-rich motif comprising SEQ ID NO: 23, a stem-loop motif in which at least one stem strand has a length of about 13 nucleotides, a 3' U-rich motif comprising SEQ ID NO: 24, and an A-rich tract comprising SEQ ID NO: 25. In some embodiments, the 3' TTD comprises SEQ ID NO: 24. In some embodiments, the 3' TTD comprises SEQ ID NO: 23.

In some embodiments, the 3' TTD is between 200 and 1000 nucleotides in length (e.g., from 200 to 900, from 200 to 800, from 200 to 700, from 200 to 600, from 200 to 500, from 200 to 400, or from 200 to 300 nucleotides in length).

Triplex-Forming Structure

The triple helix structure is, in one embodiment, formed from an A-rich motif (e.g., an A-rich tract), along with two upstream (e.g., 5') U-rich motifs and a stem-loop structure. As exemplified herein, these sequences are highly conserved evolutionarily in metastasis-associated lung adenocarcinoma transcript 1 (MALAT1), a lncRNA associated with certain cancers. Similar highly conserved A- and U-rich motifs are present at the 3' end of the MENβ long nuclear-retained noncoding RNA, also known as NEAT1_2, which is also processed at its 3' end by RNase P. It has been shown that these highly conserved A- and U-rich motifs form a triple-helical structure critical for protecting the 3' end of MALAT1 from 3'-5' exonucleases.

A number of triple-helices are useful in engineering any of the constructs described herein. Such triple-helices include ENE+A, riboswitch, and telomerase triple helices (see, e.g., Brown et al. Nature Structural and Molecular Biology, 21, 633-642, 2014, which is incorporated herein by reference). For example, ENE+A triple helices are described for human MALAT1 (Brown et al. Nat. Struct. Mol. Biol., 7, 633-40, 2014.), KSHV PAN (Mitton-Fry et al. Science, 330, 1244-7, 2010), human MENβ (Brown et al. Proc. Natl. Acad. Sci. USA, 109, 19202-7, 2012), *Acanthamoeba polyphaga* mimivirus (Tycowski et al. Cell Rep., 2, 26-32, 2012), *Cotesia congregata* bracovirus (Tycowski et al. Cell Rep., 2, 26-32, 2012), *Cotesia* sesamiae bracovirus (Tycowski et al. Cell Rep., 2, 26-32, 2012), Equine herpesvirus 2 (EHV2) (Tycowski et al. Cell Rep., 2, 26-32, 2012), *Plautia stali* intestine virus (PSIV) (Tycowski et al. Cell Rep., 2, 26-32, 2012), and Rhesus rhadinovirus PAN (RRV) (Tycowski et al. Cell Rep., 2, 26-32, 2012). Other exemplary triple helices include riboswitch triple helices which are described for the PreQi-II Riboswitch from *Lactobacillus rhamnosus* (Liberman et al. Nat. Chem. Biol., 9, 353-5, 2013) and the SAM-II Riboswitch found in the Sargasso Sea metagenome (Gilbert et al. Nat. Struct. Mol. Biol., 15, 177-82, 2008). In yet another example, telomerase triple helices are described for humans (Theimer et al. Mol Cell, 17, 671-82, 2005) and for *Kluyveromyces lactis* (Cash et al. Proc. Natl. Acad. Sci USA, 110, 10970-5, 2013.

In one embodiment, the RTM contains a triplex forming sequence comprised of a U-rich motif 1 (e.g., a 5' U-rich motif), a conserved stem-loop, a U-rich motif 2 (e.g., a 3' U-rich motif), and an A-rich tract (e.g., as part of a poly-A tail), wherein the A-rich tract and the U-rich motif 2 form a Watson-Crick stem duplex, and the U-rich motif 1 aligns with the A-rich tract to form Hoogsteen base pairs. (Buske et al. 2012; Beal and Dervan, 1991), which is incorporated herein by reference. In one embodiment, the sequences are from human MALAT1. Thus, in one embodiment, the RTM contains a triplex forming sequence comprised of a U-rich motif 1 (8292-8301 of human MALAT1), a conserved stem-loop (8302-8333 of human MALAT1), a U-rich motif 2 (8334-8343 of human MALAT1), and an A-rich tract (8369-8379 of human MALAT1), wherein the A-rich tract and the U-rich motif 2 form a Watson-Crick stem duplex, and the U-rich motif 1 aligns with the A-rich tract to form Hoogsteen base pairs.

In another embodiment, the 3' TTD described herein is of novel design, derived from theoretical modeling and/or by extension of naturally occurring sequences. In one embodiment, the TTD comprises, in order from 5' to 3', a triplex forming sequence of varying length and composition, an RNaseP cleavage site, and a tRNA-like sequence of varying length and composition. In one embodiment, the triplex forming sequence conforms to one of three known basic "motifs", and are referred to by the base composition of the third strand of the triple helix: pyrimidine motif (T,C), purine motif (G,A), and purine-pyrimidine motif (G,T) (Buske F A, Bauer D C, Mattick J S, Bailey T L. 2012. Triplexator: Detecting nucleic acid triple helices in genomic and transcriptomic data. Genome Res. 22:1372-1382; Beal P A, Dervan P B. 1991. Second structural motif for recognition of DNA by oligonucleotide-directed triple-helix formation. Science. 251:1360-1363, which are both incorporated herein by reference).

In another embodiment, the TTD is a truncated version of the human MALAT1 triple helix. In one embodiment the TTD contains a triplex forming sequence comprised of a U-rich motif 1 (8292-8301 of human MALAT1), a conserved stem-loop (8302-8310 and 8325-8333 of human MALAT1), a U-rich motif 2 (8334-8343 of human MALAT1), an A-rich tract (8369-8379 of human MALAT1), and a deletion spanning nucleotide 8345-8364 of human MALAT1 of the intervening sequence between U-rich motif 2 and the A-rich tract, wherein the A-rich tract and the U-rich motif 2 form a Watson-Crick stem duplex, and the U-rich motif 1 aligns with the A-rich tract to form Hoogsteen base pairs.

In one embodiment, the triple helix structure is derived from a lncRNA. In one embodiment, the triple helix structure is derived from MALAT1. As the MALAT1 sequences are highly conserved evolutionarily, the MALAT1 sequence can be from any species. In one embodiment, the MALAT1 sequence is from a human. In another embodiment, the MALAT1 sequence is from a mouse. In another embodiment, the MALAT1 sequence is from a non-human primate. In another embodiment, the MALAT1 sequence is from a dog. In another embodiment, the MALAT1 sequence is from an elephant. In another embodiment, the MALAT1 sequence is from an opossum. In another embodiment, the MALAT1 sequence is from fish. Such sequences are known in the art and can be found, e.g., in GenBank. In one embodiment, the MALAT1 sequence is SEQ ID NO: 7.

In another embodiment, the triple helix sequence is provided as a truncated or modified version of the native sequence, so long as the sequence retains the ability to fold into the required triple helix structure.

In one embodiment, the triple helix structure is derived from MENβ. The MENβ sequence can be from any species. In one embodiment, the MENβ sequence is from a human. In another embodiment, the MENβ sequence is from a mouse. In another embodiment, the MENβ sequence is from a non-human primate. In another embodiment, the MENβ sequence is from a dog. In another embodiment, the MENβ sequence is from an elephant. In another embodiment, the MENβ sequence is from an opossum. In another embodiment, the MENβ sequence is from fish. Such sequences are known in the art and can be found, e.g., in GenBank.

In another embodiment, the triple helix sequence is provided as a truncated or modified version of the native sequence, so long as the sequence retains the ability to fold into the required triple helix structure. In one embodiment, the MENβ sequence is SEQ ID NO: 8.

In some embodiments, the triple helix includes four to 100 consecutive adenosines paired via Hoogsteen base pairing (e.g., four to 80 consecutive adenosines paired via Hoogsteen base pairing, four to 60 consecutive adenosines paired via Hoogsteen base pairing, four to 50 consecutive adenosines paired via Hoogsteen base pairing, four to 40 consecutive adenosines paired via Hoogsteen base pairing, four to 30 consecutive adenosines paired via Hoogsteen base pairing, four to 20 consecutive adenosines paired via Hoogsteen base pairing, four to 18 consecutive adenosines paired via Hoogsteen base pairing, four to 15 consecutive adenosines paired via Hoogsteen base pairing, four to 12 consecutive adenosines paired via Hoogsteen base pairing, four to 11 consecutive adenosines paired via Hoogsteen base pairing, four to 10 consecutive adenosines paired via Hoogsteen base pairing, four to nine consecutive adenosines paired via Hoogsteen base pairing, four to eight consecutive adenosines paired via Hoogsteen base pairing, four to seven consecutive adenosines paired via Hoogsteen base pairing, or four to six consecutive adenosines paired via Hoogsteen base pairing, e.g., five to 50 consecutive adenosines paired via Hoogsteen base pairing, five to 40 consecutive adenosines paired via Hoogsteen base pairing, five to 30 consecutive adenosines paired via Hoogsteen base pairing, five to 20 consecutive adenosines paired via Hoogsteen base pairing, five to 18 consecutive adenosines paired via Hoogsteen base pairing, five to 15 consecutive adenosines paired via Hoogsteen base pairing, five to 12 consecutive adenosines paired via Hoogsteen base pairing, five to 10 consecutive adenosines paired via Hoogsteen base pairing, five to nine consecutive adenosines paired via Hoogsteen base pairing, five to eight consecutive adenosines paired via Hoogsteen base pairing, five to seven consecutive adenosines paired via Hoogsteen base pairing, or five to six consecutive adenosines paired via Hoogsteen base pairing, e.g., six to eight consecutive adenosines paired via Hoogsteen base pairing, eight to 10 consecutive adenosines paired via Hoogsteen base pairing, 10 to 12 consecutive adenosines paired via Hoogsteen base pairing, 12 to 14 consecutive adenosines paired via Hoogsteen base pairing, 14 to 16 consecutive adenosines paired via Hoogsteen base pairing, 16 to 18 consecutive adenosines paired via Hoogsteen base pairing, 18 to 20 consecutive adenosines paired via Hoogsteen base pairing, 20 to 30 consecutive adenosines paired via Hoogsteen base pairing, 30 to 40 consecutive adenosines paired via Hoogsteen base pairing, or 40 to 50 consecutive adenosines paired via Hoogsteen base pairing).

In some embodiments, the triple helix includes a strand of consecutive nucleotides in which at least 90% of the nucleotides are paired via Hoogsteen base pairing (e.g., at least 90% of the nucleotides are paired via Hoogsteen base pairing, at least 91% of the nucleotides are paired via Hoogsteen base pairing, at least 92% of the nucleotides are paired via Hoogsteen base pairing, at least 93% of the nucleotides are paired via Hoogsteen base pairing, at least 94% of the nucleotides are paired via Hoogsteen base pairing, at least 95% of the nucleotides are paired via Hoogsteen base pairing, at least 96% of the nucleotides are paired via Hoogsteen base pairing, at least 97% of the nucleotides are paired via Hoogsteen base pairing, at least 98% of the nucleotides are paired via Hoogsteen base pairing, at least 99% of the nucleotides are paired via Hoogsteen base pairing, or 100% of the nucleotides are paired via Hoogsteen base pairing).

Domain 2—tRNA-Like Structure

The tRNA-like structures described herein, are sequences which form tRNA-like clover secondary structure, allowing it to be recognized by one or more of RNase P, RNase Z, and the CCA-adding enzyme.

The tRNA-like structure of MALAT1 is termed mascRNA (MALAT1-associated small cytoplasmic RNA). This sequence is 61nt long and is shown in SEQ ID NO: 9. The tRNA-like structure of mascRNA has been preserved through evolution, as the four mismatches between the mouse and human orthologs maintain the cloverleaf secondary structure. Although similar in structure to a tRNA and containing a well-conserved B-box, the 61-nt mascRNA transcript is smaller than most tRNAs (~76-nt) and has a small, relatively poorly conserved anticodon loop. Wilusz et al, Cell. 2008 Nov. 28; 135(5):919-932, incorporated by reference herein. The tRNA-like structure of MENβ is termed menRNA. Zhang et al., 2017, Cell Reports 19, 1723-1738, which is incorporated herein by reference.

In one embodiment, the tRNA-like structure is derived from a lncRNA. In one embodiment, the tRNA-like structure is derived from MALAT1. As the MALAT1 sequences are highly conserved evolutionarily, the MALAT1 sequence can be from any species. In one embodiment, the MALAT1 sequence is from a human. In another embodiment, the MALAT1 sequence is from a mouse. In another embodiment, the MALAT1 sequence is from a non-human primate. In another embodiment, the MALAT1 sequence is from a dog. In another embodiment, the MALAT1 sequence is from an elephant. In another embodiment, the MALAT1 sequence is from an opossum. In another embodiment, the MALAT1 sequence is from fish. Such sequences are known in the art and can be found, e.g., in GenBank.

In another embodiment, the tRNA-like sequence is provided as a truncated or modified version of the native sequence, so long as the sequence retains the ability to fold into the required tRNA-like structure.

In one embodiment, the tRNA-like structure is derived from MENβ. The MENβ sequence can be from any species. In one embodiment, the MENβ sequence is from a human. In another embodiment, the MENβ sequence is from a mouse. In another embodiment, the MENβ sequence is from a non-human primate. In another embodiment, the MENβ sequence is from a dog. In another embodiment, the MENβ sequence is from an elephant. In another embodiment, the MENβ sequence is from an opossum. In another embodiment, the MENβ sequence is from fish. Such sequences are known in the art and can be found, e.g., in GenBank.

In another embodiment, the tRNA-like sequence is provided as a truncated or modified version of the native sequence, so long as the sequence retains the ability to fold into the required tRNA-like structure.

The components of the TTD can originate from the same or different lncRNA, including lncRNA homologs from different species. For example, the triple helix domain and the tRNA-like domain may originate from the same long non-coding RNA or different combinations of long non-coding RNA domains derived from human or any other species. In one embodiment, the triple helix domain and the tRNA-like domain are from MALAT1 or NEAT1/MENβ.

Targeted Genes

The targeted gene is one that contains one or multiple defects or mutations that cause an ocular disease. In one embodiment described herein, the targeted gene is a mammalian gene with defects known to cause a disease or disorder.

The wildtype sequences of the genes and encoded proteins and/or the genomic and chromosomal sequences are available from publically available databases and their accession numbers are provided herein. In addition to these published sequences, all corrections later obtained or naturally occurring conservative and non-disease-causing variants sequences that occur in the human or other mammalian population are also included. Additionally, conservative nucleotide replacements or those causing codon optimizations are also included. The sequences as provided by the database accession numbers may also be used to search for homologous sequences in the same or another mammalian organism.

It is anticipated that the target ocular nucleic acid sequences and the resulting protein truncates or amino acid fragments identified herein may tolerate certain minor modifications at the nucleic acid level to include, for example, modifications to the nucleotide bases which are silent, e.g., preference codons. In other embodiments, nucleic acid base modifications which change the amino acids, e.g. to improve expression of the resulting peptide/protein are anticipated. Also included as likely modification of fragments are allelic variations, caused by the natural degeneracy of the genetic code.

Also included as modification of the selected genes are analogs, or modified versions, of the encoded protein fragments provided herein. Typically, such analogs differ from the specifically identified proteins by only one to four codon changes. Conservative replacements are those that take place within a family of amino acids that are related in their side chains and chemical properties.

The nucleic acid sequence encoding a normal gene may be derived from any mammal which natively expresses that gene, or homolog thereof. In another embodiment, the gene sequence is derived from the same mammal that the composition is intended to treat. In another embodiment, the gene sequence is derived from a human. In other embodiments, certain modifications are made to the gene sequence in order to enhance the expression in the target cell. Such modifications include codon optimization.

In one embodiment, the gene is ABCA4, which is indicated in Stargardt's Disease. The genomic sequence of the DNA for this gene can be found in the NCBI Reference Sequence for Chromosome 1 (135313 bp) at NG_009073.1. The mRNA for the gene as well as the locations of the exons are indicated in the NCBI report. The DNA sequence of ABCA4 provided as NCBI Reference Sequence: NM_000350.2. The amino acid sequence is provided as NCBI Reference Sequence: NP000341.2.

In another embodiment, the gene is CEP290. Leber congenital amaurosis comprises a group of early-onset childhood retinal dystrophies characterized by vision loss, nystagmus, and severe retinal dysfunction. Patients usually present at birth with profound vision loss and pendular nystagmus. Electroretinogram (ERG) responses are usually nonrecordable. Other clinical findings may include high hypermetropia, photodysphoria, oculodigital sign, keratoconus, cataracts, and a variable appearance to the fundus. LCA10 is caused by mutation in the CEP290 gene on chromosome 12q21 and may account for as many as 21% of cases of LCA. Mutations in CEP290 can also result in extra-ocular findings, including kidney and CNS abnormalities, and thus can result in syndromes (Senior Loken syndrome, Joubert syndrome, Bardet-Biedl).

The genomic sequence of the DNA for this gene can be found in the NCBI Reference Sequence for Chromosome 12 from nt. 88049013-88142216 (93,204 bp) at NC_000012.12. The mRNA and the exons are identified in NCBI report. The DNA sequence of CEP290 provided as NCBI Reference Sequence: NM_025114.3. The amino acid sequence is provided as NCBI Reference Sequence: NP0789390.3. The mRNA contains 54 exons and 59 introns (due to alternative splicing). Many mutations of CEP290 and their locations in the nucleotide sequence are known.

In another embodiment, the gene is MYO7A. Mutations in this gene are related to Usher Syndrome. Usher syndrome is a condition characterized by hearing loss and progressive vision loss. The loss of vision is caused by an eye disease called retinitis pigmentosa (RP), which affects the layer of light-sensitive retina. Vision loss occurs as the light-sensing cells of the retina gradually deteriorate. Over time, these blind spots enlarge and merge to produce tunnel vision. In some cases of Usher syndrome, vision is further impaired by clouding of the lens of the eye (cataracts). Many people with retinitis pigmentosa retain some central vision throughout their lives, however. The loss of hearing is caused by disease in cochlear hair cells, which also gradually deteriorate.

Usher syndrome type I can result from mutations in the CDH23, MYO7A, PCDH15, USHIC, or USH1G gene.

More than 250 mutations in the MYO7A gene have been identified in people with Usher syndrome type 1B. Many of these genetic changes alter a single protein building block (amino acid) in critical regions of the myosin VIIA protein. Other mutations introduce a premature stop signal in the instructions for the myosin VIIA protein. As a result, an abnormally small version of this protein is made. Some mutations insert or delete small amounts of DNA in the MYO7A gene, which alters the protein. All of these changes cause the production of a nonfunctional myosin VIIA protein that adversely affects the development and function of cells in the inner ear and retina, resulting in Usher syndrome.

The genomic sequence of the DNA for this gene can be found in the NCBI Reference Sequence for Chromosome 11 from nt. 77,128,255 to 77,215,240 (86,986 bp) at NC_000011.9. The DNA sequence of MYO7A provided as NCBI Reference Sequence: NM_000260.3. The amino acid sequence is provided as NCBI Reference Sequence: NP 000251.1. The DNA sequence, amino acid sequence, exon sequences and intron sequences are provided for MYO7A online at grenada_lumc_nl/LOVD2/Usher_montpellier/refseq/MYO7A_codingDNA_html, last modified Feb. 17, 2010. The mRNA contains 49 exons and 61 introns. Many mutations of MYO7A may be found on the CCHMC Molecular Genetics Laboratory Mutation Database, LOVD v.2.0.

RTM Target Gene Coding Sequence

In one embodiment, the coding domain is a single exon of the target gene, which contains the normal wild-type sequence lacking the disease-causing mutations, e.g., Exon 27 of ABCA4. In another embodiment, the coding domain comprises multiple exons which contain multiple mutations causing disease, e.g., Exons 1-22 of ABCA4. Depending upon the location of the exon to be corrected, the RTM may contain multiple exons located at the 5' or 3' end of the target gene, or the RTM may be designed to replace an exon in the middle of the gene. For use and delivery in the rAAV, the entire coding sequence of the gene is not useful as the coding domain of RTM, unless this technique is directed to a small gene less than 3000 nucleotides in length. As described herein, to replace an entire large gene, two RTMs, a 3' and a 5' RTM can be employed in different rAAV particles.

In one embodiment, the coding domain of a 5' RTM is designed to replace the exons in the 5' portion of the targeted gene. In another embodiment, the coding domain of a 3' RTM is designed to replace the exons in the 3' portion of a gene. In another embodiment, the coding domain is one or a multiple exons located internally in the gene and the coding domain is located in a double trans-splicing RTMs.

Thus, for example, three possible types of RTMs are useful for treatment of disease caused by defects in e.g., ABCA4: 5' trans-splicing RTMs which include a 5' splice site. After trans-splicing, the 5' RTM will have changed the 5' region of the target mRNA; a 3' RTM which include a 3' splice site that is used to trans-splice and replace the 3' region of the target mRNA; and double trans-splicing RTMs, which carry multiple binding domains along with a 3' and a 5' splice site. After trans-splicing, this RTM replaces an internal exon in the processed target mRNA. In other embodiments, the coding domain can include an exon that comprises naturally occurring or artificially introduced stop-codons in order to reduce gene expression; or the RTM can contain other sequences which produce an RNAi-like effect.

For use in treating Stargardt's disease, suitable coding regions of ABCA4 are Exons 1-22 or 27-50, in separate RTMs. For use in treating LCA10, suitable coding regions of CEP290 are Exons 1-26 or exons 27-54 in separate RTMs. For use in treating Usher Syndrome, suitable coding regions of MYO7A are Exons 1-18 or 33-49, in separate RTMs.

Optional Components or Modifications of the RTM

An optional spacer region may be used to separate the splicing domain from the target binding domain in the RTM. The spacer region may be designed to include features such as (i) stop codons which would function to block translation of any unspliced RTM and/or (ii) sequences that enhance trans-splicing to the target pre-mRNA. The spacer may be between 3 to 25 nucleotides or more depending upon the lengths of the other components of the RTM and the rAAV limitations. In one embodiment a suitable 5' RTM spacer is AGA TCT CGT TGC GAT ATT AT SEQ ID NO: 10. In one embodiment a suitable 3' spacer is: 5'-GAG AAC ATT ATT ATA GCG TTG CTC GAG-3' SEQ ID NO: 11.

Still other optional components of the RTMs include mini introns, and intronic or exonic enhancers or silencers that would regulate the trans-splicing (See, e.g., the descriptions in the RTM technology publications cited herein.)

In another embodiment, the RTM further comprises at least one safety sequence incorporated into the spacer, binding domain, or elsewhere in the RTM to prevent non-specific trans-splicing. This is a region of the RTM that covers elements of the 3' and/or 5' splice site of the RTM by relatively weak complementarity, preventing non-specific trans-splicing. The RTM is designed in such a way that upon hybridization of the binding/targeting portion(s) of the RTM, the 3' and/or 5' splice site is uncovered and becomes fully active. Such "safety" sequences comprise a complementary stretch of cis-sequence (or could be a second, separate, strand of nucleic acid) which binds to one or both sides of the RTM branch point, pyrimidine tract, 3' splice site and/or 5' splice site (splicing elements), or could bind to parts of the splicing elements themselves. The binding of the "safety" may be disrupted by the binding of the target binding region of the RTM to the target pre-mRNA, thus exposing and activating the RTM splicing elements (making them available to trans-splice into the target pre-mRNA). In another embodiment, the RTM has 3'UTR sequences or ribozyme sequences added to the 3 or 5' end.

In an embodiment, splicing enhancers such as, for example, sequences referred to as exonic splicing enhancers may also be included in the structure of the synthetic RTMs. Additional features can be added to the RTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the RTM structure to prevent translation of unspliced RTMs. Further elements such as a 3' hairpin structure, circularized RNA, nucleotide base modification, or synthetic analogs can be incorporated into RTMs to promote or facilitate nuclear localization and spliceosomal incorporation, and intra-cellular stability.

The binding of the RTM nucleic acid molecule to the target pre-mRNA is mediated by complementarity (i.e. based on base-pairing characteristics of nucleic acids), triple helix formation or protein-nucleic acid interaction (as described in documents cited herein). In one embodiment, the RTM nucleic acid molecules consist of DNA, RNA or DNA/RNA hybrid molecules, wherein the DNA or RNA is either single or double stranded. Also comprised are RNAs or DNAs, which hybridize to one of the aforementioned RNAs or DNAs preferably under stringent conditions like, for example, hybridization at 60° C. in 2.5×SSC buffer and several washes at 37° C. at a lower buffer concentration like, for example, 0.5×SSC buffer and which encode proteins exhibiting lipid phosphate phosphatase activity and/or association with plasma membranes. When RTMs are synthesized in vitro (synthetic RTMs), such RTMs can be modified at the base moiety, sugar moiety, or phosphate backbone, for example, to improve stability of the molecule, hybridization to the target mRNA, transport into the cell, stability in the cells to enzymatic cleavage, etc. For example, modification of a RTM to reduce the overall charge can enhance the cellular uptake of the molecule. In addition modifications can be made to reduce susceptibility to nuclease or chemical degradation. The nucleic acid molecules may be synthesized in such a way as to be conjugated to another molecule, e.g., a peptide, hybridization triggered cross-linking agent, transport agent, hybridization-triggered cleavage agent, etc.

Various other well-known modifications to the nucleic acid molecules can be introduced as a means of increasing intracellular stability and half-life (see also above for oligonucleotides). Possible modifications are known to the art (see documents cited herein). Modifications, which may be made to the structure of the synthetic RTMs include but are not limited to backbone modifications such as described in the cited RTM technology documents.

Recombinant AAV Molecules

A variety of known nucleic acid vectors may be used in these methods to design and assemble the components of the RTM and the recombinant adeno-associated virus (AAV), intended to deliver the RTM to the target cells. A wealth of publications known to those of skill in the art discusses the use of a variety of such vectors for delivery of genes (see, e.g., Ausubel et al., Current Protocols in Molecular Biology, John Wiley & Sons, New York, 1989; Kay, M. A. et al, 2001 Nat. Medic., 7(1):33 to 40; and Walther W. and Stein U., 2000 Drugs, 60(2):249 to 71). In one embodiment described herein the vector is a recombinant AAV carrying a RTM and driven by a promoter that expresses the RTM in selected target cells of the affected subject. Methods for assembly of the recombinant vectors are well-known (see, e.g., International Patent Publication No. WO 00/15822, published Mar. 23, 2000 and other references cited herein).

In certain embodiments described herein, the RTM(s) carrying the selected gene binding and coding sequences is delivered to the target cells, e.g., photoreceptor cells, in need of treatment by means of an adeno-associated virus vector. Many naturally occurring serotypes of AAV are available. Many natural variants in the AAV capsid exist, allowing identification and use of an AAV with properties specifically suited for ocular cells. AAV viruses may be engineered by conventional molecular biology techniques, making it possible to optimize these particles for cell specific delivery of the RTM nucleic acid sequences, for minimizing immunogenicity, for tuning stability and particle lifetime, for efficient degradation, for accurate delivery to the nucleus, etc.

The expression of the RTMs described herein can be achieved in the selected cells through delivery by recombinantly engineered AAVs or artificial AAV's that contain sequences encoding the desired RTM. The use of AAVs is a common mode of exogenous delivery of DNA as it is relatively non-toxic, provides efficient gene transfer, and can be easily optimized for specific purposes. Among the serotypes of AAVs isolated from human or non-human primates (NHP) and well characterized, human serotype 2 has been widely used for efficient gene transfer experiments in different target tissues and animal models. Other AAV serotypes include, but are not limited to, AAV1, AAV3, AAV4, AAV5, AAV6, AAV7, AAV8 and AAV9. Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9, AAVrh.10, AAV8 bp, AAV7m8 or other known and unknown AAV serotypes. These ITRs or other AAV components may be readily isolated using techniques available to those of skill in the art from an AAV serotype. Such AAV may be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank, PubMed, or the like. See, e.g., WO 2005/033321 or WO2014/124282 for a discussion of various AAV serotypes, which is incorporated herein by reference.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 a useful pseudotyped vector. In another embodiment, the AAV is AAV2/8.

In one embodiment, the vectors useful in preparing the compositions and methods described herein contain, at a minimum, sequences encoding a selected AAV serotype capsid, e.g., an AAV2 capsid, or a fragment thereof. In another embodiment, useful vectors contain, at a minimum, sequences encoding a selected AAV serotype rep protein, e.g., AAV2 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV2 origin. Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

A suitable recombinant adeno-associated virus (AAV) is generated by culturing a host cell which contains a nucleic acid sequence encoding an adeno-associated virus (AAV) serotype capsid protein, or fragment thereof, as defined herein; a functional rep gene; a minigene composed of, at a minimum, AAV inverted terminal repeats (ITRs) and the RTM nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In one embodiment, the rAAV comprises a promoter (or a functional fragment of a promoter). The selection of the promoter to be employed in the rAAV may be made from among a wide number of constitutive or inducible promoters that can express the selected transgene in the desired target cell. See, e.g., the list of promoters identified in International Patent Publication No. WO2014/12482, published Aug. 14, 2014, incorporated by reference herein. In one embodiment, the promoter is "cell specific". The term "cell-specific" means that the particular promoter selected for the recombinant vector can direct expression of the selected transgene in a particular cell or ocular cell type. In one embodiment, the promoter is specific for expression of the transgene in photoreceptor cells. In another embodiment, the promoter is specific for expression in the rods and/or cones. In another embodiment, the promoter is specific for expression of the transgene in RPE cells. In another embodiment, the promoter is specific for expression of the transgene in ganglion cells. In another embodiment, the promoter is specific for expression of the transgene in Mueller cells. In another embodiment, the promoter is specific for expression of the transgene in bipolar cells. In another embodiment, the transgene is expressed in any of the above noted ocular cells.

In another embodiment, promoter is the native promoter for the target ocular gene to be expressed. Useful promoters include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein.

Other conventional regulatory sequences contained in the mini-gene or rAAV are also disclosed in documents such as WO2014/124282 and others cited and incorporated by reference herein. One of skill in the art may make a selection among these, and other, expression control sequences without departing from the scope described herein.

The desired AAV minigene is composed of, at a minimum, the RTM described herein and its regulatory sequences, and 5' and 3' AAV inverted terminal repeats (ITRs). In one embodiment, the ITRs of AAV serotype 2 are used. In another embodiment, the ITRs of AAV serotype 5 or 8 are used. However, ITRs from other suitable serotypes may be selected. It is this minigene which is packaged into the AAV capsid and delivered to a selected host cell.

The minigene, rep sequences, cap sequences, and helper functions required for producing the rAAV may be delivered to the packaging host cell in the form of any genetic element which transfers the sequences carried thereon. The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY. Similarly, methods of generating rAAV virions are well known and the selection of a suitable method is not a limitation on the present invention. See, e.g., K. Fisher et al, 1993 *J. Virol.,* 70:520 to 532 and U.S. Pat. No. 5,478,745, among others. These publications are incorporated by reference herein.

Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the AAV production plasmid carrying the minigene is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the production plasmids are cultured in the host cells which express the cap and/or rep proteins. In the host cells, the minigene consisting of the RTM with flanking AAV ITRs is rescued and packaged into the capsid protein or envelope protein to form an infectious viral particle. Thus a recombinant AAV infectious particle is produced by culturing a packaging cell carrying the proviral plasmid in the presence of sufficient viral sequences to permit packaging of the gene expression cassette viral genome into an infectious AAV envelope or capsid.

The Pharmaceutical Carrier and Pharmaceutical Compositions

The compositions described herein containing the recombinant viral vector, e.g., AAV, containing the desired RTM minigene for use in the selected target cells, e.g., photoreceptor cells for treatment of Stargardt Disease, as detailed above, is preferably assessed for contamination by conventional methods and then formulated into a pharmaceutical composition intended for a suitable route of administration. Still other compositions containing the RTM, e.g., naked DNA or as protein, may be formulated similarly with a suitable carrier. Such formulation involves the use of a pharmaceutically and/or physiologically acceptable vehicle or carrier, particularly directed for administration to the target cell. In one embodiment, carriers suitable for administration to the cells of the eye include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In other embodiments, e.g., compositions containing RTMs described herein include a surfactant. Useful surfactants, such as Pluronic F68 ((Poloxamer 188), also known as Lutrol® F68) may be included as they prevent AAV from sticking to inert surfaces and thus ensure delivery of the desired dose.

As an example, one illustrative composition designed for the treatment of the ocular diseases described herein comprises a recombinant adeno-associated vector carrying a nucleic acid sequence encoding 3'RTM as described herein, under the control of regulatory sequences which express the RTM in an ocular cell of a mammalian subject, and a pharmaceutically acceptable carrier. The carrier is isotonic sodium chloride solution and includes a surfactant Pluronic F68. In one embodiment, the RTM is that described in the examples. In another embodiment, the RTM contains the binding and coding regions for CEP290 or MYO7A.

In yet another exemplary embodiment, the composition comprises a recombinant AAV2/5 pseudotyped adeno-associated virus carrying a 3' or 5' or RTM for internal gene replacement, the nucleic acid sequence under the control of promoter which directs expression of the RTM in the target cells, wherein the composition is formulated with a carrier and additional components suitable for injection.

In still another embodiment, the composition or components for production or assembly of this composition, including carriers, rAAV particles, surfactants, and/or the components for generating the rAAV, as well as suitable laboratory hardware to prepare the composition, may be incorporated into a kit.

Methods of Treating Disorders

The compositions described above are thus useful in methods of treating one or more of the diseases associated with a selected gene. In one embodiment, the disease is an ocular disease (e.g., Stargardt Disease, Lebers Congenital Amaurosis, cone rod dystrophy, fundus flavimaculatus, retinitis pigmentosa, age-related macular degeneration, Senior Løken syndrome, Joubert syndrome, or Usher Syndrome, among others). Treatment, in one embodiment, includes delaying or ameliorating symptoms associated with the ocular diseases described herein. Such methods involve contacting a target pre-mRNA (e.g., ABCA4, CEP290, MYO7A) with one or more of a 3'RTM, 5' RTM, both 3' and 5' RTM or a double trans-splicing RTM as described herein, under conditions in which a portion of the RTM is spliced to the target pre-mRNA to replace all or a part of the targeted gene carrying one or more defects or mutations, with a "healthy", or normal or wildtype or corrected mRNA of the targeted gene, in order to correct expression of that gene in the target cell. Alternatively, a pre-miRNA (see the RTM documents cited herein) can be formed, which is designed to reduce the expression of a target mRNA. Thus, the methods and compositions are used to treat the ocular diseases/pathologies associated with the specific mutations and/or gene expression.

In one embodiment, the contacting involves direct administration to the affected subject; in another embodiment, the contacting may occur ex vivo to the cultured cell and the treated cell reimplanted in the subject. In one embodiment, the method involves administering a rAAV particle carrying a 3' RTM. In another embodiment, the method involves administering a rAAV particle carrying a 5' RTM. In another embodiment, the method involves administering a rAAV particle carrying a double trans-splicing RTM. In still another embodiment, the method involves administering a mixture of rAAV particle carrying a 3' RTM and rAAV particle carrying a 5' RTM. In still another embodiment, the method involves administering a mixture of rAAV particle carrying a 3' RTM and an rAAV particle carrying a double trans-splicing RTM. In still another embodiment, the method involves administering a mixture of rAAV particle carrying a 5' RTM and an rAAV carrying a double trans-splicing RTM. In still another embodiment, the method involves administering a mixture of an rAAV particle carrying a 3' RTM, with an rAAV particle carrying a 5' RTM and an rAAV particle carrying a double trans-splicing RTM.

These methods comprise administering to a subject in need thereof subject an effective concentration of a composition of any of those described herein. In one illustrative embodiment, such a method is provided for preventing, arresting progression of or ameliorating vision loss associated with Stargardt Disease in a subject, said method comprising administering to an ocular cell of a mammalian subject in need thereof an effective concentration of a composition comprising a recombinant adeno-associated virus (AAV) carrying a 3'RTM such as described above and in the examples, under the control of regulatory sequences which permit the RTM to function and cause trans-splicing of the defective targeted gene in an ocular cell, e.g., photoreceptor cell, of a mammalian subject. In still another embodiment, the method involves administering two rAAV particles, one carrying a 5' RTM and the other carrying the 3'RTM, such as those RTMs described in the examples to replace large portions of large genes.

By "administering" as used in the methods means delivering the composition to the target selected cell which is characterized by the disease caused by a mutation or defect in the targeted gene. For example, in one embodiment, the method involves delivering the composition by subretinal injection to the photoreceptor cells or other ocular cells. In another embodiment, intravitreal injection to ocular cells or injection via the palpebral vein to ocular cells may be employed. In another embodiment, the method involves delivering the composition by direct injection to the organ indicated, e.g., liver. In yet another embodiment, the method involves delivering the composition by intravenous injection. Still other methods of administration may be selected by one of skill in the art given this disclosure.

Furthermore, in certain embodiments, it is desirable to perform non-invasive retinal imaging and functional studies to identify areas of retained photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc. In view of the imaging and functional studies, in some embodiments one or more injections are performed in the same eye in order to target different areas of retained photoreceptors.

For use in these methods, the volume and viral titer of each injection is determined individually, as further described below, and may be the same or different from other injections performed in the same subject. In another embodiment, a single, larger volume injection is made in order to treat the entire eye. The dosages, administrations and regimens may be determined by the attending physician given the teachings of this specification.

In one embodiment, the volume and concentration of the rAAV composition is selected so that only the certain regions of photoreceptors or other ocular cell is impacted. In another embodiment, the volume and/or concentration of the rAAV composition is a greater amount, in order reach larger portions of the eye. Similarly dosages are adjusted for administration to other organs.

An effective concentration of a recombinant adeno-associated virus carrying a RTM as described herein ranges between about $10^8$ and $10^{13}$ vector genomes per milliliter (vg/mL). The rAAV infectious units are measured as described in S. K. Mclaughlin et al, 1988 *J. Virol.,* 62:1963. In another embodiment, the concentration ranges between $10^9$ and $10^{13}$ vector genomes per milliliter (vg/mL). In another embodiment, the effective concentration is about $1.5\times10^{11}$ vg/mL. In one embodiment, the effective concentration is about $1.5\times10^{10}$ vg/mL. In another embodiment, the effective concentration is about $2.8\times10^{11}$ vg/mL. In yet another embodiment, the effective concentration is about $1.5\times10^{12}$ vg/mL. In another embodiment, the effective concentration is about $1.5\times10^{13}$ vg/mL. It is desirable that the lowest effective concentration of virus be utilized in order to reduce the risk of undesirable effects, such as toxicity, and other issues related to administration to the eye, e.g., retinal dysplasia and detachment. Still other dosages in these ranges or in other units may be selected by the attending physician, taking into account the physical state of the subject, preferably human, being treated, including the age of the subject; the composition being administered and the particular disorder; the targeted cell and the degree to which the disorder, if progressive, has developed.

The composition may be delivered in a volume of from about 50 μL to about 1 mL, including all numbers within the range, depending on the size of the area to be treated, the viral titer used, the route of administration, and the desired effect of the method. In one embodiment, the volume is about 50 μL. In another embodiment, the volume is about 70 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 250 μL. In another embodiment, the volume is about 300 μL. In another embodiment, the volume is about 450 μL. In another embodiment, the volume is about 500 μL. In another embodiment, the volume is about 600 μL. In another embodiment, the volume is about 750 μL. In another embodiment, the volume is about 850 L. In another embodiment, the volume is about 1000 μL.

The examples that follow do not limit the scope of the embodiments described herein. One skilled in the art will appreciate that modifications can be made in the following examples which are intended to be encompassed by the spirit and scope of the invention.

Example 1: Splicing Dependent Reporter RTM

Figure 1F:
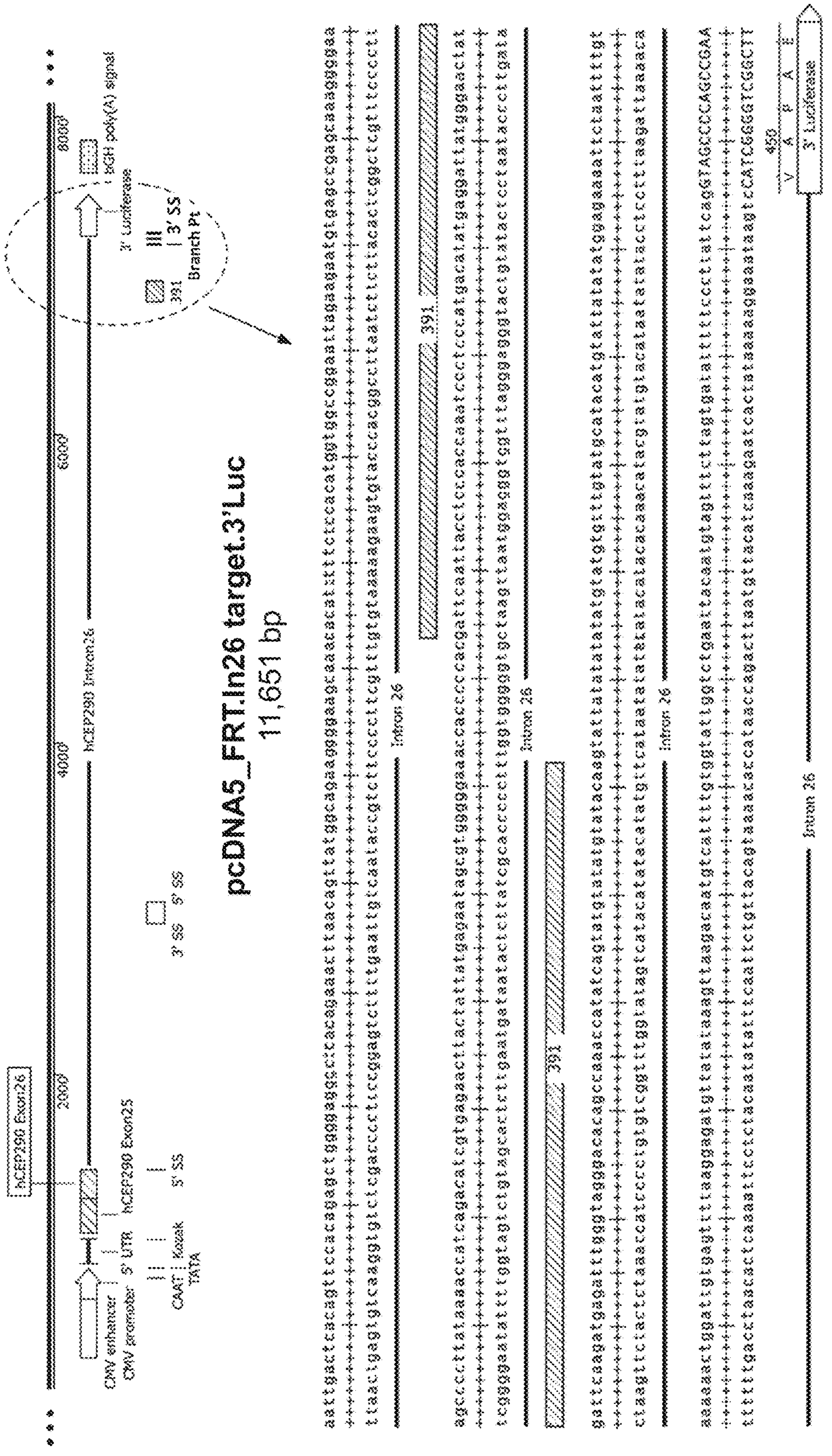
FIG. 1F shows a map and a sequence of a minigene that contains Intron26 from human CEP290 fused to the 3' half of the luciferase CDS.
Figure 2A:
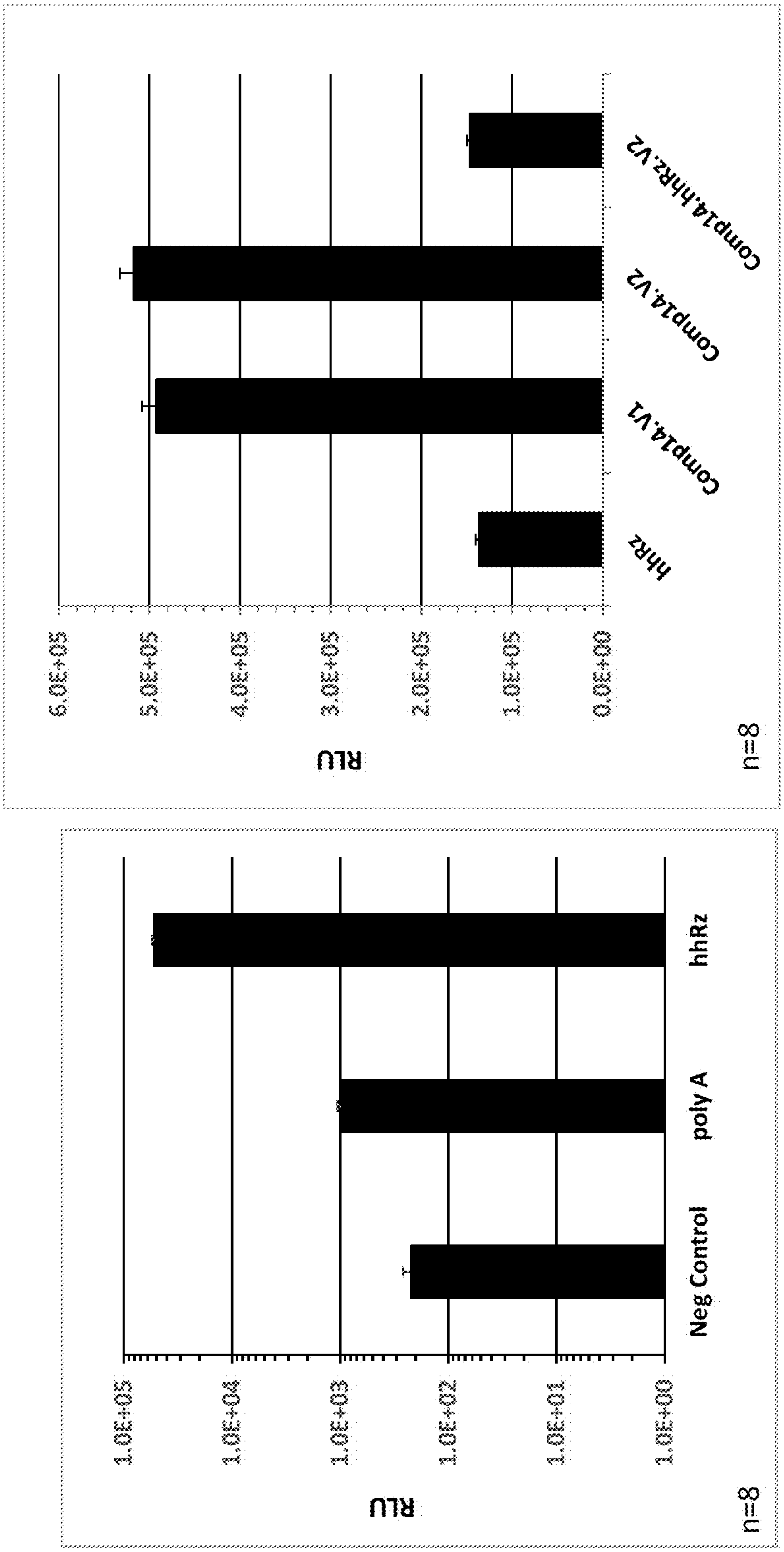
FIGS. 2A and 2B shows luciferase levels that were measured for the constructs described in FIG. 1A-1D, as discussed in Example 1. The RTM is delivered to a cell line that expresses a minigene that contains Intron26 from human CEP290 fused to the 3' half of the luciferase CDS shown in FIG. 1F.

The RTMs shown in FIGS. 1A-1D were delivered delivered to a cell line that expresses a minigene (FIG. 1F) that contains Intron26 from CEP290 fused to the 3' half of luciferase ORF. The RTM binds (via the binding domain) to the target sequence in Intron26, bringing the 5' splice site (5' SS) in the RTM in proximity to the 3' splice site (3' SS) of the CEP290 minigene. Spliceosome mediated splicing occurs, yielding luciferase expression as a direct measure of trans-splicing activity (FIG. 2A). Two reference RTMs that contain either a polyadenylation signal (polyA) or hammerhead ribozyme (hhRz) constitute prior art for transcription termination elements, and serve here to establish a baseline of activity. The data suggests the Comp14 derivative of the MALAT1 transcription terminator enhances trans-splicing relative to the reference RTM that contains a hhRz for transcription termination. Furthermore, this activity appears to be dependent on the mascRNA domain and its associated RNaseP cleavage. Evidenced by a loss of activity when the mascRNA domain is replaced with the hhRz.

Figure 2B:
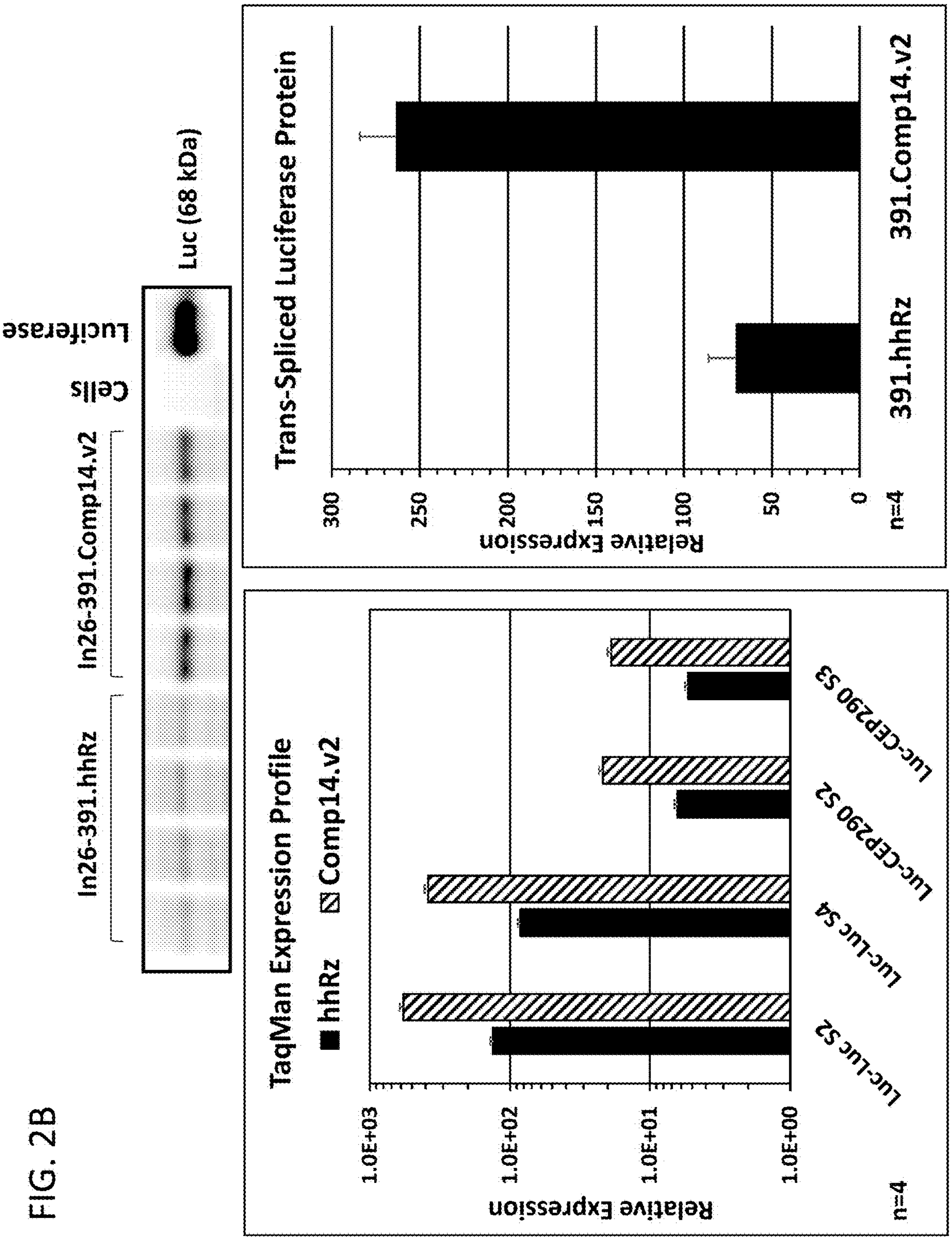

In FIG. 2B the experiment was designed to measure luciferase RNA and protein by TaqMan and Western blotting, respectively. N=4 experimental replicates were tested for each construct, revealing an increase in luciferase protein when the hhRz was replaced with the Comp14 Malat1 derivative, consistent with luciferase activity shown in FIG. 2A. TaqMan analysis of RNA extracted from treated cells showed a similar increase in trans-spliced luciferase RNA when the RTM contained the Comp14 derivative of the Malat1 terminator, according to two different primer-probe sets (S2 and S4). Because the RTM in these studies used a binding domain that targets Intron26 of the CEP290 gene, it was also possible to measure RTM trans-splicing activity against the endogenous CEP290 transcript. As shown in FIG. 2B, the RTM that carries the Comp14 derivative of the Malat1 terminator generated higher levels of the chimeric Luc-CEP290 RNA compared to an RTM with the hhRz terminator, according to two different TaqMan primer-probe sets (S2 and S3).

Example 2: Comparison of 3' Terminator Sequences

Figure 3A:
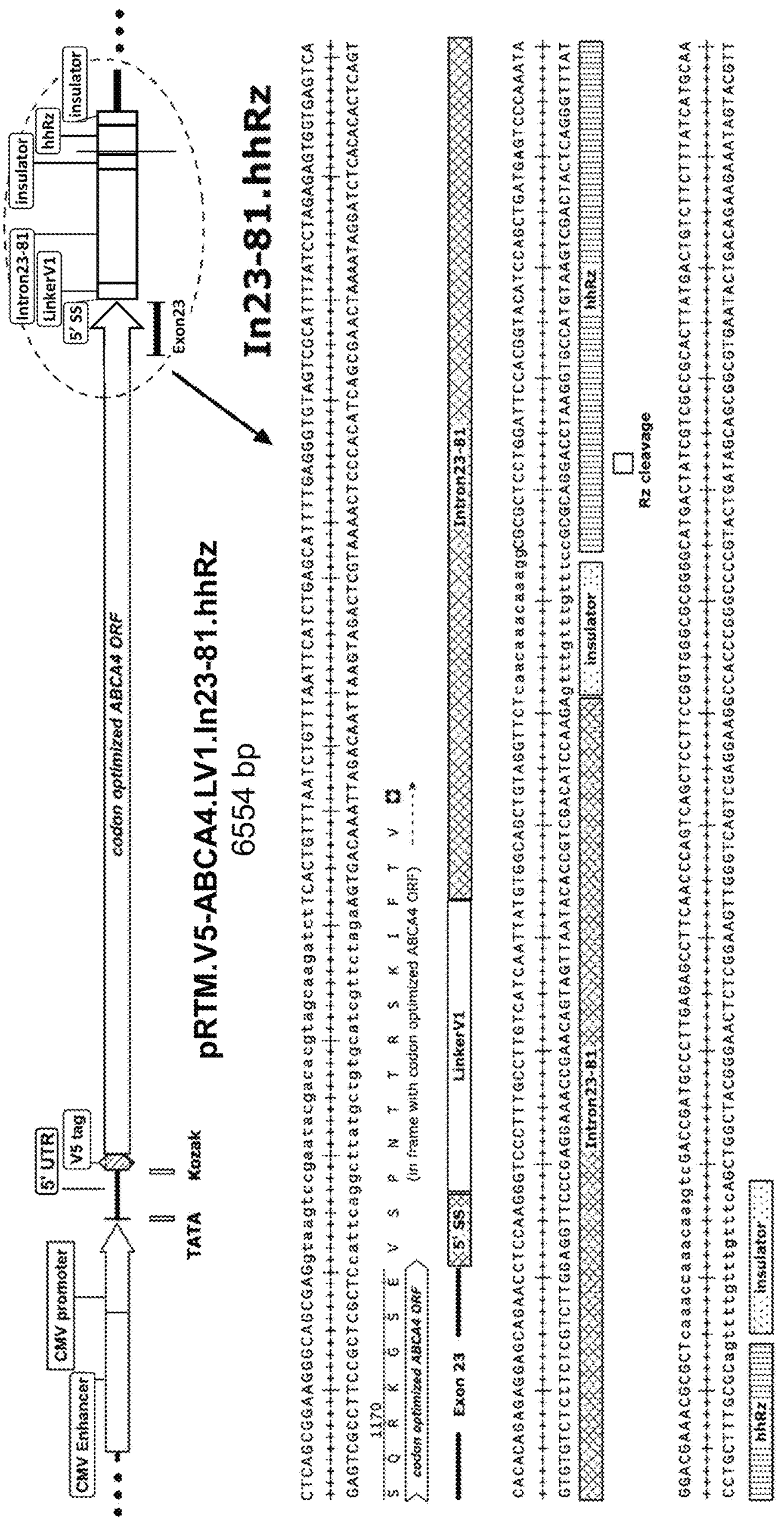
FIGS. 3A-3C show a map and partial sequence of RTM constructs that target Intron23 of human ABCA4. They include one of several terminator sequences that were tested for ABCA4 trans-splicing activity: hhz—hammerhead Ribozyme, which self cleaves to create 3' terminal end of RTM (FIG. 3A); C14 or Comp14—a truncated derivative of the MALAT1 triple helix structure, which creates 3' terminal end of RTM following RNase P cleavage (FIG. 3B); and wt—native MALAT1 triple helix terminator, which creates 3' terminal end of RTM following RNase P cleavage (FIG. 3C).
Figure 3B:
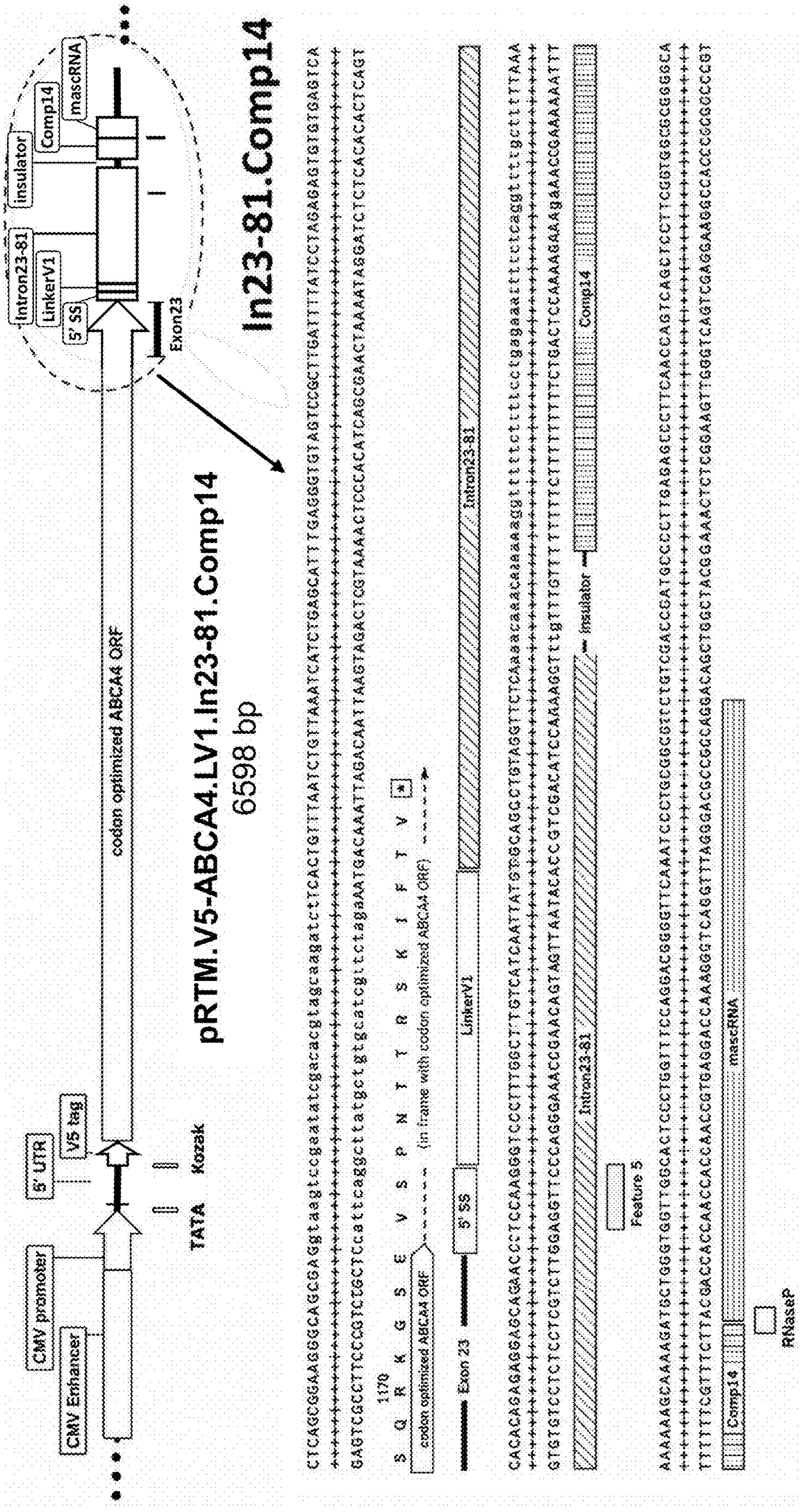
Figure 3C:
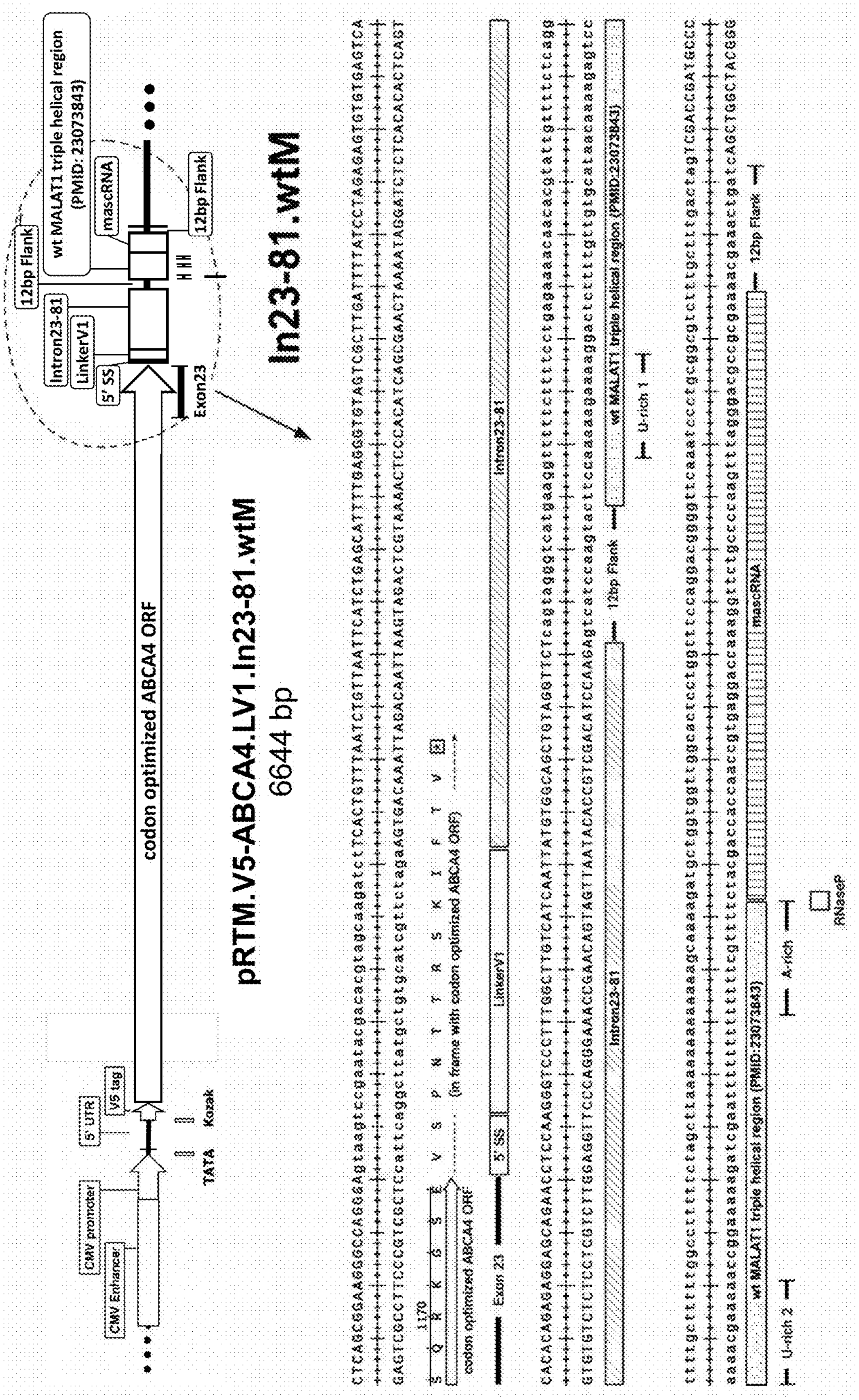

RTM constructs were made which several terminator sequences were tested for ABCA4 expression: hhz—hammerhead Ribozyme, which self cleaves to create 3' terminal end of RTM (FIG. 3A); C14 or Comp14—a truncated MALAT1 triple helix structure (SEQ ID NO: 12), which creates 3' terminal end of RTM following RNase P cleavage (FIG. 3B); and wt—native MALAT1 triple helix, which creates 3' terminal end of RTM following RNase P cleavage (FIG. 3C).

Figure 4A:
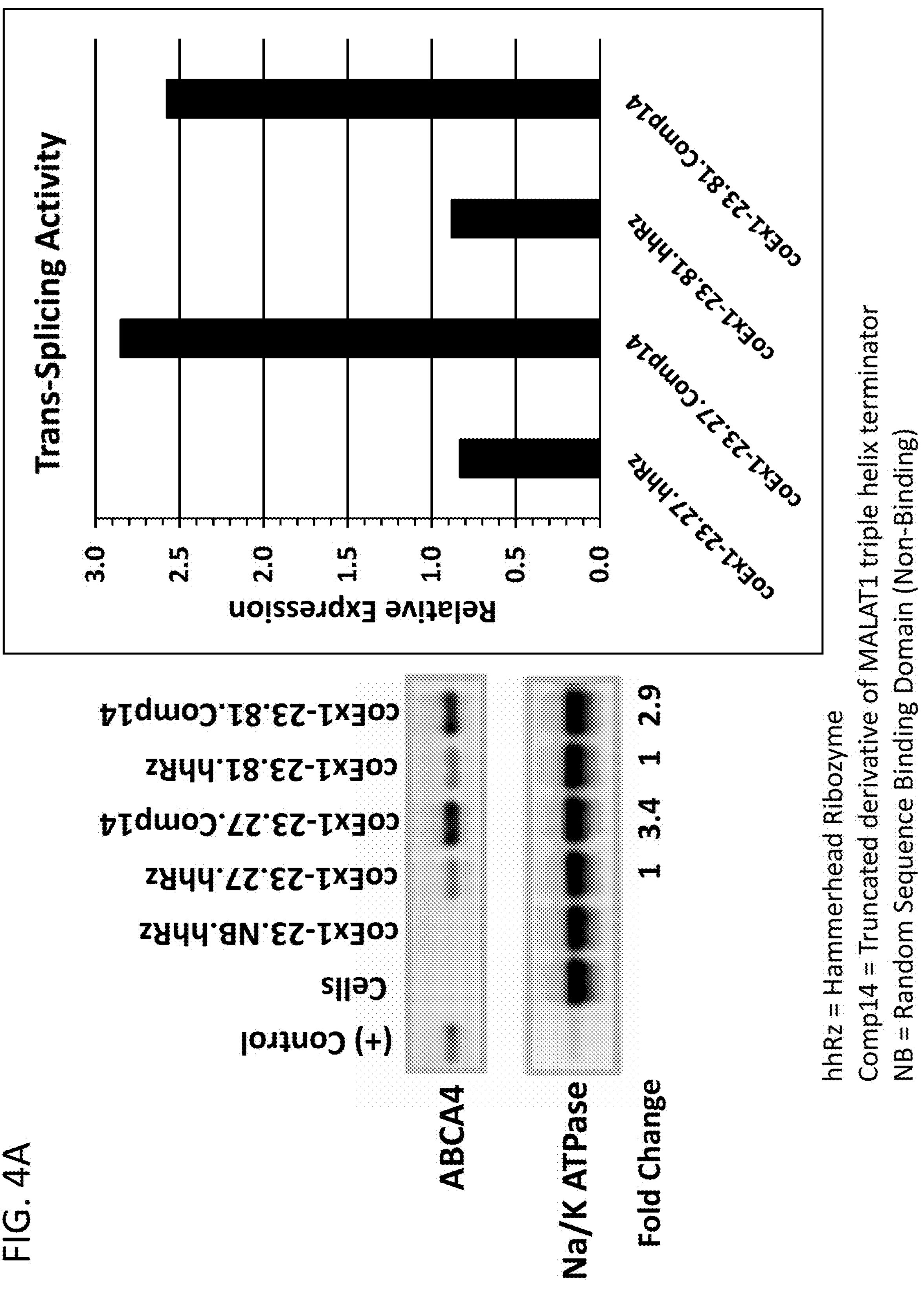
Figure 4C:
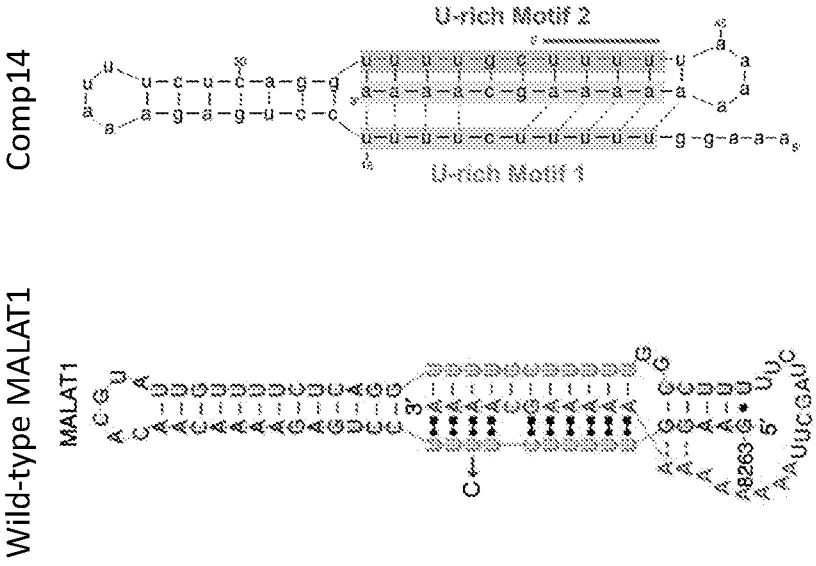
FIG. 4C shows the predicted base-pairing of the wild-type MALAT1 triple helix terminator and the Comp14 derivative.

FIGS. 4A and 4B are Western blots, and quantitation thereof, showing ABCA4 protein generated by RTM-mediated trans-splicing. RTMs of FIG. 3 that were tested include binding domains for ABCA4 intron23 (motifs 27 and 81) and intron22 (motifs 117 and 118). NB is a negative control Non-Binding motif. The data in FIG. 4A shows a marked increase in ABCA4 protein when the hhRz terminator was replaced with the Comp14 derivative. In FIG. 4B the Comp14 derivative was compared to the wild-type MALAT1 triple helix terminator, revealing an even greater increase in trans-splicing activity with the latter, ranging from 5-10 fold depending on the binding domain. In FIG. 4C the predicted base-pairing of the wild-type MALAT1 triple helix terminator and the Comp14 derivative is shown. In their design of the Comp14 derivative, Wilusz et al. suggested it should have the same base-pairing characteristics between the A-rich and U-rich domains as the wild-type MALAT1 sequence, yet with truncated flanking stem-loop domains. However, this assumption ignores the possible role of the flanking stem-loops for proper base-pairing, and could explain the lower ENE activity of Comp14 compared to the wild-type MALAT1 triple helix terminator. The higher levels of trans-splicing activity seen with the wild-type MALAT1 sequence compared to the Comp14 derivative demonstrates an important characteristic of the triple helix terminator structure and ENE function.

FIG. 5A shows Western blot analysis of RTMs containing different triple helix terminators from lncRNAs. They include the wild-type sequence from MALAT1 and NEAT1 (MENβ), as well as chimeric forms where the triple helix domain from MALAT1 was fused to the tRNA-like motif from NEAT1 (called menRNA) and one where the triple helix domain from NEAT1 was fused to the mascRNA motif from MALAT1. The data suggests trans-splicing activity is highest when an RTM contains the wild-type MALAT1 terminator.

FIG. 5B shows the predicted base-pairing for triple helix terminators from three different lncRNAs, including MALAT1, MENβ (NEAT1), and PAN RNA (produced from the Kaposi's sarcoma-associated herpesvirus, KSHV). The structural similarity across distinct lncRNAs suggests a common evolutionary strategy for protecting the 3' end of the lncRNA following transcription termination. However, X-ray crystallography of the MALAT1 triple helix domain revealed it contains 10 major groove and 2 minor groove triples, the most of any known naturally occurring triple helical structure (Brown, J. A. et al. 2014). This intricate design likely confers a level of structural stability that is greater than either NEAT1 or PAN, and could explain why the MALAT1 terminator appears to better support trans-splicing. By way of protecting the RTM from degradation in the nucleus. Importantly, the blunt-ended triple helix of MALAT1 has been shown to inhibit rapid nuclear RNA decay as shown by in vivo decay assays (Brown, J. A. 2014).

Figure 6A:
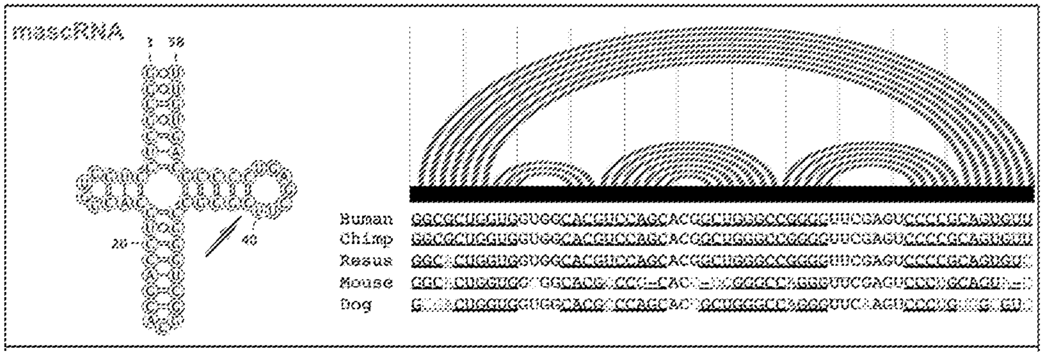
FIG. 6A shows the highly conserved mascRNA sequence of MALAT1 from several species and it's predicted folded conformation. A single G-to-A point mutation, indicated by the arrow, was inserted into the mascRNA sequence to test the importance of this domain for trans-splicing activity. As shown in the Western blot (FIG. 6B), the point mutation ablated trans-splicing activity of a validated RTM that targets ABCA4. Possibly due to the inability of the mutated sequence to assume the correct conformation required for RNaseP recognition and cleavage.
Figure 6B:
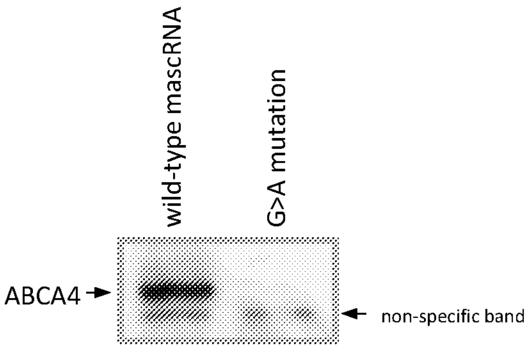
Figure 7:
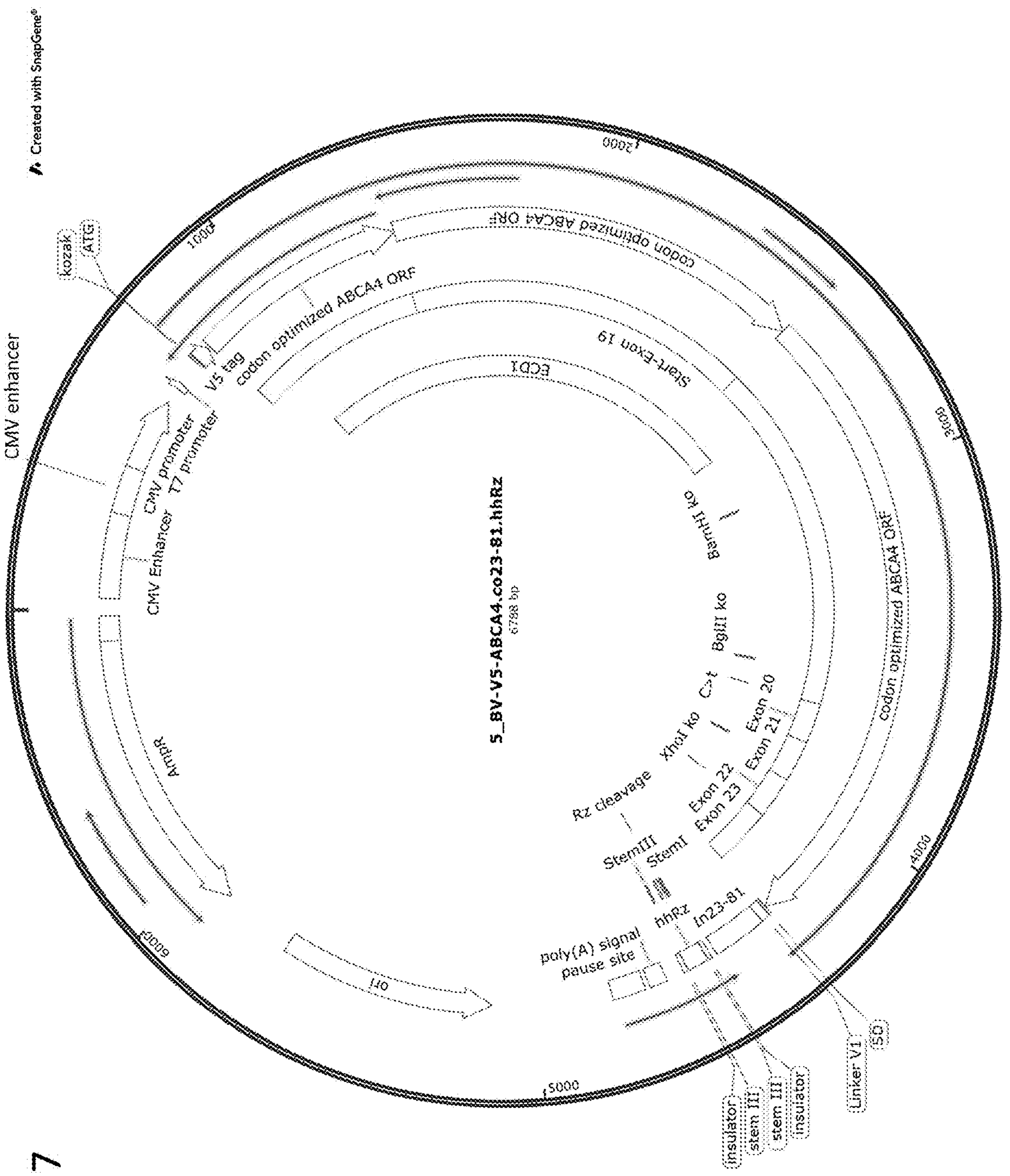
FIG. 7 shows a vector map of a vector which includes codon-optimized ABCA4 coding sequence and hammerhead ribozyme (hhRz). The sequence is shown in SEQ ID NO: 28.
Figure 8:
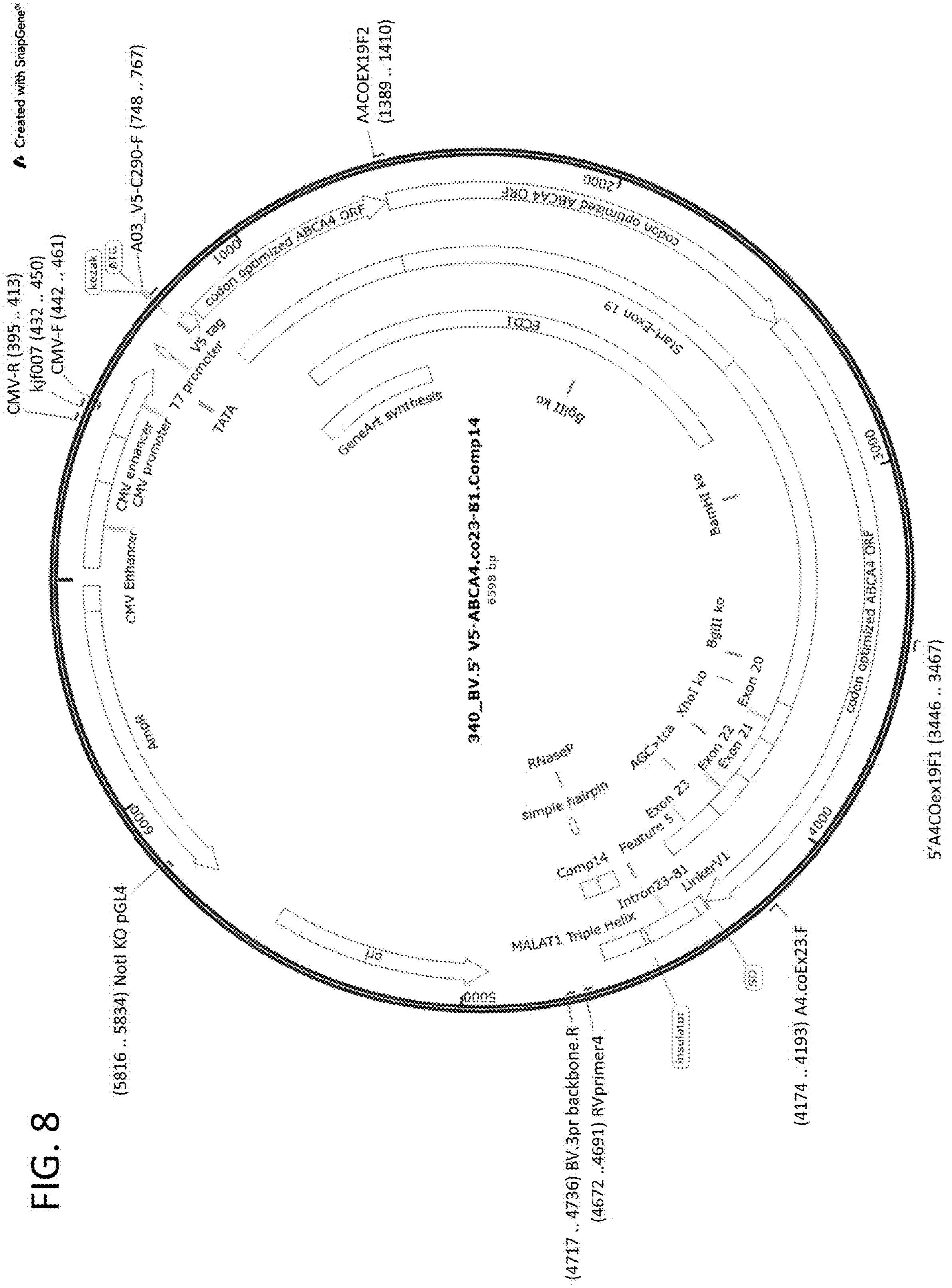
FIG. 8 shows a vector map of a vector which includes codon-optimized ABCA4 coding sequence, MALAT1, for codons 1-23 and the truncated MALAT1 Comp14 3'TTD sequences. The sequence is shown in SEQ ID NO: 29.
Figure 9:
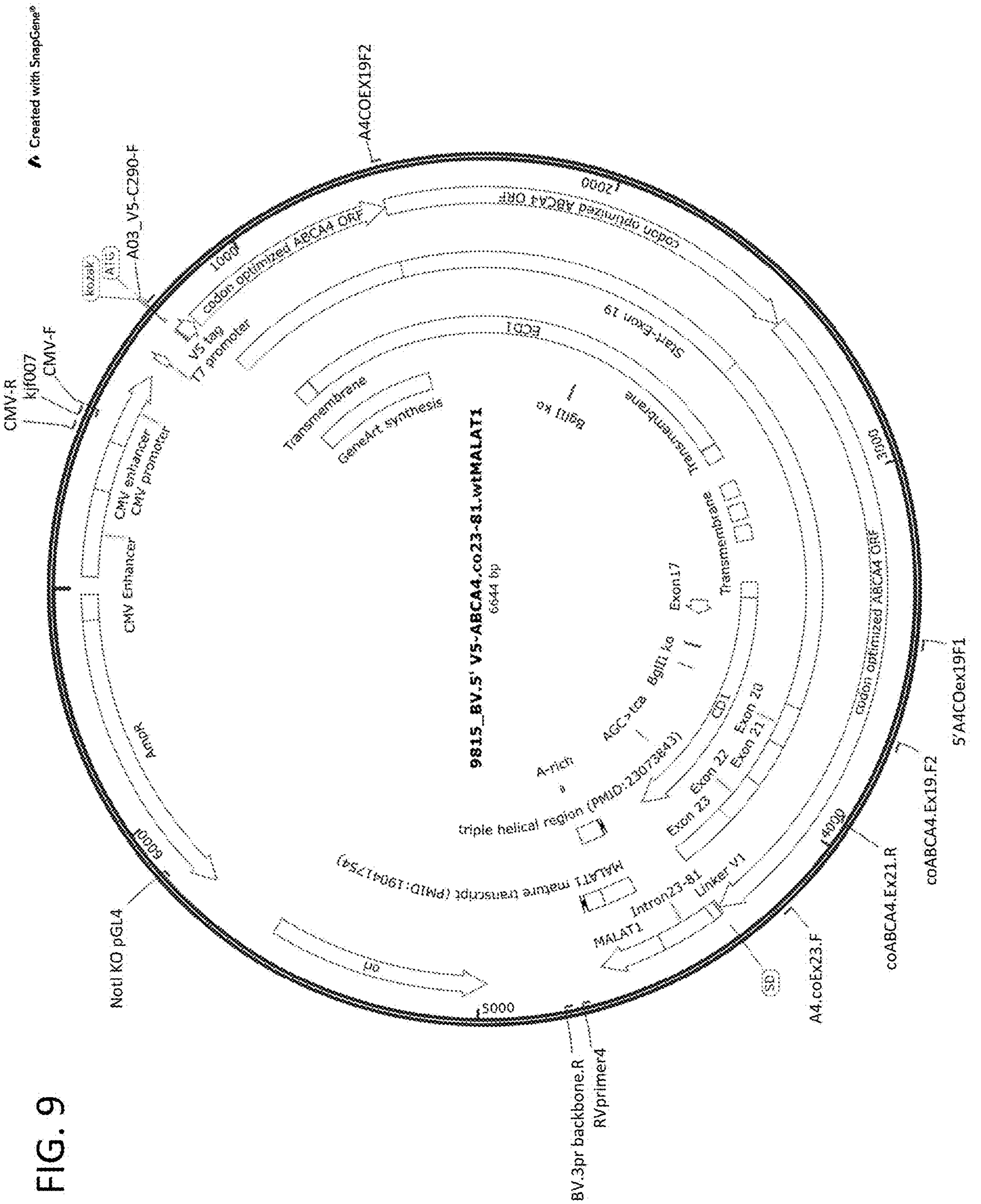
FIG. 9 shows a vector map of a vector which includes codon-optimized ABCA4 coding sequence, MALAT1, for codons 1-23 and the wt MALAT1 3'TTD sequences. The sequence is shown in SEQ ID NO: 30.
Figure 10:
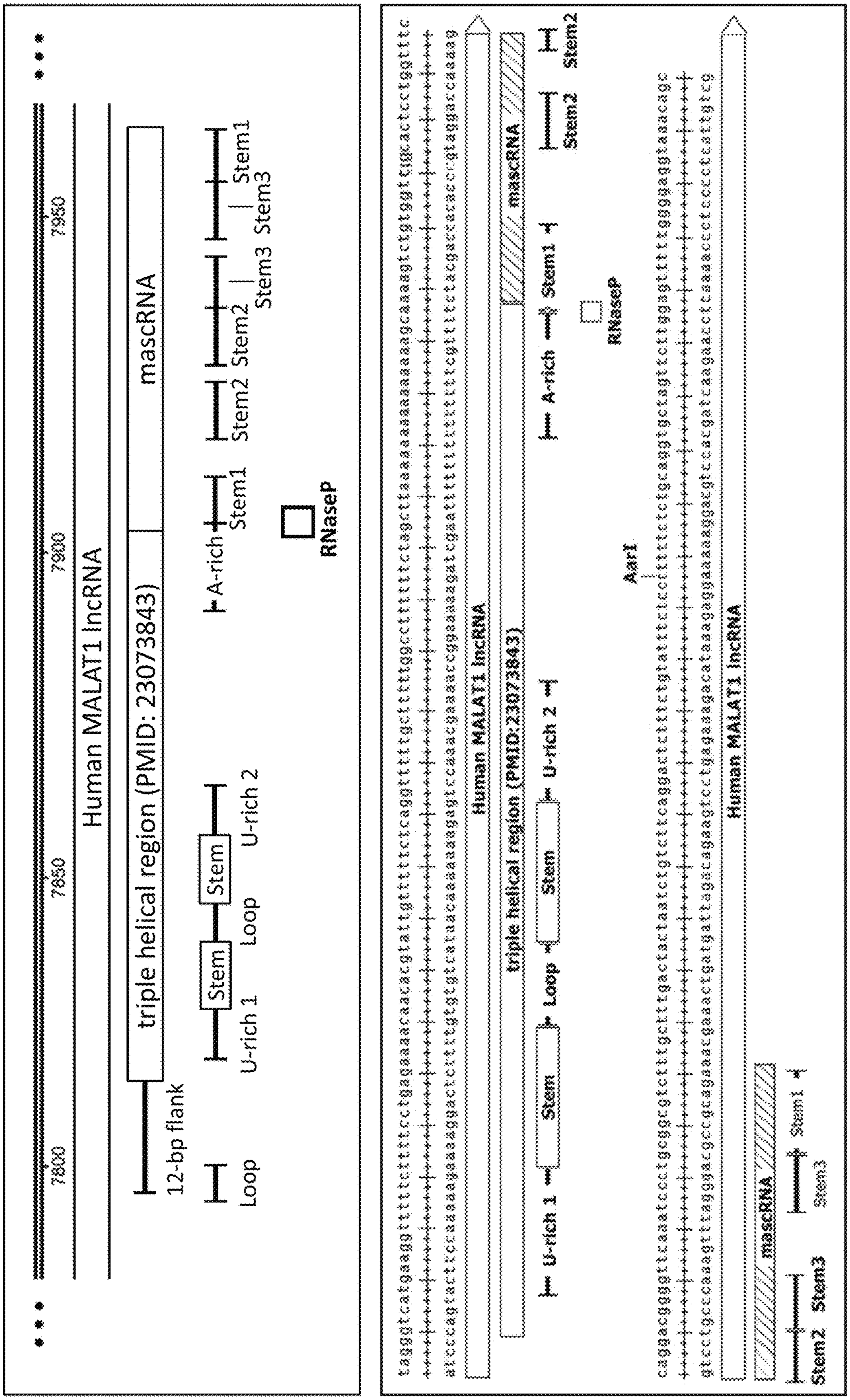
FIG. 10 shows a map and sequence of the triple helix region from the human MALAT1 lncRNA. The sequence of MALAT1 is shown in SEQ ID NO: 7. The triple helical region begins at 8287 of SEQ ID NO: 7 and the mascRNA ends at 8437 of SEQ ID NO: 7.

FIG. 6A shows the highly conserved mascRNA sequence of MALAT1 from several species and it's predicted folded conformation. A single G-to-A point mutation, indicated by the red arrow, was inserted into the mascRNA sequence to test the importance of this domain for trans-splicing activity. As shown in the Western blot (FIG. 6B), the point mutation ablated trans-splicing activity of a validated RTM that targets ABCA4. Possibly due to the inability of the mutated sequence to assume the correct conformation required for RNaseP recognition and cleavage.

The following additional numerated paragraphs further define some embodiments of the invention described herein.

1. A nucleic acid trans-splicing molecule comprising a 3' transcription terminator domain (TTD), which comprises a triple helix.

2. The nucleic acid trans-splicing molecule of embodiment 1, wherein the triple helix comprises at least five consecutive A-U Hoogsteen base pairs.

3. The nucleic acid trans-splicing molecule of embodiment 1 or 2, wherein the triple helix comprises an A-rich tract of 5-30 nucleic acids.

4. The nucleic acid trans-splicing molecule of embodiment 3, wherein the A-rich tract is at the 3' end of the TTD.

5. The nucleic acid trans-splicing molecule of any one of embodiments 1-4, wherein the triple helix comprises a strand of 10 consecutive nucleotides, wherein 9 of the 10 consecutive nucleotides are paired via Hoogsteen base pairing.

6. The nucleic acid trans-splicing molecule of any one of embodiments 1-5, wherein the TTD comprises a stem-loop motif.

7. The nucleic acid trans-splicing molecule of any one of embodiments 1-6, wherein the 3' TTD comprises, operatively linked in a 5'-to-3' direction, a 5' U-rich motif, a stem-loop motif, a 3' U-rich motif, and an A-rich tract.

8. The nucleic acid trans-splicing molecule of any one of embodiments 1-4, wherein the 3' TTD is at least 95% homologous with SEQ ID NO: 13, SEQ ID NO: 15, SEQ ID NO: 17, or SEQ ID NO: 23.

9. The nucleic acid trans-splicing molecule of embodiment 8, wherein the 3' TTD is at least 95% homologous with SEQ ID NO: 13, and wherein the triple helix comprises Hoogsteen base pairing of U7-U11 of SEQ ID NO: 13 with an A-rich tract.

10. The nucleic acid of embodiment 9, wherein the 3' TTD is the PAN ENE+A.

11. The nucleic acid trans-splicing molecule of any one of embodiments 1-8, wherein the 3' TTD is at least 95% homologous with SEQ ID NO: 15, and wherein the triple helix comprises Hoogsteen base pairing of U6-10, C11, and U12-15 of SEQ ID NO: 15 with an A-rich tract.

12. The nucleic acid of embodiment 11, wherein the 3' TTD is the MALAT1 ENE+A.

13. The nucleic acid trans-splicing molecule of embodiment 8, wherein the 3' TTD is at least 95% homologous with SEQ ID NO: 17, and wherein the triple helix comprises Hoogsteen base pairing of U6-10, C11, and U12-15 of SEQ ID NO: 17 with an A-rich tract.

14. The nucleic acid of embodiment 13, wherein the 3' TTD is the MALAT1 core ENE+A.

15. The nucleic acid trans-splicing molecule of embodiment 8, wherein the 3' TTD is at least 95% homologous with SEQ ID NO: 23, and wherein the triple helix comprises Hoogsteen base pairing of U8-10, C11, and U12-15 of SEQ ID NO: 23 with an A-rich tract.

16. The nucleic acid trans-splicing molecule of embodiment 15, wherein the 3' TTD is the MENβ ENE+A.

17. A nucleic acid trans-splicing molecule comprising, operatively linked in a 5'-to-3' direction:

(a) a coding domain sequence (CDS) comprising one or more functional exon(s) of a selected gene;

(b) a linker domain sequence (LDS) of varying length that acts as a structural connection between the coding domain and the binding domain, (c) a spliceosome recognition motif (5' Splice Site) configured to initiate spliceosome-mediated trans-splicing;

(d) a binding domain (BD) of varying length and sequence configured to hybridize to a target intron of the selected gene, wherein said gene has at least one defect or mutation in an exon 5' to the target intron; and (e) a 3' transcription terminator domain (TTD) that increases the efficiency of trans-splicing, wherein the nucleic acid trans-splicing molecule is configured to trans-splice the coding domain to an endogenous exon of the selected gene adjacent to the target intron, thereby replacing the endogenous defective or mutated exon with the functional exon and correcting a mutation in the selected gene.

18. The nucleic acid trans-splicing molecule of embodiment 17, wherein the binding domain hybridizes to the target intron of the selected gene 3' to the mutation and the coding domain comprises one or more exon(s) 5' to the target intron.

19. A nucleic acid trans-splicing molecule comprising, operatively linked in a 5'-to-3' direction:

(a) a binding domain (BD) configured to bind a target intron of a selected gene, wherein said gene has at least one defect or mutation in an exon 3' to the targeted intron;

(b) a linker sequence of varying length and composition that acts as a structural connection between the binding domain the coding region;

(c) a 3' spliceosome recognition motif (3' Splice Site) configured to mediate trans-splicing;

(d) a coding domain sequence (CDS) comprising one or more functional exon(s) of the selected gene; and (e) a 3' transcription terminator domain (TTD) that increases the efficiency of trans-splicing, wherein the nucleic acid trans-splicing molecule is configured to trans-splice the coding domain to an endogenous exon of the selected gene adjacent to the target intron, thereby replacing the endogenous defective or mutated exon with the functional exon and correcting a mutation in the selected gene.

20. The nucleic acid trans-splicing molecule of embodiment 19, wherein the binding domain binds to the target intron of the selected gene 5' to the mutation and the coding domain comprises one or more exon 3' to the target intron.

21. The nucleic acid trans-splicing molecule of any one of embodiments 17-20, wherein the 3' transcription terminator domain forms a triple helical structure that effectively caps the 3' end.

22. The nucleic acid trans-splicing molecule of any one of embodiments 1-21, wherein the 3' transcription terminator domain is a sequence from one or more long non-coding RNAs (lncRNA) or other nuclear RNA molecules that contain a 3' transcription terminator that condenses into a triple helix blund-ended structure.

23. The nucleic acid trans-splicing molecule of any one of embodiments 17-22, wherein the 3' transcription terminator domain is from the human long non-coding RNA MALAT1.

24. The nucleic acid trans-splicing molecule of embodiment 23, wherein the 3' transcription terminator domain comprises nucleotides 8287-8437 of SEQ ID NO: 7.

25. The nucleic acid trans-splicing molecule of embodiment 23, wherein the 3' transcription terminator domain comprises, in order from 5' to 3', a triplex forming sequence that comprises nucleotides 8287-8379 of SEQ ID NO: 7, an RNaseP cleavage site the comprises nucleotides 8379-8380 of SEQ ID NO: 7, and a tRNA-like sequence that comprises nucleotides 8380-8437 of SEQ ID NO: 7.

26. The nucleic acid trans-splicing molecule of embodiment 23, wherein the 3' transcription terminator domain contains a triplex forming sequence comprised of a U-rich motif 1 at nucleotides 8292-8301 of SEQ ID NO: 7, a conserved stem-loop at nucleotides 8302-8333 of SEQ ID NO: 7, a U-rich motif 2 at nucleotides 8334-8343 of SEQ ID NO: 7, and an A-rich tract at nucleotides 8369-8379 of SEQ ID NO: 7, wherein the A-rich tract and the U-rich motif 2 form a Watson-Crick stem duplex, and the U-rich motif 1 aligns with the A-rich tract to form Hoogsteen base pairs.

27. The nucleic acid trans-splicing molecule of embodiment 23, wherein the 3' transcription terminator domain is a truncated version of the human MALAT1 triple helix.

28. The nucleic acid trans-splicing molecule of embodiment 27, wherein the 3' transcription terminator domain contains a triplex forming sequence comprised of a U-rich motif 1 at nucleotides 8292-8301 of SEQ ID NO: 7, a conserved stem-loop at nucleotides 8302-8310 and 8325-8333 of SEQ ID NO: 7, a U-rich motif 2 at nucleotides 8334-8343 of SEQ ID NO: 7, an A-rich tract at nucleotides 8369-8379 of SEQ ID NO: 7, and a deletion spanning nucleotide 8345-8364 of SEQ ID NO: 7 in the intervening sequence between U-rich motif 2 and the A-rich tract, wherein the A-rich tract and the U-rich motif 2 form a Watson-Crick stem duplex, and the U-rich motif 1 aligns with the A-rich tract to form Hoogsteen base pairs.

29. The nucleic acid trans-splicing molecule of embodiment 27, wherein the 3' transcription terminator domain comprises, in order from 5' to 3', a triplex forming sequence of varying length and composition, an RNaseP cleavage site, and a tRNA-like sequence of varying length and composition.

30. The nucleic acid trans-splicing molecule of embodiment 27, wherein the 3' transcription terminator domain contains a triplex forming sequence that conforms to one of three known basic “motifs”, and are referred to by the base composition of the third strand of the triple helix: pyrimidine motif (T,C), purine motif (G,A), and purine-pyrimidine motif (G,T).

31. The nucleic acid trans-splicing molecule of embodiment 22, wherein the 3' transcription terminator domain comprises a triple helix domain and a tRNA-like domain.

32. The nucleic acid trans-splicing molecule of embodiment 31, wherein the triple helix domain and the tRNA-like domain originate from the same long non-coding RNA or different combinations of long non-coding RNA domains derived from human or any other species.

33. The nucleic acid trans-splicing molecule of embodiment 31, wherein the triple helix domain and the tRNA-like domain are from MALAT1 or NEAT1/MENβ.

34. The nucleic acid trans-splicing molecule of any one of embodiments 17-33, wherein the targeted mammalian gene is ABCA4, CEP290, or MYO7A.

35. The nucleic acid trans-splicing molecule of any one of embodiments 17-34, wherein the gene is ABCA4 and the defect or mutation is in any of Exons 1-23.

36. The nucleic acid trans-splicing molecule of any one of embodiments 1-35, further comprising one or more linker sequences.

37. The nucleic acid trans-splicing molecule of embodiment 36, comprising a linker between the splicing domain and binding domain.

38. The nucleic acid trans-splicing molecule of embodiment 36 or 37, comprising a linker between the binding domain and 3' transcription terminal domain.

39. A recombinant adeno-associated virus (rAAV) comprising the nucleic acid molecule of any one of embodiments 1-38.

40. The rAAV of embodiment 39, wherein the AAV preferentially targets a photoreceptor cell.

41. The rAAV of embodiment 39 or 40, wherein the AAV comprises an AAV5 capsid protein, an AAV8 capsid protein, an AAV8 (b) capsid protein, or an AAV9 capsid protein.

42. A method of treating a disease caused by a defect or mutation in a target gene comprising: administering to the cells of a subject having the disease a composition comprising a recombinant AAV comprising a nucleic acid trans-splicing molecule of any one of embodiments 1-38.

43. A method of treating an ocular disease caused by a defect or mutation in a target gene comprising: administering to the ocular cells of a subject having an ocular disease a composition comprising a recombinant AAV comprising a nucleic acid trans-splicing molecule of any one of embodiments 1-38.

44. The method according to embodiment 43, wherein the disease is Stargardt Disease, Leber Congenital Amaurosis (LCA), cone rod dystrophy, fundus flavimaculatus, retinitis pigmentosa, age-related macular degeneration, or Usher Syndrome.

45. The method of embodiment 43 or 44, wherein the composition is administered by subretinal injection.

46. The method of embodiment 43, wherein the disease is Stargardt's Disease, the cells are photoreceptor cells, the ocular gene is ABCA4 and the corrected exon sequence is Exons 1-19, Exons 1-22, Exons 1-23 or Exons 1-24.

47. A pharmaceutical preparation, comprising a physiologically acceptable carrier and the rAAV of any one of embodiments 39-41.

All publications cited in this specification are incorporated herein by reference in their entireties. In addition, U.S. Provisional Patent Application No. 62/835,164, filed Apr. 17, 2019, is incorporated herein by reference in its entirety. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A nucleic acid trans-splicing molecule comprising, operatively linked in a 5'-to-3' direction:

(a) a coding domain sequence (CDS) comprising one or more functional exons of a selected gene;

(b) a spliceosome recognition motif (5' splice site) configured to initiate spliceosome-mediated trans-splicing;

(c) a linker domain sequence (LDS) that acts as a structural connection between the coding domain and the binding domain, (d) a binding domain (BD) configured to bind to a target intron of the selected gene, wherein said gene has at least one mutation in an exon 5' to the target intron; and (e) a 3' transcription terminator domain (TTD), wherein the 3' TTD comprises, operatively linked in a 5'-to-3' direction: a triplex-forming sequence, an RNase P cleavage site and a tRNA-like sequence, wherein the RNase P cleavage site and the tRNA-like sequence comprise nucleotides 8379 to 8437 of SEQ ID NO: 7, and wherein the triplex-forming sequence comprises the nucleic acid sequence of SEQ ID NO: 15, wherein the nucleic acid trans-splicing molecule is configured to trans-splice the coding domain sequence to an endogenous exon of the selected gene adjacent to the target intron, thereby replacing the endogenous exon with the functional exon and correcting the mutation in the selected gene.

2. The nucleic acid trans-splicing molecule according to claim 1, wherein the binding domain hybridizes to the target intron of the selected gene 3' to the mutation and the coding domain comprises one or more exon(s) 5' to the target intron.

3. The nucleic acid trans-splicing molecule according to claim 1, wherein the 3' transcription terminator domain comprises nucleotides 8287 to 8437 of SEQ ID NO: 7.

4. The nucleic acid trans-splicing molecule according to claim 1, wherein the selected gene is ABCA4, CEP290, or MYO7A.

5. The nucleic acid trans-splicing molecule according to claim 4, wherein the selected gene is ABCA4 and has a mutation in any of Exons 1-22.

6. A recombinant adeno-associated virus (rAAV) comprising the nucleic acid molecule of claim 1, and optionally wherein the AAV targets a photoreceptor cell, and/or optionally wherein the AAV comprises an AAV5 capsid protein, an AAV8 capsid protein, an AAV8 (b) capsid protein, or an AAV9 capsid protein.

7. A method of treating a disease caused by a mutation in a target gene comprising administering to the cells of a subject having the disease a composition comprising the rAAV of claim 6, wherein the disease is Stargardt's Disease, the target gene is ABCA4 and the corrected exon sequence is Exons 1-19, Exons 1-22, Exons 1-23 or Exons 1-24.

8. A pharmaceutical preparation comprising a physiologically acceptable carrier and the nucleic acid trans-splicing molecule of claim 1.

9. A nucleic acid trans-splicing molecule comprising, operatively linked in a 5'-to-3' direction:

(a) a binding domain (BD) configured to bind a target intron of a selected gene, wherein said gene has at least one mutation in an exon 3' to the targeted intron;

(b) a linker sequence that acts as a structural connection between the binding domain and the coding domain;

(c) a 3' spliceosome recognition motif (3' splice site) configured to mediate trans-splicing;

(d) a coding domain sequence (CDS) comprising one or more functional exons of the selected gene; and (e) a 3' transcription terminator domain (TTD), wherein the 3' TTD comprises, operatively linked in a 5'-to-3' direction: a triplex-forming sequence, an RNase P cleavage site and a tRNA-like sequence, wherein the RNase P cleavage site and the tRNA-like sequence comprise nucleotides 8379 to 8437 of SEQ ID NO: 7, and wherein the triplex-forming sequence comprises the nucleic acid sequence of SEQ ID NO: 15, wherein the nucleic acid trans-splicing molecule is configured to trans-splice the coding domain to an endogenous exon of the selected gene adjacent to the target intron, thereby replacing the endogenous exon with the functional exon and correcting the mutation in the selected gene.

10. The nucleic acid trans-splicing molecule according to claim 9, wherein the binding domain binds to the target intron of the selected gene 5' to the mutation and the coding domain comprises one or more exon(s) 3' to the target intron.

11. The nucleic acid trans-splicing molecule according to claim 9, wherein the 3' transcription terminator domain comprises nucleotides 8287 to 8437 of SEQ ID NO: 7.

12. The nucleic acid trans-splicing molecule according to claim 9, wherein the selected gene is ABCA4, CEP290, or MYO7A.

13. The nucleic acid trans-splicing molecule according to claim 12, wherein the selected gene is ABCA4 and has a mutation in any of Exons 23-50.

14. A recombinant adeno-associated virus (rAAV) comprising the nucleic acid molecule of claim 9, and optionally wherein the AAV targets a photoreceptor cell, and/or optionally wherein the AAV comprises an AAV5 capsid protein, an AAV8 capsid protein, an AAV8 (b) capsid protein, or an AAV9 capsid protein.

15. A method of treating a disease caused by a mutation in a target gene comprising administering to the cells of a subject having the disease a composition comprising the rAAV of claim 14, wherein the disease is Stargardt's Disease, the target gene is ABCA4 and the corrected exon sequence is Exons 23-50, Exons 24-50, or Exons 27-50.

16. A pharmaceutical preparation comprising a physiologically acceptable carrier and the nucleic acid trans-splicing molecule of claim 9.

* * * * *